US005614624A

United States Patent [19]
Hirai et al.

[11] Patent Number: 5,614,624
[45] Date of Patent: Mar. 25, 1997

[54] CARBAPENEM

[75] Inventors: Koichi Hirai; Yuji Iwano; Takahide Nishi; Akira Yoshida; Kozo Oda, all of Tokyo, Japan; Hiroo Koyama, Westfield, N.J.

[73] Assignee: Sankyo Company, Limited, Tokyo, Japan

[21] Appl. No.: 460,209

[22] Filed: Jun. 2, 1995

Related U.S. Application Data

[60] Division of Ser. No. 289,133, Aug. 11, 1994, Pat. No. 5,541,317, which is a continuation-in-part of Ser. No. 90,489, Jul. 12, 1993, abandoned, and Ser. No. 119,008, Sep. 9, 1993, abandoned, which is a continuation of Ser. No. 888,879, May 26, 1992, abandoned.

[30] Foreign Application Priority Data

| May 31, 1991 | [JP] | Japan | 3-129576 |
| Jul. 12, 1991 | [JP] | Japan | 3-172220 |
| Sep. 9, 1992 | [JP] | Japan | 4-240825 |
| Dec. 4, 1992 | [JP] | Japan | 4-325114 |

[51] Int. Cl.$^6$ .................................. C07D 487/04
[52] U.S. Cl. ................................................ 540/350
[58] Field of Search .................................... 540/350

[56] References Cited

U.S. PATENT DOCUMENTS

| 4,772,683 | 9/1988 | Martel et al. . |
| 4,820,817 | 4/1989 | Christensen . |
| 4,895,939 | 1/1990 | Martel et al. . |
| 5,011,832 | 4/1991 | Dininno et al. . |

FOREIGN PATENT DOCUMENTS

| 0000828 | 2/1979 | European Pat. Off. . |
| 0046363 | 2/1982 | European Pat. Off. . |
| 0061231 | 9/1982 | European Pat. Off. . |
| 0060612 | 9/1982 | European Pat. Off. . |
| 0090366 | 10/1983 | European Pat. Off. . |
| 0105227 | 4/1984 | European Pat. Off. . |

OTHER PUBLICATIONS

McOmie, Protective Groups in Organic Chemistry, 1973, pp. 183–210.

Sown, et al, "Enantioselective Synthesis of the 1β–Methylcarbapenems via Cycloaddition of 3–Siloxypentadiene and 4–Acetoxyazetidinone", J.A.C.S., 53, 4154 (1988).

Guthikonda et al, "Structure–Activity Relationships in the 2–Arylcarbapenem Series: Synthesis of 1–Methyl–2–arylcarbapenems", J. Med. Chem., 30, 871 (1987).

Kim et al, "Stereoselective Synthesis of 1–β–Methylcarbapenem", Tetrahedron Letters, 28, 507–510 (1987).

Primary Examiner—Rebecca Cook
Attorney, Agent, or Firm—Frishauf, Holtz, Goodman, Langer & Chick, P.C.

[57] ABSTRACT

A compound of the formula (IV')

in which:

$R^{1'}$ is hydrogen or a carboxy-protecting group;

$R^{41'}$ is hydrogen or a hydroxy-protecting group;

$R^{42'}$ is a $C_1$–$C_6$ alkyl, a $C_1$–$C_6$ alkoxy, a halogen, an aryl or an aryloxy; $R^{43'}$ is hydrogen, a $C_1$–$C_6$ alkyl, a $C_1$–$C_6$ alkoxy, a hydroxy, a halogen, a cyano, a nitro or a group of the formula —$NR^{8'}R^{9'}$, where $R^{8'}$ and $R^{9'}$ are independently selected from the group consisting of hydrogen, amino-protecting groups, $C_1$–$C_6$ alkyl groups and phenyl groups, or $R^{8'}$ and $R^{9'}$ together represent a group —$(CH_2)_{q'}$—$O_{r'}$—$(CH_2)_{s'}$—, where q' and s' are independently 0 or an integer of from 1 to 5 and r' is 0 or 1, provided that (q'+s') is an integer of at least 2; $R^{45'}$ and $R^{46'}$ are independently selected from the group consisting of $C_1$–$C_6$ alkyl groups and aryl groups, or $R^{45'}$ and $R^{46'}$ together represent a group —$(CH_2)_{q'}$—$O_{r'}$—$(CH_2)_{s'}$—, where q' and s' are independently 0 or an integer of from 1 to 5 and r' is 0 or 1; Y' is oxygen or sulfur; and j' is 0, 1 or 2.

13 Claims, No Drawings

CARBAPENEM

This is a division of application Ser. No. 08/289,133 filed Aug. 11, 1994, now U.S. Pat. No. 5,541,317, which is a CIP of both (i) application Ser. No. 08/090,489 filed Jul. 12, 1993 abandoned which is a continuation of application Ser. No. 07/888,879 filed May 26, 1992 (abandoned) and (ii) application Ser. No. 08/119,008 filed Sep. 9, 1993 abandoned.

BACKGROUND TO THE INVENTION

The present invention relates to a series of new azetidinone derivatives which may be used as intermediates in the preparation of certain carbapenem antibiotics.

The present invention also relates to a new process for preparing a series of carbapenem and penem compounds which are useful as antibiotics. The invention also provides a series of novel intermediates used in this process.

The penam and cephem antibiotics have been known for many years and have proved of considerable value in the control and prevention of infectious diseases. More recently, penem and carbapenem antibiotics have been developed and have also been found to be of great benefit. The penem and carbapenem compounds have in common a basic structure which may be represented by the formula (A'):

in which Z' represents a sulfur atom or a group of formula >CH$_2$, which may optionally be substituted by an alkyl or alkoxy group. Those compounds in which Z' represents a sulfur atom are the penem compounds, whilst those in which Z' represents a group of formula >CH$_2$ or substituted group of formula >CH$_2$ are the carbapenem compounds. In accordance with the recommendations of the International Union of Pure and Applied Chemistry (IUPAC), the compounds referred to herein are named semi-systematically using penem and carbapenem as the parent compound. For the avoidance of doubt, the above formula (A') also shows the relevant numbers in the peripheral numbering system employed to describe the compounds herein.

Those carbapenem antibiotics having no substituent at the 1-position are potentially a very useful series of compounds which have extraordinarily potent antibacterial activity. Unfortunately, however, they are chemically unstable and, moreover, are sensitive to dehydropeptidase I in vivo. Dehydropeptidase I is an enzyme which hydrolyses the β-lactam ring in carbapenem antibiotics and which exists in mammalian tissue, for example in the renal cortex. It is responsible for the extensive metabolisation of many otherwise valuable β-lactam antibiotics in animals, including humans, thus greatly reducing their value. Despite these disadvantages, these carbapenem antibiotics are finding increasing use in the treatment of bacterial infections. On the other hand, those carbapenem antibiotics having a 1β-substituent are chemically stable and are resistant to the dehydropeptidase I enzyme. However, none of this series of compounds has been found in nature, and the compounds must, accordingly, be prepared by chemical synthesis. As with many biologically active compounds, the steric configuration of some of the atoms in the molecules of these compounds is of importance and the most interesting compounds have a multi-ring structure whose skeleton may be represented by the formula (B):

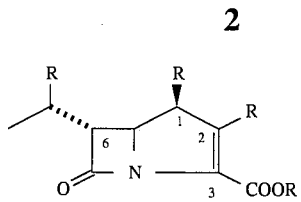

in which each of the symbols R represents any of a variety of substituent groups, some of which may be quite complex, and the different groups represented by R in this formula may be the same or different, although they are normally different from each other. The numbering system shown on this formula is that commonly used in the art for the nomenclature of such compounds and is as used herein.

In the preparation of these compounds, it is necessary to synthesise an azetidinone ring system with various substituent groups preferably in the desired final configuration. This, in general, has proven difficult, although many attempts have been made. For example, U.S. Pat. Nos. 4,895,939 and 4,772,683 describe the preparation of a compound of formula (C):

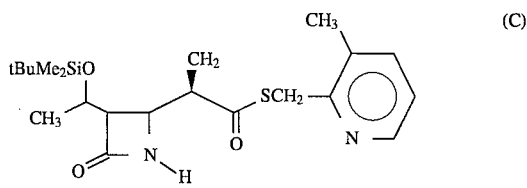

(in which tBu represents a t-butyl group and Me represents a methyl group) by reacting a compound of formula (D):

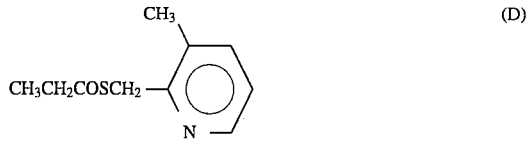

with t-butyldimethylsilyl trifluoroacetate, which has the formula CF$_3$COOSi(CH$_3$)$_2$tBu, in the presence of a base to give a 75:25 mixture of compounds of formula (E) and (F):

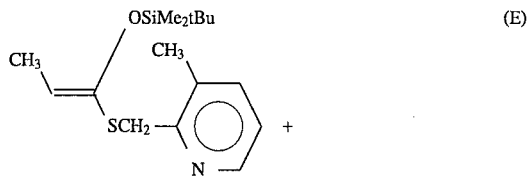

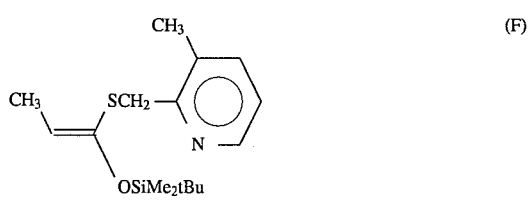

This mixture is then reacted with a compound of formula (G):

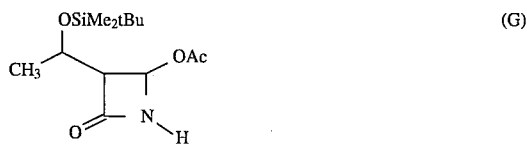

in the presence of a Lewis acid, to give the desired compound of formula (C).

It has been reported that a 2R-isomer of a compound of formula (H):

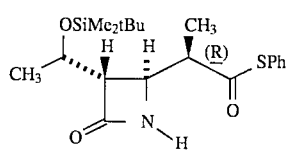

which is a key intermediate in the synthesis of 1β-methylcarbapenem antibiotics, can be synthesized by reacting a silyl enol ether prepared from S-phenyl thiopropionate with (3R,4R)-3-[(1R)-1-t-butyldimethylsilyloxy)ethyl]-4-acetoxy-2-azetidinone or with its 1-trimethylsilyl derivative [T. Shibata et al., Tetrahedron Letters, 26, 4793 (1985); C. U. Kim et al., Tetrahedron Letters, 28, 507 (1987); A. Martel et al., Can. J. Chem., 66, 1537 (1988)].

However, in the syntheses described in these reports, the 2R- and 2S-isomers of the thiopropionic acid derivative of formula (H) are produced in the ratio of 1.6:1, 1:19 and 1:9, respectively. Thus the desired 2R-isomer is prepared in relatively minor amounts and, in most cases, is produced in admixture with a much larger quantity of its less useful 2S-isomer, or, at least, with a substantial quantity of the 2S-ismoer, from which its separation is difficult, expensive and inefficient.

There is, therefore, a need for a method of preparing the desired carbapenem antibiotic precursors which allows the required compounds to be obtained in better yields and with the desired isomer as the major product and not in admixture with substantial amounts of an unwanted isomer.

Several compounds having a thiol group attached to the 2-position of a penem or carbapenem compound are known and are thought to be of value as antibiotics. Many such compounds are prepared synthetically. In particular, the 1β-methylcarbapenem derivatives, which are currently of considerable interest in this field, must be prepared synthetically, as no microorganism has been found which secretes them. An excellent method of synthesizing such compounds, which overcomes many of the disadvantages of the prior processes, is described in Japanese Patent Kokai Application No. Hei 1-25780 and involves oxidizing a sulfur atom at the carbapenem 2-position to an S-oxide (i.e. a sulfinyl or sulfonyl group) and then replacing the resulting sulfinyl or sulfonyl group by a desired mercapto group, for example as shown in the following reaction:

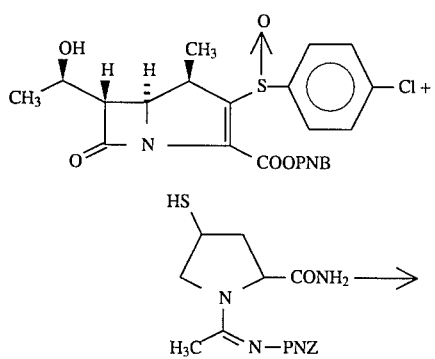

-continued

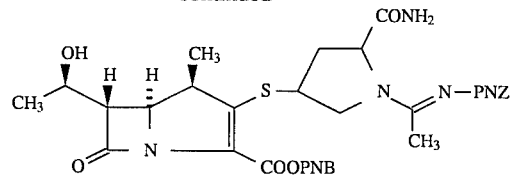

However, when this reaction is carried out by conventional means in which an organic base is employed, in many cases the sulfenic acid formed by the substitution reaction induces the production of various kinds of by-products, which results in a low reaction yield. For example, the yield of the addition-elimination reaction shown in the above reaction scheme is said to be 22% in Japanese Patent Kokai Application No. Hei 1-25780.

We have now surprisingly found that, if the reaction is effected in the presence of a metal salt of a metal of Group II or III of the Periodic Table of the Elements, in place of the organic base, yields can be much improved and yields of 40 to 80% or more (sometimes over 90%) can be achieved, instead of the yields of, at best, around 20% achievable in the prior art.

BRIEF SUMMARY OF INVENTION

It is, therefore, an object of the present invention to provide a series of novel azetidinone derivatives which can be used as intermediates in the preparation of a variety of carbapenem derivatives, including some useful antibiotics.

It is accordingly another object of the present invention to provide a process for the preparation of 2-substituted thio derivatives.

It is a further, and more specific, object of the invention to provide a process for preparing such compounds which allows them to be obtained in high yields.

Other objects and advantages will become apparent as the description proceeds.

Thus, compounds of the present invention are those compounds of formula (I):

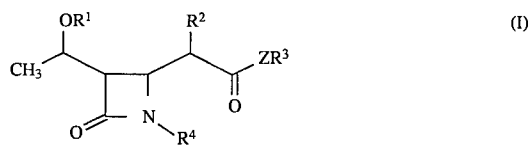

wherein:
$R^1$ represents a hydrogen atom or a hydroxy-protecting group;
$R^2$ represents an alkyl group having from 1 to 6 carbon atoms, an alkoxy group having from 1 to 6 carbon atoms, a halogen atom, an unsubstituted phenyl group, an unsubstituted phenoxy group, or a substituted phenyl or phenoxy group having at least one substituent selected from the group consisting of substituents (a), defined below;
$R^3$ represents:
  a pyridyl group which is unsubstituted or is substituted by at least one substituent selected from the group consisting of substituents (a), defined below;
  a quinolyl group which is unsubstituted or is substituted by at least one substituent selected from the group consisting of substituents (a), defined below; or
  a phenyl group which has a substituent of formula —CYNR$^5$R$^6$ and no further substituent or has at least one substituent selected from the group consisting of substituents (a), defined below, where Y represents an oxygen or sulfur atom; and $R^5$ and $R^6$ are independently selected from the group consisting of alkyl groups having from 1 to 6 carbon atoms, aryl groups as defined below, and aralkyl groups in which the alkyl part has from 1 to 6 carbon atoms and the aryl part is as defined below, or $R^5$ and $R^6$ together form a group of formula $-(CH_2)_m-(X)_p-(CH_2)_n-$, wherein m and n are independently selected from the group consisting of the cipher 0 and integers from 1 to 5, provided that (m+n) is greater than 1, p is 0 or 1, and X represents an oxygen or sulfur atom or a group of formula $=R^7$, where $R^7$ represents an alkyl group having from 1 to 6 carbon atoms, an aliphatic carboxylic acyl group having from 1 to 6 carbon atoms or an aromatic carboxylic acyl group in which the aryl part is as defined below;

$R^4$ represents a hydrogen atom or an amino-protecting group; and

Z represents a sulfur atom or an oxygen atom;

said aryl groups and the aryl parts of said aralkyl groups and said aromatic carboxylic acyl groups are carbocyclic aryl groups which have from 6 to 10 carbon atoms in at least one aromatic ring and which are unsubstituted or are substituted by at least one substituent selected from the group consisting of substituents (a), defined below;

said substituents (a) are selected from the group consisting of alkyl groups having from 1 to 6 carbon atoms, alkoxy groups having from 1 to 6 carbon atoms, halogen atoms, cyano groups, nitro groups, hydroxy groups, amino groups, alkylamino groups in which the alkyl part has from 1 to 4 carbon atoms, dialkylamino groups in which each alkyl part has from 1 to 4 carbon atoms and alkylenedioxy groups having from 1 to 3 carbon atoms.

The invention also provides processes for preparing these compounds and for using them to prepare carbapenem derivatives, which are described in greater detail hereafter.

In general terms, the present invention provides a process for preparing a compound of formula (I'):

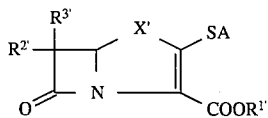

in which:

$R^{1'}$ represents a hydrogen atom or a carboxy-protecting group;

$R^{2'}$ and $R^{3'}$ are independently selected from the group consisting of hydrogen atoms, alkyl groups having from 1 to 6 carbon atoms and groups of formula

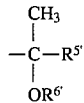

where $R^{5'}$ represents a hydrogen atom or a methyl group; and $R^{6'}$ represents a hydrogen atom or a hydroxy-protecting group; or $R^{2'}$ and $R^{3'}$ together represent a group of formula $=C(CH_3)CH_2OR^{6'}$, in which $R^{6'}$ is as defined above;

X' represents a sulfur atom or a group of formula $>CHR^{7'}$, where $R^{7'}$ represents a hydrogen atom, an alkyl group having from 1 to 6 carbon atoms or an alkoxy group having from 1 to 6 carbon atoms; and A' represents an alkyl group which has from 1 to 6 carbon atoms and which is unsubstituted or is substituted by 1 or 2 substituents selected from the group consisting of substituents A', defined below, an aryl group, as defined below, an aralkyl group in which an alkyl group having from 1 to 6 carbon atoms is substituted by at least one aryl group as defined below, a heterocyclic group which has from 3 to 10 ring atoms, at least one of said atoms being a hetero-atom selected from the group consisting of nitrogen, oxygen and sulfur hetero-atoms, said group being unsubstituted or being substituted by at least one substituent selected from the group consisting of substituents B' on carbon atoms, substituents $B^{1'}$ on nitrogen hetero-atoms, and oxygen atoms to form a sulfinyl or sulfonyl group on sulfur hetero-atoms, all as defined below;

a fused heterocyclic group in which a heterocyclic group as defined above is fused to an aryl group as defined below, or an alkyl group which has from 1 to 6 carbon atoms and which is substituted by at least one substituent selected from the group consisting of the heterocyclic groups and fused heterocyclic groups defined above;

said aryl groups are aromatic carbocyclic groups having from 6 to 14 ring carbon atoms and are unsubstituted or are substituted by at least one substituent selected from the group consisting of substituents C', defined below;

said substituents A' are selected from the group consisting of hydroxy groups, protected hydroxy groups, amino groups, protected amino groups, groups of formula $-C(=NR^{10'})NR^{11'}R^{12'}$, where $R^{10'}$, $R^{11'}$ and $R^{12'}$ are independently selected from the group consisting of hydrogen atoms, amino-protecting groups and alkyl groups having from 1 to 6 carbon atoms, or $R^{11'}$ and $R^{12'}$ together represent a group of formula $-(CH_2)_{n'}-$, where n' is an integer from 2 to 6, or $R^{10'}$ and $R^{11'}$ together represent a group of formula $-(CH_2)_{p'}-$, where p' is 2 or 3, and groups of formula $-NR^{13'}C(=NR^{14'})R^{15'}$, where $R^{13'}$ and $R^{14'}$ are independently selected from the group consisting of hydrogen atoms, amino-protecting groups and alkyl groups having from 1 to 6 carbon atoms, and $R^{15'}$ represents a hydrogen atom, an alkyl group having from 1 to 6 carbon atoms, an amino group or a protected amino group, or any two of $R^{13'}$, $R^{14'}$ and $R^{15'}$ together represent a group of formula $-(CH_2)_{p'}-$, where p' is 2 or 3;

said substituents B' are selected from the group consisting of alkyl groups having from 1 to 6 carbon atoms, alkoxy groups having from 1 to 6 carbon atoms, hydroxy groups, halogen atoms, cyano groups, nitro groups, alkoxycarbonyl groups having from 2 to 7 carbon atoms, carboxy groups, oxygen atoms, to form with a ring carbon atom a carbonyl group, cycloalkyl groups having from 3 to 7 ring carbon atoms, alkoxyalkyl groups in which the alkoxy and alkyl parts both have from 1 to 6 carbon atoms, alkoxycarbonylalkyl groups in which the alkoxy and alkyl parts both have from 1 to 6 carbon atoms, cyanoalkyl groups in which the alkyl part has from 1 to 6 carbon atoms, haloalkyl groups having from 1 to 6 carbon atoms, alkanoyloxy groups having from 1 to 6 carbon atoms, azido groups, alkylthio groups having from 1 to 6 carbon atoms, alkylsulfinyl groups having from 1 to 6 carbon atoms, alkylsulfonyl groups having from 1 to 6 carbon atoms, groups of formula —NR$^{8'}$R$^{9'}$ and groups of formula —CONR$^{8'}$R$^{9'}$, where R$^{8'}$ and R$^{9'}$ are independently selected from the group consisting of hydrogen atoms, amino-protecting groups, alkyl groups having from 1 to 6 carbon atoms and phenyl groups, or R$^{8'}$ and R$^{9'}$ together represent a group of formula —(CH$_2$)$_{q'}$—O$_{r'}$—(CH$_2$)$_{s'}$—, where q' and s' are independently selected from the group consisting of 0 and integers of from 1 to 5 and r' is 0 or 1, provided that (q'+s') is an integer of at least 2; and groups of formulae (B-I'), (B-II'), (B-III'), (B-IV'), (B-V'), (B-VI'), (B-VII'), (B-VIII') and (B-IX'):

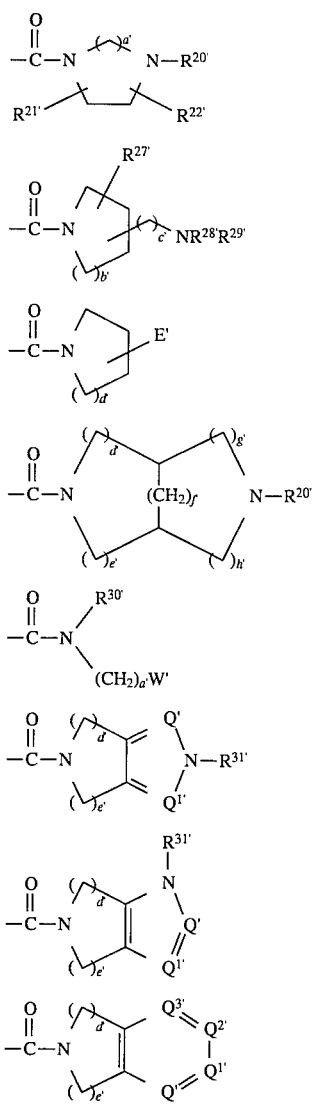

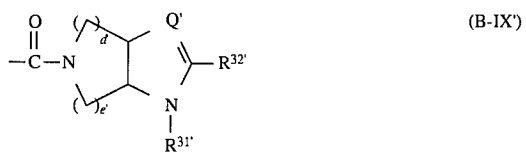

in which:

a' is 1, 2 or 3, b' is 1, 1 or 2, c' is 0 or 1, d' is 0, 1 or 2, e' is 0, 1 or 2, f' is 0, 1 or 2, g' is 0, 1 or 2, h' is 0, 1 or 2,

R$^{20'}$ represents a hydrogen atom, an amino-protecting group, a group of formula —COR$^{26'}$, where R$^{26'}$ represents an alkyl group having from 1 to 6 carbon atoms or a substituted alkyl group which has from 1 to 6 carbon atoms and which is substituted by at least one substituent selected from the group consisting of substituents A';

a group of formula —C(=NR$^{16'}$)R$^{17'}$, where

R$^{16'}$ and R$^{17'}$ are independently selected from the group consisting of hydrogen atoms, alkyl groups having from 1 to 6 carbon atoms, amino groups, protected amino groups and amino-protecting groups;

an unsubstituted alkyl group having from 1 to 6 carbon atoms, or a substituted alkyl group which has from 1 to 6 carbon atoms and which is substituted by at least one substituent selected from the group consisting of substituents D', defined below.

R$^{21'}$ and R$^{22'}$ are independently selected from the group consisting of hydrogen atoms, alkyl groups having from 1 to 6 carbon atoms, hydroxy groups and protected hydroxy groups;

R$^{27'}$ represents a hydrogen atom or an alkyl group having from 1 to 6 carbon atoms;

R$^{28'}$ and R$^{29'}$ are independently selected from the group consisting of hydrogen atoms, alkyl groups having from 1 to 6 carbon atoms, amino-protecting groups, amino groups, protected amino groups and groups of formula —C(=NR$^{16'}$)R$^{17'}$, where R$^{16'}$ and R$^{17'}$ are as defined above;

R$^{30'}$ represents a hydrogen atom, an alkyl group having from 1 to 6 carbon atoms or a substituted alkyl group which has from 1 to 6 carbon atoms and which is substituted by at least one substituent selected from the group consisting of hydroxy groups and protected hydroxy groups;

R$^{31'}$ represents a hydrogen atom, an alkyl group having from 1 to 6 carbon atoms or an amino-protecting group;

R$^{32'}$ represents a hydrogen atom, an alkyl group having from 1 to 6 carbon atoms or a group of formula —NR$^{28'}$R$^{29'}$, in which R$^{28'}$ and R$^{29'}$ are as defined above;

E' represents an imidazolyl group or a triazolyl group;

W' represents an aromatic heterocyclic group having from 5 to 8 ring atoms, of which from 1 to 4 are nitrogen atoms, said aromatic heterocyclic group being unsubstituted or being substituted by at least one alkyl group having from 1 to 6 carbon atoms;

Q', Q$^{1'}$, Q$^{2'}$ and Q$^{3'}$ are independently selected from the group consisting of groups of formula >CH and >N;

said substituents B[1'] are selected from the group consisting of alkyl groups having from 1 to 6 carbon atoms, amino-protecting groups, groups of formula —C(=NR[16'])R[17'], where R[16'] and R[17'] are as defined above, amino-protecting groups and groups of formula —CONR[18']R[19'], where R[18'] and R[19'] are independently selected from the group consisting of alkyl groups having from 1 to 6 carbon atoms and carboxylic acyl groups;

said substituents C' are selected from the group consisting of alkyl groups having from 1 to 6 carbon atoms, alkoxy groups having from 1 to 6 carbon atoms, halogen atoms, alkoxycarbonyl groups having from 2 to 7 carbon atoms, groups of formula —CONR[8']R[9'], where R[8'] and R[9'] are as defined above, cyano groups, hydroxy groups and nitro groups;

said substituents D' are selected from the group consisting of hydroxy groups, protected hydroxy groups, carboxy groups, protected carboxy groups, cyano groups, alkoxy groups having from 1 to 6 carbon atoms, alkylsulfonyl groups having from 1 to 6 carbon atoms, groups of formula —NHCOR[23'], —NR[24']R[25'], —CONR[24']R[25'] or —OCONR[24']R[25'], where R[23'], R[24'] and R[25'] are independently selected from the group consisting of hydrogen atoms and alkyl groups having from 1 to 6 carbon atoms, and pharmaceutically acceptable salts and esters thereof, which process comprises reacting a compound of formula (II):

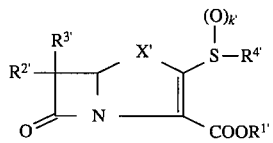

(II')

in which R[1'], R[2'], R[3'] and X' are as defined above, k' is 1 or 2, and R[4'] represents:

an alkyl group which has from 1 to 6 carbon atoms and which is unsubstituted or is substituted by at least one substituent selected from the group consisting of substituents E', defined below, an alkenyl group which has from 2 to 6 carbon atoms and which is unsubstituted or is substituted by at least one substituent selected from the group consisting of substituents E', defined below, an aryl group, as defined above, an aralkyl group in which an alkyl group having from 1 to 6 carbon atoms is substituted by at least one aryl group as defined above, a cycloalkyl group which has from 3 to 7 carbon atoms and which is unsubstituted or is substituted by at least one substituent selected from the group consisting of substituents C', defined above, an aromatic heterocyclic group which has from 5 to 7 ring atoms in an aromatic ring, at least one of said atoms being a hetero-atom selected from the group consisting of nitrogen, oxygen and sulfur hetero-atoms, said group being unsubstituted or being substituted by at least one substituent selected from the group consisting of substituents C', defined above;

a fused heterocyclic group in which an aromatic heterocyclic group as defined above is fused to an aryl group as defined above, or an alkyl group which has from 1 to 6 carbon atoms and which is substituted by at least one substituent selected from the group consisting of the aromatic heterocyclic groups and fused heterocyclic groups defined above; and said substituents E' are selected from the group consisting of hydroxy groups, protected hydroxy groups, amino groups and protected amino groups;

with a compound of formula (III'):

A'SH          (III')

in which A' is as defined above, and, if desired, removing any protecting groups, wherein the improvement comprises carrying out the reaction of said compound of formula (II') and said compound of formula (III') in the presence of a salt of a metal of Group II or III of the Periodic Table of Elements.

Certain of the compounds of formula (II') used as starting materials in the above reaction are novel compounds and also form part of the present invention. These novel compounds are those compounds of formula (IV'):

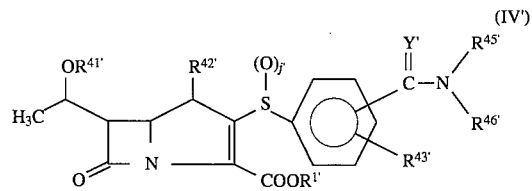

(IV')

in which:

R[1'] is as defined above;

R[41'] represents a hydrogen atom or a hydroxy-protecting group;

R[42'] represents an alkyl group having from 1 to 6 carbon atoms, an alkoxy group having from 1 to 6 carbon atoms, a halogen atom, an aryl group as defined above or an aryloxy group in which the aryl part is as defined above;

R[43'] represents a hydrogen atom, an alkyl group having from 1 to 6 carbon atoms, an alkoxy group having from 1 to 6 carbon atoms, a hydroxy group, a halogen atom, a cyano group, a nitro group or a group of formula —NR[8']R[9'], where R[8'] and R[9'] are as defined above;

R[45'] and R[46'] are independently selected from the group consisting of alkyl groups having from 1 to 6 carbon atoms and aryl groups as defined above, or R[45'] and R[46'] together represent a group of formula —(CH$_2$)$_{q'}$—O$_{r'}$—(CH$_2$)$_{s'}$—, where q' and s' are independently selected from the group consisting of 0 and integers of from 1 to 5 and r' is 0 or 1;

Y' represents an oxygen atom or a sulfur atom; and j' is 0, 1 or 2;

and pharmaceutically acceptable salts and esters thereof.

DETAILED DESCRIPTION OF INVENTION

The steric configuration of the compounds of formula (I) important and we therefore generally prefer those compounds of formula (I) whose configuration is as shown in formula (Ia):

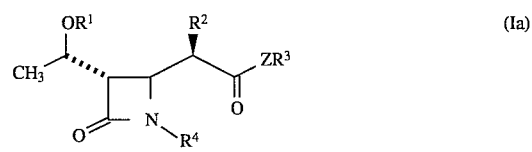

(Ia)

Since the compounds of formula (I) of the present invention are useful as intermediates in the preparation of other compounds and are not themselves used as drugs, the nature of certain groups in the compound whose only function is to protect a group or a part of the molecule from attack during the preparation of those other compounds is not critical. These are the hydroxy-protecting groups which may be represented by $R^1$ and the amino-protecting groups which may be represented by $R^4$.

Where $R^1$ represents a hydroxy-protecting group, the nature of the group is not critical to the invention, and it may be selected from a wide range of known groups having regard to criteria usually employed in the art and well known to those skilled in the art, without any particular restriction. Examples of such groups include:

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups preferably having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic aromatic group, which is unsubstituted or has from 1 to 5, preferably from 1 to 3 substituents, selected from the group consisting of substituents (b), defined and exemplified below, preferably: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 5, preferably from 1 to 4, carbon atoms (such as the 4-anisoyl group); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents (b), defined and exemplified below, and oxygen atoms; examples include: the tetrahydropyranyl groups, which may be substituted or unsubstituted, such as the tetrahydropyran-2-yl, 3-bromotetrahydropyran-2-yl and 4-methoxytetrahydropyran-4-yl groups; the tetrahydrothiopyranyl groups, which may be substituted or unsubstituted, such as the tetrahydrothiopyran-2-yl and 4-methoxytetrahydrothiopyran-4-yl groups; the tetrahydrofuranyl groups, which may be substituted or unsubstituted, such as the tetrahydrofuran-2-yl group; and the tetrahydrothienyl groups, which may be substituted or unsubstituted, such as the tetrahydrothien-2-yl group;

tri-substituted silyl groups, in which all three or two or one of the substituents are alkyl groups having from 1 to 5, preferably from 1 to 4, carbon atoms, and, correspondingly, none, one or two of the substituents are aryl groups, as defined above, but preferably phenyl or substituted phenyl groups, preferably: tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutylsilyl, diphenyl-t-butylsilyl, diphenylisopropylsilyl and phenyldiisopropylsilyl groups);

alkoxylakyl groups, in which the alkoxy and alkyl parts each have from 1 to 5, preferably from 1 to 4, carbon atoms, especially the alkoxymethyl and alkoxyethyl groups, more especially the alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, 1,1-dimethyl-1-methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)methyl groups] and lower alkoxy-substituted ethyl groups (such as the 1-ethoxyethyl, 1-methyl-1-methoxyethyl and 1-isopropoxyethyl groups);

other substituted ethyl groups, preferably: halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups (in which the aryl group has from 6 to 14 ring carbon atoms, but is otherwise as defined above), which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or may be substituted on the aryl part with a lower alkyl group ("lower" meaning "having from 1 to 6 carbon atoms"), a lower alkoxy group, a nitro group, a halogen atom, a cyano group, or an alkylenedioxy group having from 1 to 3 carbon atoms, preferably a methylenedioxy group [such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups];

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or may be substituted with a halogen atom or a tri-substituted silyl group (as defined above), e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups);

sulfo groups; and aralkyloxycarbonyl groups, in which the aralkyl part is as defined and exemplified above, but is preferably a benzyl or phenethyl group, more preferably a phenethyl group, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups).

Of the protecting groups listed above, we prefer: the tri-substituted silyl groups, such as the t-butyldimethylsilyl, trimethylsilyl and triethylsilyl groups; the optionally substituted benzyloxycarbonyl groups, such as the benzyloxycarbonyl and 4-nitrobenzyloxycarbonyl group; and the aliphatic acyl groups, such as the acetyl, chloroacetyl and methoxyacetyl groups. Still more preferred are the tri-substituted silyl groups, especially the t-butyldimethylsilyl and trimethylsilyl groups, more especially the t-butyldimethylsilyl group.

However, the corresponding carbapenem compounds prepared from the compounds of the present invention normally have a hydroxy group in the position corresponding to the group of formula —$OR^1$, i.e. $R^1$ is preferably hydrogen, and so the protecting group will be removed before the resulting compound is used in therapy. Its function is, therefore, simply to protect the hydroxy group during preparation of the compounds of the present invention and during conversion of those compounds to the desired carbapenem compounds.

Where $R^2$ represents an alkyl group having from 1 to 6 carbon atoms, this may be a straight or branched chain group having from 1 to 6, preferably from 1 to 5, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, more preferably a methyl or ethyl group and most preferably the methyl group.

Where $R^2$ represents an alkoxy group having from 1 to 6 carbon atoms, this may be a straight or branched chain group having from 1 to 6, preferably from 1 to 5, carbon atoms, and examples include the methoxy, ethoxy, propoxy, isopropoxy, butoxy, isobutoxy, sec-butoxy, t-butoxy, pentyloxy, isopentyloxy, neopentyloxy, 2-methylbutoxy,1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups. Of these, we prefer those alkoxy groups having from 1 to 4 carbon atoms, preferably the methoxy, ethoxy, propoxy, isopropoxy, butoxy, sec-butoxy and t-butoxy groups, and most preferably the methoxy group.

Where $R^2$ represents a halogen atom, this may be a fluorine, chlorine, bromine or iodine atom, preferably a fluorine or chlorine atom, and most preferably a chlorine atom.

Where $R^2$ represents a phenyl or phenoxy group, this may be a substituted or unsubstituted group. If substituted, the substituents are preferably selected from the group consisting of substituents (a) defined above and exemplified below. Examples of such substituted groups include the 2-chlorophenyl, 3-chlorophenyl, 4-chlorophenyl, 4-cyanophenyl, 4-nitrophenyl, 2,4-dichlorophenyl, 2,5-dichlorophenyl, 2,4,5-trichlorophenyl, 2-methylphenyl, 3-methylphenyl, 4-methylphenyl, 2,4-dichloro-3-methylphenyl, 4-aminophenyl, 4-methylaminophenyl, 4-dimethylaminophenyl, 4-hydroxyphenyl, 4-methoxyphenyl, 3-methoxyphenyl, 2-methoxyphenyl, 3-chloro-4-methoxyphenyl, 2-chlorophenoxy, 3-chlorophenoxy, 4-chlorophenoxy, 4-cyanophenoxy, 4-nitrophenoxy, 2,4-dichlorophenoxy, 2,5-dichlorophenoxy, 2,4,5-trichlorophenoxy, 2-methylphenoxy, 3-methylphenoxy, 4-methylphenoxy, 2,4-dichloro-3-methylphenoxy, 4-aminophenoxy, 4-methylaminophenoxy, 4-dimethylaminophenoxy, 4-hydroxyphenoxy, 4-methoxyphenoxy, 3-methoxyphenoxy, 2-methoxyphenoxy, and piperonyl (3,4-methylenedioxyphenyl) groups. However, the unsubstituted phenyl and phenoxy groups are preferred.

Of the groups and atoms listed above, $R^2$ preferably represents a methyl group, an ethyl group, a methoxy group or a chlorine atom, most preferably a methyl group.

Where $R^3$ represents a pyridyl group, this may be unsubstituted or it may be substituted by at least one substituent selected from the group consisting of substituents (a), defined above and exemplified below. The pyridyl group itself may be a 2-, 3- or 4-pyridyl group and, if it is substituted, the number of substituents is limited only by the number of substitutable positions (four) and possibly by steric constraints. In general the number of substituents is preferably 1 or 2, and more preferably 1. The pyridyl group, whether unsubstituted or substituted, is preferably the 2-pyridyl group. Although the group may be substituted by any one or more of substituents (a), exemplified below, preferred examples of substituted groups include the 3-methyl-2-pyridyl, 4-methyl-2-pyridyl, 5-methyl-2-pyridyl, 2-methyl-3-pyridyl, 4-methyl-3-pyridyl, 5-methyl-3-pyridyl, 2-methyl-4-pyridyl, 3-methyl-4-pyridyl, 5-methyl-4-pyridyl, 3-ethyl-2-pyridyl, 4-ethyl-2-pyridyl, 5-ethyl-2-pyridyl, 2-ethyl-3-pyridyl, 4-ethyl-3-pyridyl, 5-ethyl-3-pyridyl, 2-ethyl-4-pyridyl, 3-ethyl-4-pyridyl, 5-ethyl-4-pyridyl, 3-chloro-2-pyridyl, 4-chloro-2-pyridyl, 5-chloro-2-pyridyl, 2-chloro-3-pyridyl, 4-chloro-3-pyridyl, 5-chloro-3-pyridyl, 2-chloro-4-pyridyl, 3-chloro-4-pyridyl, 5-chloro-4-pyridyl, 3-methoxy-2-pyridyl, 4-methoxy-2-pyridyl, 5-methoxy-2-pyridyl, 2-methoxy-3-pyridyl, 4-methoxy-3-pyridyl, 5-methoxy-3-pyridyl, 2-methoxy-4-pyridyl, 3-methoxy-4-pyridyl, 5-methoxy-4-pyridyl, 3-nitro-2-pyridyl, 4-nitro-2-pyridyl, 5-nitro-2-pyridyl, 2-nitro-3-pyridyl, 4-nitro-3-pyridyl, 5-nitro-3-pyridyl, 2-nitro-4-pyridyl, 3-nitro-4-pyridyl and 5-nitro-4-pyridyl groups, of which the 3-methyl-2-pyridyl, 4-methyl-2-pyridyl and 5-methyl-2-pyridyl groups are more preferred.

Where $R^3$ represents a quinolyl group, this may be unsubstituted or it may be substituted by at least one substituent selected from the group consisting of substituents (a), defined above and exemplified below. The quinolyl group itself may be a 2-, 3- or 4-quinolyl group and, if it is substituted, the number of substituents is limited only by the number of substitutable positions (four) and possibly by steric constraints. In general the number of substituents is preferably 1 or 2, and more preferably 1. The quinolyl group, whether unsubstituted or substituted, is preferably the 2-quinolyl group. Although the group may be substituted by any one or more of substituents (a), exemplified below, preferred examples of substituted groups include the 3-methyl-2-quinolyl, 4-methyl-2-quinolyl, 5-methyl-2-quinolyl, 2-methyl-3-quinolyl, 4-methyl-3-quinolyl, 5-methyl-3-quinolyl, 2-methyl-4-quinolyl, 3-methyl-4-quinolyl, 5-methyl-4-quinolyl, 3-ethyl-2-quinolyl, 4-ethyl-2-quinolyl, 5-ethyl-2-quinolyl, 2-ethyl-3-quinolyl, 4-ethyl-3-quinolyl, 5-ethyl-3-quinolyl, 2-ethyl-4-quinolyl, 3-ethyl-4-quinolyl, 5-ethyl-4-quinolyl, 3-chloro-2-quinolyl, 4-chloro-2-quinolyl, 5-chloro-2-quinolyl, 2-chloro-3-quinolyl, 4-chloro-3-quinolyl, 5-chloro-3-quinolyl, 2-chloro-4-quinolyl, 3-chloro-4-quinolyl, 5-chloro-4-quinolyl, 3-methoxy-2-quinolyl, 4-methoxy-2-quinolyl, 5-methoxy-2-quinolyl, 2-methoxy-3-quinolyl, 4-methoxy-3-quinolyl, 5-methoxy-3-quinolyl, 2-methoxy-4-quinolyl, 3-methoxy-4-quinolyl, 5-methoxy-4-quinolyl, 3-nitro-2-quinolyl, 4-nitro-2-quinolyl, 5-nitro-2-quinolyl, 2-nitro-3-quinolyl, 4-nitro-3-quinolyl, 5-nitro-3-quinolyl, 2-nitro-4-quinolyl, 3-nitro-4-quinolyl and 5-nitro-4-quinolyl groups, of which the 3-methyl-2-quinolyl, 4-methyl-2-quinolyl and 5-methyl-2-quinolyl groups are more preferred.

However, the unsubstituted pyridyl and quinolyl groups are preferred, and the pyridyl group is most preferred.

Where $R^3$ represents a phenyl group, this is substituted by a carbamoyl or heterocyclic-carbonyl group of formula —CONR$^5$R$^6$ or a (thiocarbamoyl) or heterocyclic-(thiocarbonyl) group of formula —CSNR$^5$R$^6$, in which $R^5$ and $R^6$ are as defined above. In addition, the phenyl group may optionally be substituted by one or more further substitutents selected from the group consisting of substituents (a), defined above and exemplified below.

Where $R^5$ or $R^6$ represents an alkyl group, this has from 1 to 6 carbon atoms and may be a straight or branched chain group. Examples of such groups are as given above in relation to the groups which may be represented by $R^2$. Of these, the methyl, ethyl, propyl, isopropyl, butyl, isobutyl and pentyl groups are preferred, and the methyl, ethyl and propyl groups are more preferred, the ethyl group being most preferred.

Where $R^5$ or $R^6$ represents an aryl group, this has from 6 to 10, preferably 6 or 10, carbon atoms, and may be, for example, a phenyl or naphthyl (1- or 2-naphthyl) group. The group may be unsubstituted or it may be substituted by one or more substituents selected from the group consisting of substituents (a), defined above and exemplified below. Examples of such substituted aryl groups include the 2-chlorophenyl, 3-chlorophenyl, 4-chlorophenyl, 2-chloro-1-naphthyl, 1-chloro-2-naphthyl, 1-methyl-2-naphthyl, 4-cyanophenyl, 4-nitrophenyl, 2,4-dichlorophenyl, 2,5-dichlorophenyl, 2,4,5-trichlorophenyl, 2-methylphenyl, 3-methylphenyl, 4-methylphenyl, 2,4-dichloro-3-methylphenyl, 4-aminophenyl, 4-methylaminophenyl, 4-dimethylaminophenyl, 4-hydroxyphenyl, 4-methoxyphenyl, 3-methoxyphenyl, 2-methoxyphenyl, 3-chloro-4-methoxyphenyl and piperonyl groups, of which the 2-methylphenyl, 4-methoxyphenyl, 3-chlorophenyl, 4-fluorophenyl, 4-methylphenyl and 4-chlorophenyl groups are preferred. However, the unsubstituted phenyl and naphthyl groups are more preferred and the phenyl group is most preferred.

Where $R^5$ or $R^6$ represents an aralkyl group, the aryl group may be any of those exemplified above in relation to the aryl groups which may be represented by $R^5$ and $R^6$, and the alkyl part may be any of those alkyl groups exemplified above in relation to the alkyl groups which may be represented by $R^2$. Preferred examples of such groups include the benzyl, phenethyl (i.e. 2-phenylethyl), 1-phenylethyl, 3-phenylpropyl, 4-phenylbutyl, 5-phenylpentyl, 6-phenylhexyl, 2-phenylpropyl, 1-phenylpropyl, 1-naphthylmethyl, 2-naphthylmethyl, 2-(2-naphthyl)ethyl, benzhydryl (i.e. diphenylmethyl) and trityl (i.e. triphenylmethyl) groups and analogs of such groups in which the phenyl and naphthyl groups are replaced by the substituted groups exemplified above in relation to $R^5$ and $R^6$. Of these, the benzyl and phenethyl groups are preferred and the benzyl group is most preferred.

Where $R^5$ and $R^6$ represent separate groups, these groups may be the same or different, although it is generally most convenient if they are the same.

Alternatively, $R^5$ and $R^6$ may together represent a group of formula $-(CH_2)_m-(X)_l-(CH_2)_n-$, wherein m and n are independently selected from the group consisting of the cipher 0 and integers from 1 to 5, provided that (m+n) is greater than 1, l is 0 or 1, and X represents an oxygen or sulfur atom or a group of formula $=NR^7$, where $R^7$ represents an alkyl group having from 1 to 6 carbon atoms, an aliphatic carboxylic acyl group having from 1 to 6 carbon atoms or an aromatic carboxylic acyl group in which the aryl part is as defined above. In this group, (m+n) must be greater than 1, and, when l is 0, preferably total 4, 5, 6 or 7, to form, with the nitrogen atom to which they are attached, a pyrrolidinyl, piperidyl, azepinyl or azocinyl group, respectively. When l is 1, (m+n) preferably totals 3, 4, 5 or 6, and (m–n) is preferably −1, 0 or +1; more preferably m and n are each 2. Where X represents a group of formula $=NR^7$, and $R^7$ represents an alkyl group having from 1 to 6 carbon atoms, these may be any of the alkyl groups exemplified above in relation to the alkyl groups which may be represented by $R^2$, but the methyl and ethyl groups are preferred. Examples of aliphatic acyl groups and aromatic acyl groups which may be represented by $R^7$ include the corresponding groups exemplified above in relation to the hydroxy-protecting groups which may be represented by $R^1$. Of these, the alkanoyl groups having from 1 to 4 carbon atoms (particularly the formyl, acetyl, propionyl and butyryl groups) and the benzoyl and methyl-substituted benzoyl groups (particularly the p-toluoyl group) are preferred.

Particularly preferred groups of formula $-(CH_2)_m-(X)_p-(CH_2)_n-$ include those groups of formula:
—(CH$_2$)$_2$—,
—(CH$_2$)$_3$—,
—(CH$_2$)$_4$—,
—(CH$_2$)$_5$—,
—(CH$_2$)$_6$—,
—(CH$_2$)$_7$—,
—(CH$_2$)$_8$—,
—(CH$_2$)$_2$O(CH$_2$)$_2$—,
—(CH$_2$)$_2$O(CH$_2$)$_3$—,
—(CH$_2$)$_3$O(CH$_2$)$_3$—,
—(CH$_2$)$_4$O(CH$_2$)$_4$—,
—(CH$_2$)$_2$S(CH$_2$)$_2$—,
—(CH$_2$)$_3$S(CH$_2$)$_3$—,
—(CH$_2$)$_2$S(CH$_2$)$_3$—,
—(CH$_2$)$_2$NMe(CH$_2$)$_2$—,
—(CH$_2$)$_2$NBoz(CH$_2$)$_2$—,
—(CH$_2$)$_2$NAc(CH$_2$)$_2$—,
—(CH$_2$)$_2$NAc(CH$_2$)$_3$—, and
—(CH$_2$)$_2$NEt(CH$_2$)$_3$—,
where Ac represents an acetyl group, Boz represents a benzoyl group, Et represents an ethyl group and Me represents a methyl group. Of these, the more preferred groups are those of formula:
—(CH$_2$)$_4$—,
—(CH$_2$)$_5$—, —(CH$_2$)$_6$—, and
—(CH$_2$)$_2$O(CH$_2$)$_2$—, Where R$^4$ represents a amino-protecting group, the nature of the group is not critical to the invention, and it may be selected having regard to criteria usually employed in the art and well known to those skilled in the art, without any particular restriction. Examples of such groups include:

tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably: tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutylsilyl, diphenyl-t-butylsilyl, diphenylisopropylsilyl and phenyldiisopropylsilyl groups);

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butanoyl groups]; and aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents (b), defined and exemplified below, preferably: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 5, preferably from 1 to 4, carbon atoms (such as the 4-anisoyl group); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group).

Of these, the tri-substituted silyl groups are preferred and the trimethylsilyl and t-butyldimethylsilyl groups are most preferred.

Examples of the groups and atoms which may be included in substituents (a) are:

alkyl groups having from 1 to 6 carbon atoms, such as those exemplified above in relation to R$^2$;

alkoxy groups having from 1 to 6 carbon atoms, such as those exemplified above in relation to R$^2$;

halogen atoms, such as those exemplified above in relation to R$^2$;

cyano groups, nitro groups, hydroxy groups and amino groups;

alkylamino groups in which the alkyl part has from 1 to 4 carbon atoms, such as the methylamino, ethylamino, propylamino, isopropylamino, butylamino, isobutylamino, sec-butylamino and t-butylamino groups;

dialkylamino groups in which each alkyl part has from 1 to 4 carbon atoms, such as the dimethylamino, diethylamino, dipropylamino, diisopropylamino, dibutylamino, diisobutylamino, methylethylamino and methylbutylamino groups; and alkylenedioxy groups having from 1 to 3 carbon atoms, such as the methylenedioxy, ethylenedioxy, trimethylenedioxy and propylenedioxy groups, of which the methylenedioxy group is most preferred.

Examples of the groups and atoms which may be included in substituents (b) are those groups and atoms exemplified above in relation to substituents (a), and:

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups); and aryl groups, such as those exemplified above in relation to R$^5$ and R$^6$.

Of the compounds of the present invention, one class of preferred compounds are those compounds of formulae (I) and (Ia), in which:

R$^1$ represents a hydrogen atom or a hydroxy-protecting group;

R$^2$ represents an alkyl group having from 1 to 6 carbon atoms, an alkoxy group having from 1 to 6 carbon atoms, a halogen atom, an unsubstituted phenyl group or an unsubstituted phenoxy group;

R$^3$ represents:

a pyridyl group which is unsubstituted or is substituted by at least one substituent selected from the group consisting of substituents (a$_1$), defined below; or a quinolyl group which is unsubstituted or is substituted by at least one substituent selected from the group consisting of substituents (a$_1$), defined below;

R$^4$ represents a hydrogen atom or an amino-protecting group; and

Z represents a sulfur atom;

said substituents (a$_1$) are selected from the group consisting of alkyl groups having from 1 to 6 carbon atoms, alkoxy groups having from 1 to 6 carbon atoms and halogen atoms.

Of these, a more preferred class of compounds of the present invention are those compounds of formulae (I) and (Ia), in which:

R$^1$ represents:

a hydrogen atom;

a tri-substituted silyl group, in which all three or two or one of the substituents are alkyl groups having from 1 to 5 carbon atoms, and none, one or two of the substituents are aryl groups, as defined above;

an aliphatic acyl group having from 1 to 6 carbon atoms;

a halogenated alkanoyl group having from 2 to 6 carbon atoms;

an alkoxyalkanoyl group in which the alkoxy part has from 1 to 5 carbon atoms and the alkanoyl part has from 2 to 6 carbon atoms; or an aralkyloxycarbonyl group, in which the aryl part is as defined above, and the alkyl part has from 1 to 4 carbon atoms;

$R^2$ represents a methyl, ethyl, methoxy or ethoxy group;

$R^3$ represents:

a pyridyl group which is unsubstituted or is substituted by at least one substituent selected from the group consisting of substituents ($a_2$), defined below; or a quinolyl group which is unsubstituted or is substituted by at least one substituent selected from the group consisting of substituents ($a_2$), defined below;

$R^4$ represents a hydrogen atom or a tri-substituted silyl group, in which all three or two or one of the substituents are alkyl groups having from 1 to 5 carbon atoms, and none, one or two of the substituents are aryl groups, as defined above; and Z represents a sulfur atom;

said substituents ($a_2$) are selected from the group consisting of methyl, ethyl, methoxy and ethoxy groups.

Of these, the most preferred class of compounds of the present invention are those compounds of formulae (I) and (Ia), in which:

$R^1$ represents:

a hydrogen atom;

a tri-substituted silyl group, in which all three or two or one of the substituents are alkyl groups having from 1 to 5 carbon atoms, and none, one or two of the substituents are aryl groups, as defined above;

an aliphatic acyl group having from 1 to 6 carbon atoms;

a halogenated alkanoyl group having from 2 to 6 carbon atoms;

an alkoxyalkanoyl group in which the alkoxy part has from 1 to 5 carbon atoms and the alkanoyl part has from 2 to 6 carbon atoms; or an aralkyloxycarbonyl group, in which the aryl part is as defined above, and the alkyl part has from 1 to 4 carbon atoms;

$R^2$ represents a methyl or ethyl group;

$R^3$ represents:

a pyridyl group which is unsubstituted or is substituted by at least one methyl group; or a quinolyl group which is unsubstituted or is substituted by at least one methyl group;

$R^4$ represents a hydrogen atom or a tri-substituted silyl group, in which all three or two or one of the substituents are alkyl groups having from 1 to 5 carbon atoms, and none, one or two of the substituents are aryl groups, as defined above; and Z represents a sulfur atom.

An alternative preferred class of compounds of the present invention are those compounds of formulae (I) and (Ia), in which:

$R^1$ represents a hydrogen atom or a hydroxy-protecting group;

$R^2$ represents a methyl group;

$R^3$ represents a phenyl group which has a substituent of formula —$CYNR^5R^6$ and no further substituent or has at least one substituent selected from the group consisting of substituents ($a_1$), defined below, where Y represents an oxygen or sulfur atom; and $R^5$ and $R^6$ are independently selected from the group consisting of alkyl groups having from 1 to 6 carbon atoms, aryl groups as defined above, and aralkyl groups in which the alkyl part has from 1 to 6 carbon atoms and the aryl part is as defined above, or $R^5$ and $R^6$ together form a group of formula —$(CH_2)_m$—$(X)_p$—$(CH_2)_n$—, wherein m and n are independently selected from the group consisting of the cipher 0 and integers from 1 to 5, provided that (m+n) is greater than 1. l is 0 or 1, and X represents an oxygen or sulfur atom or a group of formula =$NR^7$, where $R^7$ represents an alkyl group having from 1 to 6 carbon atoms, an aliphatic carboxylic acyl group having from 1 to 6 carbon atoms or an aromatic carboxylic acyl group in which the aryl part is as defined above;

$R^4$ represents a hydrogen atom or an amino-protecting group; and

Z represents a sulfur atom;

said substituents ($a_1$) are selected from the group consisting of alkyl groups having from 1 to 6 carbon atoms, alkoxy groups having from 1 to 6 carbon atoms and halogen atoms.

An alternative more preferred class of compounds of the present invention are those compounds of formulae (I) and (Ia), in which:

$R^1$ represents:

a hydrogen atom;

a tri-substituted silyl group, in which all three or two or one of the substituents are alkyl groups having from 1 to 5 carbon atoms, and none, one or two of the substituents are aryl groups, as defined above;

an aliphatic acyl group having from 1 to 6 carbon atoms;

a halogenated alkanoyl group having from 2 to 6 carbon atoms;

an alkoxyalkanoyl group in which the alkoxy part has from 1 to 5 carbon atoms and the alkanoyl part has from 2 to 6 carbon atoms; or an aralkyloxycarbonyl group, in which the aryl part is as defined above, and the alkyl part has from 1 to 4 carbon atoms;

$R^2$ represents a methyl group;

$R^3$ represents a phenyl group which has a substituent of formula —$CONR^5R^6$ and no further substituent or has at least one substituent selected from the group consisting of substituents ($a_2$), defined below, where $R^5$ and $R^6$ are independently selected from the group consisting of alkyl groups having from 1 to 3 carbon atoms, phenyl groups which are unsubstituted or are substituted by at least one substituent selected from the group consisting of substituents ($a_2$), defined below, and aralkyl groups in which the alkyl part has 1 or 2 carbon atoms and the aryl part is a phenyl group which is unsubstituted or is substituted by at least one substituent selected from the group consisting of substituents ($a_2$), defined below, or $R^5$ and $R^6$ together form a group of formula —$(CH_2)_m$—$(X)_p$—$(CH_2)_n$—, wherein m and n are independently selected from the group consisting of the cipher 0 and integers from 1 to 5, provided that (m+n) is greater than 1, l is 0 or 1, and X represents an oxygen or sulfur atom or a group of formula =$NR^7$, where $R^7$ represents a methyl group, an ethyl group, an aliphatic carboxylic acyl group having from 2 to 4 carbon atoms or a benzoyl group which is unsubstituted or is substituted by at least one substituent selected from the group consisting of substituents (a$_2$), defined below;

R$^4$ represents a hydrogen atom or a tri-substituted silyl group, in which all three or two or one of the substituents are alkyl groups having from 1 to 5 carbon atoms, and none, one or two of the substituents are aryl groups, as defined above; and Z represents a sulfur atom;

said substituents (a$_2$) are selected from the group consisting of methyl, ethyl, methoxy and ethoxy groups.

An alternative most preferred class of compounds of the present invention are those compounds of formulae (I) and (Ia), in which:

R$^1$ represents:

a hydrogen atom;

a tri-substituted silyl group, in which all three or two or one of the substituents are alkyl groups having from 1 to 5 carbon atoms, and none, one or two of the substituents are aryl groups, as defined above;

an aliphatic acyl group having from 1 to 6 carbon atoms;

a halogenated alkanoyl group having from 2 to 6 carbon atoms;

an alkoxyalkanoyl group in which the alkoxy part has from 1 to 5 carbon atoms and the alkanoyl part has from 2 to 6 carbon atoms; or an aralkyloxycarbonyl group, in which the aryl part is as defined above, and the alkyl part has from 1 to 4 carbon atoms;

R$^2$ represents a methyl group;

R$^3$ represents a phenyl group which has a substituent of formula —CONR$^5$R$^6$ and no further substituent or has at least one substituent selected from the group consisting of methyl and methoxy groups, where R$^5$ and R$^6$ are independently selected from the group consisting of alkyl groups having from 1 to 3 carbon atoms, or R$^5$ and R$^6$ together form a group of formula
—(CH$_2$)$_4$—
—(CH$_2$)$_5$—
—(CH$_2$)$_6$— or
—(CH$_2$)$_2$—O—(CH$_2$)$_2$—;

R$^4$ represents a hydrogen atom; and

Z represents a sulfur atom.

The compounds of the present invention necessarily contain several assymetric carbon atoms and can, therefore, form optical isomers, including, for example, that shown above as formula (Ia). In addition, depending upon the nature of the various substituent groups, other optical and geometric isomers may be possible. Although all such isomers are shown herein by a single formula, the present invention embraces the use of all such isomers as well as mixtures thereof. Where a mixture of the compounds of the present invention is obtained, these may be separated by conventional resolution techniques. Alternatively, in appropriate cases, a mixture of isomers may be used. However, it should be remembered that it is an advantage of the present invention that the desired 1β-isomer can be obtained readily and in a good yield.

Specific examples of compounds of the present invention are shown in the following formulae (I-1) to (I-3), in which the various substituent groups are as defined in the corresponding one of Tables 1 to 3, i.e Table 1 relates to formula (I-1), Table 2 relates to formula (I-2) and Table 3 relates to formula (I-3). In the Tables 1 to 3, the following abbreviations are used:

| Ac | acetyl |
|---|---|
| Boz | benzoyl |
| Bu | buty |
| iBu | isobutyl |
| tBu | t-butyl |
| Bz | benzyl |
| Et | ethyl |
| Me | methyl |
| Ph | phenyl |
| Pn | pentyl |
| Pr | propyl |
| iPr | isopropyl |
| Prn | propionyl |
| Pyr | pyridyl |
| Quin | quinolyl |

(I-1)

(I-2)

(I-3)

TABLE 1

| Cpd. No. | R$^1$ | R$^2$ | R$^3$ | R$^4$ |
|---|---|---|---|---|
| 1-1 | tBuMe$_2$Si— | Me | 2-Pyr | H |
| 1-2 | tBuMe$_2$Si— | Me | 3-Me-2-Pyr | H |
| 1-3 | tBuMe$_2$Si— | Me | 4-Me-2-Pyr | H |
| 1-4 | tBuMe$_2$Si— | Me | 5-Me-2-Pyr | H |
| 1-5 | tBuMe$_2$Si— | Me | 2-Quin | H |
| 1-6 | tBuMe$_2$Si— | Et | 2-Pyr | H |
| 1-7 | tBuMe$_2$Si— | Me | 3-MeO-2-Pyr | H |
| 1-8 | tBuMe$_2$Si— | Cl | 2-Pyr | H |
| 1-9 | tBuMe$_2$Si— | OMe | 2-Pyr | H |
| 1-10 | Me$_3$Si— | Me | 2-Pyr | H |
| 1-11 | Me$_3$Si— | Me | 3-Me-2-Pyr | H |
| 1-12 | BzO.CO— | Me | 2-Pyr | H |
| 1-13 | p-NO$_2$BzO.CO— | Me | 2-Pyr | H |
| 1-14 | Ac | Me | 2-Pyr | H |
| 1-15 | ClCH$_2$CO— | Me | 2-Pyr | H |
| 1-16 | BzO.CO— | Me | 3-Me-2-Pyr | H |
| 1-17 | p-NO$_2$BzO.CO— | Me | 3-Me-2-Pyr | H |
| 1-18 | BzO.CO— | Me | 2-Quin | H |
| 1-19 | Me$_3$Si— | Et | 2-Pyr | H |
| 1-20 | tBuMe$_2$Si— | Me | 2-Pyr | tBuMe$_2$Me$_2$Si— |
| 1-21 | tBuMe$_2$Si— | Me | 2-Pyr | Ac |
| 1-22 | tBuMe$_2$Si— | Me | 2-Pyr | Boz |
| 1-23 | tBuMe$_2$Si— | Me | 2-Pyr | Prn |
| 1-24 | tBuMe$_2$Si— | Me | 3-Me-2-Pyr | tBuMe$_2$Si— |
| 1-25 | tBuMe$_2$Si— | Me | 3-Me-2-Pyr | Ac |
| 1-26 | tBuMe$_2$Si— | Me | 3-Me-2-Pyr | Boz |
| 1-27 | tBuMe$_2$Si— | Me | 3-Me-2-Pyr | Prn |
| 1-28 | H | Me | 2-Pyr | H |

TABLE 1-continued

| Cpd. No. | R¹ | R² | R³ | R⁴ |
|---|---|---|---|---|
| 1-29 | H | Me | 3-Me-2-Pyr | H |
| 1-30 | H | Me | 4-Me-2-Pyr | H |
| 1-31 | H | Me | 5-Me-2-Pyr | H |
| 1-32 | H | Me | 2-Quin | H |
| 1-33 | H | Et | 2-Pyr | H |
| 1-34 | H | Me | 3-MeO-2-Pyr | H |
| 1-35 | H | Cl | 2-Pyr | H |
| 1-36 | H | OMe | 2-Pyr | H |
| 1-37 | H | Me | 2-Pyr | tBuMe₂Si— |
| 1-38 | H | Me | 2-Pyr | Ac |
| 1-39 | H | Me | 2-Pyr | Boz |
| 1-40 | H | Me | 2-Pyr | Prn |
| 1-41 | H | Me | 3-Me-2-Pyr | tBuMe₂Si— |
| 1-42 | H | Me | 3-Me-2-Pyr | Ac |
| 1-43 | H | Me | 3-Me-2-Pyr | Boz |
| 1-44 | H | Me | 3-Me-2-Pyr | Prn |

TABLE 2

| Cpd. No. | R¹ | R³ᵃ | R⁵ | R⁶ | Y | Z |
|---|---|---|---|---|---|---|
| 2-1 | tBuMe₂Si— | H | Me | Me | O | S |
| 2-2 | tBuMe₂Si— | H | Et | Et | O | S |
| 2-3 | tBuMe₂Si— | H | Pr | Pr | O | S |
| 2-4 | tBuMe₂Si— | H | iPr | iPr | O | S |
| 2-5 | tBuMe₂Si— | H | Me | Et | O | S |
| 2-6 | tBuMe₂Si— | H | iBu | iBu | O | S |
| 2-7 | tBuMe₂Si— | H | Bu | Bu | O | S |
| 2-8 | tBuMe₂Si— | H | Et | Pr | O | S |
| 2-9 | tBuMe₂Si— | H | Pn | Pn | O | S |
| 2-10 | Me₃Si— | H | Et | Et | O | S |
| 2-11 | Me₃Si— | H | Me | Me | O | S |
| 2-12 | Me₃Si— | H | Pr | Pr | O | S |
| 2-13 | Me₃Si— | H | Me | Et | O | S |
| 2-14 | Me₃Si— | H | Et | Pr | O | S |
| 2-15 | Me₃Si— | H | iBu | iBu | O | S |
| 2-16 | tBuMe₂Si— | H | Me | Ph | O | S |
| 2-17 | tBuMe₂Si— | H | Et | Ph | O | S |
| 2-18 | tBuMe₂Si— | H | Pr | Ph | O | S |
| 2-19 | tBuMe₂Si— | H | Bu | Ph | O | S |
| 2-20 | tBuMe₂Si— | H | Et | 2-MePh | O | S |
| 2-21 | tBuMe₂Si— | H | Et | 4-MeOPh | O | S |
| 2-22 | tBuMe₂Si— | H | Et | 3-ClPh | O | S |
| 2-23 | tBuMe₂Si— | H | Bu | 4-FPh | O | S |
| 2-24 | tBuMe₂Si— | H | Me | 4-MePh | O | S |
| 2-25 | tBuMe₂Si— | H | Me | 4-ClPh | O | S |
| 2-26 | p-NO₂BzO.CO— | H | Me | Et | O | S |
| 2-27 | p-NO₂BzO.CO— | H | Et | Et | O | S |
| 2-28 | p-NO₂BzO.CO— | H | Et | Pr | O | S |
| 2-29 | p-NO₂BzO.CO— | H | Me | Me | O | S |
| 2-30 | p-NO₂BzO.CO— | H | Pr | Pr | O | S |
| 2-31 | p-NO₂BzO.CO— | H | Et | Bu | O | S |
| 2-32 | tBuMe₂Si— | H | Et | Bz | O | S |
| 2-33 | tBuMe₂Si— | H | Et | 2-PhEt | O | S |
| 2-34 | tBuMe₂Si— | H | Me | Bz | O | S |
| 2-35 | tBuMe₂Si— | H | Me | 2-PhEt | O | S |
| 2-36 | tBuMe₂Si— | H | Et | Bz | O | S |
| 2-37 | tBuMe₂Si— | 3-Cl | Et | Et | O | S |
| 2-38 | tBuMe₂Si— | 3-Me | Et | Et | O | S |
| 2-39 | tBuMe₂Si— | 3-OMe | Et | Et | O | S |
| 2-40 | tBuMe₂Si— | 6-Me | Et | Et | O | S |
| 2-41 | tBuMe₂Si— | 6-Cl | Et | Et | O | S |
| 2-42 | tBuMe₂Si— | 6-OMe | Et | Et | O | S |
| 2-43 | tBuMe₂Si— | 3-Cl | Me | Me | O | S |
| 2-44 | tBuMe₂Si— | 3-Me | Me | Me | O | S |
| 2-45 | tBuMe₂Si— | 3-OMe | Me | Me | O | S |
| 2-46 | tBuMe₂Si— | 6-Cl | Me | Me | O | S |
| 2-47 | tBuMe₂Si— | 6-OMe | Me | Me | O | S |
| 2-48 | tBuMe₂Si— | 6-Me | Me | Me | O | S |
| 2-49 | tBuMe₂Si— | 3-Cl | Me | Et | O | S |
| 2-50 | tBuMe₂Si— | 3-Me | Me | Et | O | S |
| 2-51 | tBuMe₂Si— | 3-OMe | Me | Et | O | S |
| 2-52 | tBuMe₂Si— | 3-Cl | Et | Pr | O | S |
| 2-53 | tBuMe₂Si— | 3-Me | Et | Pr | O | S |
| 2-54 | tBuMe₂Si— | 3-OMe | Et | Pr | O | S |
| 2-55 | tBuMe₂Si— | 6-Me | Et | Et | O | O |
| 2-56 | tBuMe₂Si— | H | Et | Et | O | O |
| 2-57 | tBuMe₂Si— | H | Me | Me | O | O |
| 2-58 | tBuMe₂Si— | H | Pr | Pr | O | O |
| 2-59 | tBuMe₂Si— | 3-Me | Et | Et | O | O |
| 2-60 | tBuMe₂Si— | H | Et | Et | S | S |
| 2-61 | tBuMe₂Si— | H | Me | Me | S | S |
| 2-62 | tBuMe₂Si— | H | Pr | Pr | S | S |
| 2-63 | tBuMe₂Si— | 6-Me | Et | Et | S | S |
| 2-64 | tBuMe₂Si— | 6-Me | Pr | Pr | S | S |
| 2-65 | tBuMe₂Si— | 6-Me | Me | Me | S | S |
| 2-66 | H | H | Me | Me | O | S |
| 2-67 | H | H | Et | Et | O | S |
| 2-68 | H | H | Pr | Pr | O | S |
| 2-69 | H | H | iPr | iPr | O | S |
| 2-70 | H | H | Me | Et | O | S |
| 2-71 | H | H | iBu | iBu | O | S |
| 2-72 | H | H | Bu | Bu | O | S |
| 2-73 | H | H | Et | Pr | O | S |
| 2-74 | H | H | Pn | Pn | O | S |
| 2-75 | H | 3-Me | Et | Et | O | S |
| 2-76 | H | 6-Me | Et | Et | O | S |
| 2-77 | H | 3-OMe | Me | Me | O | S |
| 2-78 | H | 6-OMe | Me | Me | O | S |
| 2-79 | H | 3-Cl | Et | Pr | O | S |
| 2-80 | H | H | Et | Et | O | O |
| 2-81 | H | H | Me | Me | O | O |
| 2-82 | H | H | Pr | Pr | O | O |
| 2-83 | H | 3-Me | Et | Et | O | O |
| 2-84 | H | H | Et | Et | S | S |
| 2-85 | H | H | Me | Me | S | S |
| 2-86 | H | H | Pr | Pr | S | S |
| 2-87 | H | 6-Me | Et | Et | S | S |
| 2-88 | H | 6-Me | Pr | Pr | S | S |
| 2-89 | H | 6-Me | Me | Me | S | S |

TABLE 3

| Cpd. No. | R¹ | R³ᵃ | A | Y | Z |
|---|---|---|---|---|---|
| 3-1 | tBuMe₂Si— | H | —(CH₂)₂— | O | S |
| 3-2 | tBuMe₂Si— | H | —(CH₂)₃— | O | S |
| 3-3 | tBuMe₂Si— | H | —(CH₂)₄— | O | S |
| 3-4 | tBuMe₂Si— | H | —(CH₂)₅— | O | S |
| 3-5 | tBuMe₂Si— | H | —(CH₂)₆— | O | S |
| 3-6 | tBuMe₂Si— | H | —(CH₂)₇— | O | S |
| 3-7 | tBuMe₂Si— | H | —(CH₂)₈— | O | S |
| 3-8 | tBuMe₂Si— | H | —(CH₂)₂O(CH₂)₂— | O | S |
| 3-9 | tBuMe₂Si— | H | —(CH₂)₂O(CH₂)₃— | O | S |
| 3-10 | tBuMe₂Si— | H | —(CH₂)₃O(CH₂)₃— | O | S |
| 3-11 | tBuMe₂Si— | H | —(CH₂)₄O(CH₂)₄— | O | S |
| 3-12 | tBuMe₂Si— | H | —(CH₂)₂S(CH₂)₂— | O | S |
| 3-13 | tBuMe₂Si— | H | —(CH₂)₃S(CH₂)₃— | O | S |
| 3-14 | tBuMe₂Si— | H | —(CH₂)₂S(CH₂)₃— | O | S |
| 3-15 | tBuMe₂Si— | H | —(CH₂)₃S(CH₂)₃— | O | S |
| 3-16 | tBuMe₂Si— | H | —(CH₂)₂NMe(CH₂)₂— | O | S |
| 3-17 | tBuMe₂Si— | H | —(CH₂)₂NBoz(CH₂)₂— | O | S |
| 3-18 | tBuMe₂Si— | H | —(CH₂)₂NAc(CH₂)₂— | O | S |
| 3-19 | tBuMe₂Si— | H | —(CH₂)₂NAc(CH₂)₃— | O | S |
| 3-20 | tBuMe₂Si— | H | —(CH₂)₂NEt(CH₂)₃— | O | S |
| 3-21 | tBuMe₂Si— | 3-Me | —(CH₂)₂O(CH₂)₂— | O | S |
| 3-22 | tBuMe₂Si— | 3-OMe | —(CH₂)₂O(CH₂)₂— | O | S |
| 3-23 | tBuMe₂Si— | 3-Cl | —(CH₂)₂O(CH₂)₂— | O | S |
| 3-24 | tBuMe₂Si— | 3-OEt | —(CH₂)₂O(CH₂)₂— | O | S |
| 3-25 | tBuMe₂Si— | 6-Me | —(CH₂)₂O(CH₂)₂— | O | S |
| 3-26 | tBuMe₂Si— | 6-OMe | —(CH₂)₂O(CH₂)₂— | O | S |
| 3-27 | tBuMe₂Si— | 6-Cl | —(CH₂)₂O(CH₂)₂— | O | S |
| 3-28 | tBuMe₂Si— | 3-Me | —(CH₂)₂— | O | S |
| 3-29 | tBuMe₂Si— | 3-OMe | —(CH₂)₂— | O | S |
| 3-30 | tBuMe₂Si— | 3-Cl | —(CH₂)₂— | O | S |
| 3-31 | tBuMe₂Si— | 6-OMe | —(CH₂)₆— | O | S |

TABLE 3-continued

| Cpd. No. | R¹ | R³ᵃ | A | Y | Z |
|---|---|---|---|---|---|
| 3-32 | tBuMe₂Si— | 6-Me | —(CH₂)₆— | O | S |
| 3-33 | tBuMe₂Si— | 6-Cl | —(CH₂)₆— | O | S |
| 3-34 | tBuMe₂Si— | 3-Me | —(CH₂)₃— | O | S |
| 3-35 | tBuMe₂Si— | 3-OMe | —(CH₂)₃— | O | S |
| 3-36 | tBuMe₂Si— | 3-Cl | —(CH₂)₃— | O | S |
| 3-37 | tBuMe₂Si— | 3-Me | —(CH₂)₃— | O | S |
| 3-38 | tBuMe₂Si— | 6-OMe | —(CH₂)₃— | O | S |
| 3-39 | tBuMe₂Si— | 6-Cl | —(CH₂)₃— | O | S |
| 3-40 | tBuMe₂Si— | 3-Me | —(CH₂)₄— | O | S |
| 3-41 | tBuMe₂Si— | 3-OMe | —(CH₂)₄— | O | S |
| 3-42 | tBuMe₂Si— | 3-Cl | —(CH₂)₄— | O | S |
| 3-43 | tBuMe₂Si— | 6-Me | —(CH₂)₄— | O | S |
| 3-44 | tBuMe₂Si— | 6-OMe | —(CH₂)₄— | O | S |
| 3-45 | tBuMe₂Si— | 6-Cl | —(CH₂)₄— | O | S |
| 3-46 | tBuMe₂Si— | 3-Me | —(CH₂)₅— | O | S |
| 3-47 | tBuMe₂Si— | 3-OMe | —(CH₂)₅— | O | S |
| 3-48 | tBuMe₂Si— | 3-Cl | —(CH₂)₅— | O | S |
| 3-49 | tBuMe₂Si— | 6-Me | —(CH₂)₅— | O | S |
| 3-50 | tBuMe₂Si— | 6-OMe | —(CH₂)₅— | O | S |
| 3-51 | tBuMe₂Si— | 6-Cl | —(CH₂)₅— | O | S |
| 3-52 | tBuMe₂Si— | 3-Me | —(CH₂)₆— | O | S |
| 3-53 | tBuMe₂Si— | 3-OMe | —(CH₂)₆— | O | S |
| 3-54 | tBuMe₂Si— | 3-Cl | —(CH₂)₆— | O | S |
| 3-55 | tBuMe₂Si— | 3-Me | —(CH₂)₂S(CH₂)₂— | O | S |
| 3-56 | tBuMe₂Si— | 3-OMe | —(CH₂)₂S(CH₂)₂— | O | S |
| 3-57 | tBuMe₂Si— | 3-Cl | —(CH₂)₂S(CH₂)₂— | O | S |
| 3-58 | tBuMe₂Si— | 3-Cl | —(CH₂)₂NAc(CH₂)₂— | O | S |
| 3-59 | tBuMe₂Si— | 3-OMe | —(CH₂)₂NAc(CH₂)₂— | O | S |
| 3-60 | tBuMe₂Si— | 3-Me | —(CH₂)₂NAc(CH₂)₂— | O | S |
| 3-61 | tBuMe₂Si— | H | —(CH₂)₅— | O | O |
| 3-62 | tBuMe₂Si— | H | —(CH₂)₄— | O | O |
| 3-63 | tBuMe₂Si— | H | —(CH₂)₅— | S | S |
| 3-64 | tBuMe₂Si— | H | —(CH₂)₄— | S | S |
| 3-65 | tBuMe₂Si— | 3-Me | —(CH₂)₅— | S | S |
| 3-66 | tBuMe₂Si— | 6-Me | —(CH₂)₆— | S | S |
| 3-67 | tBuMe₂Si— | H | —(CH₂)₆— | O | O |
| 3-68 | tBuMe₂Si— | 6-Me | —(CH₂)₆— | O | O |
| 3-69 | tBuMe₂Si— | H | —(CH₂)₄— | O | S |
| 3-70 | tBuMe₂Si— | H | —(CH₂)₅— | O | S |
| 3-71 | tBuMe₂Si— | H | —(CH₂)₆— | O | S |
| 3-72 | tBuMe₂Si— | H | —(CH₂)₂O(CH₂)₂— | O | S |
| 3-73 | tBuMe₂Si— | H | —(CH₂)₂S(CH₂)₂— | O | S |
| 3-74 | tBuMe₂Si— | H | —(CH₂)₂NBoz(CH₂)₂— | O | S |
| 3-75 | tBuMe₂Si— | H | —(CH₂)₂NAc(CH₂)₂— | O | S |
| 3-76 | tBuMe₂Si— | 3-Me | —(CH₂)₂O(CH₂)₂— | O | S |
| 3-77 | tBuMe₂Si— | 3-OMe | —(CH₂)₂O(CH₂)₂— | O | S |
| 3-78 | H | 3-Me | —(CH₂)₄— | O | S |
| 3-79 | H | 3-OMe | —(CH₂)₄— | O | S |
| 3-80 | H | 3-Cl | —(CH₂)₄— | O | S |
| 3-81 | H | 6-Me | —(CH₂)₄— | O | S |
| 3-82 | H | 6-OMe | —(CH₂)₄— | O | S |
| 3-83 | H | 6-Cl | —(CH₂)₄— | O | S |
| 3-84 | H | 3-Me | —(CH₂)₅— | O | S |
| 3-85 | H | 3-OMe | —(CH₂)₅— | O | S |
| 3-86 | H | 3-Cl | —(CH₂)₅— | O | S |
| 3-87 | H | 6-Me | —(CH₂)₅— | O | S |
| 3-88 | H | 6-OMe | —(CH₂)₅— | O | S |
| 3-89 | H | 6-Cl | —(CH₂)₅— | O | S |
| 3-90 | H | 3-Me | —(CH₂)₂S(CH₂)₂— | O | S |
| 3-91 | H | 3-Me | —(CH₂)₂NAc(CH₂)₂— | O | S |
| 3-92 | H | H | —(CH₂)₅— | O | O |
| 3-93 | H | H | —(CH₂)₄— | O | O |
| 3-94 | H | H | —(CH₂)₅— | S | S |
| 3-95 | H | H | —(CH₂)₄— | S | S |
| 3-96 | H | 3-Me | —(CH₂)₅— | S | S |
| 3-97 | H | 6-Me | —(CH₂)₆— | S | S |
| 3-98 | H | H | —(CH₂)₆— | O | O |
| 3-99 | H | 6-Me | —(CH₂)₆— | O | O |

Of the compounds listed above, the following are preferred, that is to say Compounds No. 1-1, 1-5, 1-10, 1-13, 1-14, 1-16, 1-20, 1-22, 1-24, 1-26, 1-28, 1-32, 1-37, 1-39, 1-41, 1-43, 2-1, 2-2, 2-3, 2-6, 2-16, 2-26, 2-27, 2-28, 2-29, 2-30, 2-31, 2-37, 2-38, 2-39, 2-40, 2-41, 2-42, 2-55, 2-56, 2-59, 2-60, 2-63, 2-66, 2-68, 2-69, 2-70, 2-71, 2-75, 3-3, 3-4, 3-5, 3-8, 3-21, 3-25, 3-46, 3-47, 3-48, 3-49, 3-50, 3-51, 3-61, 3-63, 3-65, 3-69, 3-70, 3-71, 3-72, 3-76, 3-84, 3-85, 3-86, 3-87, 3-88, 3-89, 3-92, 3-94 and 3-96, and the following are more preferred, that is to say Compounds No. 1-1, 1-5, 1-10, 1-13, 1-20, 1-22, 1-24, 1-26, 1-28, 1-32, 1-37, 1-39, 1-41, 1-43, 2-1, 2-2, 2-3, 2-6, 2-16, 2-26, 2-27, 2-28, 2-29, 2-30, 2-31, 2-40, 2-56, 2-60, 2-63, 2-66, 2-68, 2-69, 2-70, 2-71, 3-3, 3-4, 3-5, 3-8, 3-21, 3-25, 3-61, 3-63, 3-65, 3-69, 3-70, 3-71 and 3-72. The most preferred specific compounds of the present invention are Compounds No.:

1-1. (3S,4S)-3[(1R)-1-t-Butyldimethylsilyloxyethyl]-4-[(1R)-(2-pyridylthiocarbonyl)ethyl]azetidin-2-one;

1-5. (3S,4S)-3-[(1R)-1-t-Butyldimethylsilyloxyethyl]-4-[(1R)-2-quinolinethiocarbonyl)ethyl]azetidin-2-one;

1-10. (3S,4S)-3[(1R)-1-Trimethylsilyloxyethyl]-4-[(1R)-(2-pyridylthiocarbonyl)ethyl]azetidin-2-one;

1-13. (3S,4S)-3[(1R)-1-p-Nitrobenzyloxycarbonyloxyethyl]-4-[(1R)-(2-pyridylthiocarbonyl)ethyl]azetidin-2-one;

1-28. (3S,4S)-3[(1R)-1-Hydroxyethyl]-4-[(1R)-(2-pyridylthiocarbonyl)ethyl]azetidin-2-one;

1-32. (3S,4S)-3-[(1R)-1-Hydroxyethyl]-4-[(1R)-(2-quinolinethiocarbonyl)ethyl]azetidin-2-one;

2-2. S-2-Diethylcarbamoylphenyl 2(R)-{(3S,4S)-3-[1(R)-(t-butyldimethylsilyloxy)ethyl]-2-oxo-4-azetidinyl}thiopropionate;

2-3. S-2-Dipropylcarbamoylphenyl 2(R)-{(3S,4S)-3-[1(R)-(t-butyldimethylsilyloxy)ethyl]-2-oxo-4-azetidinyl}thiopropionate;

2-56. 2-Diethylcarbamoylphenyl 2(R)-{(3S,4S)-3-[1(R)-(t-butyldimethylsilyloxy)ethyl]-2-oxo-4-azetidinyl}propionate;

2-60. S-2-[Diethyl(thiocarbamoyl)]phenyl 2(R)-{(3S,4S)-3-[1(R)-(t-butyldimethylsilyloxy)ethyl]-2-oxo-4-azetidinyl}thiopropionate;

2-67. S-2-Diethylcarbamoylphenyl 2(R)-{(3S,4S)-3-[1(R)-hydroxyethyl]-2-oxo-4-azetidinyl}thiopropionate;

3-3. S-2-(1-Pyrrolidinylcarbonyl)phenyl 2(R)-{(3S,4S)-3-[1(R)-(t-butyldimethylsilyloxy)ethyl]-2-oxo-4-azetidinyl}thiopropionate;

3-4. S-2-(1-Piperidylcarbonyl)phenyl 2(R)-{(3S,4S)-3-[1(R)-(t-butyldimethylsilyloxy)ethyl]-2-oxo-4-azetidinyl}thiopropionate;

3-5. S-2-(1-Azepinylcarbonyl)phenyl 2(R)-{(3S,4S)-3-[1(R)-(t-butyldimethylsilyloxy)ethyl]-2-oxo-4-azetidinyl}thiopropionate;

3-8. S-2-Morpholinocarbonylphenyl 2(R)-{(3S,4S)-3-[1(R)-(t-butyldimethylsilyloxy)ethyl]-2-oxo-4-azetidinyl}thiopropionate.

The compounds of the present invention can be prepared by a variety of methods, whose general techniques are known in the art for the preparation of compounds of this type. For example, they may be prepared by reacting a compound of formula (II):

in which $R^2$, $R^3$ and Z are as defined above, and $R^8$, $R^9$ and $R^{10}$ are the same or different and each represents an alkyl group having from 1 to 4 carbon atoms or a phenyl group, with a compound of formula (III):

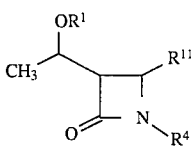

in which $R^1$ and $R^4$ are as defined above, and $R^{11}$ represents an acyloxy, alkylsulfonyl, arylsulfonyl, alkylsufinyl or arylsulfinyl group, all of which are as more precisely defined and exemplified below.

More preferably, the compound of formula (III) has the configuration shown in formula (IIIa):

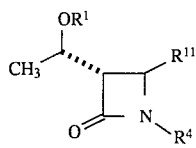

to produce a compound of formula (Ia):

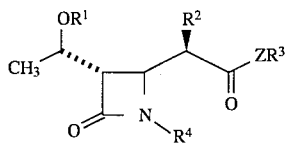

Examples of the alkyl groups which may be represented by $R^8$, $R^9$ and $R^{10}$ include the methyl, ethyl, propyl, isopropyl, butyl, sec-butyl and t-butyl groups. Examples of preferred groups of formula $SiR^8R^9R^{10}$ include the t-butyldimethylsilyl, trimethylsilyl, triethylsilyl, triisopropylsilyl and t-butyldiphenylsilyl groups.

The acyloxy groups which may be represented by $R^{11}$ are carboxylic acyloxy groups which may be aliphatic or aromatic. In the case of the aliphatic acyloxy groups, these preferably have from 1 to 6, more preferably from 2 to 4, carbon atoms and may be alkanoyloxy, haloalkanoyloxy or alkenoyloxy groups, the alkanoyloxy groups being preferred. Examples of such groups include the acetoxy, propionyloxy and butyryloxy groups. In the case of the aromatic acyloxy groups, these are arylcarbonyloxy groups and the aryl part may be as defined and exemplified above. A preferred such group is the benzoyloxy group. In the case of the alkylsulfonyl and alkylsulfinyl groups, the alkyl parts have from 1 to 6, preferably from 1 to 4, carbon atoms and examples of the alkyl moieties of such groups include the methyl, ethyl, propyl and isopropyl groups. In the case of the arylsulfonyl and arylsulfinyl groups, the aryl part may be as defined and exemplified above, and examples of the aryl moieties of such groups include the phenyl and p-tolyl groups. Preferably $R^{11}$ represents an acetoxy, benzoyloxy, phenylsulfonyl, phenylsulfinyl, tolylsulfinyl or methylsulfinyl group.

In this reaction, a silyl enol ether of formula (II) is reacted with an azetidinone derivative of formula (III). This reaction normally and preferably takes place in the presence of a solvent and in the presence of a Lewis acid.

Examples of Lewis acids which may be used in the reaction include: zinc chloride, zinc bromide, zinc iodide and boron trifluoride etherate. Of these, we prefer to use zinc chloride or zinc iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride, chloroform and 1,2-dichloroethane; ethers such as tetrahydrofuran and 1,2-dimethoxyethane; and nitriles, such as acetonitrile. Of these, we prefer to use methylene chloride, chloroform or 1,2-dichloroethane.

The reaction can take place over a wide range of temperatures, and the precise reaction temperature is not critical to the invention. In general, we find it convenient to carry out the reaction at a temperature of from −10° C. to 70° C. and more preferably from 10° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

The compound of formula (I) thus obtained can be recovered from the reaction mixture by any conventional method. For example, one suitable recovery procedure comprises adding a solvent, such as methylene chloride or ethyl acetate, to the reaction mixture, separating and washing the organic layer with water and finally separating the desired compound by suitable means, such as thin layer chromatography or flash chromatography through silica gel, or purifying it by means of crystallization or recrystallization.

The silyl enol ether of formula (II), used as a starting material in this reaction, can be prepared by reacting a compound of formula (IV):

$$R^2CH_2.CO.ZR^3 \qquad (IV)$$

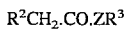

in which $R^2$, $R^3$ and Z are as defined above, with an active silyl compound of formula (V):

$$R^8R^9R^{10}SiW \qquad (V)$$

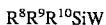

in which $R^8$, $R^9$ and $R^{10}$ are as defined above, and W represents a leaving group, for example a halogen atom, such as a chlorine atom, or a sulfonyloxy group, such as a trifluoromethanesulfonyloxy group, in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers such as diethyl ether, 1,2-dimethoxyethane and tetrahydrofuran; and hydrocarbons, especially aliphatic hydrocarbons, such as hexane or cyclohexane; mixtures of of any two or more of these solvents may also be employed.

The yield of the reaction can be improved by adding one or more of the following solvents to one or more of the solvents listed above. Examples of such additional solvents include: hexamethylphosphoric triamide (HMPA), N,N-dimethylformamide, N,N-dimethylacetamide, N,N'-dimethylpropyleneurea, N-methylpyrrolidone and N-methylpiperidone.

Examples of bases which may be used in the reaction include lithium, sodium or potassium salts of diisopropylamine, hexamethyldisilazane, dicyclohexylamine or 2,2,6,6-tetramethylpiperidine.

In some cases, the addition of one or more additional bases as well as the bases listed above will improve the yield of the compound of formula (II). Examples of such bases include tertiary amines, such as triethylamine.

The reaction can take place over a wide range of temperatures, and the precise reaction temperature is not critical to the invention. In general, we find it convenient to carry out the reaction at a temperature of from −90° C. to 20° C. and more preferably from −78° C. to −20° C. The time required for the reaction may also vary widely, depending on many factors, notably the reaction temperature and the nature of the reagents and solvent employed. However, provided that the reaction is effected under the preferred conditions outlined above, a period of from 5 minutes to 4 hours and more preferably from 10 minutes to 30 minutes will usually suffice.

The resulting compound of formula (II) can then be recovered from the reaction mixture by conventional means. For example, it can be recovered in a good yield by adding water, a saturated aqueous solution of sodium hydrogencarbonate or triethylamine to the reaction mixture, extracting the mixture with an organic solvent and then purifying it by means of column chromatography or distillation.

Where $R^3$ represents a phenyl group $R^2$ represents a methyl group and Z represents a sulfur atom, the resulting compound of formula (IV) is a substituted S-phenyl thiopropionate, which can be used as a starting compound in the above reaction. This may be prepared as shown in the following Reaction Schemes A and B:

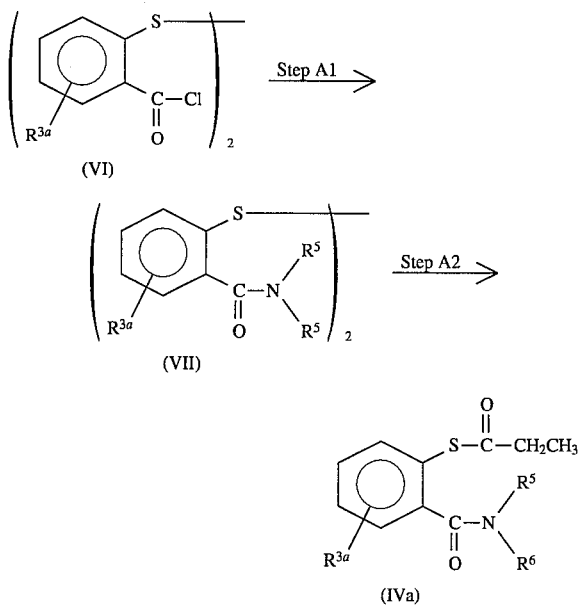

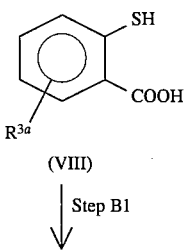

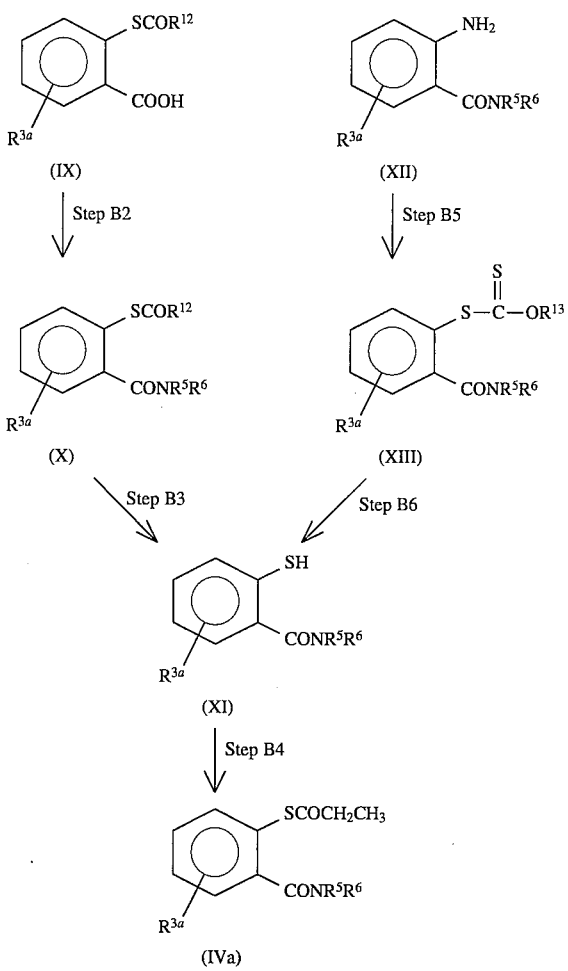

In the above formulae, $R^{3a}$, $R^5$ and $R^6$ are as defined above. $R^{12}$ represents an aryl group (as defined above), such as a phenyl or tolyl group, and $R^{13}$ represents a lower alkyl group having from 1 to 6 carbon atoms, preferably from 1 to 4 carbon atoms, such as a methyl or ethyl group.

In Reaction Scheme A, a substituted S-phenyl thiopropionate, that is to say a compound of formula (IVa), can be prepared from a compound of formula (VI), which, in turn, can readily be obtained by reacting a 2,2'-dithiobenzoic acid derivative with a halogenating agent, such as thionyl chloride.

In Step A1, a secondary amine, $R^5R^6NH$, is reacted with the compound of formula (VI) in the presence of an organic amine, such as triethylamine, or an inorganic base such, as sodium carbonate, to give the compound of formula (VII). In Step A2, this compound of formula (VII) is reacted with propionic anhydride in the presence of a metal having reducing activity, such as zinc.

Alternatively, in Reaction Scheme B, a compound of formula (IVa) is prepared using a thiosalicylic acid derivative of formula (VIII) as the starting material.

In Step B1 of this reaction scheme, the thiol group of a compound of formula (VIII) is protected by reacting the compound of formula (VIII) with an aromatic acyl halide, such as benzoyl chloride, to give the protected compound of formula (IX).

In Step B2, the compound of formula (IX) is reacted with a secondary amine, $R^5R^6NH$, in the presence of a dehydrating condensing agent, such as 2-chloro-1-methylpyridinium iodide, to produce an amide compound of formula (X).

In Step B3, the aromatic acyl protecting group, $R^{12}CO$, is removed by treating the compound of formula (X) with a base, such as sodium methoxide, to give a compound of formula (XI).

In Step B4, the thiol group of the compound of formula (XI) is propionylated by reacting it with an active derivative of propionic acid, such as propionyl chloride or propionic anhydride, in the presence of a base, to give the desired substituted S-phenyl thiopropionate of formula (IVa).

Alternatively, the compound of formula (XI) can also be prepared from an anthranilic acid derivative of formula (XII) by conventional means (e.g. as disclosed in Organic Syntheses Coll. Vol. III, page 809, the disclosure of which is incorporated herein by reference) via Steps B5 and B6. In Step B5, a compound of formula (XII) is diazotized and then reacted with potassium S-ethyl dithiocarbonate, to give a compound of formula (XIII). In Step B6, this compound of formula (XIII) is hydrolysed with a base, such as potassium hydroxide, to give the compound of formula (XI).

Reaction Scheme B illustrates the preparation of compounds of formula (IV) in which $R^3$ represents a substituted phenyl group, Y represents an oxygen atom and Z represents a sulfur atom, that is a compound of formula (IVa). Corresponding compounds in which Y represents a sulfur atom or Z represents an oxygen atom can be prepared as illustrated in the following Reaction Schemes C and D:

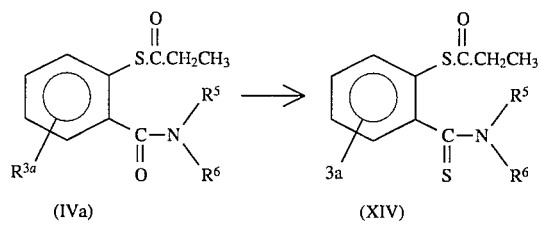

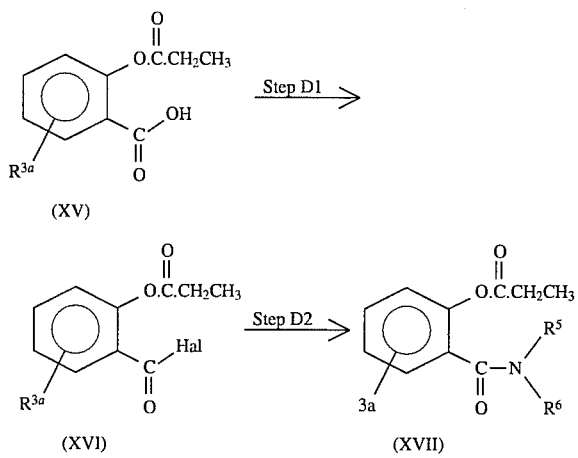

In the above formulae, $R^{3a}$, $R^5$ and $R^6$ are as defined above and Hal represents a halogen atom.

In Reaction Scheme C, the carbonyl group forming part of the amido group at the 2-position of the compound of formula (IVa) is converted to a thiocarbonyl group by reaction with a thiolating agent, such as Lawesson's reagent or phosphorus pentasulfide. This reaction is well known in the art and may be carried out using solvents, reaction temperatures and reaction times as are conventional and well known.

In Step D1 of Reaction Scheme D, the carboxy group at the 2-position of the compound of formula (IVa) is halogenated, preferably chlorinated, using a conventional halogenating agent, such as oxalyl chloride, oxalyl bromide, thionyl chloride or thionyl bromide, and using conventional halogenating conditions, to give the compound of formula (XVI). This compound of formula (XVI) is then reacted with a secondary amine of formula $R^5R^6NH$ in the presence of an organic tertiary amine, such as triethylamine, or of an inorganic base, such as sodium carbonate, to give the desired compound of formula (XVII).

The azetidinone derivatives of formula (I) in accordance with the present invention can readily be converted to the corresponding carbapenem compounds by reaction with an appropriate mercaptan derivative of formula $R^{14}SH$, which may be effected by conventional means (e.g. as described in Japanese Patent Application Kokai No. Sho 60-19764) to produce a compound of formula (XVIII), which can then be cyclised by conventional means (e.g. as described in Japanese Patent Publication No. Sho 62-54427), to give a carbapenem derivative of formula (XIX), as shown in the following Reaction Schemes E and Ea:

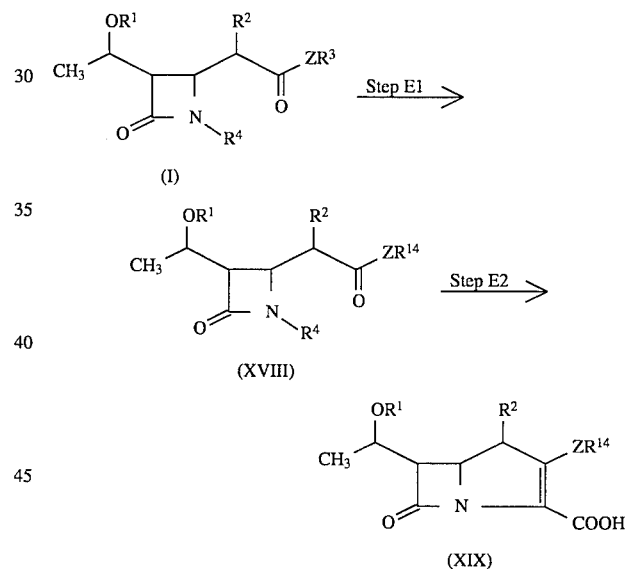

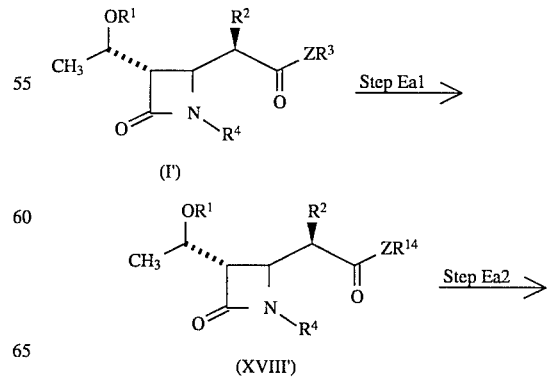

Reaction Scheme Ea:

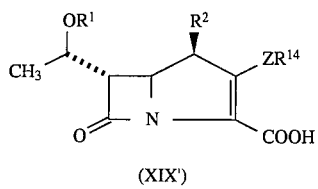

(XIX')

In these formulae, Z, $R^1$, $R^2$, $R^3$ and $R^4$ are as defined above and $R^{14}$ represents a variety of organic groups of a type commonly employed, at the indicated position, in carbapenem derivatives. As can be seen from Reaction Scheme E', the configuration at the azetidine 3-position and at the carbon atom to which the group represented by $R^2$ is attached are conserved, and so this provides a convenient and efficient way of producing these valuable compounds.

In contrast, the compound of formula (C), described in U.S. Pat. Nos. 4,895,939 and 4,772,683, referred to above, does not appear suitable for this reaction because it does not easily react with a mercaptan of formula $R^{14}SH$ in the first step of Reaction Scheme E, and cannot, therefore, readily form the compound of formula (XVII). On the other hand, in the reactions described by T. Shibata et al. [Tetrahedron Letters, 26, 4793 (1985)], C. U. Kim et al. [Tetrahedron Letters, 28, 507 (1987)] and A. Martel et al. [Can. J. Chem., 66, 1537 (1988)] the desired 2R-isomer is produced in a relatively low yield in admixture with a large quantity of the unwanted 2S-isomer, and so is difficult and expensive to isolate.

In the compounds of formula (I'), (II') and (IV'), where $R^{1'}$ represents a carboxy-protecting group, this may be any group commonly employed in the synthesis of β-lactam antibiotics, and, in the case of the compounds of formulae (II') and (IV'), which are simply intermediates, there is no particular restriction; in the case of the desired compounds of formula (I'), which may be used in therapy, care may need to be taken in selecting the protecting group, if a protecting group is present. More preferably, in the case of the compounds of formula (I'), $R^{1'}$ represents a hydrogen atom or is an ester group, as described in greater detail hereafter. Examples of such protecting groups include:

lower alkyl groups having from 1 to 6, preferably from 1 to 4, carbon atoms, such as the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methyl-pentyl, 1-methylpentyl, 3,3-dimethylbutyl, 2,2-dimethyl-butyl, 1,1-dimethylbutyl, 1,2-dimethylbutyl, 1,3-dimethylbutyl, 2,3-dimethylbutyl, 2-ethylbutyl, hexyl and isohexyl groups; of these, we prefer those alkyl groups having from 1 to 4 carbon atoms, preferably the methyl, ethyl and t-butyl groups;

aralkyl groups, which are preferably alkyl groups which have from 1 to 4, preferably 1 to 3, more preferably 1 or 2, and most preferably 1, carbon atoms and which are substituted by at least one (more preferably 1, 2 or 3) aryl groups, as defined above, such as the benzyl, diphenylmethyl, triphenylmethyl, 4-nitrobenzyl, 2-nitrobenzyl, 1-naphthylmethyl, α-methylbenzyl, α,α-dimethylbenzyl, 1-phenylethyl, phenethyl (i.e. 2-phenylethyl), 3-phenylpropyl and 4-phenylbutyl groups, of which the benzyl, diphenylmethyl, 4-nitrobenzyl and 2-nitrobenzyl groups are preferred;

alkenyl groups having from 2 to 6, preferably 3 or 4, carbon atoms, and which are optionally substituted by one or more halogen atoms, such as the vinyl, allyl, 2-chloroallyl or 2-methylallyl groups;

haloalkyl groups having from 1 to 6, preferably from 1 to 4, carbon atoms, such as the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2,2-dibromoethyl, 3-chloropropyl, 3,3,3-trichloropropyl, perfluoroethyl, 4-fluorobutyl, 5-bromopentyl, 6-chlorohexyl and 6,6,6-trifluorohexyl groups, preferably the 2,2,2-trichloroethyl or 2,2,2-tribromoethyl group; and tri-substituted silylethyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably: 1- or 2-[tri(lower alkyl)silyl]ethyl groups, such as the 2-(trimethylsilyl)ethyl, 2-(triethylsilyl)ethyl, 2-(isopropyldimethylsilyl)ethyl, 2-(t-butyldimethylsilyl)ethyl, 2-(methyldiisopropylsilyl)ethyl, 2-(methyldi-t-butylsilyl)ethyl and 2-(triisopropylsilyl)ethyl groups; and 1- or 2-[tri(lower alkyl)silyl]ethyl groups in which one or two of the alkyl groups have been replaced by aryl groups, such as the 2-(diphenylmethylsilyl)ethyl, 2-(diphenylbutylsilyl)ethyl, 2-(diphenyl-t-butylsilyl)ethyl, 2-(diphenylisopropylsilyl)ethyl and 2-(phenyldiisopropylsilyl)ethyl groups, especially the 2-(trimethylsilyl)ethyl group;

acyloxyalkyl groups, in which the acyl part is an alkanoyl group having from 1 to 6, preferably from 1 to 5, carbon atoms and the alkyl part has from 1 to 6, preferably 1 or 2, carbon atoms, such as the formyloxymethyl, acetoxymethyl, propionyloxymethyl, butyryloxymethyl, valeryloxymethyl, isovaleryloxymethyl, pivaloyloxymethyl, hexanoyloxymethyl, 1-formyloxyethyl, 1-acetoxyethyl, 1-propionyloxyethyl, 1-butyryloxyethyl, 1-valeryloxyethyl, 1-isovaleryloxyethyl, 1-pivaloyloxyethyl, 1-hexanoyloxyethyl, 1-formyloxypropyl, 1-acetoxypropyl, 1-pivaloyloxypropyl, 1-acetoxybutyl, 1-acetoxypentyl and 1-acetoxyhexyl groups, preferably the acetoxymethyl, pivaloyloxymethyl and 1-acetoxyethyl groups;

alkoxycarbonyloxyalkyl groups in which the alkoxy and alkyl parts each have from 1 to 6, preferably from 1 to 4, carbon atoms, such as the ethoxycarbonyloxymethyl, 1-(ethoxycarbonyloxy)ethyl, 1-(isopropoxycarbonyloxy)ethyl and t-butoxycarbonyloxymethyl groups;

cycloalkoxycarbonyloxyalkyl groups in which the cycloalkyl part has from 3 to 7, preferably 5 or 6, ring carbon atoms and may be unsubstituted or substituted by at least one substituent selected from the group consisting of substituents C', defined above and exemplified below, but particularly an alkyl group having from 1 to 6, preferably from 1 to 4 and more preferably 1 or 2, carbon atoms, and the alkyl part has from 1 to 6, preferably from 1 to 4 and more preferably 1 or 2, carbon atoms, such the 1-(cyclohexyloxycarbonyloxy)ethyl and (1-methylcyclohexyl)oxycarbonyloxymethyl groups;

(5-alkyl or 5-aryl-2-oxo-1,3-dioxolen-4-yl)methyl groups in which the alkyl part has from 1 to 4, preferably 1 or 2, carbon atoms and the aryl part is as defined above, but is preferably a phenyl group, such as the (5-methyl-2-oxo-1,3-dioxolen-4-yl)methyl and (5-phenyl-2-oxo-1,3-dioxolen-4-yl)methyl groups; and the 3-phthalidyl group.

The above acyloxyalkyl groups, alkoxycarbonyloxyalkyl groups, cycloalkoxycarbonyloxyalkyl groups, (5-alkyl or 5-aryl-2-oxo-1,3-dioxolen-4-yl)methyl groups and 3-phthalidyl group are capable of hydrolysis in vivo and are therefore particularly preferred, especially for those cases where they are to be retained in the final product for therapeutic use.

Where $R^{2'}$, $R^{3'}$ or $R^{4'}$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, and most preferably the methyl and ethyl groups.

Where $R^{2'}$ or $R^{3'}$ represents a group of formula

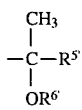

and $R^{6'}$ represents a hydroxy-protecting group, the hydroxy-protecting group may be selected from any protecting groups known in the art for use in β-lactam antibiotics. Examples of such groups are given by T. W. Green in "Protective Groups in Organic Synthesis", John Wiley & Sons; and by J. F. W. McOmie in "Protective Groups in Organic Chemistry", Plenum Press, the disclosures of which are incorporated herein by reference. More specifically, preferred such protecting groups include the:

substituted silyl groups, in which the silyl group has up to 3, and preferably 3, substituents selected from alkyl groups having from 1 to 6 carbon atoms and phenyl groups which are unsubstituted or have at least one substituent selected from substituents C' defined above and exemplified below, for example a trimethylsilyl, triethylsilyl, t-butyldimethylsilyl or t-butyldiphenylsilyl group;

aralkyl groups, which are preferably alkyl groups which have from 1 to 4, preferably from 1 to 3, more preferably 1 or 2, and most preferably 1, carbon atoms and which are substituted by at least one (more preferably 1, 2 or 3) aryl groups, as defined above, such as the benzyl, diphenylmethyl, triphenylmethyl, 4-methoxybenzyl, 4-nitrobenzyl, 2-nitrobenzyl, 1-naphthylmethyl, α-methylbenzyl, α,α-dimethylbenzyl, 1-phenylethyl, phenethyl, 3-phenylpropyl and 4-phenylbutyl groups, of which the benzyl, 4-methoxybenzyl, 4-nitrobenzyl and 2-nitrobenzyl groups are preferred;

oxycarbonyl groups, including:
 aralkyloxycarbonyl groups, in which the aralkyl part may be as defined and exemplified above, preferably the benzyloxycarbonyl, 4-nitrobenzyloxycarbonyl, 2-nitrobenzyloxycarbonyl and benzhydryloxycarbonyl groups;
 alkenyloxycarbonyl groups in which the alkenyl part has from 2 to 6, preferably 2 or 3, carbon atoms and may be unsubstituted or may be substituted by at least one (preferably from 1 to 3, more preferably 1) halogen atom, such as the allyloxycarbonyl, 2-chloroallyloxycarbonyl and 2-methylallyloxycarbonyl groups;
 alkoxycarbonyl groups which have in total from 2 to 7 carbon atoms, that is in which the alkyl part has from 1 to 6 carbon atoms and may be any of the alkyl groups exemplified above, and which may be unsubstituted or may be substituted by at least one (preferably from 1 to 3, more preferably 1 or 3) halogen atom, such as the 2,2,2-trichloroethoxycarbonyl, 2,2,2-tribromoethoxycarbonyl and t-butoxycarbonyl groups; and
 substituted silylalkoxycarbonyl groups, in which the alkoxycarbonyl part is as defined and exemplified above and the substituted silyl part is also as defined and exemplified above, such as the 2-(trimethylsilyl)ethoxycarbonyl group;
ether groups, including:
 oxygen-containing heterocyclic groups, for example the substituted and unsubstituted tetrahydropyranyl and tetrahydrofuranyl groups, such as the tetrahydropyranyl group;
 alkoxyalkyl groups in which the alkoxy and alkyl parts each have from 1 to 6, preferably from 1 to 4 and more preferably 1 or 2, carbon atoms, such as the methoxymethyl and 1-ethoxyethyl groups;
 substituted silylalkoxyalkyl groups, in which the alkoxyalkyl part is as defined and exemplified above and the substituted silyl part is also as defined and exemplified above, such as the 2-(trimethylsilyl)ethoxymethyl group; and
and alkanoyl and haloalkanoyl groups which have from 1 to 6 carbon atoms (2 to 6, in the case of the haloalkanoyl groups), such as the acetyl, propionyl, butyryl, isobutyryl, valeryl, isovaleryl, pivaloyl and chloroacetyl groups.

Where $R^{7'}$ represents an alkyl group having from 1 to 6 carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and sec-butyl groups, and most preferably the methyl group.

Where $R^{7'}$ represents an alkoxy group having from 1 to 6 carbon atoms, this may be a straight or branched chain group, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups. Of these, we prefer those alkoxy groups having from 1 to 4 carbon atoms, preferably the methoxy, ethoxy, propoxy, isopropoxy, butoxy and sec-butoxy groups, and most preferably the methoxy group.

Where A' represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, and most preferably the methyl and ethyl groups.

Where A' represents a substituted alkyl group, the alkyl part may be any of the unsubstituted groups defined and exemplified above, and the substituents are selected from substituents A', which include:
 hydroxy groups,
 protected hydroxy groups, such as those defined and exemplified above in relation to $R^{6'}$, amino groups, protected amino groups, in which the protecting group may be chosen from any amino-protecting group well known in the field of β-lactam chemistry, and there may be one or two such groups, preferably one such group, for example acyl groups, including alkanoyl and haloalkanoyl groups as defined above in relation to the hydroxy-protecting groups which may be represented by $R^{6'}$, preferably the formyl, acetyl, chloroacetyl and propionyl groups, and arylcarbonyl groups (in which the aryl part may be as defined above and exemplified below), preferably the benzoyl group, and oxycarbonyl groups, which may be as defined above in relation to the hydroxy-protecting groups which may be represented by $R^{6'}$, preferably the benzyloxycarbonyl, 4-nitrobenzyloxycarbonyl, 2-nitrobenzyloxycarbonyl, allyloxycarbonyl, 2,2,2-trichloroethoxycarbonyl, 2,2,2-tribromoethoxycarbonyl, t-butoxycarbonyl and 2-(trimethylsilyl)ethoxycarbonyl groups;

groups of formula $-C(=NR^{10'})NR^{11'}R^{12'}$ and $-NR^{13'}C(=NR^{14'})R^{15'}$, where $R^{10'}$, $R^{11'}$, $R^{12'}$, $R^{13'}$ and $R^{14'}$ are independently selected from the group consisting of hydrogen atoms, amino-protecting groups (for example as defined and exemplified above) and alkyl groups having from 1 to 6 carbon atoms (for example as defined and exemplified in relation to the alkyl groups which may be represented by A', preferably a methyl or ethyl group), or $R^{11'}$ and $R^{12'}$ together represent a group of formula $-(CH_2)_{n'}-$, where n' is an integer from 2 to 6, or $R^{10'}$ and $R^{11'}$ together represent a group of formula $-(CH_2)_{p'}-$, where p' is 2 or 3, and $R^{15'}$ represents a hydrogen atom, an alkyl group having from 1 to 6 carbon atoms (for example as defined and exemplified in relation to the alkyl groups which may be represented by A, preferably a methyl, ethyl or propyl group), an amino group or a protected amino group (for example as defined and exemplified above), or any two of $R^{13'}$, $R^{14'}$ and $R^{15'}$ together represent a group of formula $-(CH_2)_{p'}-$, where p' is 2 or 3.

Where A' represents an aryl group, this is a carbocyclic aromatic group having from 6 to 14, preferably from 6 to 10, more preferably 6 or 10, and most preferably 6, ring carbon atoms in one or more aromatic rings. The group may also be unsubstituted or substituted, and, if substituted, the substituents are selected from the group consisting of substituents C', defined above and exemplified below. In the case of the substituted groups, there is no particular limitation on the number of substituents on the aryl group, except such as may be imposed by the number of substitutable positions or possibly by steric constraints, but, in general, from 1 to 5 substituents are preferred, from 1 to 4 being more preferred and 1, 2 or 3 being most preferred. Also, where the group is substituted, it is preferred that it should not be further substituted by a group which is also substituted by another aryl group. Specific examples of the aromatic groups include the phenyl, α- or β-naphthyl, indenyl, phenanthrenyl and anthracenyl groups, of which we prefer those aromatic hydrocarbon groups having from 6 to 10 ring carbon atoms, particularly the phenyl, α-naphthyl and β-naphthyl groups, the phenyl group being most preferred.

Where the aryl group is substituted, the substituents are selected from the group consisting of substituents C', which include:

alkyl groups having from 1 to 6 carbon atoms, which may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups; of these, we prefer those alkyl groups having from 1 to 4 carbon atoms, preferably the methyl, ethyl, propyl, isopropyl, butyl and isobutyl groups, more preferably the methyl, ethyl, propyl and isopropyl groups, and most preferably the methyl group;

alkoxy groups having from 1 to 6 carbon atoms, which may be a straight or branched chain group, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups; of these, we prefer those alkoxy groups having from 1 to 4 carbon atoms, preferably the methoxy, ethoxy, propoxy, isopropoxy, butoxy and isobutoxy groups, more preferably the methoxy, ethoxy and propoxy groups, and most preferably the methoxy group;

halgen atoms, such as the fluorine, chlorine, bromine and iodine atoms, particularly the fluorine, chlorine and bromine atoms;

alkoxycarbonyl groups having from 2 to 7 carbon atoms, that is the alkoxy part has from 1 to 6 carbon atoms and may be any of the alkoxy groups defined ande exemplified above; examples of such alkoxycarbonyl groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups; of these, we prefer those alkoxycarbonyl groups having from 1 to 4 carbon atoms, preferably the methoxycarbonyl, ethoxycarbonyl, propoxycarbonyl, isopropoxycarbonyl, butoxycarbonyl and isobutoxycarbonyl groups, more preferably the methoxycarbonyl and ethoxycarbonyl groups;

groups of formula $-CONR^{8'}R^{9'}$, where $R^{8'}$ and $R^{9'}$ are the same or different and each represents:

a hydrogen atom, an amino-protecting group (for example as defined and exemplified above in relation to the groups which may be included in substituents A'), an alkyl group having from 1 to 6 carbon atoms (such as those exemplified above in relation to substituents C') or a phenyl group, or $R^{8'}$ and $R^{9'}$ together represent a group of formula $-(CH_2)_{q'}-O_{r'}-(CH_2)_{s'}-$, where q' and s' are independently selected from the group consisting of 0 and integers of from 1 to 5 and r' is 0 or 1, provided that (q'+s') is an integer of at least 2; and cyano groups, hydroxy groups and nitro groups.

Where A' represents an aralkyl group, this is as defined above, and examples include any of the alkyl groups having from 1 to 6, preferably from 1 to 4, carbon atoms exemplified above and substituted by at least one aryl group, such as those exemplified above. There is no particular limitation on the number of aryl substituents on the alkyl group, except such as may be imposed by the number of substitutable positions or possibly by steric constraints, but, in general, from 1 to 3 aryl groups are preferred, 2 or 1 being more preferred and 1 being most preferred. The aryl group forming part of the aralkyl group may itself be unsubstituted or it may be substituted by at least one substituent selected from the group consisting of substituents C', defined above and exemplified below. Again, there is no particular limitation on the number of substituents on the aryl group, except such as may be imposed by the number of substitutable positions or possibly by steric constraints, but, in general, from 1 to 5 substituents are preferred, from 1 to 3 being more preferred and 1 being most preferred. Specific examples of such groups include the benzyl, α-naphthylmethyl, β-naphthylmethyl, 2-methylbenzyl, 3-methylbenzyl, 4-methylbenzyl, 2,4,6-trimethylbenzyl, 3,4,5-trimethylbenzyl, 2-methoxybenzyl, 3-methoxybenzyl, 4-methoxybenzyl, 3,4-dimethoxybenzyl, 2-nitrobenzyl, 4-nitrobenzyl, 2-chlorobenzyl, 3-chlorobenzyl, 4-chlorobenzyl, 4-bromobenzyl, 4-cyanobenzyl, α or β-naphthylmethyl, benzhydryl (i.e. diphenylmethyl), trityl (i.e. triphenylmethyl), phenethyl, 1-phenylethyl, 1-(α or β-naphthyl)ethyl, 2-(α or β-naphthyl)ethyl, 1-phenylpropyl, 2-phenylpropyl, 3-phenylpropyl, 1-(α or β-naphthyl)propyl, 2-(α or β-naphthyl) propyl, 3-(α or β-naphthyl)propyl, 1-phenylbutyl, 2-phenylbutyl, 3-phenylbutyl, 4-phenylbutyl, 1-(α or β-naphthyl)butyl, 2-(α or β-naphthyl)butyl, 3-(α or β-naphthyl)butyl, 4-(α or β-naphthyl)butyl, 1-phenylpentyl, 2-phenylpentyl, 3-phenylpentyl, 4-phenylpentyl, 5-phenylpentyl, 1-(α or β-naphthyl)pentyl, 2-(α or β-naphthyl)pentyl, 3-(α or β-naphthyl) pentyl, 4-(α or β-naphthyl)pentyl, 5-(α or β-naphthyl)pentyl, 1-phenylhexyl, 2-phenylhexyl, 3-phenylhexyl, 4-phenylhexyl, 5-phenylhexyl, 6-phenylhexyl, 1-(α or β-naphthyl)hexyl, 2-(α or β-naphthyl)hexyl, 3-(α or β-naphthyl)hexyl, 4-(α or β-naphthyl)hexyl, 5-(α or β-naphthyl)hexyl and 6-(α or β-naphthyl)hexyl groups. Of these, we prefer the benzyl, phenethyl, 3-phenylpropyl and 4-phenylpentyl groups, the unsubstituted aralkyl groups being more preferred, and the unsubstituted benzyl and phenethyl groups being most preferred.

Where A' represents a heterocyclic group, this has from 3 to 10, more preferably from 5 to 7, ring atoms in one or more heterocyclic rings, at least one of said atoms, preferably from 1 to 4 and more preferably from 1 to 3 of said atoms, being a hetero-atom selected from the group consisting of nitrogen, oxygen and sulfur hetero-atoms, said group being unsubstituted or being substituted by at least one substituent selected from the group consisting of substituents B' on carbon atoms, substituents $B^{1'}$ on nitrogen hetero-atoms, and oxygen atoms to form a sulfinyl or sulfonyl group or sulfur hetero-atoms, all as defined and exemplified below, or it may represent a fused heterocyclic group in which a heterocyclic group as defined above is fused to an aryl group as defined above, preferably a phenyl group. The heterocyclic group may be aromatic or non-aromatic, but is preferably non-aromatic. The group may be a monocyclic group or it may consist of two or more rings attached to each other by fusion or by a spiro attachment. In the case of those groups having 4 hetero-atoms in a ring, we prefer that 3 or 4 of them should be nitrogen atoms and 1 or 0 should be an oxygen or sulfur atom. In the case of those groups having 3 hetero-atoms in a ring, we prefer that 1, 2 or 3 should be nitrogen atoms and, correspondingly, 2, 1 or 0 should be oxygen and/or sulfur atoms. In the case of those groups having 1 or 2 hetero-atoms in a ring, the hetero-atoms may be freely chosen from nitrogen, oxygen and sulfur atoms. Preferably, however, the group contains at least one nitrogen atom. The group may be substituted or unsubstituted and, if substituted, the substituents are selected from the group consisting of substituents B', $B^{1'}$ and oxygen atoms, as defined above and exemplified below.

The groups may also be saturated, unsaturated or partially saturated and, if fully unsaturated, may be aromatic in character. Examples of such non-aromatic groups include the azetidinyl, pyrrolidinyl, oxopyrrolidinyl, piperidyl, oxopiperidyl, morpholinyl (especially morpholino), thiomorpholinyl, tetrahydropyrimidinyl, thiazolidinyl, oxazolidinyl, hexahydropyrimidinyl, imidazolidinyl, octahydroazocinyl and pyrazolidinyl groups. Of these, we prefer the saturated heterocyclic groups having 5 or 6 ring atoms and containing at least one nitrogen atom, and optionally an oxygen or sulfur atom or atoms.

These heterocyclyl groups may optionally be condensed with one or more other cyclic groups such as, for example, the aryl groups and cycloalkyl groups defined and exemplified herein. Examples of such groups include: the 1,2,3,4-tetrahydroisoquinolyl, pyrazolotriazolyl decahydroisoquinolyl, 1,2,3,4-tetrahydroquinolyl, decahydroquinolyl, isoindolinyl and indolinyl groups.

Where A' represents a substituted alkyl group, this has from 1 to 6 carbon atoms and is substituted by at least one substituent selected from the group consisting of the heterocyclic groups and fused heterocyclic groups defined and exemplified above.

Such heterocyclic groups and heterocyclic groups which are substituents on alkyl groups represented by A' may be unsubstituted or they may be substituted by one or more of the following groups and atoms. There is no particular restriction upon the number of substituents which may be present, except such as may be imposed by the number of substitutable atoms and possibly by steric constraints. In general, from 1 to 5 substituents are preferred, from 1 to 3 being more preferred.

In the case of carbon atoms or sulfur atoms, these may be substituted by 1 (carbon atoms) or 1 or 2 (sulfur atoms) oxygen atoms, to form a carbonyl group or a sulfinyl or sulfonyl group.

In the case of carbon atoms, these may be substituted by one or more of substituents B':
alkyl groups having from 1 to 6 carbon atoms, such as the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups, preferably the methyl, ethyl, propyl, isopropyl, butyl, isobutyl, sec-butyl, t-butyl, pentyl and isopentyl groups;
alkoxy groups having from 1 to 6 carbon atoms, such as the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups, preferably the methoxy, ethoxy, propoxy, isopropoxy, butoxy, isobutoxy, sec-butoxy and t-butoxy groups;

hydroxy groups, cyano groups, nitro groups, halogen atoms, such as fluorine, chlorine, bromine and iodine atoms;

alkoxycarbonyl groups having from 2 to 7 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups, preferably the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups;

carboxy groups, cycloalkyl groups having from 3 to 7 ring carbon atoms, preferably 5 or 6 ring carbon atoms, such as the cyclopropyl, cyclobutyl, cyclopentyl and cyclohexyl groups;

alkoxyalkyl groups in which the alkoxy and alkyl parts both have from 1 to 6 carbon atoms, and each may be as defined and exemplified above in relation to those groups included in substituents B', for example the methoxymethyl, ethoxymethyl, propoxymethyl, isopropoxymethyl, butoxymethyl, 2-methoxyethyl, 3-methoxypropyl, 2-methoxypropyl or 4-ethoxybutyl;

alkoxycarbonylalkyl groups in which the alkoxy and alkyl parts both have from 1 to 6 carbon atoms, and each may be as defined and exemplified above in relation to those groups included in substituents B', for example the methoxycarbonylmethyl, ethoxycarbonylmethyl, propoxycarbonylmethyl, isopropoxycarbonylmethyl, butoxycarbonylmethyl, 2-methoxycarbonylethyl, 3-methoxycarbonylpropyl, 2-methoxycarbonylpropyl and 4-ethoxycarbonylbutyl groups; cyanoalkyl groups in which the alkyl part has from 1 to 6 carbon atoms, such as the cyanomethyl, 2-cyanoethyl, 3-cyanopropyl, 2-cyanopropyl and 4-cyanobutyl groups;

haloalkyl groups having from 1 to 6 carbon atoms, in which the alkyl part may be any of those alkyl groups exemplified above and has at least one halogen substituent; there is no restriction on the number of halogen substituents, and the group may be anything from a monohaloalkyl group to a perhaloalkyl group; preferably there are from 1 to 3 halogen atoms; examples of such groups include the trifluoromethyl, trichloromethyl, fluoromethyl, chloromethyl, bromomethyl, iodomethyl, 2-fluoroethyl, 2,2,2-trifluoroethyl, 2-chloroethyl, 2-bromoethyl, 3-fluoropropyl, 2-fluoropropyl, 4-chlorobutyl and 3-fluorobutyl groups;

alkanoyloxy groups having from 1 to 6 carbon atoms, such as the acetoxy, propionyloxy, butyryloxy, isobutyryloxy, valeryloxy, isovaleryloxy, pivaloyloxy and hexanoyloxy groups, preferably the acetoxy, propionyloxy, butyryloxy or isobutyryloxy;

azido groups, alkylthio groups having from 1 to 6 carbon atoms, such as the methylthio, ethylthio, propylthio, isopropylthio, butylthio, isobutylthio, sec-butylthio, t-butylthio, pentylthio, isopentylthio, neopentylthio, 2-methylbutylthio, 1-ethylpropylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, hexyl and isohexylthio groups, preferably the methylthio, ethylthio, propylthio, isopropylthio, butylthio and isobutylthio groups;

alkylsulfinyl groups having from 1 to 6 carbon atoms, such as the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, neopentylsulfinyl, 2-methylbutylsulfinyl, 1-ethylpropylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl, 2-ethylbutylsulfinyl, hexylsulfinyl and isohexylsulfinyl groups, preferably the methylsulfinyl, ethylsulfinyl, propylsulfinyl, isopropylsulfinyl, butylsulfinyl and isobutylsulfinyl groups;

alkylsulfonyl groups having from 1 to 6 carbon atoms, such as the methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, neopentylsulfonyl, 2-methylbutylsulfonyl, 1-ethylpropylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl, 2-ethylbutylsulfonyl, hexylsulfonyl and isohexylsulfonyl groups, preferably the methylsulfonyl, ethylsulfonyl, propylsulfonyl, isopropylsulfonyl, butylsulfonyl and isobutylsulfonyl groups;

groups of formula —$NR^{8'}R^{9'}$ and groups of formula —$CONR^{8'}R^{9'}$, where $R^{8'}$ and $R^{9'}$ are independently selected from the group consisting of hydrogen atoms, amino-protecting groups, alkyl groups having from 1 to 6 carbon atoms and phenyl groups, or $R^{8'}$ and $R^{9'}$ together represent a group of formula —$(CH_2)_{q'}$—$O_{r'}$—$(CH_2)_{s'}$—, where q' and s' are independently selected from the group consisting of 0 and integers of from 1 to 5 and r' is 0 or 1, provided that (q'+s') is an integer of at least 2, all as defined and exemplified above; and groups of formulae (B-I'), (B-II'), (B-III'), (B-IV'), (B-V'), (B-VI'), (B-VII'), (B-VIII') and (B-IX'), as shown above.

In formulae (B-I') to (B-IX'):

$R^{20'}$ represents a hydrogen atom, an amino-protecting group (such as those exemplified above in relation to A'), a group of formula —$COR^{26'}$, where $R^{26'}$ represents an alkyl group having from 1 to 6 carbon atoms (such as those exemplified above in relation to $R^{1'}$, preferably a methyl group), or a substituted alkyl group which has from 1 to 6 carbon atoms and which is substituted by at least one substituent selected from the group consisting of substituents A';

a group of formula —$C(=NR^{16'})R^{17'}$, where $R^{16'}$ and $R^{17'}$ are independently selected from the group consisting of hydrogen atoms, alkyl groups having from 1 to 6 carbon atoms (such as those exemplified above in relation to $R^{1'}$, preferably a methyl group), amino groups, protected amino groups (such as those exemplified above in relation to A') and amino-protecting groups (such as those exemplified above in relation to A');

an unsubstituted alkyl group having from 1 to 6 carbon atoms (such as those exemplified above in relation to $R^{1'}$, preferably a methyl group), or a substituted alkyl group which has from 1 to 6 carbon atoms and which is substituted by at least one substituent selected from the group consisting of substituents D, defined and exemplified below.

$R^{21'}$ and $R^{22'}$ are independently selected from the group consisting of hydrogen atoms, alkyl groups having from 1 to 6 carbon atoms (such as those exemplified above in relation to $R^{1'}$, preferably a methyl group), hydroxy groups and protected hydroxy groups (such as those defined and exemplified above in relation to $R^{6'}$);

$R^{28'}$ and $R^{29'}$ are independently selected from the group consisting of hydrogen atoms, alkyl groups having from 1 to 6 carbon atoms (such as those exemplified above in relation to $R^{1'}$, preferably a methyl group), amino-protecting (such as those exemplified above in relation to A') groups, amino groups, protected amino groups (such as those exemplified above in relation to A') and groups of formula —C(=NR$^{16'}$)R$^{17'}$, where $R^{16'}$ and $R^{17'}$ are as defined above.

$R^{30'}$ represents a hydrogen atom, an alkyl group having from 1 to 6 carbon atoms (such as those exemplified above in relation to $R^{1'}$, preferably a methyl group) or a substituted alkyl group which has from 1 to 6 carbon atoms and which is substituted by at least one substituent selected from the group consisting of hydroxy groups (for example a 1-hydroxyethyl group) and protected hydroxy groups (such as those defined and exemplified above in relation to $R^{6'}$).

$R^{31'}$ represents a hydrogen atom, an alkyl group having from 1 to 6 carbon atoms (such as those exemplified above in relation to $R^{1'}$, preferably a methyl group) or an amino-protecting group (such as those exemplified above in relation to A').

$R^{32'}$ represents a hydrogen atom, an alkyl group having from 1 to 6 carbon atoms (such as those exemplified above in relation to $R^{1'}$, preferably a methyl group) or a group of formula —NR$^{28'}$R$^{29'}$, in which $R^{28'}$ and $R^{29'}$ are as defined above.

E' represents an imidazolyl group or a triazolyl group.

W' represents an aromatic heterocyclic group having from 5 to 8, preferably 5 or 6, ring atoms, of which from 1 to 4 are nitrogen atoms, said aromatic heterocyclic group being unsubstituted or being substituted by at least one alkyl group having from 1 to 6 carbon atoms (such as those exemplified above in relation to $R^{1'}$, preferably a methyl group); specific examples of such aromatic heterocyclic groups include the pyridyl, pyridazinyl, pyrazinyl, pyrrolyl, imidazolyl, triazolyl and tetrazolyl groups.

Where there is, as is preferred, a nitrogen atom in the heterocyclic group, this may also be substituted, and the substituents are selected from the group consisting of substituents $B^{1'}$, which include:

alkyl groups having from 1 to 6 carbon atoms, such as those exemplified above in relation to $R^{1'}$, preferably a methyl group; groups of formula —C(=NR$^{16'}$)R$^{17'}$, where $R^{16'}$ and $R^{17'}$ are as defined and exemplified above;

amino-protecting groups, such as those exemplified above in relation to A'; and groups of formula —CONR$^{18'}$R$^{19'}$, where $R^{18'}$ and $R^{19'}$ are independently selected from the group consisting of alkyl groups having from 1 to 6 carbon atoms (such as those exemplified above in relation to $R^{1'}$, preferably a methyl, ethyl, propyl or isopropyl group) and carboxylic acyl groups (preferably oxycarbonyl groups, as defined and exemplified above in relation to the oxycarbonyl groups which may be represented by $R^{6'}$.

Substituents D' are selected from the group consisting of hydroxy groups, protected hydroxy groups (such as those defined and exemplified above in relation to $R^{6'}$), carboxy groups, protected carboxy groups (such as those defined and exemplified above in relation to $R^{1'}$), cyano groups, alkoxy groups having from 1 to 6 carbon atoms (such as those defined and exemplified above in relation to $R^{7'}$, preferably a methoxy group), alkylsulfonyl groups having from 1 to 6 carbon atoms (such as those exemplified above in relation to substituents B), and groups of formula —NHCOR$^{23'}$, —NR$^{24'}$R$^{25'}$, —CONR$^{24'}$R$^{25'}$ or —OCONR$^{24'}$R$^{25'}$, where $R^{23'}$, $R^{24'}$ and $R^{25'}$ are independently selected from the group consisting of hydrogen atoms and alkyl groups having from 1 to 6 carbon atoms (such as those exemplified above in relation to $R^{1'}$, preferably a methyl, ethyl, propyl or isopropyl group).

Where $R^{4'}$ represents an alkyl group, this may be as defined and exemplified above. The group may be unsubstituted or it may be substituted by one or more substituents selected from the group consisting of substituents E', which include: hydroxy groups, protected hydroxy groups (such as those defined and exemplified above in relation to $R^{6'}$), amino groups and protected amino groups (such as those exemplified above in relation to A').

Where $R^{4'}$ represents an alkenyl group, this has from 2 to 6, preferably 3 or 4, carbon atoms and is unsubstituted or is substituted by at least one substituent selected from the group consisting of substituents E', defined and exemplified above. Examples include the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the vinyl, allyl, 1-propenyl, and 1-butenyl groups are preferred, the vinyl, allyl and 1-butenyl groups being most preferred.

Where $R^{4'}$ represents an aryl or aralkyl group, this may be any one of the aryl or aralkyl groups defined and exemplified above in relation to A', and, as with A', it may be substituted or unsubstituted.

Where $R^{4'}$ represents a cycloalkyl group, this has from 3 to 7 carbon atoms and is unsubstituted or is substituted by at least one substituent selected from the group consisting of substituents C', defined and exemplified above. Preferred cycloalkyl groups have from 4 to 6 carbon atoms, and examples of such groups include the cyclopropyl, cyclobutyl, cyclopentyl, cyclohexyl and cycloheptyl groups, of which the cyclobutyl, cyclopentyl and cyclohexyl groups are preferred.

Where $R^{4'}$ represents an aromatic heterocyclic group, this has from 5 to 7, preferably 5 or 6, ring atoms in an aromatic heterocyclic ring, and this may optionally be fused to an aryl group, as defined and exemplified above, preferably a phenyl group. It has at least one hetero-atom selected from the group consisting of nitrogen, oxygen and sulfur heteroatoms, and preferably has from 1 to 4, more preferably from 1 to 3 and most preferably 1 or 2, such hetero-atoms. In the case of those groups having 4 hetero-atoms in a ring, we prefer that 3 or 4 of them should be nitrogen atoms and 1 or 0 should be an oxygen or sulfur atom. In the case of those groups having 3 hetero-atoms in a ring, we prefer that 1, 2 or 3 should be nitrogen atoms and, correspondingly, 2, 1 or 0 should be oxygen and/or sulfur atoms. In the case of those groups having 1 or 2 hetero-atoms in a ring, the heteroatoms may be freely chosen from nitrogen, oxygen and sulfur atoms. Preferably, however, the group contains at least one nitrogen atom. Examples of such aromatic heterocyclic groups include the 2-pyridyl, 3-pyridyl, 2-pyrimidinyl, 2-imidazolyl, 3-thiazolyl, 2-thienyl and 2-furyl groups.

These groups may be unsubstituted or they may have one or more substituents selected from the group consisting of substituents C', defined and exemplified above.

Where $R^{4'}$ represents an alkyl group which has from 1 to 6 carbon atoms and which is substituted by at least one substituent selected from the group consisting of aromatic heterocylic groups and fused heterocyclic groups, the heterocyclic groups may be as defined and exemplified above; and the alkyl groups may be any of the alkyl groups having from 1 to 6, preferably from 1 to 4 and more preferably 1, 2 or 3, carbon atoms defined and exemplified above in relation to $R^{2'}$ etc., the methyl and ethyl groups being most preferred.

In the compounds of formula (IV'), $R^{1'}$ may be the same as in the compounds of formula (I') and (II'). In these compounds, particularly preferred groups are the:

alkyl groups, especially the methyl, ethyl and t-butyl groups, aralkyl groups, especially the benzyl, benzhydryl, 4-nitrobenzyl and 2-nitrobenzyl groups, alkenyl groups, especially the allyl, 2-chloroallyl and 2-methylallyl groups, haloalkyl groups, especially the 2,2,2-trichloroethyl and 2,2,2-tribromoethyl groups, and the 2-trimethylsilylethyl group.

Also, $R^{41'}$ may be a hydrogen atom or a hydroxy-protecting group, which latter may be any of the groups defined and exemplified above in relation to $R^{6'}$. Particularly preferred such groups in the case of $R^{41'}$ are:

tri-substituted silyl groups, such as those previously exemplified, particularly the t-butyldimethylsilyl, t-butyldiphenylsilyl, trimethylsilyl and triethylsilyl groups;

aralkyloxycarbonyl groups, such as those defined and exemplified above, preferably the benzyloxycarbonyl and 4-nitrobenzyloxycarbonyl groups; and unsubstituted and substituted acetyl groups, particularly those in which the substituents are selected from the group consisting of substituents C', defined and exemplified above, and especially the acetyl, chloroacetyl and methoxyacetyl groups.

$R^{42'}$, $R^{43'}$, $R^{45'}$ and $R^{46'}$ may represent an alkyl group having from 1 to 6 carbon atoms, which may be as defined and exemplified above in relation to $R^{2'}$ and $R^{3'}$. Particularly preferred such groups are the methyl, ethyl, propyl, isobutyl, pentyl and hexyl groups, of which the methyl, ethyl and propyl groups are most preferred.

$R^{42'}$ and $R^{43'}$ may represent an alkoxy group having from 1 to 6 carbon atoms, which may be as defined and exemplified above in relation to $R^{7'}$. Particularly preferred such groups are the methoxy, ethoxy, propoxy, isobutoxy, pentyloxy and hexyloxy groups, of which the methoxy, ethoxy and propoxy groups are most preferred.

$R^{42'}$ and $R^{43'}$ may represent a halogen atom, for example a fluorine, chlorine, bromine or iodine atom, of which the fluorine, chlorine and bromine atoms are preferred and the fluorine and chlorine atoms are more preferred.

$R^{42'}$, $R^{45'}$ and $R^{46'}$ may represent an aryl group, which may be as defined and exemplified above in relation to $R^{4'}$. A particularly preferred such group is the phenyl group.

Where $R^{42'}$ represents an aryloxy group, this may be the aryloxy equivalent of any of the aryl groups defined and exemplified above in relation to $R^{4'}$. A particularly preferred such group is the phenoxy group.

Preferred compounds of formula (I') are those in which:
(1) $R^{1'}$ represents:
a hydrogen atom,
an alkyl group having from 1 to 6 carbon atoms,
an aralkyl group which is an alkyl group having from 1 to 4 carbon atoms and which is substituted by at least one aryl group, as defined above,
an alkenyl group having from 2 to 6 carbon atoms, and which is unsubstituted or is substituted by one or more halogen atoms,
a haloalkyl group having from 1 to 6 carbon atoms,
a tri-substituted silylethyl group, in which all three or two or one of the substituents are alkyl groups having from 1 to 5 carbon atoms, and none, one or two of the substituents are aryl groups, as defined above,
an acyloxyalkyl group, in which the acyl part is an alkanoyl group having from 1 to 6 carbon atoms and the alkyl part has from 1 to 6 carbon atoms,
an alkoxycarbonyloxyalkyl group in which the alkoxy and alkyl parts each have from 1 to 6 carbon atoms,
a cycloalkoxycarbonyloxyalkyl groups in which the cycloalkyl part has from 3 to 7 ring carbon atoms and may be unsubstituted or substituted by at least one substituent selected from the group consisting of substituents C', defined above and the alkyl part has from 1 to 6 carbon atoms
a (5-alkyl or 5-aryl -2-oxo-1,3-dioxolen-4-yl)methyl group in which the alkyl part has from 1 to 4 carbon atoms and the aryl part is as defined above; or
the 3-phthalidyl group;
(2) $R^{2'}$ and $R^{3'}$ are independently selected from the group consisting of hydrogen atoms, alkyl groups having from 1 to 4 carbon atoms and groups of formula

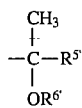

where $R^{5'}$ represents a hydrogen atom or a methyl group; and $R^{6'}$ represents:
a hydrogen atom,
a substituted silyl group, in which the silyl group has 3 substituents selected from alkyl groups having from 1 to 6 carbon atoms and phenyl groups,
an aralkyl group, in which an alkyl group having from 1 to 4 carbon atoms is substituted by at least one aryl group, as defined above,
an aralkyloxycarbonyl group, in which the aralkyl part is as defined above,
an alkenyloxycarbonyl group in which the alkenyl part has from 2 to 6 carbon atoms and is unsubstituted or is substituted by at least one halogen atom,
an alkoxycarbonyl group which has from 2 to 7 carbon atoms,
a substituted silylalkoxycarbonyl group, in which the alkoxycarbonyl part and the substituted silyl part are as defined above,
an oxygen-containing heterocyclic group,
an alkoxyalkyl group in which the alkoxy and alkyl parts each have from 1 to 6 carbon atoms,
a substituted silylalkoxyalkyl group, in which the alkoxyalkyl part and the substituted silyl part are as defined above, or
an alkanoyl or haloalkanoyl group which has no more than 6 carbon atoms; or
$R^{2'}$ and $R^{3'}$ together represent a group of formula $=C(CH_3)CH_2OR^{6'}$, in which $R^{6'}$ is as defined above;
(3) X' represents a sulfur atom or a group of formula $>CHR^{7'}$, where $R^{7'}$ represents a hydrogen atom, an alkyl group having from 1 to 4 carbon atoms or an alkoxy group having from 1 to 4 carbon atoms; and (4) A' represents an alkyl group which has from 1 to 4 carbon atoms and which is unsubstituted or is substituted by 1 or 2 substituents selected from the group consisting of substituents $A^{a'}$, defined below, an aryl group, as defined below, an aralkyl group in which an alkyl group having from 1 to 3 carbon atoms is substituted by at least one aryl group as defined below, a heterocyclic group which has from 4 to 7 ring atoms, at least one of said atoms being a hetero-atom selected from the group consisting of nitrogen, oxygen and sulfur hetero-atoms, said group being unsubstituted or being substituted by at least one substituent selected from the group consisting of substituents $B^{a'}$ on carbon atoms, substituents $B^{a1'}$ on nitrogen hetero-atoms, and oxygen atoms to form a sulfinyl or sulfonyl group on sulfur hetero-atoms, all as defined below;

an alkyl group which has from 1 to 3 carbon atoms and which is substituted by at least one substituent selected from the group consisting of the heterocyclic groups defined above;

said aryl groups are aromatic carbocyclic groups having from 6 to 10 ring carbon atoms and are unsubstituted or are substituted by at least one substituent selected from the group consisting of substituents $C^{a'}$, defined below;

said substituents $A^{a'}$ are selected from the group consisting of hydroxy groups, protected hydroxy groups, amino groups, protected amino groups, groups of formula $-C(=NR^{10'})NR^{11'}R^{12'}$, where $R^{10'}$, $R^{11'}$ and $R^{12'}$ are independently selected from the group consisting of hydrogen atoms, amino-protecting groups and alkyl groups having from 1 to 4 carbon atoms, or $R^{11'}$ and $R^{12'}$ together represent a group of formula $-(CH_2)_{n'}-$, where n is an integer from 2 to 6, or $R^{10'}$ and $R^{11'}$ together represent a group of formula $-(CH_2)_{p'}-$, where p' is 2 or 3, and groups of formula $-NR^{13'}C(=NR^{14'})R^{15'}$, where $R^{13'}$ and $R^{14'}$ are independently selected from the group consisting of hydrogen atoms, amino-protecting groups and alkyl groups having from 1 to 6 carbon atoms, and $R^{15'}$ represents a hydrogen atom, an alkyl group having from 1 to 4 carbon atoms, an amino group or a protected amino group, or any two of $R^{13'}$, $R^{14'}$ and $R^{15'}$ together represent a group of formula $-(CH_2)_{p'}-$, where p' is 2 or 3;

said substituents $B^{a'}$ are selected from the group consisting of alkyl groups having from 1 to 4 carbon atoms,
alkoxy groups having from 1 to 6 carbon atoms,
hydroxy groups,
halogen atoms,
cyano groups,
nitro groups,
alkoxycarbonyl groups having from 2 to 5 carbon atoms,
carboxy groups,
oxygen atoms, to form with a ring carbon atom a carbonyl group,
alkoxyalkyl groups in which the alkoxy and alkyl parts both have from 1 to 6 carbon atoms,
haloalkyl groups having from 1 to 6 carbon atoms,
alkanoyloxy groups having from 1 to 6 carbon atoms,
groups of formula $-NR^{8'}R^{9'}$ and groups of formula $-CONR^{8'}R^{9'}$, where $R^{8'}$ and $R^{9'}$ are independently selected from the group consisting of hydrogen atoms, amino-protecting groups, alkyl groups having from 1 to 4 carbon atoms and phenyl groups, or $R^{8'}$ and $R^{9'}$ together represent a group of formula $-(CH_2)_{q'}-O_{r'}-(CH_2)_{s'}-$, where q' and s' are independently selected from the group consisting of 0 and integers of from 1 to 5 and r' is 0 or 1, provided that (q'+s') is an integer of at least 2; and groups of formulae (B-I'), (B-II'), (B-III'), (B-IV'), (B-V'), (B-VI'), (B-VII'), (B-VIII') and (B-IX') as defined above;

said substituents $B^{a1'}$ are selected from the group consisting of alkyl groups having from 1 to 4 carbon atoms, amino-protecting groups, groups of formula $-C(=NR^{16'})R^{17'}$, where $R^{16'}$ and $R^{17'}$ are as defined above, amino-protecting groups and groups of formula $-CONR^{18'}R^{19'}$, where $R^{18'}$ and $R^{19'}$ are independently selected from the group consisting of alkyl groups having from 1 to 4 carbon atoms, alkanoyl groups having from 2 to 5 carbon atoms and benzoyl groups;

said substituents C' are selected from the group consisting of alkyl groups having from 1 to 4 carbon atoms, alkoxy groups having from 1 to 4 carbon atoms, halogen atoms, alkoxycarbonyl groups having from 2 to 5 carbon atoms, groups of formula $-CONR^{8'}R^{9'}$, where $R^{8'}$ and $R^{9'}$ are as defined above, cyano groups, hydroxy groups and nitro groups.

More preferred compounds of formulae (I') and (II') of the present invention are those compounds in which:

(5) $R^{1'}$ represents:

a hydrogen atom, an alkyl group having from 1 to 4 carbon atoms, an aralkyl group which is an alkyl group having 1 or 2 carbon atoms and which is substituted by at least one phenyl group a haloalkyl group having from 1 to 4 carbon atoms, a tri-substituted silylethyl group, in which all three or two of the substituents are alkyl groups having from 1 to 4 carbon atoms, and none or one of the substituents are phenyl groups, an acyloxyalkyl group, in which the acyl part is an alkanoyl group having from 2 to 5 carbon atoms and the alkyl part has 1 or 2 carbon atoms, an alkoxycarbonyloxyalkyl group in which the alkoxy and alkyl parts each have from 1 to 4 carbon atoms, a (5-methyl-2-oxo-1,3-dioxolen-4-yl)methyl group, or a 3-phthalidyl group;

(6) $R^{2'}$ and $R^{3'}$ are independently selected from the group consisting of hydrogen atoms, alkyl groups having from 1 to 4 carbon atoms and groups of formula

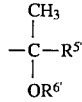

where $R^{5'}$ represents a hydrogen atom or a methyl group; and $R^{6'}$ represents:

a hydrogen atom, a substituted silyl group, in which the silyl group has 3 substituents selected from alkyl groups having from 1 to 4 carbon atoms and phenyl groups, an aralkyl group, in which an alkyl group having from 1 to 4 carbon atoms is substituted by at least one aryl group, as defined above, an alkoxycarbonyl group which has from 2 to 7 carbon atoms, a tetrahydropyranyl group, an alkoxyalkyl group in which the alkoxy and alkyl parts each have from 1 to 4 carbon atoms, an alkanoyl or haloalkanoyl group which has from 2 to 5 carbon atoms; or $R^{2'}$ and $R^{3'}$ together represent a group of formula $=C(CH_3)CH_2OR^{6'}$, in which $R^{6'}$ is as defined above;

(7) X' represents a sulfur atom or a group of formula >CHR$^{7'}$, where R$^{7'}$ represents a hydrogen atom, an alkyl group having 1 or 2 carbon atoms or an alkoxy group having 1 or 2 carbon atoms; and (8) A' represents an alkyl group which has 1 or 2 carbon atoms and which is unsubstituted or is substituted by 1 or 2 substituents selected from the group consisting of substituents A$^{b'}$, defined below, a phenyl group, which is unsubstituted or is substituted by 1 or 2 substituents selected from the group consisting of substituents C$^{b'}$, defined below, an aralkyl group in which an alkyl group having from 1 to 3 carbon atoms is substituted by at least one phenyl group, which is unsubstituted or is substituted by 1 or 2 substituents selected from the group consisting of substituents C$^{b'}$, defined below, a heterocylic group which has 5 or 6 ring atoms, from 1 to 3 of said atoms being a hetero-atom selected from the group consisting of nitrogen, oxygen and sulfur hetero-atoms, said group being unsubstituted or being substituted by at least one substituent selected from the group consisting of substituents B$^{b'}$ on carbon atoms, substituents B$^{b1'}$ on nitrogen hetero-atoms, and oxygen atoms to form a sulfinyl or sulfonyl group on sulfur hetero-atoms, all as defined below;

said substituents A$^{b'}$ are selected from the group consisting of hydroxy groups, protected hydroxy groups, amino groups and protected amino groups;

said substituents B$^{b'}$ are selected from the group consisting of alkyl groups having 1 or 2 carbon atoms,
alkoxy groups having 1 or 2 carbon atoms,
hydroxy groups,
halogen atoms,
cyano groups,
nitro groups,
alkoxycarbonyl groups having from 2 to 5 carbon atoms,
carboxy groups,
haloalkyl groups having from 1 to 6 carbon atoms,
alkanoyloxy groups having from 1 to 6 carbon atoms,
groups of formula —NR$^{8'}$R$^{9'}$ and groups of formula —CONR$^{8'}$R$^{9'}$, where R$^{8'}$ and R$^{9'}$ are independently selected from the group consisting of hydrogen atoms, amino-protecting groups, alkyl groups having 1 or 2 carbon atoms and phenyl groups, or R$^{8'}$ and R$^{9'}$ together represent a group of formula —(CH$_2$)$_{q'}$—O$_{r'}$—(CH$_2$)$_{s'}$—, where q' and s' are independently selected from the group consisting of 0 and integers of from 1 to 5 and r' is 0 or 1, provided that (q'+s') is an integer of at least 2; and groups of formulae (B-I'), (B-II'), (B-III'), (B-IV'), (B-V'), (B-VI'), (B-VII'), (B-VIII') and (B-IX') as defined above;

said substituents B$^{b1'}$ are selected from the group consisting of alkyl groups having 1 or 2 carbon atoms, amino-protecting groups, groups of formula —C(=NR$^{16'}$)R$^{17'}$, where R$^{16'}$ and R$^{17'}$ are as defined above, amino-protecting groups and groups of formula —CONR$^{18'}$R$^{19'}$, where R$^{18'}$ and R$^{19'}$ are independently selected from the group consisting of alkyl groups having 1 or 2 carbon atoms, alkanoyl groups having from 2 to 5 carbon atoms and benzoyl groups;

said substituents C$^{b'}$ are selected from the group consisting of alkyl groups having 1 or 2 carbon atoms, alkoxy groups having 1 or 2 carbon atoms, halogen atoms, groups of formula —CONR$^{8'}$R$^{9'}$, where R$^{8'}$ and R$^{9'}$ are as defined above, cyano groups, hydroxy groups and nitro groups.

Preferred compounds of formula (IV') of the present invention are those compounds in which:

(9) R$^{1'}$ represents:
a hydrogen atom,
an alkyl group having from 1 to 6 carbon atoms,
an aralkyl group which is an alkyl group having from 1 to 4 carbon atoms and which is substituted by at least one aryl group, as defined above,
an alkenyl group having from 2 to 6 carbon atoms, and which is unsubstituted or is substituted by one or more halogen atoms,
a haloalkyl group having from 1 to 6 carbon atoms,
a tri-substituted silylethyl group, in which all three or two or one of the substituents are alkyl groups having from 1 to 5 carbon atoms, and none, one or two of the substituents are aryl groups, as defined above,
an acyloxyalkyl group, in which the acyl part is an alkanoyl group having from 1 to 6 carbon atoms and the alkyl part has from 1 to 6 carbon atoms,
an alkoxycarbonyloxyalkyl group in which the alkoxy and alkyl parts each have from 1 to 6 carbon atoms,
a cycloalkoxycarbonyloxyalkyl groups in which the cycloalkyl part has from 3 to 7 ring carbon atoms and may be unsubstituted or substituted by at least one substituent selected from the group consisting of substituents C', defined above and alkyl part has from 1 to 6 carbon atoms,
a (5-alkyl or 5-aryl -2-oxo-1,3-dioxolen-4-yl)methyl group in which the alkyl part has from 1 to 4 carbon atoms and the aryl part is as defined above; or
the 3-phthalidyl group;

(10) R$^{41'}$ represents:
a hydrogen atom,
a substituted silyl group, in which the silyl group has 3 substituents selected from alkyl groups having from 1 to 6 carbon atoms and phenyl groups,
an aralkyl group, in which an alkyl group having from 1 to 4 carbon atoms is substituted by at least one aryl group, as defined above,
an aralkyloxycarbonyl group, in which the aralkyl part is as defined above,
an alkenyloxycarbonyl group in which the alkenyl part has from 2 to 6 carbon atoms and is unsubstituted or is substituted by at least one halogen atom,
an alkoxycarbonyl group which has from 2 to 7 carbon atoms,
a substituted silylalkoxycarbonyl group, in which the alkoxycarbonyl part and the substituted silyl part are as defined above,
an oxygen-containing heterocyclic group,
an alkoxyalkyl group in which the alkoxy and alkyl parts each have from 1 to 6 carbon atoms,
a substituted silylalkoxyalkyl group, in which the alkoxyalkyl part and the substituted silyl part are as defined above, or
an alkanoyl or haloalkanoyl group which has no more than 6 carbon atoms;

(11) R$^{42'}$ represents an alkyl group having from 1 to 4 carbon atoms, an alkoxy group having from 1 to 4 carbon atoms, a halogen atom, an aryl group as defined below or an aryloxy group in which the aryl part is as defined below;

(12) R$^{43'}$ represents a hydrogen atom, an alkyl group having from 1 to 4 carbon atoms, an alkoxy group having from 1 to 4 carbon atoms, a hydroxy group, a halogen atom, a cyano group, a nitro group or a group of formula —NR$^{8'}$R$^{9'}$, where R$^{8'}$ and R$^{9'}$ are independently selected from the group consisting of hydrogen atoms, amino-protecting groups, alkyl groups having from 1 to 4 carbon atoms and phenyl groups, or R$^{8'}$ and R$^{9'}$ together represent a group of formula —(CH$_2$)$_{q'}$—O$_{r'}$—(CH$_2$)$_{s'}$—, where q' and s are independently selected from the group consisting of 0 and integers of from 1 to 5 and r' is 0 or 1, provided that (q'+s') is an integer of at least 2; and

(13) $R^{45'}$ and $R^{46'}$ are independently selected from the group consisting of alkyl groups having from 1 to 4 carbon atoms and aryl groups as defined below, or $R^{45'}$ and $R^{46'}$ together represent a group of formula $-(CH_2)_{q'}-O_{r'}-(CH_2)_{s'}-$, where q' and s' are independently selected from the group consisting of 0 and integers of from 1 to 5 and r' is 0 or 1.

More preferred compounds of formula (IV') are those in which:

(14) $R^{1'}$ represents:

a hydrogen atom;

an alkyl group having from 1 to 4 carbon atoms, an aralkyl group which is an alkyl group having 1 or 2 carbon atoms and which is substituted by at least one phenyl group, a haloalkyl group having from 1 to 4 carbon atoms, a tri-substituted silylethyl group, in which all three or two of the substituents are alkyl groups having from 1 to 4 carbon atoms, and none or one of the substituents are phenyl groups, an acyloxyalkyl group, in which the acyl part is an alkanoyl group having from 2 to 5 carbon atoms and the alkyl part has 1 or 2 carbon atoms, an alkoxycarbonyloxyalkyl group in which the alkoxy and alkyl parts each have from 1 to 4 carbon atoms, a (5-methyl-2-oxo-1,3-dioxolen-4-yl)methyl group, or a 3-phthalidyl group;

said aryl groups are aromatic carbocyclic groups having from 6 to 10 ring carbon atoms and are unsubstituted or are substituted by at least one substituent selected from the group consisting of substituents $C^{a'}$, defined above;

(15) $R^{41'}$ represents:

a hydrogen atom, a substituted silyl group, in which the silyl group has 3 substituents selected from alkyl groups having from 1 to 4 carbon atoms and phenyl groups, an aralkyl group, in which an alkyl group having 1 or 2 carbon atoms is substituted by at least one aryl group, as defined above, an aralkyloxycarbonyl group, in which the aralkyl part is as defined above, an alkoxycarbonyl group which has from 2 to 5 carbon atoms, a tetrahydropyranyl group, an alkoxyalkyl group in which the alkoxy and alkyl parts each have from 1 to 4 carbon atoms, an alkanoyl or haloalkanoyl group which has from 2 to 5 carbon atoms;

(16) $R^{42'}$ represents an alkyl group having 1 or 2 carbon atoms, an alkoxy group having 1 or 2 carbon atoms, a halogen atom, a phenyl group or a phenoxy group;

(17) $R^{43'}$ represents a hydrogen atom, an alkyl group having 1 or 2 carbon atoms, an alkoxy group having 1 or 2 carbon atoms, a hydroxy group, a halogen atom, a cyano group, a nitro group or a group of formula $-NR^{8'}R^{9'}$, where $R^{8'}$ and $R^{9'}$ are independently selected from the group consisting of hydrogen atoms, amino-protecting groups, alkyl groups having 1 or 2 carbon atoms and phenyl groups, or $R^{8'}$ and $R^{9'}$ together represent a group of formula $-(CH_2)_{q'}-O_{4'}-(CH_2)_{s'}-$, where q' and s' are independently selected from the group consisting of 0 and integers of from 1 to 5 and r' is 0 or 1, provided that (q'+s') is an integer of at least 2; and

(18) $R^{45'}$ and $R^{46'}$ are independently selected from the group consisting of alkyl groups having 1 or 2 carbon atoms and phenyl groups, or $R^{45'}$ and $R^{46'}$ together represent a group of formula $-(CH_2)_{q'}-O_{r'}-(CH_2)_{s'}-$, where q' and s' are independently selected from the group consisting of 0 and integers of from 1 to 5 and r' is 0 or 1.

Specific examples of compounds of formulae (I') and (II') are given in the following Tables 4 and 5, and specific examples of compounds of formula (IV') of the present invention are shown in formulae (I-3') and (I-4'), in which the substituents are as shown in the respective one of the following Tables 6 and 7, that is Table 6 relates to formula (I-3') and Table 7 relates to formula (I-4'). Preferred compounds of the present invention are those having the configuration shown in formulae (I-3a') and (Io4a'). Certain of the groups represented by $R^{4'}$ are shown by the following formulae (1-1') to (1-30').

(1-1')

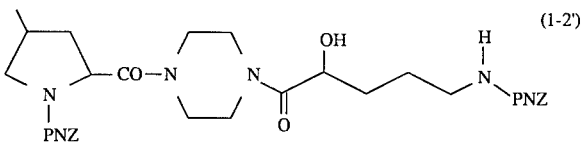

(1-2')

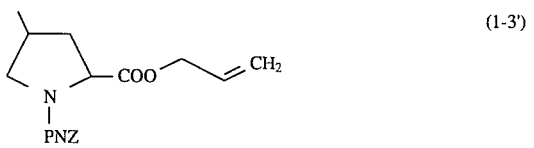

(1-3')

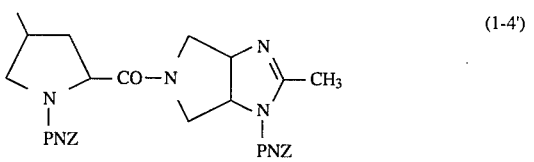

(1-4')

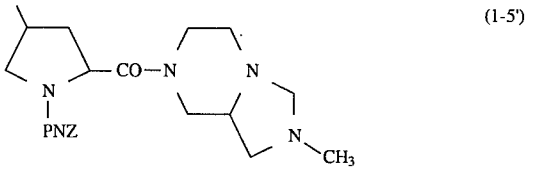

(1-5')

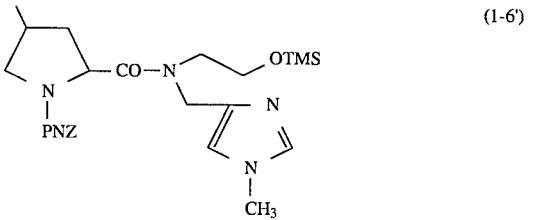

(1-6')

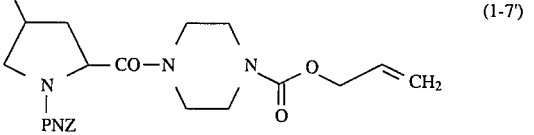

(1-7')

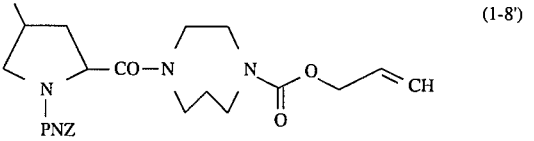

(1-8')

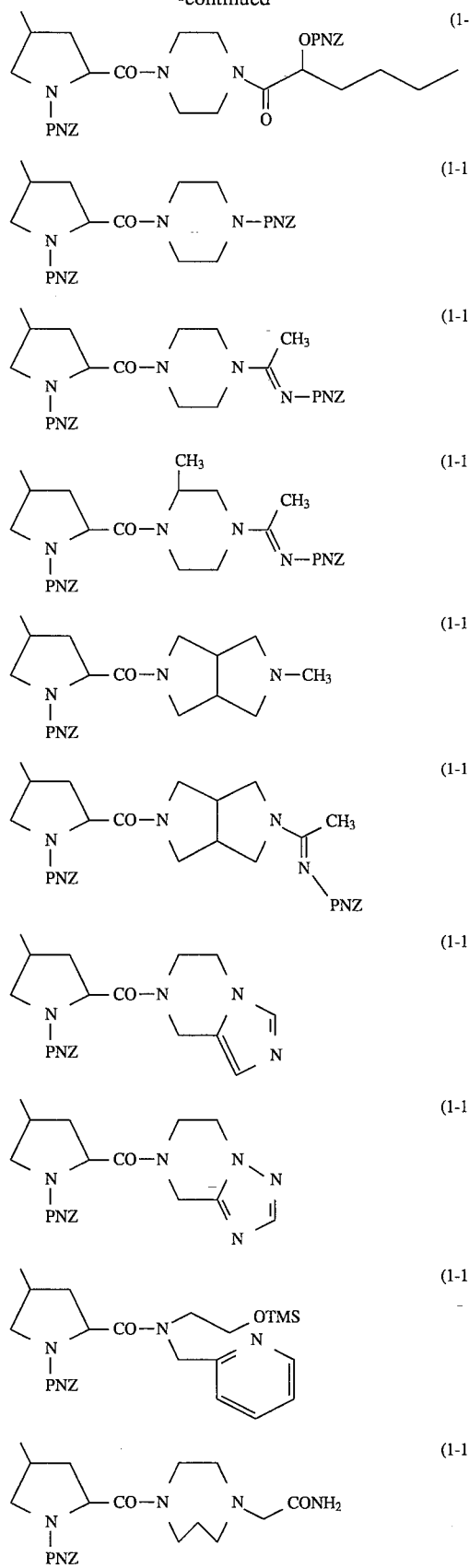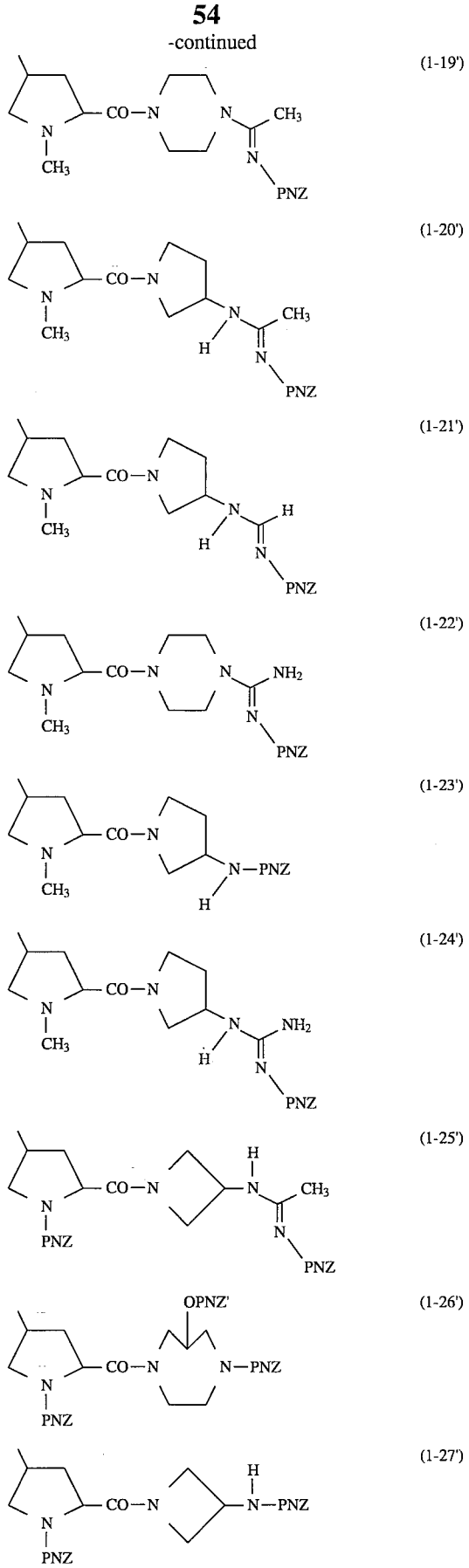

 (1-28')

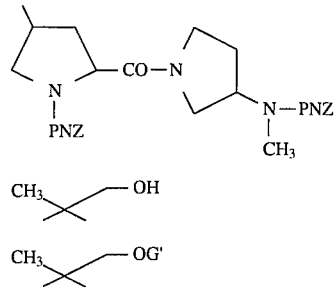

(1-29')

(1-30')

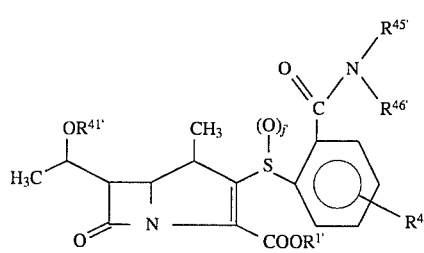 (I-3')

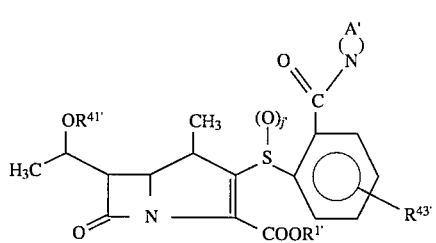 (I-4')

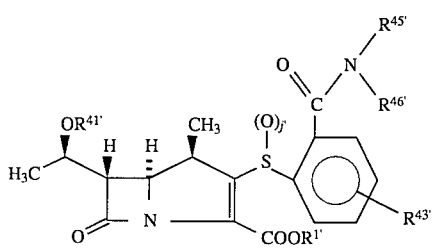 (I-3a')

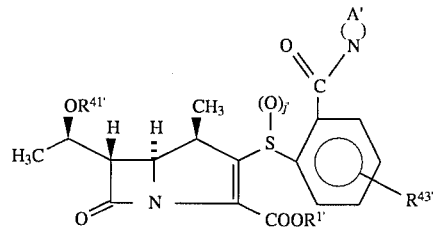 (I-4a')

In the Tables 4 to 7, the following abbreviations are used:

| | |
|---|---|
| Ac | acetyl |
| All | allyl |
| Azp | perhydroazepinyl |
| Bu | butyl |
| iBu | isobutyl |
| Bz | benzyl |
| Et | ethyl |
| Imid | imidazolyl |
| Ithiz | isothiazolyl |
| Me | methyl |
| Ph | phenyl |
| Piz | piperazinyl |
| PNB | 4-nitrobenzyl |
| PNZ | 4-nitrobenzyloxycarbonyl |
| Pr | propyl |
| iPr | isopropyl |
| Pyr | pyridyl |
| Pyrd | pyrrolidinyl |
| Pyrz | pyrazolidinyl |
| TBS | t-butyldimethylsilyl |
| Tht | 1-oxotetrahydrothien-3-yl |
| TMS | trimethylsilyl |
| G | hydrogen, TMS, TBS, or PNZ |

TABLE 4

| Cpd. No. | $R^{1'}$ | $R^{2'}$ | $R^{3'}$ | $R^{4'}$ | $X'$ |
|---|---|---|---|---|---|
| 1-1' | PNB | H | 1-(G—O)Et | 1-PNZ-5-Me$_2$NCO-3-Pyrd | >CH(CH$_3$) |
| 1-2' | PNB | H | 1-(G—O)Et | —CH$_2$CH$_2$NH.PNZ | >CH(CH$_3$) |
| 1-3' | PNB | H | 1-(G—O)Et | 4-NO$_2$Bz | >CH(CH$_3$) |
| 1-4' | PNB | H | 1-(G—O)Et | Ph | >CH(CH$_3$) |
| 1-5' | PNB | H | 1-(G—O)Et | 1-{1-(PNZ.N═)Et]-3-Pyrd | >CH(CH$_3$) |
| 1-6' | PNB | H | 1-(G—O)Et | 2-[1-Azp.CO]Ph | >CH(CH$_3$) |
| 1-7' | PNB | H | 1-(G—O)Et | 1-PNZ-5-[4-(2-PNZ.OEt)PizCO]Pyrd | >CH(CH$_3$) |
| 1-8' | PNB | H | 1-(G—O)Et | —CH$_2$—C(NMe$_2$)═N.PNZ | >CH(CH$_3$) |
| 1-9' | PNB | H | 1-(G—O)Et | 1,2-di(PNZ)-4-Pyrz | >CH(CH$_3$) |
| 1-10' | PNB | H | 1-(G—O)Et | formula (1-1') | >CH(CH$_3$) |
| 1-11' | PNB | H | 1-(G—O)Et | formula (1-2') | >CH(CH$_3$) |
| 1-12' | PNB | H | 1-(G—O)Et | formula (1-3') | >CH(CH$_3$) |
| 1-13' | PNB | H | 1-(G—O)Et | 1-PNZ-5-PhSCO-3-Pyrd | >CH(CH$_3$) |
| 1-14' | PNB | H | 1-(G—O)Et | 5-oxo-2-Pyrd | >CH(CH$_3$) |
| 1-15' | PNB | H | 1-(G—O)Et | 5-oxo-3-Pyrid | >CH(CH$_3$) |
| 1-16' | PNB | H | 1-(G—O)Et | 2-oxo-3-Pip | >CH(CH$_3$) |
| 1-17' | PNB | H | 1-(G—O)Et | formula (1-4') | >CH(CH$_3$) |
| 1-18' | PNB | H | 1-(G—O)Et | formula (1-5') | >CH(CH$_3$) |
| 1-19' | PNB | H | 1-(G—O)Et | formula (1-6') | >CH(CH$_3$) |
| 1-20' | PNB | H | 1-(G—O)Et | formula (1-7') | >CH(CH$_3$) |
| 1-21' | PNB | H | 1-(G—O)Et | formula (1-8') | >CH(CH$_3$) |
| 1-22' | PNB | H | 1-(G—O)Et | 1-PNZ-5-[4-(2-HOEt)-1-PizCO]-3-Pyrd | >CH(CH$_3$) |
| 1-23' | PNB | H | 1-(G—O)Et | formula (1-9') | >CH(CH$_3$) |
| 1-24' | PNB | H | 1-(G—O)Et | formula (1-10') | >CH(CH$_3$) |
| 1-25' | PNB | H | 1-(G—O)Et | formula (1-11') | >CH(CH$_3$) |

TABLE 4-continued

| Cpd. No. | R¹' | R²' | R³' | R⁴' | X' |
|---|---|---|---|---|---|
| 1-26' | PNB | H | 1-(G—O)Et | formula (1-12') | >CH(CH₃) |
| 1-27' | PNB | H | 1-(G—O)Et | formula (1-13') | >CH(CH₃) |
| 1-28' | PNB | H | 1-(G—O)Et | formula (1-14') | >CH(CH₃) |
| 1-29' | PNB | H | 1-(G—O)Et | formula (1-15') | >CH(CH₃) |
| 1-30' | PNB | H | 1-(G—O)Et | formula (1-16') | >CH(CH₃) |
| 1-31' | PNB | H | 1-(G—O)Et | formula (1-17') | >CH(CH₃) |
| 1-32' | PNB | H | 1-(G—O)Et | formula (1-18') | >CH(CH₃) |
| 1-33' | PNB | H | 1-(G—O)Et | formula (1-19') | >CH(CH₃) |
| 1-34' | PNB | H | 1-(G—O)Et | formula (1-20') | >CH(CH₃) |
| 1-35' | PNB | H | 1-(G—O)Et | formula (1-21') | >CH(CH₃) |
| 1-36' | PNB | H | 1-(G—O)Et | formula (1-22') | >CH(CH₃) |
| 1-37' | PNB | H | 1-(G—O)Et | formula (1-23') | >CH(CH₃) |
| 1-38' | PNB | H | 1-(G—O)Et | formula (1-24') | >CH(CH₃) |
| 1-39' | PNB | H | 1-(G—O)Et | formula (1-25') | >CH(CH₃) |
| 1-40' | PNB | H | 1-(G—O)Et | formula (1-26') | >CH(CH₃) |
| 1-41' | PNB | H | 1-(G—O)Et | formula (1-27') | >CH(CH₃) |
| 1-42' | PNB | H | 1-(G—O)Et | formula (1-28') | >CH(CH₃) |
| 1-43' | PNB | H | 1-(G—O)Et | 1-[1-(PNZ.N=Et]-3-Pyrd | >CH₂ |
| 1-44' | PNB | H | 1-(G—O)Et | 2-(PNZ—N=CH—NH)Et | >CH₂ |
| 1-45' | PNB | H | 1-(G—O)Et | —CH₂CH₂NH.PNZ | >CH₂ |
| 1-46' | PNB | H | 1-(G—O)Et | 1-PNZ-5-Me₂NCO-3-Pyrd | >CH₂ |
| 1-47' | All | H | 1-(G—O)Et | 1-PNZ-5-Me₂NCO-3-Pyrd | >CH(CH₃) |
| 1-48' | All | H | 1-(G—O)Et | formula (1-11) | >CH(CH₃) |
| 1-49' | All | H | 1-(G—O)Et | 2-oxo-3-Pip | >CH(CH₃) |
| 1-50' | All | H | 1-(G—O)Et | 5-oxo-3-Pyrd | >CH(CH₃) |
| 1-51' | PNB | formula (1-29') | | 1-[1-(PNZ.N=)Et]-3-Pyrd | >CH₂ |
| 1-52' | PNB | H | Et | 1-[1-(PNZ.N=)Et]-3-Pyrd | >CH₂ |
| 1-53' | PNB | H | 1-HO-1-MeEt | 1-[1-(PNZ.N=)Et]-3-Pyrd | >CH₂ |
| 1-54' | PNB | H | 1-(G—O)Et | 1-[1-(PNZ.N=)Et]-3-Pyrd | >S |
| 1-55' | PNB | H | 1-(G—O)Et | —CH₂CH₂NH.PNZ | >S |
| 1-56' | PNB | H | 1-(G—O)Et | 1-PNZ-5-Me₂NCO-3-Pyrd | >S |
| 1-57' | PNB | H | 1-(G—O)Et | Tht | >S |
| 1-58' | PNB | H | 1-(G—O)Et | Et | >CH(CH₃) |

TABLE 5

| Cpd. No. | k' | R¹' | R²' | R³' | R⁴' | X' |
|---|---|---|---|---|---|---|
| 2-1' | 1 | PNB | H | 1-(G—O)Et | 2-(Et₂NCO)Ph | >CH(CH₃) |
| 2-2' | 2 | PNB | H | 1-(G—O)Et | 2-(Et₂NCO)Ph | >CH(CH₃) |
| 2-3' | 1 | PNB | H | 1-(G—O)Et | 2-[1-Azp.CO)Ph | >CH(CH₃) |
| 2-4' | 2 | PNB | H | 1-(G—O)Et | 2-[1-Azp.CO)Ph | >CH(CH₃) |
| 2-5' | 1 | PNB | H | 1-(G—O)Et | 2-PyrMe | >CH(CH₃) |
| 2-6' | 2 | PNB | H | 1-(G—O)Et | 2-PyrMe | >CH(CH₃) |
| 2-7' | 1 | PNB | H | 1-(G—O)Et | (3-Me-2-Pyr)Me | >CH(CH₃) |
| 2-8' | 2 | PNB | H | 1-(G—O)Et | (3-Me-2-Pyr)Me | >CH(CH₃) |
| 2-9' | 1 | PNB | H | 1-(G—O)Et | (1-Me-2-Imid)Me | >CH(CH₃) |
| 2-10' | 2 | PNB | H | 1-(G—O)Et | (1-Me-2-Imid)Me | >CH(CH₃) |
| 2-11' | 1 | PNB | H | 1-(G—O)Et | (3-Ithiz)Me | >CH(CH₃) |
| 2-12' | 2 | PNB | H | 1-(G—O)Et | (3-Ithiz)Me | >CH(CH₃) |
| 2-13' | 1 | PNB | H | 1-(G—O)Et | 2-Pyr | >CH(CH₃) |
| 2-14' | 2 | PNB | H | 1-(G—O)Et | 2-Pyr | >CH(CH₃) |
| 2-15' | 1 | PNB | H | 1-(G—O)Et | —CH₂CH₂NH.PNZ | >CH(CH₃) |
| 2-16' | 2 | PNB | H | 1-(G—O)Et | —CH₂CH₂NH.PNZ | >CH(CH₃) |
| 2-17' | 1 | PNB | H | 1-(G—O)Et | Ph | >CH(CH₃) |
| 2-18' | 2 | PNB | H | 1-(G—O)Et | Ph | >CH(CH₃) |
| 2-19' | 1 | PNB | H | 1-(G—O)Et | Et | >CH(CH₃) |
| 2-20' | 2 | PNB | H | 1-(G—O)Et | Et | >CH(CH₃) |
| 2-21' | 1 | PNB | H | 1-(G—O)Et | Bz | >CH(CH₃) |
| 2-22' | 2 | PNB | H | 1-(G—O)Et | Bz | >CH(CH₃) |
| 2-23' | 1 | PNB | H | 1-(G—O)Et | —CH₂CH₂NH.Ac | >CH₂ |
| 2-24' | 1 | PNB | H | 1-(G—O)Et | —CH₂CH₂NH.PNZ | >CH₂ |
| 2-25' | 1 | PNB | H | 1-(G—O)Et | —CH₂CH₂OH | >CH₂ |
| 2-26' | 1 | PNB | H | 1-(G—O)Et | —CH=CH—NH.Ac | >CH₂ |
| 2-27' | 1 | PNB | formula (1-30) | | —CH₂CH₂NH.Ac | >CH₂ |
| 2-28' | 1 | PNB | H | 1-HO-1-MeEt | —CH₂CH₂NH.Ac | >CH₂ |
| 2-29' | 1 | PNB | H | Et | —CH₂CH₂NH.Ac | >CH₂ |
| 2-30' | 1 | PNB | H | 1-(G—O)Et | Ph | >CH₂ |
| 2-31' | 1 | PNB | H | 1-(G—O)Et | Et | >CH₂ |
| 2-32' | 1 | PNB | H | 1-(G—O)Et | Bz | >CH₂ |
| 2-33' | 1 | PNB | H | 1-(G—O)Et | Et | >S |
| 2-34' | 1 | PNB | H | 1-(G—O)Et | —CH₂CH₂NH.PNZ | >S |
| 2-35' | 1 | All | H | 1-(G—O)Et | 2-(Et₂NCO)Ph | >CH(CH₃) |

TABLE 5-continued

| Cpd. No. | k' | R¹' | R²' | R³' | R⁴' | X' |
|---|---|---|---|---|---|---|
| 2-36' | 2 | All | H | 1-(G—O)Et | 2-(Et₂NCO)Ph | >CH(CH₃) |
| 2-37' | 1 | All | H | 1-(G—O)Et | (3-Me-2-Pyr)Me | >CH(CH₃) |
| 2-38' | 2 | All | H | 1-(G—O)Et | (3-Me-2-Pyr)Me | >CH(CH₃) |
| 2-39' | 1 | All | H | 1-(G—O)Et | (2-Pyr)Me | >CH(CH₃) |
| 2-40' | 2 | All | H | 1-(G—O)Et | (2-Pyr)Me | >CH(CH₃) |
| 2-41' | 1 | All | H | 1-(G—O)Et | 2-Pyr | >CH(CH₃) |
| 2-42' | 2 | All | H | 1-(G—O)Et | 2-Pyr | >CH(CH₃) |
| 2-43' | 1 | All | H | 1-(G—O)Et | Ph | >CH(CH₃) |
| 2-44' | 2 | All | H | 1-(G—O)Et | Ph | >CH(CH₃) |
| 2-45' | 1 | All | H | 1-(G—O)Et | Et | >CH(CH₃) |
| 2-46' | 2 | All | H | 1-(G—O)Et | Et | >CH(CH₃) |
| 2-47' | 1 | All | H | 1-(G—O)Et | Bz | >CH(CH₃) |
| 2-48' | 2 | All | H | 1-(G—O)Et | Bz | >CH(CH₃) |

TABLE 6

| Cpd. No. | R⁴¹' | R⁴³' | R¹' | R⁴⁵' | R⁴⁶' | i' |
|---|---|---|---|---|---|---|
| 3-1' | TBS | H | PNB | Me | Me | 0 |
| 3-2' | TBS | H | PNB | Me | Me | 1 |
| 3-3' | TBS | H | PNB | Me | Me | 2 |
| 3-4' | TBS | H | PNB | Et | Et | 0 |
| 3-5' | TBS | H | PNB | Et | Et | 1 |
| 3-6' | TBS | H | PNB | Et | Et | 2 |
| 3-7' | TBS | H | PNB | Pr | Pr | 0 |
| 3-8' | TBS | H | PNB | Pr | Pr | 1 |
| 3-9' | TBS | H | PNB | Pr | Pr | 2 |
| 3-10' | TBS | H | PNB | iPr | Pr | 0 |
| 3-11' | TBS | H | PNB | iPr | Pr | 1 |
| 3-12' | TBS | H | PNB | iPr | Pr | 2 |
| 3-13' | TBS | H | PNB | Me | Et | 0 |
| 3-14' | TBS | H | PNB | Me | Et | 1 |
| 3-15' | TBS | H | PNB | Me | Et | 2 |
| 3-16' | TBS | H | PNB | iBu | iBu | 0 |
| 3-17' | TBS | H | PNB | iBu | iBu | 1 |
| 3-18' | TBS | H | PNB | iBu | iBu | 2 |
| 3-19' | TBS | H | PNB | Bu | Bu | 0 |
| 3-20' | TBS | H | PNB | Bu | Bu | 1 |
| 3-21' | TBS | H | PNB | Bu | Bu | 2 |
| 3-22' | TBS | H | PNB | Et | Pr | 0 |
| 3-23' | TBS | H | PNB | Et | Pr | 1 |
| 3-24' | TBS | H | PNB | Et | Pr | 2 |
| 3-25' | TBS | H | PNB | Me | Bu | 0 |
| 3-26' | TBS | H | PNB | Me | Bu | 1 |
| 3-27' | TBS | H | PNB | Me | Bu | 2 |
| 3-28' | TMS | H | PNB | Me | Me | 0 |
| 3-29' | TMS | H | PNB | Me | Me | 1 |
| 3-30' | TMS | H | PNB | Me | Me | 2 |
| 3-31' | TMS | H | PNB | Et | Et | 0 |
| 3-32' | TMS | H | PNB | Et | Et | 1 |
| 3-33' | TMS | H | PNB | Et | Et | 2 |
| 3-34' | TMS | H | PNB | Pr | Pr | 0 |
| 3-35' | TMS | H | PNB | Pr | Pr | 1 |
| 3-36' | TMS | H | PNB | Pr | Pr | 2 |
| 3-37' | TMS | H | PNB | iBu | iBu | 0 |
| 3-38' | TMS | H | PNB | iBu | iBu | 1 |
| 3-39' | TMS | H | PNB | iBu | iBu | 2 |
| 3-40' | TMS | H | PNB | Bu | Bu | 0 |
| 3-41' | TMS | H | PNB | Bu | Bu | 1 |
| 3-42' | TMS | H | PNB | Bu | Bu | 2 |
| 3-43' | TMS | H | PNB | iPr | Et | 0 |
| 3-44' | TMS | H | PNB | iPr | Et | 1 |
| 3-45' | TMS | H | PNB | iPr | Et | 2 |
| 3-46' | H | H | PNB | Me | Me | 0 |
| 3-47' | H | H | PNB | Me | Me | 1 |
| 3-48' | H | H | PNB | Me | Me | 2 |
| 3-49' | H | H | PNB | Et | Et | 0 |
| 3-50' | H | H | PNB | Et | Et | 1 |
| 3-51' | H | H | PNB | Et | Et | 2 |
| 3-52' | H | H | PNB | Pr | Pr | 0 |
| 3-53' | H | H | PNB | Pr | Pr | 1 |
| 3-54' | H | H | PNB | Pr | Pr | 2 |
| 3-55' | H | H | PNB | iBu | iBu | 0 |
| 3-56' | H | H | PNB | iBu | iBu | 1 |
| 3-57' | H | H | PNB | iBu | iBu | 2 |
| 3-58' | H | H | PNB | Bu | Bu | 0 |
| 3-59' | H | H | PNB | Bu | Bu | 1 |
| 3-60' | H | H | PNB | Bu | Bu | 2 |
| 3-61' | H | H | PNB | iPr | Et | 0 |
| 3-62' | H | H | PNB | iPr | Et | 1 |
| 3-63' | H | H | PNB | iPr | Et | 2 |
| 3-64' | H | H | All | Me | Me | 0 |
| 3-65' | H | H | All | Me | Me | 1 |
| 3-66' | H | H | All | Me | Me | 2 |
| 3-67' | H | H | All | Et | Et | 0 |
| 3-68' | H | H | All | Et | Et | 1 |
| 3-69' | H | H | All | Et | Et | 2 |
| 3-70' | H | H | All | Pr | Pr | 0 |
| 3-71' | H | H | All | Pr | Pr | 1 |
| 3-72' | H | H | All | Pr | Pr | 2 |
| 3-73' | H | H | All | iBu | iBu | 0 |
| 3-74' | H | H | All | iBu | iBu | 1 |
| 3-75' | H | H | All | iBu | iBu | 2 |
| 3-76' | H | H | All | Bu | Bu | 0 |
| 3-77' | H | H | All | Bu | Bu | 1 |
| 3-78' | H | H | All | Bu | Bu | 2 |
| 3-79' | TMS | H | All | Me | Me | 0 |
| 3-80' | TMS | H | All | Me | Me | 1 |
| 3-81' | TMS | H | All | Me | Me | 2 |
| 3-82' | TMS | H | All | Et | Et | 0 |
| 3-83' | TMS | H | All | Et | Et | 1 |
| 3-84' | TMS | H | All | Et | Et | 2 |
| 3-85' | TMS | H | All | Pr | Pr | 0 |
| 3-86' | TMS | H | All | Pr | Pr | 1 |
| 3-87' | TMS | H | All | Pr | Pr | 2 |
| 3-88' | TMS | H | All | iBu | iBu | 0 |
| 3-89' | TMS | H | All | iBu | iBu | 1 |
| 3-90' | TMS | H | All | iBu | iBu | 2 |
| 3-91' | TMS | H | All | Bu | Bu | 0 |
| 3-92' | TMS | H | All | Bu | Bu | 1 |
| 3-93' | TMS | H | All | Bu | Bu | 2 |
| 3-94' | TBS | H | All | Me | Me | 0 |
| 3-95' | TBS | H | All | Me | Me | 1 |
| 3-96' | TBS | H | All | Me | Me | 2 |
| 3-97' | TBS | H | All | Et | Et | 0 |
| 3-98' | TBS | H | All | Et | Et | 1 |
| 3-99' | TBS | H | All | Et | Et | 2 |
| 3-100' | TBS | H | All | Pr | Pr | 0 |
| 3-101' | TBS | H | All | Pr | Pr | 1 |
| 3-102' | TBS | H | All | Pr | Pr | 2 |
| 3-103' | TBS | H | All | iBu | iBu | 0 |
| 3-104' | TBS | H | All | iBu | iBu | 1 |
| 3-105' | TBS | H | All | iBu | iBu | 2 |
| 3-106' | TBS | H | All | Bu | Bu | 0 |
| 3-107' | TBS | H | All | Bu | Bu | 1 |
| 3-108' | TBS | H | All | Bu | Bu | 2 |

TABLE 6-continued

| Cpd. No. | R⁴¹' | R⁴³' | R¹' | R⁴⁵' | R⁴⁶' | i' |
|---|---|---|---|---|---|---|
| 3-109' | TBS | H | All | Me | Et | 0 |
| 3-110' | TBS | H | All | Me | Et | 1 |
| 3-111' | TBS | H | All | Me | Et | 2 |
| 3-112' | TMS | H | All | Me | Et | 0 |
| 3-113' | TMS | H | All | Me | Et | 1 |
| 3-114' | TMS | H | All | Me | Et | 2 |
| 3-115' | H | H | All | Me | Et | 0 |
| 3-116' | H | H | All | Me | Et | 1 |
| 3-117' | H | H | All | Me | Et | 2 |
| 3-118' | H | H | All | Et | Pr | 0 |
| 3-119' | H | H | All | Et | Pr | 1 |
| 3-120' | H | H | All | Et | Pr | 2 |
| 3-121' | TMS | H | All | Et | Pr | 0 |
| 3-122' | TMS | H | All | Et | Pr | 1 |
| 3-123' | TMS | H | All | Et | Pr | 2 |
| 3-124' | TBS | H | All | Et | Pr | 0 |
| 3-125' | TBS | H | All | Et | Pr | 1 |
| 3-126' | TBS | H | All | Et | Pr | 2 |
| 3-127' | TMS | H | PNB | Me | Et | 0 |
| 3-128' | TMS | H | PNB | Me | Et | 1 |
| 3-129' | TMS | H | PNB | Me | Et | 2 |
| 3-130' | H | H | PNB | Me | Et | 0 |
| 3-131' | H | H | PNB | Me | Et | 1 |
| 3-132' | H | H | PNB | Me | Et | 2 |
| 3-133' | H | H | PNB | Et | Pr | 0 |
| 3-134' | H | H | PNB | Et | Pr | 1 |
| 3-135' | H | H | PNB | Et | Pr | 2 |
| 3-136' | TMS | H | PNB | Et | Pr | 0 |
| 3-137' | TMS | H | PNB | Et | Pr | 1 |
| 3-138' | TMS | H | PNB | Et | Pr | 2 |
| 3-139' | PNZ | H | PNB | Et | Et | 0 |
| 3-140' | PNZ | H | PNB | Et | Et | 1 |
| 3-141' | PNZ | H | PNB | Et | Et | 2 |
| 3-142' | PNZ | H | PNB | Me | Me | 0 |
| 3-143' | PNZ | H | PNB | Me | Me | 1 |
| 3-144' | PNZ | H | PNB | Me | Me | 2 |
| 3-145' | PNZ | H | PNB | iBu | iBu | 0 |
| 3-146' | PNZ | H | PNB | iBu | iBu | 1 |
| 3-147' | PNZ | H | PNB | iBu | iBu | 2 |
| 3-148' | PNZ | H | PNB | Bu | Bu | 0 |
| 3-149' | PNZ | H | PNB | Bu | Bu | 1 |
| 3-150' | PNZ | H | PNB | Bu | Bu | 2 |
| 3-151' | PNZ | H | PNB | Ph | Pr | 0 |
| 3-152' | PNZ | H | PNB | Ph | Pr | 1 |
| 3-153' | PNZ | H | PNB | Ph | Pr | 2 |
| 3-154' | PNZ | H | All | Et | Et | 0 |
| 3-155' | PNZ | H | All | Et | Et | 1 |
| 3-156' | PNZ | H | All | Et | Et | 2 |
| 3-157' | TBS | H | PNB | Me | Ph | 0 |
| 3-158' | TBS | H | PNB | Me | Ph | 1 |
| 3-159' | TBS | H | PNB | Me | Ph | 2 |
| 3-160' | TMS | H | PNB | Me | Ph | 0 |
| 3-161' | TMS | H | PNB | Me | Ph | 1 |
| 3-162' | TMS | H | PNB | Me | Ph | 2 |
| 3-163' | H | H | PNB | Me | Ph | 0 |
| 3-164' | H | H | PNB | Me | Ph | 1 |
| 3-165' | H | H | PNB | Me | Ph | 2 |
| 3-166' | TBS | H | PNB | Et | Ph | 0 |
| 3-167' | TBS | H | PNB | Et | Ph | 1 |
| 3-168' | TBS | H | PNB | Et | Ph | 2 |
| 3-169' | TMS | H | PNB | Et | Ph | 0 |
| 3-170' | TMS | H | PNB | Et | Ph | 1 |
| 3-171' | TMS | H | PNB | Et | Ph | 2 |
| 3-172' | H | H | PNB | Et | Ph | 0 |
| 3-173' | H | H | PNB | Et | Ph | 1 |
| 3-174' | H | H | PNB | Et | Ph | 2 |
| 3-175' | TBS | 6-Me | PNB | Et | Et | 1 |
| 3-176' | TBS | 5-Me | PNB | Et | Et | 1 |
| 3-177' | TBS | 4-Me | PNB | Et | Et | 1 |
| 3-178' | TBS | 5-NO₂ | PNB | Et | Et | 1 |
| 3-179' | TBS | 5-Cl | PNB | Et | Et | 1 |
| 3-180' | TBS | 4-OMe | PNB | Et | Et | 1 |
| 3-181' | TBS | 6-Cl | PNB | Et | Et | 1 |
| 3-182' | TBS | 3-Me | PNB | Et | Et | 1 |

TABLE 7

| Cpd. No. | R⁴¹' | R⁴³' | R¹' | A' | i' |
|---|---|---|---|---|---|
| 4-1' | TBS | H | PNB | —(CH₂)₂— | 0 |
| 4-2' | TBS | H | PNB | —(CH₂)₃— | 0 |
| 4-3' | TBS | H | PNB | —(CH₂)₄— | 0 |
| 4-4' | TBS | H | PNB | —(CH₂)₅— | 0 |
| 4-5' | TBS | H | PNB | —(CH₂)₆— | 0 |
| 4-6' | TBS | H | PNB | —(CH₂)₇— | 0 |
| 4-7' | TBS | H | PNB | —(CH₂)₂O(CH₂)₂— | 0 |
| 4-8' | TBS | H | PNB | —(CH₂)₂— | 1 |
| 4-9' | TBS | H | PNB | —(CH₂)₃— | 1 |
| 4-10' | TBS | H | PNB | —(CH₂)₄— | 1 |
| 4-11' | TBS | H | PNB | —(CH₂)₅— | 1 |
| 4-12' | TBS | H | PNB | —(CH₂)₆— | 1 |
| 4-13' | TBS | H | PNB | —(CH₂)₇— | 1 |
| 4-14' | TBS | H | PNB | —(CH₂)₂O(CH₂)₂— | 1 |
| 4-15' | TBS | H | PNB | —(CH₂)₂— | 2 |
| 4-16' | TBS | H | PNB | —(CH₂)₃— | 2 |
| 4-17' | TBS | H | PNB | —(CH₂)₄— | 2 |
| 4-18' | TBS | H | PNB | —(CH₂)₅— | 2 |
| 4-19' | TBS | H | PNB | —(CH₂)₆— | 2 |
| 4-20' | TBS | H | PNB | —(CH₂)₇— | 2 |
| 4-21' | TBS | H | PNB | —(CH₂)₂O(CH₂)₂— | 2 |
| 4-22' | TMS | H | PNB | —(CH₂)₂— | 0 |
| 4-23' | TMS | H | PNB | —(CH₂)₃— | 0 |
| 4-24' | TMS | H | PNB | —(CH₂)₄— | 0 |
| 4-25' | TMS | H | PNB | —(CH₂)₅— | 0 |
| 4-26' | TMS | H | PNB | —(CH₂)₆— | 0 |
| 4-27' | TMS | H | PNB | —(CH₂)₇— | 0 |
| 4-28' | TMS | H | PNB | —(CH₂)₂O(CH₂)₂— | 0 |
| 4-29' | TMS | H | PNB | —(CH₂)₂— | 1 |
| 4-30' | TMS | H | PNB | —(CH₂)₃— | 1 |
| 4-31' | TMS | H | PNB | —(CH₂)₄— | 1 |
| 4-32' | TMS | H | PNB | —(CH₂)₅— | 1 |
| 4-33' | TMS | H | PNB | —(CH₂)₆— | 1 |
| 4-34' | TMS | H | PNB | —(CH₂)₇— | 1 |
| 4-35' | TMS | H | PNB | —(CH₂)₂O(CH₂)₂— | 1 |
| 4-36' | TMS | H | PNB | —(CH₂)₂— | 2 |
| 4-37' | TMS | H | PNB | —(CH₂)₃— | 2 |
| 4-38' | TMS | H | PNB | —(CH₂)₄— | 2 |
| 4-39' | TMS | H | PNB | —(CH₂)₅— | 2 |
| 4-40' | TMS | H | PNB | —(CH₂)₆— | 2 |
| 4-41' | TMS | H | PNB | —(CH₂)₇— | 2 |
| 4-42' | TMS | H | PNB | —(CH₂)₂O(CH₂)₂— | 2 |
| 4-43' | H | H | PNB | —(CH₂)₂— | 0 |
| 4-44' | H | H | PNB | —(CH₂)₃— | 0 |
| 4-45' | H | H | PNB | —(CH₂)₄— | 0 |
| 4-46' | H | H | PNB | —(CH₂)₅— | 0 |
| 4-47' | H | H | PNB | —(CH₂)₆— | 0 |
| 4-48' | H | H | PNB | —(CH₂)₇— | 0 |
| 4-49' | H | H | PNB | —(CH₂)₂O(CH₂)₂— | 0 |
| 4-50' | H | H | PNB | —(CH₂)₂— | 1 |
| 4-51' | H | H | PNB | —(CH₂)₃— | 1 |
| 4-52' | H | H | PNB | —(CH₂)₄— | 1 |
| 4-53' | H | H | PNB | —(CH₂)₅— | 1 |
| 4-54' | H | H | PNB | —(CH₂)₆— | 1 |
| 4-55' | H | H | PNB | —(CH₂)₇— | 1 |
| 4-56' | H | H | PNB | —(CH₂)₂O(CH₂)₂— | 1 |
| 4-57' | H | H | PNB | —(CH₂)₂— | 2 |
| 4-58' | H | H | PNB | —(CH₂)₃— | 2 |
| 4-59' | H | H | PNB | —(CH₂)₄— | 2 |
| 4-60' | H | H | PNB | —(CH₂)₅— | 2 |
| 4-61' | H | H | PNB | —(CH₂)₆— | 2 |
| 4-62' | H | H | PNB | —(CH₂)₇— | 2 |
| 4-63' | H | H | PNB | —(CH₂)₂O(CH₂)₂— | 2 |
| 4-64' | H | H | All | —(CH₂)₄— | 0 |
| 4-65' | H | H | All | —(CH₂)₅— | 0 |
| 4-66' | H | H | All | —(CH₂)₆— | 0 |
| 4-67' | H | H | All | —(CH₂)₆— | 1 |
| 4-68' | H | H | All | —(CH₂)₅— | 1 |
| 4-69' | H | H | All | —(CH₂)₄— | 1 |
| 4-70' | H | H | All | —(CH₂)₄— | 2 |
| 4-71' | H | H | All | —(CH₂)₅— | 2 |
| 4-72' | H | H | All | —(CH₂)₆— | 2 |
| 4-73' | TMS | H | All | —(CH₂)₆— | 0 |
| 4-74' | TMS | H | All | —(CH₂)₅— | 0 |
| 4-75' | TMS | H | All | —(CH₂)₄— | 0 |
| 4-76' | TMS | H | All | —(CH₂)₄— | 1 |

TABLE 7-continued

| Cpd. No. | R⁴¹' | R⁴³' | R¹' | A' | i' |
|---|---|---|---|---|---|
| 4-77' | TMS | H | All | —(CH₂)₅— | 1 |
| 4-78' | TMS | H | All | —(CH₂)₆— | 1 |
| 4-79' | TMS | H | All | —(CH₂)₆— | 2 |
| 4-80' | TMS | H | All | —(CH₂)₅— | 2 |
| 4-81' | TMS | H | All | —(CH₂)₄— | 2 |
| 4-82' | TBS | H | All | —(CH₂)₄— | 0 |
| 4-83' | TBS | H | All | —(CH₂)₅— | 0 |
| 4-84' | TBS | H | All | —(CH₂)₆— | 0 |
| 4-85' | TBS | H | All | —(CH₂)₆— | 1 |
| 4-86' | TBS | H | All | —(CH₂)₅— | 1 |
| 4-87' | TBS | H | All | —(CH₂)₄— | 1 |
| 4-88' | TBS | H | All | —(CH₂)₄— | 2 |
| 4-89' | TBS | H | All | —(CH₂)₅— | 2 |
| 4-90' | TBS | H | All | —(CH₂)₆— | 2 |
| 4-91' | PNZ | H | PNB | —(CH₂)₆— | 0 |
| 4-92' | PNZ | H | PNB | —(CH₂)₅— | 0 |
| 4-93' | PNZ | H | PNB | —(CH₂)₄— | 0 |
| 4-94' | PNZ | H | PNB | —(CH₂)₄— | 1 |
| 4-95' | PNZ | H | PNB | —(CH₂)₅— | 1 |
| 4-96' | PNZ | H | PNB | —(CH₂)₆— | 1 |
| 4-97' | PNZ | H | PNB | —(CH₂)₆— | 2 |
| 4-98' | PNZ | H | PNB | —(CH₂)₅— | 2 |
| 4-99' | TBS | 4-Me | PNB | —(CH₂)₆— | 1 |
| 4-100' | TBS | 5-Cl | PNB | —(CH₂)₆— | 1 |
| 4-101' | TBS | 5-NO₂ | PNB | —(CH₂)₆— | 1 |
| 4-102' | TBS | 6-Cl | PNB | —(CH₂)₆— | 1 |
| 4-103' | TBS | 4-Me | PNB | —(CH₂)₆— | 0 |
| 4-104' | TBS | 5-Cl | PNB | —(CH₂)₆— | 0 |
| 4-105' | TBS | 5-NO₂ | PNB | —(CH₂)₆— | 0 |
| 4-106' | TBS | 6-Cl | PNB | —(CH₂)₆— | 0 |
| 4-107' | TBS | 4-Me | PNB | —(CH₂)₆— | 2 |
| 4-108' | TBS | 5-Cl | PNB | —(CH₂)₆— | 2 |
| 4-109' | TBS | 5-NO₂ | PNB | —(CH₂)₆— | 2 |
| 4-110' | TBS | 6-Cl | PNB | —(CH₂)₆— | 2 |
| 4-111' | TBS | 4-Me | PNB | —(CH₂)₄— | 1 |
| 4-112' | TBS | 5-Cl | PNB | —(CH₂)₄— | 1 |
| 4-113' | TBS | 5-NO₂ | PNB | —(CH₂)₄— | 1 |

Of the compounds listed in above preferred compounds are Compounds No. 3-1', 3-2', 3-3', 3-4', 3-5', 3-6', 3-7', 3-8', 3-9', 3-28', 3-29', 3-30', 3-31', 3-32', 3-33', 3-34', 3-35', 3-36', 3-47', 3-48', 3-40', 3-50', 3-51', 3-52', 3-53', 3-54', 3-64', 3-65', 3-66', 3-67', 3-68', 3-69', 3-79', 3-80', 3-81', 3-82', 3-83', 3-84', 4-3', 4-4', 4-5', 4-7', 4-10', 4-11', 4-12', 4-14', 4-17', 4-18', 4-19', 4-21', 4-24', 4-26', 4-4-28', 4-31', 4-33', 4-35', 4-38', 4-40', 4-42', 4-45', 4-47', 4-49', 4-52', 4-54', 4-56', 4-59', 4-61' and 4-63'. More preferred compounds are Compounds No. 3-4', 3-5', 3-6', 3-31', 3-32', 3-33', 3-49', 3-50', 3-51', 4-5', 4-12', 4-19', 4-26', 4-33', 4-40', 4-47', 4-54' and 4-61'. The most preferred compounds are Compounds No.

3-31'. 4-Nitrobenzyl 2-(2-diethylcarbamoylphenylthio)-1-methyl-6-(1-trimethylsilyloxyethyl)-1-carbapen-2-em-3-carboxylate;

3-32'. 4-Nitrobenzyl 2-(2-diethylcarbamoylphenylsulfinyl)-1-methyl-6-(1-trimethylsilyloxyethyl)-2-carbapen-2-em-3-carboxylate;

3-33'. 4-Nitrobenzyl 2-(2-diethylcarbamoylphenylsulfonyl)-1-methyl-6-(1-trimethylsilyloxyethyl)-1-carbapen-2-em-3-carboxylate;

3-40'. 4-Nitrobenzyl- 2-(2-diethylcarbamoylphenylthio)-2-methyl-6-(1-hydroxyethyl)-1-carbapen-2-em-3-carboxylate;

3-50'. 4-Nitrobenzyl 2-(2-diethylcarbamoylphenylsulfinyl)-1-methyl-6-(1-hydroxyethyl)-1-carbapen-2-em-3-carboxylate;

3-51'. 4-Nitrobenzyl 2-(2-diethylcarbamoylphenylsulfonyl)-1-methyl-6-(1-hydroxyethyl)-1-carbapen-2-em-3-carboxylate;

4-26'. 4-Nitrobenzyl 2-[2-(1-perhydroazepinylcarbonyl)-phenylthio]-1-methyl-6-(1-trimethylsilyloxyethyl)-1-carbapen-2-em-3-carboxylate;

4-33'. 4-Nitrobenzyl 2-[2-(1-perhydroazepinylcarbonyl)-phenylsulfinyl]-1-methyl-6-(1-trimethylsilyloxyethyl)-1-carbapen-2-em-3-carboxylate;

4-40'. 4-Nitrobenzyl 2-[2-(1-perhydroazepinylcarbonyl)-phenylsulfonyl]-1-methyl-6-(1-trimethylsilyloxyethyl)-1-carbapen-2-em-3-carboxylate;

4-47'. 4-Nitrobenzyl 2-[2-(1-perhydroazepinylcarbonyl)-phenylthio]-1-methyl-6-(1-hydroxyethyl)-1-carbapen-2-em-3-carboxylate; and 4-54'. 4-Nitrobenzyl 2-[2-(1-perhydroazepinylcarbonyl)-phenylsulfinyl]-1-methyl-6-(1-hydroxyethyl)-1-carbapen-2-em-3-carboxylate; and 4-61'. 4-Nitrobenzyl 2-[2-(1-perhydroazepinylcarbonyl)-phenylsulfonyl]-1-methyl-6-(1-hydroxyethyl)-1-carbapen-2-em-3-carboxylate.

In accordance with the present invention, compounds of formula (II'), which include the novel compounds of formula (IV'), may be converte to the desired compounds of formula (I') by reaction with a compound of formula (III'), A'SH (in which A' is as defined above), in the presence of a metal salt. The metal salt is a salt of a metal from Group II or III of the Periodic Table.

In the case of salts of a metal belonging to Group II, the metal may be from sub-Group A or B. The metals of sub-Group A include beryllium, magnesium, calcium, strontium, barium and radium. The metals of sub-Group B of Group II include zinc, cadmium and mercury, but these are not preferred for use in the process of the present invention. Accordingly, the metals of sub-Group A are preferred, magnesium or calcium salts being especially preferred and the salts of magnesium being most preferred. Of these, we particularly prefer:

a metal halide, such as magnesium chloride, magnesium bromide, magnesium iodide or calcium bromide;

a complex of the metal with an ether such as magnesium bromide—diethyl ether complex;

a mixture of the metal halide or of the ether complex with an organic base such as triethylamine, diisopropylethylamine, 1-ethylpiperidine, 1,5-diazabicyclo[5,4,0]-5-undecene, 1,4-diazabicyclo[2,2,2]octane or 1,5-diazabicyclo[4,3,0]-5-nonene [which mixture can, for example, be prepared by suspending a halide of a metal belonging to Group II or its ether complex in a solvent, and then adding an organic base (The molar ratio of the metal salt to the organic base is preferably from 10:1 to 1:1];

an amide of a metal belonging to Group II and having the formula (V'):

$$R^{33'}R^{34'}N.M—X' \qquad (V)$$

in which:

each of $R^{33'}$ and $R^{34'}$ independently represents a straight or branched chain alkyl group, preferably having from 1 to 6, more preferably from 1 to 4, carbon atoms, such as the methyl, ethyl and isopropyl groups; a cycloalkyl group, preferably having from 3 to 7, more preferably 5 or 6, carbon atoms, such as the cyclohexyl and cyclopentyl groups; a phenyl group; or a trialkylsilyl group in which each alkyl part preferably has from 1 to 6, more preferably from 1 to 4, carbon atoms, such as the trimethylsilyl group; or $R^{33'}$ and $R^{34'}$ together represent a group of formula —(CH₂)$_{d'}$—, in which d' represents 4 or 5, or a group of formula —(CH₂)₂O(CH₂)₂—;

M' represents a metal belonging to Group II; and

X' represents a halogen atom, such as a chlorine, bromine or iodine atom;

an alcoholate of a metal belonging to Group II and having the formula (VI'):

$$R^{35'}—O—M'—X' \qquad (VI')$$

in which:

$R^{35'}$ represents a straight or branched chain alkyl group, preferably having from 1 to 6, more preferably from 1 to 4, carbon atoms, such as the methyl, ethyl, isopropyl and t-butyl groups; a cycloalkyl group, preferably having from 3 to 7, more preferably 5 or 6, carbon atoms, such as the cyclohexyl and cyclopentyl groups; or a phenyl group;

M' represents a metal belonging to Group II; and

X' represents a halogen atom, such as a chlorine, bromine or iodine atom;

this compound of formula (VI') may be prepared by dissolving a compound of formula $R^{35'}OH$ corresponding to the solvent employed for the reaction, and then allowing it to react with a Grignard reagent, such as methyl magnesium bromide or phenyl magnesium bromide] or;

a mixture prepared by adding an alkali metal amide [such as lithium bis(trimethylsilyl)amide, lithium diisopropylamide or sodium bis(trimethylsilyl)amide] or an alkali metal alcoholate (such as potassium t-butoxide or lithium ethoxide) to a halide of a metal or an ether complex of a halide of a metal belonging to Group II suspended in the solvent to be employed for the reaction.

In the case of Group III of the Periodic Table, sub-Group A includes scandium, yttrium and the lanthanides, but it is not certain that they will be effective in the process of the present invention. Group IIIB includes boron, aluminum, gallium, indium and thallium, and a salt of a metal from this sub-Group is preferred, a salt of aluminum or boron being more preferred and aluminum being most preferred. Examples of salts of metals belonging to Group III employable for the reaction include compounds of formula (VII'):

$$R^{33'}R^{34'}N—Al(R^{36'})_3 \qquad (VII')$$

in which:

$R^{33'}$ and $R^{34'}$ are as defined above, and $R^{36'}$ represents an alkyl group, preferably having from 1 to 6, more preferably from 1 to 4, carbon atoms, such as the methyl or ethyl groups.

From all of the metals of Groups II and III, we prefer magnesium, aluminum, beryllium, calcium and boron.

Of all of these salts, the most preferred are: magnesium bromide—diethyl ether complex; a mixture of magnesium bromide—diethyl ether complex with diisopropylethylamine, 1-ethylpiperidine or 1,4-diazabicyclo[5,4,0]-5-undecene; bromomagnesium cyclohexylisopropylamide, bromomagnesium diisopropylamide, bromomagnesium diethylamide or bromomagnesium hexamethyldisilazide; bromomagnesium t-butoxide; a mixture of lithium diisopropylamide or lithium bistrimethylsilylamide with magnesium bromide—diethyl ether complex; or diethylaluminium diisopropylamide.

There is no particular restriction on the relative amounts of the reagents and of the metal salt employed. However, in general, we prefer to employ the compound of formula (II') and the mercaptan of formula (III') in a molar ration of from 1:1 to 1:3. The salt of a metal of Group II or III is preferably present in an amount of from 1 to 20 moles per mole of the compound of formula (II').

The reaction is normally and preferably carried out in the presence of a solvent, the nature of which is not critical, provided that it has no adverse effect upon the reaction and that it can dissolve the reagents, at least to some extent. Examples of suitable solvents include: hydrocarbons, especially alicyclic and aromatic hydrocarbons, such as cyclohexane, benzene, toluene or xylene; halogenated hydrocarbons, especially halogenated aliphatic hydrocarbons, such as methylene chloride, 1,2-dichloroethane or carbon tetrachloride; ethers, such as diethyl ether, 1,2-dimethoxyethane, tetrahydrofuran or dioxane; amides, such as dimethylformamide, dimethylacetamide, N-methyl-2-pyrrolidone or hexamethylphosphoric triamide; and sulfoxides, such as dimethyl sulfoxide. Of these, we prefer the hydrocarbons, the halogenated hydrocarbons, the ethers or the amides, the ethers being particularly preferred.

The reaction will take place over a wide range of temperatures, and the precise reaction temperature chosen is not critical to the invention. In general, we find it convenient to carry out the reaction at a temperature in the range of from −70° C. to 60° C., more preferably from 0° C. to 30° C. The time required for the reaction may likewise vary widely, depending on many factors, notably the reaction temperature and the nature of the reagents. However, in most cases, a period of from 10 minutes to 48 hours will normally suffice if a sulfinyl derivative is used, and from 10 minutes to several days will normally suffice if a sulfonyl derivative is used.

A sulfinyl derivative of formula (IX') or a sulfonyl derivative of formula (X'), which may be used as the starting material for this reaction, can be synthesized by oxidation of a compound of formula (XI') according to a known method using a suitable oxidizing agent, for example a peroxide, such as m-chloroperbenzoic acid, peracetic acid or t-butyl peroxide, as shown in the following Reaction Scheme 2:

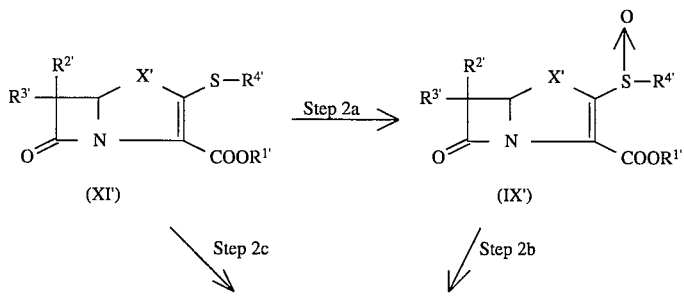

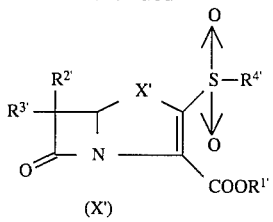

(X')

In the above formulae, $R^{1'}$, $R^{2'}$, $R^{3'}$ and $R^{4'}$ are as defined above.

When t-butyl peroxide is used, we prefer to employ vanadyl acetylacetonate [VO(acac)$_2$] as a catalyst. In addition, in order to remove any acidic substances originating from the peroxides which are formed in this reaction, the oxidation reaction is preferably conducted in the presence of a base, for example an alkali metal carbonate or an aqueous solution thereof.

A sulfonyl derivative of formula (X') can be synthesized either by further oxidation of the sulfinyl derivative of formula (IX') according to the method mentioned above or by direct oxidation of the compound of formula (XI').

These oxidation reactions are described in more detail in relation to Step 3d of Reaction Scheme 3.

The compound of formula (XI') employed as the starting material can be synthesized from a natural substance when X' represents CH$_2$ (for example, as described by S. M. Schmitt et al.: J. Org. Chem. 1980, 45, 1142); or according to the reported method when X represents CH$_2$ or CH(CH$_3$) [for example, as described by S. Oida et al.: Tetrahedron Letters 25, 2793 (1984); B. G. Christensen et al.: Heterocycles 21, 29 (1984)].

When X' represents a sulfur atom in the compound of formula (XI'), the compound can be synthesized, for example, according to the following reported methods [S. Oida et al.: Chem. Pharm. Bull. 29, 3158 (1981); A. Yoshida et al.: Chem. Pharm. Bull. 31, 768 (1983)].

Preferred examples of compounds of formula A'SH (III') employed in the present invention are those compounds of formula (IIIa') to (IIIf'):

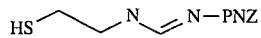 (IIIa')

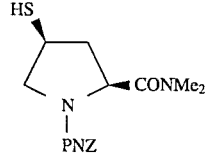 (IIIb')

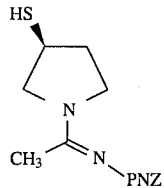 (IIIc')

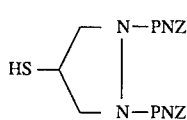 (IIId')

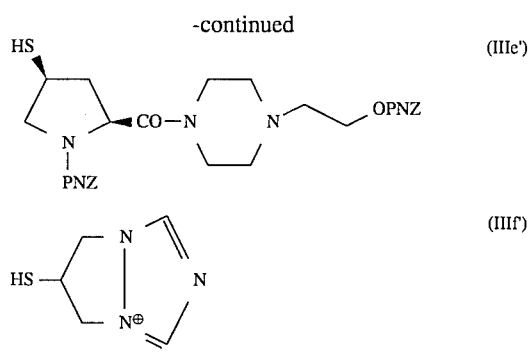

(IIIe')

(IIIf')

The compound of formula (I') which is obtainable by the method of the present invention can be converted into a corresponding carbapenem or penem derivative having excellent antibacterial activity, by removal of a carboxy-protecting group shown by $R^{1'}$, and in some cases by removal of hydroxy-protecting groups shown by $R^{2'}$ and $R^{3'}$ at position 6 and any protecting group in A' by conventional means.

The compounds of formula (IV') of the present invention may be prepared, for example, as illustrated by the following Reaction Scheme 3:

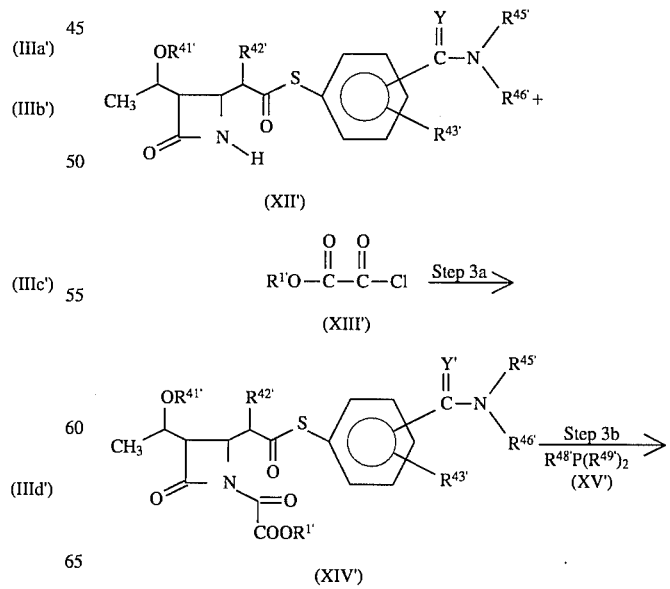

-continued

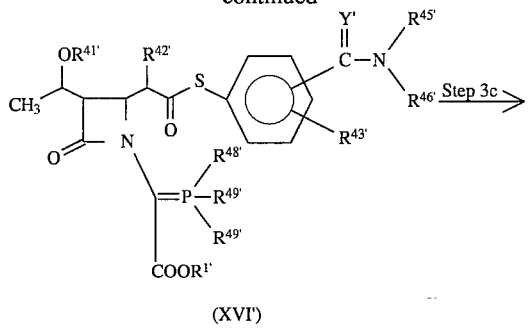

(XVI')

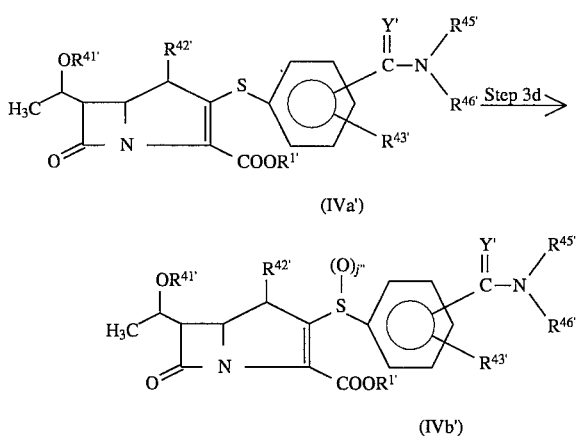

(IVa')

(IVb')

In the above formulae, $R^{1'}$, $R^{41'}$, $R^{42'}$, $R^{43'}$, $R^{45'}$, $R^{46'}$ and $Y'$ are as defined above.

$R^{48'}$ represents an alkyl group having from 1 to 6 carbon atoms or an alkoxy group having from 1 to 6 carbon atoms. Where $R^{48'}$ represents an alkyl group having from 1 to 6 carbon atoms, it may be, for example, any of those groups exemplified above in relation to $R^2$, particularly a methyl, ethyl, propyl, isopropyl, butyl or isobutyl group.

Where $R^{48'}$ represents an alkoxy group having from 1 to 6 carbon atoms, it may be, for example, any of those groups exemplified above in relation to $R^7$, particularly a methoxy, ethoxy, propoxy, isopropoxy, butoxy, isobutoxy or t-butoxy group.

$R^{49'}$ represents an alkoxy group having from 1 to 6 carbon atoms or an aryloxy group (in which the aryl part may be as generally defined and exemplified above). Where $R^{49'}$ represents an alkoxy group, it may be the same alkoxy group as defined and exemplified for $R^{48'}$.

Where $R^{49'}$ represents an aryloxy group, it may be, for example, a phenoxy, 4-methylphenoxy or 4-methoxyphenoxy group.

i" is 1 or 2.

A compound of formula (XII'), wherein $R^{41'}$ represents a t-butyldimethylsilyl group, $R^{42'}$ represents a methyl group, the group of formula $—C(=Y')NR^{45'}R^{46'}$ represents a group of formula $—CONEt_2$ at the 2-position and $R^{43'}$ represents a hydrogen atom, (disclosed in Japanese Patent Application No. Hei 4-174099) which may be be used as a starting material in Reaction Scheme 3, can be prepared by reacting Z(O)-1-t-butyldimethylsilyloxy-1-(diethylcarbamoylphenylthio)-1-propene with (3R, 4R)-3-(1(R)-[t-butyldimethylsilyloxy)ethyl]-4-acetoxyazetidinone, and is obtained in a 77% yield. It may be purified by recrystallization only without carrying out column chromatography. Accordingly this compound is a valuable intermediate in the industrial preparation of 13-methylcarbapenem derivatives.

Reaction Scheme 3 involves the preparation of a compound of formula (IVa') by reacting a compound of formula (XII') with an acid chloride of formula (XIII') to produce a N-oxalyl derivative of formula (XIV') and then treating the product with a phosphorous acid triester or phosphonous acid diester. The reaction can be accomplished by the well known method described in Tetrahedron Letters, 25, 2793 (1984) or Japanese Patent Application No. Hei 4-180779.

Step 3a:

A compound of formula (XIV') can be prepared by reacting a compound of formula (XII') with an acid chloride or formula (XIII') in the presence of a base. We prefer to employ from 2 to 5 equivalents of the acid chloride of formula (XIII') per equivalent of the compound of formula (XII').

There is no particular limitation upon the nature of the base used, provided that it has no adverse effect upon the reaction. Examples of suitable bases include: cyclic or linear tertiary amines, such as diisopropylethylamine, diisopropylmethylamine, triethylamine, 1-ethylpiperidine, 1-methylmorpholine, 1-ethylpyrrolidine, 1,4-diazabicyclo[2,2,2]octane, 1,5-diazabicyclo[5,4,0]undec-5-ene or 1,5-diazabicyclo[4,3,0]-non-5-ene.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride, chloroform or dichloroethane; ethers, such as diethyl ether or tetrahydrofuran; hydrocarbons, especially aromatic hydrocarbons, such as benzene or toluene; and nitriles such as acetonitrile or propionitrile.

The reaction can take place over a wide range of temperatures, and the precise reaction temperature is not critical to the invention. In general, we find it convenient to carry out the reaction at a temperature of from −78° C. to 50° C., more preferably from −30° C. to 30° C. The time required for the reaction may also vary widely, depending on many factors, notably the reaction temperature and the nature of the reagents and solvent employed. However, provided that the reaction is effected under the preferred conditions outlined above, a period of from 5 minutes to 3 hours will usually suffice.

After completion of the reaction, the desired compound can be recovered from the reaction mixture by conventional means after, if necessary, decomposing any excess of the acid halide with an alcohol. An example of one such technique comprises: adding water to the reaction mixture; extracting the desired compound of formula (XIV') with a water-insoluble organic solvent such as the said reaction solvent or ethyl acetate; and distilling off the solvent from the extract. The compound thus obtained can, if necessary, by purified by conventional means, such as column chromatography.

Step 3b:

A phosphorane of formula (XVI') can be prepared by reacting a compound of formula (XIV') with a tri-valent phosphorous compound of formula (XV') in the presence or absence of a solvent. There is no particular restriction on the relative proportions of the reagents. However, we generally prefer to employ from 2 to 6 equivalents of the tri-valent phosphorous compound of formula (XV') per equivalent of the compound of formula (XIV').

The reaction may be effected in the absence or the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, especially aromatic hydrocarbons, such as benzene, toluene or xylane; halogenated hydrocarbons, especially halogenated aliphatic hydrocarbons, such as chloroform, methylene chloride or 1,2-dichloroethane; ethers, such as tetrahydrofuran or dioxane; nitriles, such as acetonitrile; esters, such as ethyl acetate; and amides, such as dimethylformamide.

The reaction can take place over a wide range of temperatures, and the precise reaction temperature is not critical to the invention. In general, we find it convenient to carry out the reaction at a temperature of from −10° C. to 100° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 30 hours will usually suffice.

After completion of the reaction, the desired phosphorane of formula (XVI') can be recovered from the reaction mixture by distilling off any excess of a phosphorous compound of formula (XV') and its oxygen-aduct under reduced pressure, or by precipitating the product by adding a nonpolar solvent, such as hexane, to the reaction mixture.

The crude product of formula (XVI') thus obtained can be used in the subsequent step without any purification. However, the product can, if necessary, be purified by conventional means, such as column chromatography.

Step 3c:

The compound of formula (IVa') can be prepared by heating the phosphorane of formula (XVI').

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: substituted aromatic hydrocarbons, such as toluene, xylene, mesitylene or chlorobenzene.

The reaction can take place over a wide range of temperatures, and the precise reaction temperature is not critical to the invention. In general, we find it convenient to carry out the reaction at a temperature of from 100° C. to 200° C., more preferably from 120° C. to 170° C. The time required for the reaction may also vary widely, depending on many factors, notably the reaction temperature and the nature of the reagents and solvent employed. However, provided that the reaction is effected under the preferred conditions outlined above, a period of from 1 to 30 hours will usually suffice.

After completion of the reaction, the product of formula (IVa') can be recovered from the reaction mixture by distilling off the solvent and recrystallizing or chromatographing the residue.

Step 3d:

This optional step for the preparation of a compound of formula (Ib') involves oxidizing a compound of formula (IVa').

An S-oxide compound of formula (IVb') can be prepared by reacting the compound of formula (IVa') with an oxidizing agent. Examples of oxidizing agents which may be used include: peroxides, such as 3-chloroperoxybenzoic acid, peracetic acid, hydrogen peroxide or t-butyl hydroperoxide, perferably 3-chloroperoxybenzoic acid or t-butyl peroxide. When t-butyl peroxide is used as an oxidizing agent in the reaction, the reaction is preferably carried out in the presence of a catalyst, such as vanadyl acetylacetonate or molybdenyl acetylacetonate, preferably vanadyl acetylacetonate. In order to remove any acidic substance arising from such oxidizing agents in the course of the reaction, the oxidation reaction can be carried out in the presence of a base, such as an alkali metal carbonate or an aqueous solution thereof.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and halogenated hydrocarbons, especially halogenated aliphatic hydrocarbons, such as methylene chloride, chloroform or 1,2-dichloroethane, of which the halogenated hydrocarbons are preferred.

The reaction can take place over a wide range of temperatures, and the precise reaction temperature is not critical to the invention. In general, we find it convenient to carry out the reaction at a temperature of from −10° C. to 50° C., more preferably from 0° C. to 25° C. The time required for the reaction may also vary widely, depending on many factors, notably the reaction temperature and the nature of the reagents and solvent employed. However, provided that the reaction is effected under the preferred conditions outlined above, a period of from 30 minutes to 6 hours will usually suffice.

After completion of the reaction, the compound of formula (IVb') can be recovered from the reaction mixture by the following means. Any excess of the oxidizing agent is decomposed by adding a 10% aqueous solution of sodium sulfite and then the reaction mixture is diluted with a solvent such as methylene chloride, washed with water and dried, after which the solvent is distilled off.

The resulting residue may be purified by conventional means, such as recrystallization or chromatography to give the compound of formula (IVb').

It is possible to prepare either the sulfinyl compound of formula (IVb') (i" is 1) or the sulfonyl compound of formula (IVb') (i" is 2) by varying the amount of oxidizing agent. An excess of oxidizing agent will favor the production of a compound where i" is 2.

Alternatively, the compound where i" is 2 may be prepared by oxidizing the corresponding compound where i" is 1, using the same conditions as described above.

If desired, after completion of these reactions, the hydroxy-protecting group represented by $R^{41"}$ in any of the compounds of formula (IVa') or (IVb') may be deprotected. This can be accomplished by the well known methods described in T. W. Green and P. G. M. Wuts, "Protective Groups in Organic Synthesis. 2nd Edition", edited by John Wiley and Sons, Inc., 1991, pp. 10.

The invention is further illustrated by the following non-limiting Examples, which illustrate the preparation of compounds of the present invention. The subsequent Preparations 1 to 12, 19 to 38 and 41 to 43 illustrate the preparation of starting materials for use in these Examples, and Preparations 13 to 18, 39 and 40 illustrate the use of compounds of the present invention to prepare other compounds, leading ultimately to the desired carbapenem compounds.

In the formulae in the Examples, the following abbreviations are used for certain groups:

Et: ethyl group
Me: methyl group
PNB: 4-nitrobenzyl group
PNZ: 4-nitrobenzyloxycarbonyl group
TMS: trimethylsilyl group
TBS: t-butyldimethylsilyl group

EXAMPLE 1

(3S,4S)-3[(1R)-1-t-Butyldimethylsilyloxyethyl]-4-[(1R)-(2-pyridylthiocarbonyl)ethyl]azetidin-2-one (Compound No. 1-1)

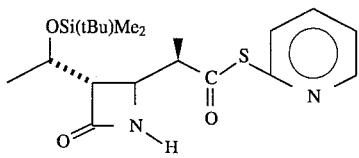

1(a)  Z(O)-2-(1-t-Butyldimethylsilyloxy-1-propenylthio)-pyridine

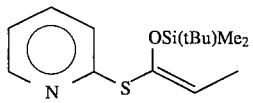

22.5 ml of a solution containing 1.2 equivalents of butyllithium in hexane were added at room temperature to a solution of 7.5 ml of hexamethyldisilazane in 50 ml of tetrahydrofuran, and the resulting mixture was stirred for 30 minutes, to prepare 1.2 equivalents of lithium hexamethyldisilazane. The reaction mixture was then cooled to 31 κ° C., and 6.25 ml (1.2 equivalents) of hexamethyldisilazane. The reaction mixture was then cooled to −78° C., and 6.25 ml (1.2 equivalents) of hexamethylphosphoric triamide, 8.37 ml (2 equivalents) of triethylamine and 9.60 g(2 equivalents) of t-butyldimethylsilyl chloride were added, in that order, followed by a solution of 5 g of 2-propionylthiopyridine (prepared as described in Preparation 1) in 10 ml of tetrahydrofuran. The reaction mixture was then stirred for 10 minutes, after which it was diluted with ethyl acetate. The organic layer was separated, washed twice with water and then dried over anhydrous magnesium sulfate. The solvent was then removed by distillation under reduced pressure, and the residue was subjected to fractional distillation, to give 8.4 g (yield 88%) of the title compound, boiling at 130° C./0.1 mmHg (13.3 Pa).

$^1$H Nuclear Magnetic Resonance Spectrum (CDCl$_3$, 270 MHz), δ ppm:

0.09 (6H, singlet);
0.88 (9H, singlet);
1.73 (3H, doublet, J=6.6 Hz);
5.45 (1H, quartet, J=6.6 Hz);
6.97–7.02 (1H, multiplet);
7.32 (1H, doublet, J=8.6 Hz);
7.51–7.57 (1H, multiplet);
8.42 (1H, doublet, J=4 Hz).

This procedure was repeated, except that the hexamethylphoshporic triamide was replaced by the additives shown below. In all cases, the amount of lithium hexamethyldisilazane was 1.2 equivalents, and 2 equivalents each of triethylamine and t-butyldimethylsilyl chloride were employed. The reaction temperature was −78° C. Using 1,3-dimethyl-3,4,5,6-tetrahydro-2(1H)-pyrimidinone as the additive, and carrying out the reaction for 10 minutes, the title compound was obtained in a yield of 88%. Using N,N-dimethylformamide as the additive, and carrying out the reaction for 10 minutes, the title compound was obtained in a yield of 80%. Using N,N-dimethylacetamide as the additive, and carrying out the reaction for 1 hour, the title compound was obtained in a yield of 46%.

1(b)  (3S,4S)-3[(1R)-1-t-Butyldimethylsilyloxyethyl]-4-[(1R)-(2-pyridylthiocarbonyl)ethyl]azetidin-2-one 163 mg (2 equivalents) of anhydrous zinc chloride (freshly fused) were added to a solution of 171 mg of Z(O)-(3S,4R)-3-[(1R)-1-t-butyldimethylsilyloxyethyl]-4-acetoxyazetidin-2-one and 337 mg (2 equivalents) of 2-(1-t-butyldimethylsilyloxy-1-propenylthio)pyridine [prepared as described in step (a) above] in 15 ml of methylene chloride, and the mixture was stirred at a bath temperature of 12° C. for 15 hours. At the end of this time, the reaction mixture was mixed with methylene chloride, and the organic layer was washed three times with water. It was then dried over anhydrous magnesium sulfate, and the solvent was removed by distillation under reduced pressure. The residue was purified by flash chromatography through silica gel, using a 1:1 by volume mixture of cyclohexane and ethyl acetate as the eluent, to give 170 mg (yield 72%) of the title compound having an Rf value of 0.2 and melting at 109° C. Infrared Absorption Spectrum (KBr), ν$_{max}$ cm$^{-1}$: 1757, 1718, 1696, 1564, 3181, 3099.

$^1$H Nuclear Magnetic Resonance Spectrum (CDCl$_3$, 270 MHz), δ ppm:

0.07 (6H, singlet);
0.87 (9H, singlet);
1.19 (3H, doublet, J=5.9 Hz);
1.35 (3H, doublet, J=7.2 Hz);
3.0–3.05 (2H, multiplet);
3.99 (1H, doublet of doublets, J=1.98 & 5.28 Hz);
4.19–4.23 (1H, multiplet);
5.90 (1H, singlet);
7.3–7.32 (1H, multiplet);
7.60 (1H, doublet, J=7.9 Hz);
7.73–7.93 (1H, multiplet);
8.63 (1H, doublet, J=3.9 Hz).

1(c)  (3S,4S)-3-[(1R)-1-t-Butyldimethylsilyloxyethyl]-4-[(1$)-(2-pyridylthiocarbonyl)ethyl]azetidin-2-one This provides an alternative method of preparing the same compound as was prepared in step (b) above.

200 mg (5.7 mmole) of Z(O)-(3S,4S)-3-[(1R)-1-t-butyldimethylsilyloxyethyl]-4-phenylsulfinylazetidin-2-one (prepared by a procedure similar to that described in Preparation 3) were added to a solution of 160 mg (5.7 mmole)of 2-(2-t-butyldimethylsilyloxy-1-propenylthio)pyridine [prepared as described in step (a) above] in 18 ml of methylene chloride, and the resulting mixture was stirred at 15° C. for 4 hours. At the end of this time, the reaction mixture was mixed with methylene chloride, and the organic layer was separated and then washed with water and with a saturated aqueous solution of sodium chloride, in that order. The solution was then dried over anhydrous magnesium sulfate, and the solvent was removed by distillation under reduced pressure. The resulting residue was purified by column chromatography using a 1:1 by volume mixture of cyclohexane and ethyl acetate as the eluent, to give 60 mg (yield 28.7%) of a 18:1 mixture of the title compound and an isomer thereof, in which the methyl group forming part of the ethyl group at the 4 position of the azetidinone ring is in the α-configuration, instead of the β-configuration.

EXAMPLE 2

(3S,4S)-3-[(1R)-1-t-Butyldimethylsilyloxyethyl]-4-[(1R)-(2-quinolinethiocarbonyl)ethyl]azetidin-2-one (Compound No. 1-5

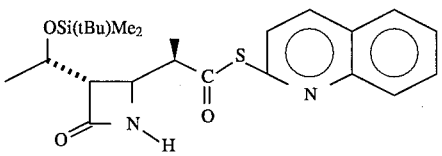

2(a) Z(O)-2-(1-t-Butyldimethylsilyloxy-1-propenylthio)quinoline

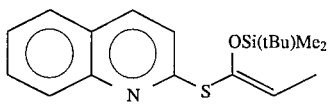

0.9 ml of a solution containing 1.2 equivalents of butyllithium in hexane was added at room temperature to a solution of 0.3 ml of hexamethyldisilazane in 10 ml of anhydrous tetrahydrofuran, and the resulting mixture was stirred for 30 minutes. The reaction mixture was then cooled to −78° C., and 0.25 ml⁻ (1.2 equivalents) of hexamethylphosphoric triamide, 0.33 ml (2 equivalents) of triethylamine and 360 mg (2 equivalents) of t-butyldimethylsilyl chloride were added, in that order, to the mixture, followed by 300 mg of 2-propionylthioquinoline (prepared as described in Preparation 2). The reaction mixture was then stirred for 10 minutes, after which it was mixed with ethyl acetate and the organic layer was separated and washed with water. The solvent was removed by distillation under reduced pressure, and the resulting residue was purified by flash column chromatography, using a 10:1 by volume mixture of cyclohexane and ethyl acetate as the eluent, to give 320 mg (yield 80%) of the title compound having an Rf value of 0.8.

$^1$H Nuclear Magnetic Resonance Spectrum (CDCl$_3$, 270 MHz), δ ppm:
 0.10 (6H, singlet);
 0.89 (9H, singlet);
 1.73 (3H, doublet, J=6.9 Hz);
 5.53 (1H, quartet, J=6.9 Hz);
 7.43–7.50 (2H, multiplet);
 7.66–7.73 (1H, multiplet);
 7.74 (1H, doublet, J=8 Hz);
 7.96 (1H, doublet, J=8.6 Hz);
 8.00 (1H, doublet, J=8.6 Hz).

2(b) (3S,4S)-3-[(1R)-1-t-Butyldimethylsilyloxyethyl]-4-[(1R)-(2-quinolinethiocarbonyl)ethyl]azetidin-2-one 120 mg (2 equivalents) of anhydrous zinc chloride were added to a solution of 126 mg of Z(O)-(2S,4R)-3-[(1R)-1-t-butyldimethylsilyloxyethyl]-4-acetoxyazetidin-2-one and 320 mg (2 equivalents) of 2-(1-t-butyldimethylsilyloxy-1-propenylthio)quinoline [prepared as described in step (a) above] in 15 ml of anhydrous methylene chloride, and the resulting mixture was stirred at a bath temperature of 29°–30° C. for 3 hours. At the end of this time, the reaction mixture was mixed with mthylene chloride. The organic layer was then separated, washed with water and dried over anhydrous magnesium sulfate. The solvent was then removed by distillation under reduced pressure. The resulting residue was purified by flash chromatography using a 1:1 by volume mixture of cyclohexane and ethyl acetate as the eluent, to give 62 mg (yield 32%) of the title compound having an Rf value of 0.2.

$^1$H Nuclear Magnetic Resonance Spectrum (CDCl$_3$, 270 MHz), δ ppm:
 0.01 (6H, singlet);
 0.88 (9H, singlet);
 1.22 (3H, doublet, J=6 Hz);
 1.40 (3H, doublet, J=7.2 Hz);
 3.07–3.11 (2H, multiplet);
 4.04 (1H, doublet of doublets, J=2 & 5.28 Hz);
 4.22–4.26 (1H, multiplet);
 5.91 (1H, singlet);
 7.63–7.68 (2H, multiplet);
 7.7–7.8 (1H, multiplet);
 7.87 (1H, doublet, J=8.5 Hz);
 8.11 (1H, doublet, J=8.5 Hz);
 8.22 (1H, doublet, J=8.58 Hz);

EXAMPLE 3

(3S,4S)-3[(1R)-1-t-Butyldimethylsilyloxyethyl]-4-{(1R)-1-[3-methyl-2-pyridylthiocarbonyl]ethyl}azetidin-2-one (Compound No. 1-2)

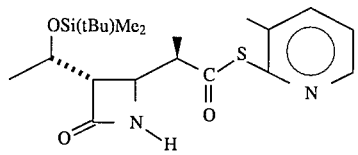

3(a) Z(O)-2-(1-t-Butyldimethylsilyloxy-1-propenylthio)-3-methylpyridine

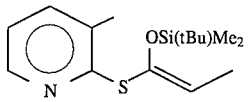

15.17 ml (24.3 mmole) of a 1.6 M solution of butyllithium in hexane were added dropwise at −78° C. to a solution of 5.59 ml (26.5 mmole) of hexamethyldisilazane in a mixture of 40 ml of tetrahydrofuran and 4.61 ml (26.5 mmole) of hexamethylphosphoric triamide, and then 6.65 g (44.1 mmole) of t-bityldimethylsilyl chloride and 9.25 ml (66.3 mmole) of triethylamine were added to the resulting mixture. The reaction mixture was then stirred for a further 10 minutes, after which a solution of 4.00 g (22.1 mmole) of 2-propionylthio-3-methylpyridine in 10 ml of anhydrous tetrahydrofuran was added dropwise to the reaction mixture. The mixture was then stirred at −78° C. for 10 minutes, and the temperature of the reaction mixture was allowed to rise to room temperature. A saturated aqueous solution of sodium hydrogencarbonate was then mixed with the mixture, and the resulting mixture was extracted three times, each time with 60 ml of pentane. The extract was dried over anhydrous magnesium sulfate, and then the solvent was removed by distillation under reduced pressure. The resulting residue was purified by column chromatography through alumina, using a 5:1 by volume mixture of hexane and ethyl acetate as the eluent, to give 3.38 g (yield 52%) of the title compound as a colorless oil.

$^1$H Nuclear Magnetic Resonance Spectrum (CDCl$_3$), δ ppm:
 0.04 (6H, singlet);
 0.85 (9H, singlet);
 1.74 (3H, doublet, J=7 Hz);
 2.25 (3H, singlet);
 5.33 (3H, quartet, J=7 Hz);
 6.95 (1H, doublet of doublets, J=7 & 5 Hz);
 7.33 (1H, doublet of doublets, J=7 & 1 Hz);
 8.37 (1H, doublet of doublets, J=5 & 1 Hz);

3(b) (3S,4S)-3[(1R)-1-t-Butyldimethylsilyloxyethyl]-4-{(1R)-1-[3-methyl-2-pyridylthiocarbonyl]ethyl}azetidin-2-one 190 mg (1.39 mmole) of zinc chloride were added to a solution of 200 mg (0.70 mmole) of Z(O)-(2S,4S)-3-[(1R)-1-t-butyldimethylsilyloxyethyl]-4-acetoxyazetidin-2-one in 5 ml of methylene chloride, and then a solution of 411 mg of 2-(1-t-butyldimethylsilyloxy-1-propenylthio)-3-methylpyridine [prepared as described in step (a) above] in 2 ml of methylene chloride was added thereto, whilst ice-cooling and under an atmosphere of nitrogen. The resulting mixture was then stirred at room temperature for 8 hours, after which 50 ml of methylene chloride were added. The organic layer was washed with ice-water and dried over anhydrous magnesium sulfate, and the solvent was removed by distillation under reduced pressure. The resulting residue was purified by medium pressure column chromatography through silica gel, using a 1:2 by volume mixture of hexane and ethyl acetate as the eluent, to give 246 mg (yield 87%) of the title compound as colorless crystals. A specimen for analysis was recrystallized from diisopropyl ether and was found to melt at 120°–122° C.

$^1$H Nuclear Magnetic Resonance Spectrum (CDCl$_3$), δ ppm:
  0.07 (6H, singlet);
  0.87 (9H, singlet);
  1.20 (3H, doublet, J=6 Hz);
  1.35 (3H, doublet, J=7 Hz);
  2.36 (3H, singlet);
  3.02–3.13 (2H, multiplet);
  4.00 (1H, doublet of doublets, J=4 & 2 Hz);
  4.20 (1H, multiplet);
  5.89 (1H, broad singlet);
  7.28 (1H, doublet of doublets, J=8 & 5 Hz);
  7.64 (1H, doublet of doublets, J=8 & 1 Hz);
  8.50 (1H, doublet of doublets, J=5 & 1 Hz).

EXAMPLE 4

(3S,4S)-3[(1R)-1-t-Butyldimethylsilyloxyethyl]-4-{(1R)-1-[4-methyl-2-pyridylthiocarbonyl]ethyl}azetidin-2-one (Compound No. 1-3)

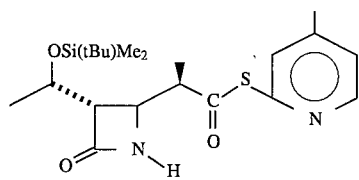

4(a) Z(O)-2-(1-t-Butyldimethylsilyloxy-1-propenylthio)-4-methylpyridine

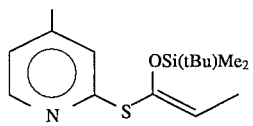

Following a procedure similar to that described in Example 3(a), but using 1.51 g (8.33 mmole) of 2-propionylthio-4-methylpyridine, 1.25 g (yield 51%) of the title compound was obtained as a colorless oil.

$^1$H Nuclear Magnetic Resonance Spectrum (CDCl$_3$), δ ppm:
  0.09 (6H, singlet);
  0.89 (9H, singlet);
  1.74 (3H, doublet, J=7 Hz);
  2.30 (3H, singlet);
  5.43 (1H, quartet, J=7 Hz);
  6.82 (1H, doublet, J=5 Hz);
  7.14 (1H, singlet);
  8.27 (1H, doublet, J=5 Hz).

4(b) (3S,4S)-3[(1R)-1-t-Butyldimethylsilyloxyethyl]-4-{(1R)-1-[4-methyl-2-pyridylthiocarbonyl]ethyl}azetidin-2-one Following a procedure similar to that described in Example 3(b), but using 500 mg (1.74 mmole) of Z(O)-(3S, 4S)-3-[(1R)-1-t-butyldimethylsilyloxyethyl]-4-acetoxyazetidin-2-one, 1.03 g (3.49 mmole) of 2-(1-t-butyldimethylsilyloxy-1-propenylthio)-4-methylpyridine [prepared as described in step (a) above] and 474 mg (3.48 mmole) of zinc chloride, 502 mg (yield 71%) of the title compound were obtained as colorless crystals. A specimen for analysis was recrystallized from diisopropyl ether and melted at 123°–125° C.

$^1$H Nuclear Magnetic Resonance Spectrum (CDCl$_3$), δ ppm:
  0.07 (6H, singlet);
  0.87 (9H, singlet);
  1.19 (3H, doublet, J=6 Hz);
  1.35 (3H, doublet, J=7 Hz);
  2.40 (3H, singlet);
  2.95–3.10 (2H, multiplet);
  3.98 (1H, doublet of doublets, J=5 & 2 Hz);
  4.21 (1H, multiplet);
  5.92 (1H, broad);
  7.13 (1H, doublet of doublets, J=5 & 1 Hz);
  7.42 (1H, doublet, J=1 Hz);
  8.48 (1H, doublet, J=5 Hz).

EXAMPLE 5

(3S,4S)-3[(1R)-1-t-Butyldimethylsilyloxyethyl]-4-{(1R)-1-[5-methyl-2-pyridylthiocarbonyl]ethyl}azetidin-2-one (Compound No. 1-4)

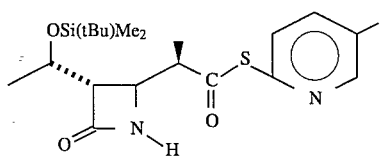

5(a) Z(O)-2-(1-t-Butyldimethylsilyloxy-1-propenylthio)-5-methylpyridine

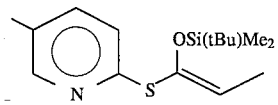

Following a procedure similar to that described in Example 3(a), but using 1.80 g (9.93 mmole) of 2-propionylthio-5-methylpyridine, 1.50 g (yield 51%) of the title compound was obtained as a colorless oil.

$^1$H Nuclear Magnetic Resonance Spectrum (CDCl$_3$). δ ppm:
  0.09 (6H, singlet);
  0.88 (9H, singlet);
  1.72 (3H, doublet, J=7 Hz);
  2.27 (3H, singlet);
  5.42 (1H, quartet, J=7 Hz);
  7.22 (1H, doublet, J=8 Hz);
  7.36 (1H, doublet of doublets, J=8 & 2 Hz);
  8.26 (1H, doublet, J=2 Hz).

5(b) (3S,4S)-3[(1R)-1-t-Butyldimethylsilyloxyethyl]-4-{(1R)-1-[5-methyl-2-pyridylthiocarbonyl]ethyl}azetidin-2-one Following a procedure similar to that described in Example 3(b), but using 500 mg (1.74 mmole) of Z(O)-(3S, 4S)-3-[(1R)-1-t-butyldimethylsilyloxyethyl]-4-acetoxyazetidin-2-one, 1.03 g (3.49 mmole) of 2-(1-t-butyldimethylsilyloxy-1-propenylthio)-5-methylpyridine [prepared as described in step (a) above] and 474 mg (3.48 mmole) of zinc chloride, 583 mg (yield 82%) of the title compound were obtained as colorless crystals. A specimen for analysis was recrystallized from diisopropyl ether and melted at 86°–88° C.

$^1$H Nuclear Magnetic Resonance Spectrum (CDCl$_3$), δ ppm:

0.07 (6H, singlet);
0.87 (9H, singlet);
1.19 (3H, doublet, J=6 Hz);
1.34 (3H, doublet, J=7 Hz);
2.37 (3H, singlet);
2.95–3.08 (2H, multiplet);
3.98 (1H, doublet of doublets, J=5 & 2 Hz);
4.21 (1H, multiplet);
5.90 (1H, broad singlet);
7.46 (1H, doublet, J=8 Hz);
7.56 (1H, doublet of doublets, J=8 & 2 Hz);
8.47 (1H, doublet, J=2 Hz).

EXAMPLE 6

S-2-Diethylcarbamoylphenyl 2(R)-{(3S,4S)-3-[1-(R)-(t-butyldimethylsilyloxy)ethyl]-2-oxo-4-azetidinyl}thiopropionate and its 2(S)-isomer (Compound No. 2-2)

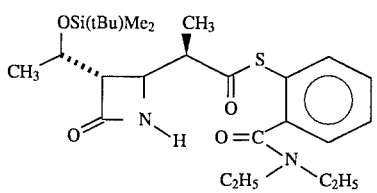

330 mg (2.42 mmole) of anhydrous zinc chloride were added to a solution of 911 mg (2.40 mmole) of 1-t-butyldimethylsilyloxy-1-(2-diethylcarbamoyl)phenylthio-1-propene (prepared as described in Preparation 19) and 347 mg (1.21 mmole) of (3R,4R)-3-[1(R)-(t-butyldimethylsilyloxy)ethyl]-4-acetoxy-2-azetidinone in 12 ml of methylene chloride, and the resulting mixture was stirred at room temperature for 2 hours. At the end of this time, the reaction mixture was diluted with ethyl acetate and the mixture was washed with water and dried over anhydrous magnesium sulfate. The solvent was then removed by distillation under reduced pressure. The resulting residue was purified by chromatography through a Lobar column, using a 1:1 by volume mixture of hexane and ethyl acetate as the eluent, to give 61 mg (yield 10%) of the 2S-isomer of the title compound, melting at 125°–126.5° C. (after recrystallization from a mixture of hexane and ethyl acetate), and 487 mg (yield 82%) of the 2R-isomer of the title compound, melting at 130.5°–132° C. (after recrystallization from diisopropyl ether).
Infrared Absorption Spectrum (KBr), $v_{max}$ cm$^{-1}$
(2S-isomer):
 3182, 1765, 1711, 1629, 953, 774;
(2R-isomer):
 3086, 1762, 1700, 1637, 965, 829.
Nuclear Magnetic Resonance Spectrum (CDCl$_3$, 270 MHz), δ ppm:
(2S-isomer):
 0.06 (3H, singlet);
 0.07 (3H, singlet);
 0.87 (9H, singlet);
 1.05 (3H, triplet, J=7 Hz);
 1.26 (3H, doublet, J=6 Hz);
 1.26 (3H, triplet, J=7 Hz);
 1.28 (3H, doublet, J=7 Hz);
 2.71–2.83 (2H, multiplet);
 3.00–3.21 (2H, nonet-like, J=7 Hz);
 3.35–3.80 (2H, broad);
 3.63 (1H, doublet, J=9 Hz);
 4.14 (1H, quintet, J=6 Hz);
 7.00–7.30 (1H, broad singlet);
 7.30–7.35 (1H, multiplet);
 7.42–7.53 (3H, multiplet);
(2R-isomer):
 0.08 (6H, singlet);
 0.87 (9H, singlet);
 1.03 (3H, triplet, J=7 Hz);
 1.21 (3H, doublet, J=6 Hz);
 1.25 (3H, triplet, J=7 Hz);
 1.29 (3H, doublet, J=7 Hz);
 2.96–3.15 (4H, multiplet);
 3.20–3.85 (2H, broad);
 3.96 (1H, doublet of doublets, J=2 & 4 Hz);
 4.19 (1H, quintet, J=6 Hz);
 5.90–6.10 (1H, broad singlet);
 7.30–7.35 (1H, multiplet);
 7.41–7.51 (3H, multiplet).
Mass spectrum (m/z): (2R- and 2S-isomers) 492 (M$^+$, $C_{25}H_{40}N_2O_4SSi$).
Elemental analysis:
 Calculated for $C_{25}H_{40}N_2O_4SSi$: C, 60.94%; H, 8.18%; N, 5.69%; S, 6.51%.
 Found, 2S-isomer: C, 60.72%; H, 8.01%; N, 5.70%; S, 6.57%.
 Found, 2R-isomer: C, 60.85%; H, 8.10%; N, 5.62%; S, 6.50%.

EXAMPLES 7 to 17

Following a similar procedure to that described in Example 6, the following compounds were also synthesized.

EXAMPLE 7

S-2-Dimethylcarbamoylphenyl 2(R)-{(3S,4S)-3-[1(R)-(t-butyldimethylsilyloxy)ethyl]-2-oxo-4-azetidinyl}thiopropionate (Compound No. 2-1)

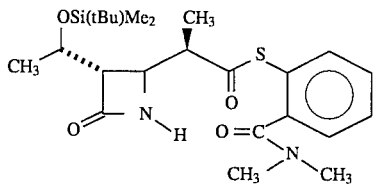

The yield of the 2R-isomer was 79%, and the ratio of the yields of 2R-isomer to 2S-isomer was 4.9:1.
Nuclear Magnetic Resonance Spectrum (CDCl$_3$), δ ppm:
 0.08 (6H, singlet);
 0.88 (9H, singlet);
 1.21 (3H, doublet, J=6 Hz);
 1.29 (3H, doublet, J=7 Hz);
 2.79 (3H, singlet);
 2.96–3.08 (2H, multiplet);
 3.10 (3H, singlet);
 3.94 (1H, doublet of doublets, J=2 & 5 Hz);
 4.19 (1H, doublet of quartets, J=5 & 6 Hz);
 6.10–6.20 (1H, broad singlet);
 7.31–7.36 (1H, multiplet);
 7.40–7.70 (3H, multiplet).
The 2R-isomer was in the form of needle-like crystals, melting at 99°–101° C. (after recrystallization from a mixture of ethyl acetate and hexane).

EXAMPLE 8

S-2-Dipropylcarbamoylphenyl 2(R)-{(3S,4S)-3-[1(R)-(t-butyldimethylsilyloxy)ethyl]-2-oxo-4-acetidinyl}-thiopropionate (Compound No. 2-3)

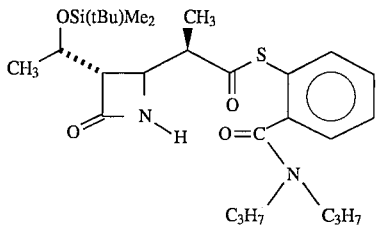

The yield of the 2R-isomer was 74%, and the ratio of the yields of 2R-isomer to 2S-isomer was 3.5:1.
Nuclear Magnetic Resonance Spectrum (CDCl$_3$), δ ppm:
 0.08 (6H, singlet);
 0.72 (3H, triplet, J=7 Hz);
 0.88 (9H, singlet);
 1.00 (3H, triplet, J=7 Hz);
 1.22 (3H, doublet, J=6 Hz);
 120–1.40 (3H, broad);
 1.46 (2H, sextet, J=7 Hz);
 1.70 (2H, sextet, J=7 Hz);
 2.91–3.06 (2H, multiplet);
 3.10–3.80 (2H, broad);
 3.96 (2H, doublet of doublets, J=2 & 4 Hz);
 4.19 (1H, doublet of quartets, J=5 & 6 Hz);
 5.90–6.20 (1H, broad singlet);
 7.92–7.35 (1H, multiplier);
 7.40–7.52 (3H, multiplet).

The 2R-isomer was in the form of needle-like crystals, melting at 112°–113° C. (after recrystallization from a mixture of ethyl acetate and hexane).

EXAMPLE 9

S-2-Diisobutylcarbamoylphenyl 2(R)-{(3S,4S)-3-[1(R)-(t-butyldimethylsilyloxy)ethyl]-2-oxo-4-azetidinyl}thiopropionate (Compound No. 2-6)

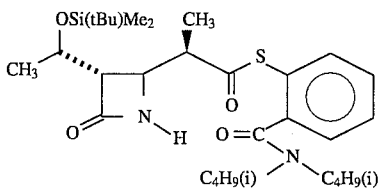

The yield of the 2R-isomer was 70%, and the ratio of the yields of 2R-isomer to 2S-isomer was 4.6:1.
Nuclear Magnetic Resonance Spectrum (CDCl$_3$), δ ppm:
 0.08 (6H, singlet);
 0.74 (6H, doublet, J=7 Hz);
 0.87 (9H, singlet);
 1.02 (6H, doublet, J=7 Hz);
 1.21 (3H, doublet, J=6 Hz);
 1.20–1.40 (3H, broad);
 1.81 (1H, septet, J=7 Hz);
 2.12 (1H, septet, J=7 Hz);
 2.80–3.06 (4H, multiplet);
 3.20–3.57 (2H, broad);
 3.92–4.05 (1H, broad singlet);
 4.13–4.28 (1H, broad);
 5.95–6.15 (1H, broad);
 7.29–7.35 (1H, multiplet);
 7.42–7.50 (3H, multiplet).

The 2R-isomer was in the form of needle-like crystals, melting at 144°–146° C. (after recrystallization from a mixture of ethyl acetate and hexane).

EXAMPLE 10

S-2-(N-Methyl-N-phenylcarbamoyl)phenyl 2(R)-{(3S,4S)-3-[1(R)-(t-butyldimethylsilyloxy)ethyl]-2-oxo-4-azetidinyl}thiopropionate (Compound No. 2-16)

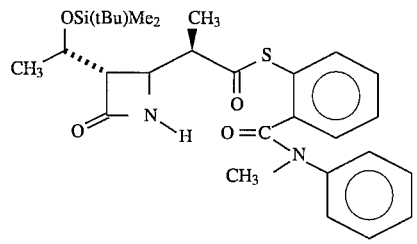

The yield of the 2R-isomer was 64%, and the ratio of the yields of 2R-isomer to 2S-isomer was 2.6:1.
Nuclear Magnetic Resonance Spectrum (CDCl$_3$), δ ppm:
 0.08 & 0.09 (together 6H, each singlet);
 0.88 (9H, singlet);
 1.23 (3H, doublet, J=6 Hz);
 1.34 (3H, doublet, J=7 Hz);
 3.01–3.12 (2H, multiplet);
 3.49 (3H, singlet);
 4.00–4.08 (1H, broad singlet);
 4.20 (1H, doublet of quartets, J=6 & 6 Hz);
 6.05–6.20 (1H, broad singlet);
 6.95–7.63 (9H, multiplet).

The 2R-isomer was in the form of needle-like crystals, melting at 158°–159.5° C. (after recrystallization from a mixture of ethyl acetate and hexane).

EXAMPLE 11

S-2-(1-Pyrrolidinylcarbonyl)phenyl 2(R)-{(3S,4S)-3-[1(R)-(t-butyldimethylsilyloxy)ethyl]-2-oxo-4-azetidinyl}thiopropionate (Compound No. 3-3)

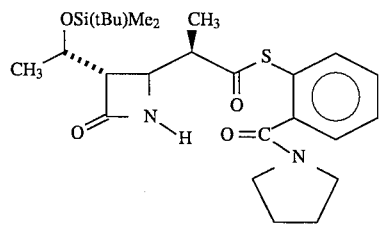

The yield of the 2R-isomer was 85%, and the ratio of the yields of 2R-isomer to 2S-isomer was 7.1:1.
Nuclear Magnetic Resonance Spectrum (CDCl$_3$), δ ppm:
 0.08 (6H, singlet);
 0.88 (9H, singlet);
 1.21 (3H, doublet, J=6 Hz);
 1.29 (3H, doublet, J=7 Hz);
 1.75–2.00 (4H, multiplet);
 2.95–3.06 (2H, multiplet);
 3.18 (2H, triplet, J=7 Hz);
 3.60 (2H, triplet, J=7 Hz);
 3.96 (1H, doublet of doublets, J=2 & 4 Hz);
 4.20 (1H, doublet of quartets, J=5 & 6 Hz);
 6.10–6.25 (1H, broad singlet);
 7.37–7.53 (4H, multiplet).

The 2R-isomer was in the form of a foam-like substance.

EXAMPLE 12

S-2-(1-Piperidylcarbonyl)phenyl 2(R)-{(3S,4S)-3-[1(R)-(t-butyldimethylsilyloxy)ethyl]-2-oxo-4-azetidinyl}thiopropionate (Compound No. 3-4)

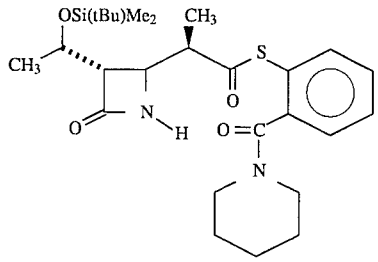

The yield of the 2R-isomer was 75%, and the ratio of the yields of 2R-isomer to 2S-isomer was 4.8:1.
nuclear Magnetic Resonance Spectrum (CDCl$_3$), δ ppm:
  0.07 & 0.08 (together 6H, two singlets);
  0.87 & 0.88 (together 9H, two singlets);
  1.16–1.25 (3H, multiplet);
  1.28 & 1.33 (together 3H, two doublets, J=7 & 7 Hz);
  1.37–1.52 (2H, broad);
  1.54–1.77 (4H, broad);
  2.95–3.26 (4H, multiplet);
  3.47–3.60 (1H, broad);
  3.80–3.95 (1H, broad);
  3.97 (1H, doublet of doublets, J=2 & 4 Hz);
  4.12–4.26 (1H, broad);
  6.00–6.16 (1H, broad);
  7.26–7.52 (4H, multiplet).
The 2R-isomer was in the form of a glassy substance.

EXAMPLE 13

S-2-Morpholinocarbonylphenyl 2(R)-{(3S,4S)-3-[1(R)-(t-butyldimethylsilyloxy)ethyl]-2-oxo-4-azetidinyl}thiopropionate (Compound No. 3-8)

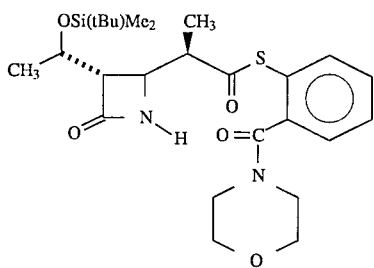

The yield of the 2R-isomer was 83%, and the ratio of the yields of 2R-isomer to 2S-isomer was 7.9:1.
Nuclear Magnetic Resonance Spectrum (CDCl$_3$), δ ppm:
  0.08 (6H, singlet);
  0.88 (9H, singlet);
  1.21 (3H, doublet, J=7 Hz);
  1.22–1.38 (3H, multiplet);
  2.97–3.08 (2H, multiplet);
  3.12–3.32 (2H, multiplet);
  3.50–3.60 (2H, multiplet);
  3.70–3.84 (4H, broad);
  3.93–4.01 (1H, broad singlet);
  4.19 (1H, doublet of quartets, J=5 & 5 Hz);
  5.90–6.10 (1H, broad);
  7.20–7.38 (1H, multiplet);
  7.42–7.55 (3H, multiplet).
The 2R-isomer was in the form of a glassy substance.

EXAMPLE 14

S-2-(1-Azepinylcarbonyl)phenyl 2(R)-{(3S,4S)-3-[1(R)-(t-butyldimethylsilyloxy)ethyl]-2-oxo-4-azetidinyl}thiopropionate (Compound No. 3-5)

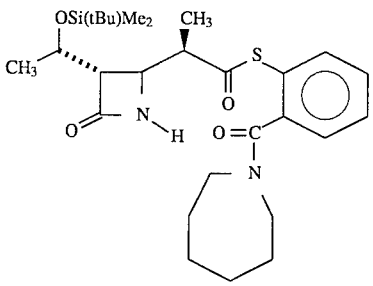

The yield of the 2R-isomer was 87%, and the ratio of the yields of 2R-isomer to 2S-isomer was 9.5:1.
Nuclear Magnetic Resonance Spectrum (CDCl$_3$), δ ppm:
  0.08 (6H, singlet);
  0.88 (9H, singlet);
  1.22 (3H, doublet, J=6 Hz);
  1.20–1.40 (3H, broad);
  1.50–1.96 (8H, broad);
  2.97–3.10 (2H, multiplet);
  3.06–3.32 (2H, broad);
  3.40–3.90 (2H, broad);
  3.96 (1H, doublet of doublets, J=2 & 4 Hz);
  4.20 (1H, doublet of quartets, J=6 & 6 Hz);
  6.05–6.25 (1H, broad);
  7.30–7.37 (1H, multiplet);
  7.42–7.52 (3H, multiplet).
The 2R-isomer was in the form of a glassy substance.

EXAMPLE 15

S-2-Diethylcarbamoyl-6-methylphenyl 2(R)-{(3S,4S)-3-[1(R)-(t-butyldimethylsilyloxy)ethyl]-2-oxo-4-azetidinyl}thiopropionate (Compound No. 2-40)

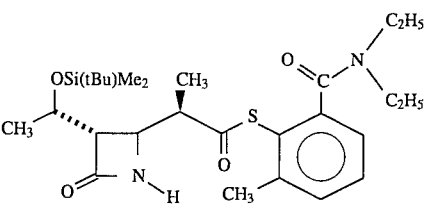

The yield of the 2R-isomer was 88%, and the ratio of the yields of 2R-isomer to 2S-isomer was 12.3:1.
Nuclear Magnetic Resonance Spectrum (CDCl$_3$), δ ppm:
  0.06 (3H, singlet);
  0.86 (9/2H, singlet);
  0.89 (9/2H, singlet);
  1.02 (3H, triplet, J=7 Hz);
  1.19–1.29 (7.5H, multiplet);
  1.35 (1.5H, doublet, J=7 Hz);
  2.35 (3H, singlet);
  2.92–3.16 (4H, multiplet);
  3.28–3.41 (1H, multiplet);
  3.74 (1H, doublet of quartets, J=14 & 7 Hz);
  3.95–4.00 (1H, multiplet);

4.17 (1H, quintet, J=6 Hz);
6.00–6.30 (1H, broad singlet);
7.14 (1H, doublet of doublets, J=3 & 6 Hz);
7.34–7.41 (2H, multiplet).

The 2R-isomer was in the form of needle-like crystals, melting at 150°–150.5° C. (after recrystallization from diisopropyl ether).

EXAMPLE 16

S-2-[Diethyl(thiocarbamoyl)]-6-methylphenyl 2(R)-{(3S, 4S)-3-[1(R)-(t-butyldimethylsilyloxy)ethyl]-2-oxo-4-azetidinyl}thiopropionate (Compound No. 2-63)

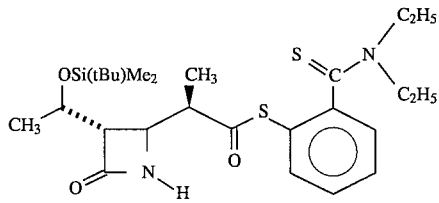

The yield of the 2R-isomer was 81%, and the ratio of the yields of 2R-isomer to 2S-isomer was 4.8:1.
Nuclear Magnetic Resonance Spectrum (CDCl$_3$), δ ppm:
  0.09 (6H, singlet);
  0.89 (9H, singlet);
  1.09 (3H, triplet, J=7 Hz);
  1.22 (3H, doublet, J=6 Hz);
  1.26 (3H, doublet, J=7 Hz);
  1.38 (3H, triplet, J=7 Hz);
  2.96–3.06 (2H, multiplet);
  3.20 (1H, doublet of quartets, J=14 & 7 Hz);
  3.36 (1H, doublet of quartets, J=14 & 7 Hz);
  3.76 (1H, doublet of quartets, J=14 & 7 Hz);
  3.97 (1H, doublet of doublets, J=2 & 5 Hz);
  4.20 (1H, doublet of quartets, J=5 & 6 Hz);
  4.46 (1H, doublet of quartets, J=14 & 7 Hz);
  7.22–7.26 (1H, multiplet);
  7.33–7.46 (3H, multiplet).

The 2R-isomer was in the form of needle-like crystals, melting at 163°–165° C. (after recrystallization from a mixture of ethyl acetate and hexane).

EXAMPLE 17

S-2-Diethylcarbamoylphenyl 2(R)-{(3S,4S)-3-[1(R)-(t-butyldimethylsilyloxy)ethyl]-2-oxo-4-azetidinyl}propionate (Compound No. 2-56)

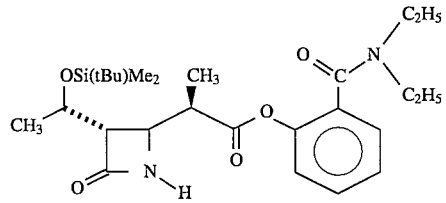

The yield of the 2R-isomer was 61%, and the ratio of the yields of 2R-isomer to 2S-isomer was 6.8:1.
Nuclear Magnetic Resonance Spectrum (CDCl$_3$), δ ppm:
  0.09 (6H, singlet);
  0.88 (9H, singlet);
  1.10 (3H, triplet, J=7 Hz);
  1.22 (3H, triplet, J=7 Hz);
  1.25 (3H, doublet, J=6 Hz);
  1.32 (3 Hz, doublet, J=7 Hz);
  2.95 (1H, doublet of quartets, J=4 & 7 Hz);
  3.00 (1H, doublet, j=6 Hz);
  3.22 (2H, quartet, J=7 Hz);
  3.42–3.63 (1H, multiplet);
  4.08–4.16 (1H, multiplet);
  4.18 (1H, quintet, J=6 Hz);
  6.45 (1H, broad singlet);
  7.17 (1H, doublet, J=8 Hz);
  7.26–7.28 (2H, multiplet);
  7.38–7.43 (1H, multiplet).

The 2R-isomer was in the form of a glassy substance.

PREPARATION 1

2-Propionylthiopyridine 15.6 ml (1.2 equivalents) of propionyl chloride were slowly added at room temperature to a solution of 20 g of 2-pyridinethiol and 25.1 ml (1.2 equivalents) of triethylamine in 200 ml of anhydrous methylene chloride, and the resulting mixture was stirred for 1 hour. At the end of this time, the solvent was removed by distillation under reduced pressure, and the resulting residue was mixed with ethyl acetate. The organic solution thus obtained was washed twice with a dilute aqueous solution of sodium hydrogencarbonate and then with water. The organic layer was separated and then dried over anhydrous magnesium sulfate, after which the solvent was removed by distillation under reduced pressure. The residue was subjected to fractional distillation in vacuo, to give 27 g (yield 90%) of the title compound, boiling at 93° C./0.05 mmHg (6.7 Pa).
$^1$H Nuclear Magnetic Resonance Spectrum (CDCl$_3$, 270 MHz), δ ppm:
  1.24 (3H, doublet, J=7.5 Hz);
  2.74 (2H, quartet, J=7.5 Hz);
  7.30–7.63 (1H, multiplet);
  7.62 (1H, doublet, J=7.9 Hz);
  7.70–7.76 (1H, multiplet);
  8.61–8.63 (1H, multiplet);

PREPARATION 2

2-Propionylthioquinoline 480 mg (1.2 equivalents) of propionyl chloride were added, whilst ice-cooling, to a solution of 1 g of 2-quinolinethiol and 0.83 ml (1.2 equivalents) of triethylamine in 20 ml of anhydrous methylene chloride, and the resulting mixture was stirred for 30 minutes. At the end of this time, the solvent was removed by distillation under reduced pressure, and the resulting residue was mixed with ethyl acetate. This mixture was washed twice with a dilute aqueous solution of sodium hydrogencarbonate and was then washed with water. The organic layer was separated and dried over anhydrous magnesium sulfate and the solvent was removed by distillation under reduced pressure. The residue was purified by flash chromatography through silica gel, using a 1:1 by volume mixture of cyclohexane and ethyl acetate as the eluent, to give 600 mg of the title compound having an Rf value of 0.4.
$^1$H Nuclear Magnetic Resonance Spectrum (CDCl$_3$, 270 MHz), δ ppm:
  1.27 (3H, triplet, J=7.2 Hz);
  2.79 (2H, quartet, J=7.2 Hz);
  7.53–7.61 (1H, multiplet);
  7.67–7.76 (2H, multiplet);
  7.49 (1H, doublet, J=7.9 Hz);
  8.09 (1H, doublet, J=8.5 Hz);
  8.19 (1H, doublet, J=8.5 Hz).

PREPARATION 3

(3S,4R)-3-[(1R)-1-t-Butyldimethylsilyloxyethyl]-4-phenylsulfinylazetidin-2-one

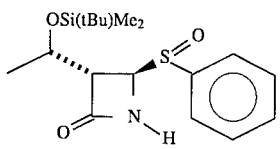

3(i) (3S,4R)-3-[(1R)-1-t-butyldimethylsilyloxyethyl]-4-phenylthio-2-azetidinone 0.7 g of sodium thiophenolate was added, whilst ice-cooling, to a solution of 2 g of (3S,4R)-3-[(1R)-1-t-butyldimethylsilyloxyethyl]-4-acetoxyazetidin-2-one in 20 ml of ethanol, and the resulting mixture was stirred at room temperature for 3 hours. At the end of this time, the reaction mixture was mixed with 50 ml of ethyl acetate, and the organic layer was separated and washed with water, with a saturated aqueous solution of sodium hydrogencarbonate and with water, in that order. It was then dried over anhydrous magnesium under reduced pressure, to give 2 g of the title compound as colorless crystals, melting at 110°–112.5° C.

Rf=0.5 (thin layer chromatography through silica gel; developing solvent: a 3:1 by volume mixture of cyclohexane and ethyl acetate).

$^1$H Nuclear Magnetic Resonance Spectrum (CDCl$_3$, 270 MHz), δ ppm:
0.06 (6H, singlet);
0.87 (9H, singlet);
1.20 (3H, doublet, J=6.6 Hz);
3.02–3.04 (1H, multiplet);
4.18–4.26 (1H, multiplet);
5.07 (1H, doublet, J=2.6 Hz);
6.05 (1H, singlet);
7.33–7.48 (5H, multiplet).

3(ii) (3S,4R)-3-[(1R)-1-t-Butyldimethylsilyloxyethyl]-4-phenylsulfinylazetidin-2-one 1.5 g of 3-chloroperoxybenzoic acid was added, whilst ice-cooling, to a solution of 2 g of (3S,4R)-3-[(1R)-1-t-butyldimethylsilyloxyethyl]-4-phenylthio-2-azetidinone [prepared as described in step (i) above] in 30 ml of methylene chloride, and the resulting mixture was stirred at room temperature for 6 hours. At the end of this time, the reaction mixture was mixed with 30 ml of methylene chloride, and the organic layer was separated and washed with water, with a saturated aqueous solution of sodium hydrogencarbonate and again with water, in that order. It was then dried over anhydrous magnesium sulfate, and the solvent was removed by distillation under reduced pressure. The resulting residue was purified by flash chromatography, using a 1:1 by volume mixture of cyclohexane and ethyl acetate as the eluent, to give 1.9 g of the title compound consisting of two diastereomers, differing in the configuration of the sulfoxide group, as colorless crystals, melting at 65°–70° C.

Rf=0.4 (developing solvent: a 1:1 by volume mixture of cyclohexane and ethyl acetate).

$^1$H Nuclear Magnetic Resonance Spectrum (CDCl$_3$, 270 MHz), δ ppm:
0.02–0.04 (6H, multiplet);
0.82–0.84 (9H, multiplet);
1.43 (3H, singlet);
3.35–3.36 (0.4H, multiplet);
3.51 (0.6H, singlet);
4.16–4.25 (1H, multiplet);
4.53 (1H, singlet);
6.57 (0.4H, singlet);
6.69 (0.6H, singlet);
7.51–7.72 (5H, multiplet).

PREPARATION 4

2-Hydroxy-3-methylpyridine

A solution of 2.30 g (33.3 mmole) of sodium nitrite in 5 ml of water was added dropwise at room temperature to a solution of 3.60 g (33.3 mmole) of 2-amino-3-picoline in a mixture of 65 ml of water and 4 ml of concentrated sulfuric acid, and the resulting mixture was stirred at room temperature for 2 hours. At the end of this time, the pH of the reaction mixture was adjusted to a value of 7 by the addition of sodium carbonate, and the water was removed by distillation under reduced pressure. The mixture was then extracted three times, each time with 80 ml of warm ethanol. The extract was then freed from the ethanol by distillation under reduced pressure, and the resulting residue was recrystallized from ethyl acetate, to give 3.38 g (yield 93%) of the title compound as colorless crystals, melting at 137°–139° C.

$^1$H Nuclear Magnetic Resonance Spectrum (CDCl$_3$), δ ppm:
2.18 (3H, singlet);
6.22 (1H, doublet of doublets, J=7 & 7 Hz);
7.3–7.4 (2H, multiplet);
13.14 (1H, singlet).

PREPARATION 5

2-Hydroxy-4-methylpyridine

Following a procedure similar to that described in Preparation 4, but using 3.60 g (33.3 mmole) of 2-amino-4-picoline, 2.32 g (yield 64%) of the title compound were obtained as colorless crystals, melting at 121°–123° C.

$^1$H Nuclear Magnetic Resonance Spectrum (CDCl$_3$), δ ppm:
2.28 (3H, singlet);
6.14 (1H, doublet, J=6 Hz);
6.39 (1H, singlet);
7.27 (1H, doublet, J=6 Hz);
13.24 (1H, singlet).

PREPARATION 6

2-Hydroxy-5-methylpyridine

Following a procedure similar to that described in Preparation 4, but using 3.60 g (33.3 mmole) of 2-amino-5-picoline, 2.56 g (yield 71%) of the title compound were obtained as colorless crystals, melting at 175°–177° C.

$^1$H Nuclear Magnetic Resonance Spectrum (CDCl$_3$), δ ppm:
2.10 (3H, singlet);
6.53 (1H, doublet, J=9 Hz);
7.16 (1H, broad singlet);
7.33 (1H, doublet of doublets, J=9 & 3 Hz);
13.35 (1H, singlet).

PREPARATION 7

2-Mercapto-3-methylpyridine

A mixture of 2.00 g (18.3 mmole) of 2-hydroxy-3-methylpyridine (prepared as described in Preparation 4) and 2.17 g (9.76 mmole) of phosphorus pentasulfide was heated at 160° C. for 4 hours. At the end of this time, the reaction mixture was diluted with 200 ml of water, and the pH of the mixture was adjusted to a value of 6 by the addition of potassium carbonate. The mixture was then extracted twice, each time with 100 ml of chloroform. The extract was washed with a saturated aqueous solution of sodium chloride and dried over anhydrous magnesium sulfate. The solvent was then removed by distillation under reduced pressure. The resulting residue was recrystallized from benzene to give 2.15 g (yield 94%) of the title compound as yellow crystals, melting at 163°–165° C.
H Nuclear Magnetic Resonance Spectrum (CDCl$_3$), δ ppm:
2.44 (3H, singlet);
6.74 (1H, doublet of doublets, J=7 & 7 Hz);
7.45 (1H, broad doublet, J=7 Hz);
7.53 (1H, broad doublet, J=7 Hz);
13.82 (1H, singlet).
Mass Spectrum m/e: 125 (M$^+$)

PREPARATION 8

2-Mercapto-4-methylpyridine

Following a procedure similar to that described in Preparation 7, but using 2.26 g (20.7 mmole) of 2-hydroxy-4-methylpyridine (prepared as described in Preparation 5), 2.01 g (yield 78%) of the title compound were obtained as yellow crystals, melting at 174°–176° C.
$^1$H Nuclear Magnetic Resonance Spectrum (CDCl$_3$), δ ppm:
2.27 (3H, singlet);
6.63 (1H, doublet, J=6 Hz);
7.42 (1H, singlet);
7.51 (1H, doublet, J=6 Hz);
13.69 (1H, singlet).

PREPARATION 9

2-Mercapto-5-methylpyridine

Following a procedure similar to that described in Preparation 7, but using 2.48 g (22.7 mmole) of 2-hydroxy-5-methylpyridine (prepared as described in Preparation 6), 2.43 g (yield 86%) of the title compound were obtained as yellow crystals, melting at 178°–181° C.
$^1$H Nuclear Magnetic Resonance Spectrum (CDCl$_3$), δ ppm:
2.20 (3H, singlet);
7.26 (1H, doublet of doublets, J=9 & 2 Hz);
7.43 (1H, broad singlet);
7.49 (1H, doublet, J=9 Hz);
13.89 (1H, singlet).

PREPARATION 10

2-Propionylthio-3-methylpyridine 1.21 ml (13.9 mmole) of propionyl chloride were added dropwise, whilst ice-cooling and under an atmosphere of nitrogen, to a solution of 1.46 g (11.7 mmole) of 2-mercapto-3-methylpyridine (prepared as described in Preparation7) and 1.94 ml (13.9 mmole) of triethylamine in 15 ml of methylene chloride, and the resulting mixture was stirred for 1 hour. At the end of this time, the reaction mixture was mixed with 50 ml of methylene chloride, and the mixture was washed with a saturated aqueous solution of sodium hydrogencarbonate. It was then dried over anhydrous magnesium sulfate, and the solvent was removed by distillation under reduced pressure. The residue was purified by medium pressure column chromatography through silica gel, using a 5:1 by volume mixture of hexane and ethyl acetate as the eluent, to give 1.89 g (yield 89%) of the title compound as a light yellow oil.
$^1$H Nuclear Magnetic Resonance Spectrum (CDCl$_3$), δ ppm:
1.24 (3H, triplet, J=7 Hz);
2.37 (3H, singlet);
2.73 (2H, quartet, J=7 Hz);
7.25 (1H, doublet of doublets, J=8 & 5 Hz);
7.61 (1H, doublet, J=8 Hz);
8.48 (1H, doublet, J=5 Hz).
Mass Spectrum m/e: 182 (M$^+$+H)

PREPARATION 11

2-Propionylthio-4-methylpyridine

Following a procedure similar to that described in Preparation 10, but using 1.20 g (9.59 mmole) of 2-mercapto-4-methylpyridine (prepared as described in Preparation 8), 1.62 g (yield 93%) of the title compound were obtained as a light yellow oil.
$^1$H Nuclear Magnetic Resonance Spectrum (CDCl$_3$), δ ppm:
1.24 (3H, triplet, J=7 Hz);
2.38 (3H, singlet);
2.72 (2H, quartet, J=7 Hz);
7.10 (1H, doublet, J=5 Hz);
7.44 (1H, singlet);
8.47 (1H, doublet, J=5 Hz).

PREPARATION 12

2-Propionylthio-5-methylpyridine

Following a procedure similar to that described in Preparation 10, but using 1.40 g (11.2 mmole) of 2-mercapto-5-methylpyridine (prepared as described in Preparation 9), 1.97 g (yield 97%) of the title compound were obtained as a light yellow oil.
$^1$H Nuclear Magnetic Resonance Spectrum (CDCl$_3$), δ ppm:
1.23 (3H, triplet, J=7 Hz);
2.35 (3H, singlet);
2.71 (2H, quartet, J=7 Hz);
7.47 (1H, doublet, J=8 Hz);
7.54 (1H, doublet of doublets, J=8 & 2 Hz);
8.45 (1H, doublet, J=2 Hz).
Mass Spectrum m/e: 181 (M$^+$)

PREPARATION 13

(3S,4S)-3-[(1R)-1-t-Butyldimethyloxyethyl]-4-{2(S)-[4-(2-p-nitrobenzyloxycarbonyloxyethyl)piperazin-1-ylcarbonyl]-1-(p-nitrobenzyloxycarbonyl)pyrrolidin-4(S)-yl]thiocarbonylethyl}azetidin-2-one

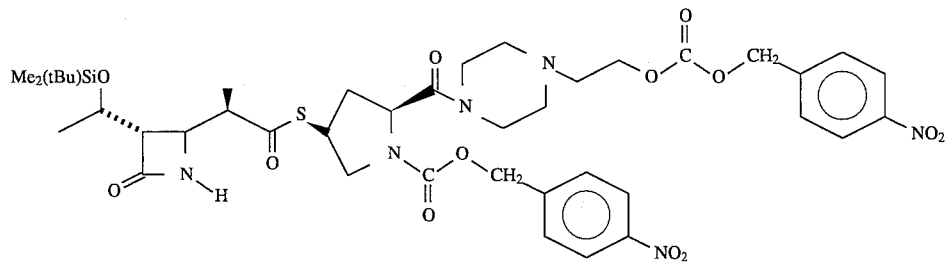

0.75 ml (5.38 mmole) of triethylamine was added, whilst ice-cooling and under an atmosphere of nitrogen, to a solution of 1.76 g (4.47 mmole) of (3S,4S)-3-[(1R)-1-t-butyldimethylsilyloxyethyl]-4-[1(R)-(2-pyridylthiocarbonyl)ethyl]azetidin-2-one prepared as described in Example 1) and 2.79 g (4.52 mmole) of (2S,4S)-2-{4-[2-(p-nitrobenzyloxycarbonyloxy)ethyl]-1-piperazinylcarbonyl}-4-mercapto-1-(p-nitrobenzyloxycarbonyl)pyrrolidine in 40 ml of methylene chloride, and the resulting mixture was stirred at room temperature for 7 hours. At the end of this time, the reaction mixture was mixed with 100 ml of methylene chloride, and the organic mixture was then washed twice, each time with 50 ml of a cooled 1N aqueous solution of sodium hydroxide, after which it was washed with a saturated aqueous solution of sodium chloride. It was then dried over anhydrous magnesium sulfate, and the solvent was removed by distillation under reduced pressure. The resulting residue was recrystallized from 40 ml of ethyl acetate, to give 3.03 g (yield 75%) of the title compound as colorless crystals, melting at 141°–143° C.

PREPARATION 14

(3S,4S)-3-[(1R)-1-Hydroxyethyl]-4-{2(S)-[4-(2-p-nitrobenzyloxycarbonyloxyethyl) piperazin-1-ylcarbonyl]-1-(p-nitrobenzyloxycarbonyl)pyrrolidin-4(S)-yl]-thiocarbonylethyl}azetidin-2-one

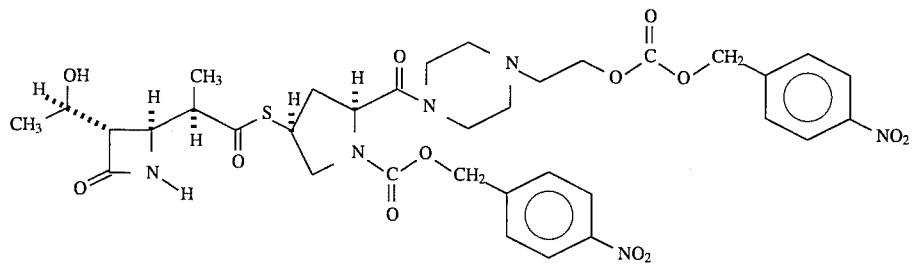

24 ml of 3N aqueous hydrochloric acid were added dropwise, whilst ice-cooling, to a solution of 8.1 g of (3S,4S)-3-[(1R)-1-t-butyldimethyloxyethyl]-4-{2(S) -[4-(2-p-nitrobenzyloxycarbonyloxyethyl)piperazin-1-ylcarbonyl] -1-(p-nitrobenzyloxycarbonyl) pyrrolidin-4(S)-yl] thiocarbonylethyl}azetidin-2-one (prepared as described in Preparation 13) in 80 ml of methanol, after which the resulting mixture was stirred at the same temperature for 30 minutes and then allowed to stand overnight in a refrigerator. At the end of this time, the pH of the reaction mixture was adjusted to a value of 5 to 6 by the addition of sodium hydrogencarbonate, whilst ice-cooling. The mixture was then concentrated by evaporation under reduced pressure, and the concentrate was mixed with a small amount of water and extracted with ethyl acetate. The aqueous layer was separated, saturated with sodium chloride and extracted with ethyl acetate. The extracts were combined and the solvent was then removed by distillation under reduced pressure. The resulting residue was purified by flash chromatography through 150 g of silica gel (Merck Art No. 9385) using a gradient elution method with mixtures of ethyl acetate and methanol ranging from 20:1 to 10:1 by volume as the eluent, to give 5.9 g of the title compound as a colorless foam.

Infrared Absorption Spectrum (CHCl$_3$), $v_{max}$ cm$^{-1}$: 1752, 1710, 1650, 1607, 1522, 1443, 1405, 1347, 1263.

Nuclear Magnetic Resonance Spectrum (CDCl$_3$, 270 MHz), δ ppm:

1.27 (3H, doublet, J=6.83 Hz);
1.28 (3H, doublet, J=6.35 Hz);
1.82–1.99 (1H, multiplet);
2.10–2.18 (1H, multiplet);
2.40–2.95 (7H, multiplet);
3.03 (1H, doublet of doublets, J=1.95 & 6.35 Hz);
3.37–3.80 (5H, multiplet);
3.78 (1H, doublet of doublets, J=1.95 & 6.84 Hz);
3.95–4.48 (6H, multiplet);
4.68 & 4.73 (together 1H, two triplets, J=8.06 & 7.33 Hz);
5.06 & 5.32 (together 1H, two doublets, J=13.43 & 13.43 Hz);
5.21 (1H, singlet);
5.26 (2H, singlet);
5.99 (1H, broad singlet);
7.45 & 7.50 (together 2H, two doublets, J=8.30 & 8.79 Hz);
7.56 ((2H, doublet, J=8.79 Hz);
8.18–8.26 (4H, multiplet).

PREPARATION 15

(3S,4S)-3-[(1R)-1-(Trimethylsilyloxy)ethyl]-4-{2(S)-[4-(2-p-nitrobenzyloxycarbonyloxyethyl) piperazin-1-ylcarbonyl]-1-(p-nitrobenzyloxycarbonyl)pyrrolidin-4(S)-yl]-thiocarbonylethyl}azetidin-2-one

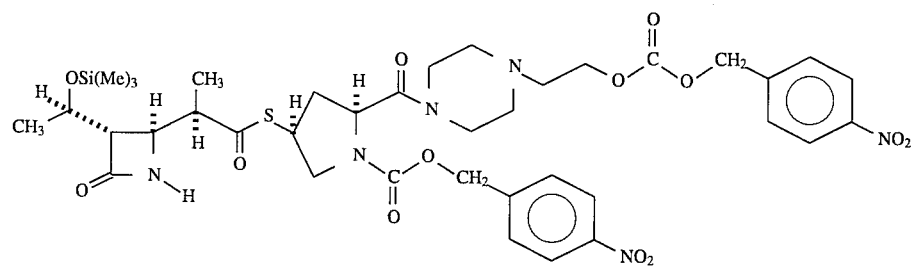

3.6 g of triethylamine and then 2.76 g of chlorotrimethylsilane were added dropwise, whilst ice-cooling and under a stream of nitrogen, to a solution of 4.0 g of (3S,4S)-3-[(1R)-1-hydroxyethyl]-4-{2(S)-[4-(2-p-nitrobenzyloxycarbonyloxyethyl) -piperazin-1-ylcarbonyl]-1-(p-nitrobenzyloxycarbonyl)-pyrrolidin-4(S)-yl]-thiocarbonylethyl}azetidin-2-one (prepared as described in Preparation 14) in 40 ml of methylene chloride, and the resulting mixture was stirred at room temperature for 20 minutes. The reaction mixture was then again cooled, and 25 ml of methanol and 3.3 g of silica gel (Merck Art. No. 7734) were added to the mixture, after which it was stirred at room temperature for 3 hours. The mixture was then concentrated by evaporation under reduced pressure, and the concentrate was mixed with water and extracted with ethyl acetate. The extract was then washed with a saturated aqueous solution of sodium chloride and dried over anhydrous magnesium sulfate, after which the solvent was removed by distillation under reduced pressure. The resulting residue was purified by flash chromatography through 40 g of silica gel (Merck Art No. 9385), using a gradient elution method with mixtures of ethyl acetate and methanol ranging from 40:1 to 20:1 by volume as the eluent, to give 3.63 g of the title compound as a colorless foam.

Infrared Absorption Spectrum (KBr), $v_{max}$ cm$^{-1}$: 1756, 1713, 1656, 1529, 1443, 1405, 1347, 1251.

Nuclear Magnetic Resonance Spectrum (CDCl$_3$, 270 MHz), δ ppm:

0.11 (9H, singlet);
1.18 (3H, doublet, J=6.34 Hz);
1.23 (3H, doublet, J=6.84 Hz);
1.84–1.92 (1H, multiplet);
2.30–2.80 (8H, multiplet);
2.82–2.92 (1H, multiplet);
3.01 & 3.03 (together 1H, two doublets, J=1.71 & 5.13 Hz);
3.35–3.65 (4H, multiplet);
3.77 & 3.79 (together 1H, two doublets, J=1.71 & 5.86 Hz);
3.93–4.03 (1H, multiplet);
4.09–4.17 (2H, multiplet);
4.22–4.37 (2H, multiplet);
4.64–4.77 (1H, multiplet);
5.06 & 5.32 (together 1H, two doublets, J=13.67 & 13.67 Hz);
5.22 (1H, doublet, J=1.95 Hz);
5.26 (2H, singlet);
5.86 (1H, broad singlet);
7.44 & 7.50 (together 2H, two doublets, J=8.79 & 8.79 Hz);
7.55 (2H, doublet, J=8.79 Hz);
8.15–8.27 (4H, multiplet).

PREPARATION 16

(3S,4S)-3-[(1R)-1-(Trimethylsilyloxy)ethyl]-4-{2(S) -[4-(2-p-nitrobenzyloxycarbonyloxyethyl)piperazin-1-ylcarbonyl]-1-(p-nitrobenzyloxycarbonyl)pyrrolidin-4(S)-yl] thiocarbonylethyl}-1-(4-nitrobenzyloxyoxalyl)azetidin-2-one

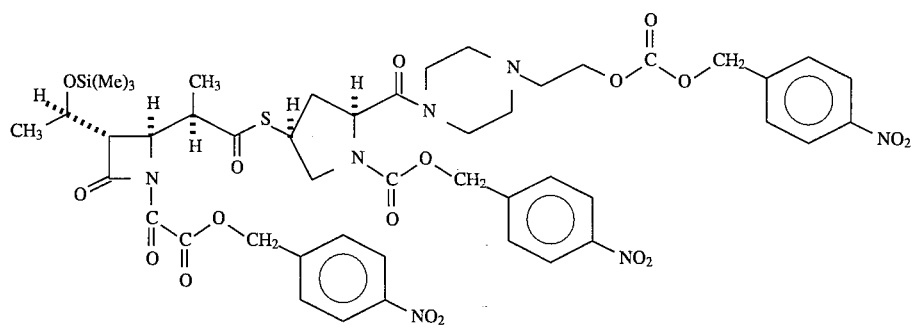

1.39 g of triethylamine were added dropwise, whilst ice-cooling and under a stream of nitrogen, to a solution of 3.94 g of (3S,4S)-3-[(1R)-1-(trimethylsilyloxy)ethyl]-4-{2(S) -[4-(2-p-nitrobenzyloxycarbonyloxyethyl)piperazin-1-ylcarbonyl]-1-(p-nitrobenzyloxycarbonyl)pyrrolidin-4(S)-yl]thiocarbonylethyl}-azetidin-2-one (prepared as described in Preparation 15) in 30 ml of methylene chloride. A solution of 3.35 g of p-nitrobenzyloxyoxalyl chloride in 30 ml of methylene chloride was then added to the mixture at a temperature below 5° C. over a period of 15 minutes, and the resulting mixture was stirred at the same temperature for 10 minutes. After this, 1.04 ml of isopropanol were added dropwise, and the mixture was stirred for a further 10 minutes. At the end of this time, the solvent was removed by distillation under reduced pressure, and the resulting residue was diluted with 50 ml of ethyl acetate. The mixture was washed with cold water and with a saturated aqueous solution of sodium chloride, in that order, and the organic layer was separated and dried over anhydrous magnesium sulfate. The solvent was then removed by distillation under reduced pressure, to give 6.89 g of the title compound as an oil.

Infrared Absorption Spectrum (KBr), $v_{max}$ cm$^{-1}$: 1809, 1754, 1708, 1524, 1348, 1253.

Nuclear Magnetic Resonance Spectrum (CDCl$_3$, 270 MHz), δ ppm:

0.03 (9H, singlet);
1.20 (3H, doublet, J=6.35 Hz);
1.28 (3H, doublet, J=6.83 Hz);
1.81–1.92 (1H, multiplet);
2.25–2.39 (1H, multiplet);
2.40–2.75 (6H, multiplet);
3.35–3.60 (6H, multiplet);
3.63–3.75 (1H, multiplet);
3.85–4.02 (1H, multiplet);
4.50–4.18 (1H, multiplet);
4.20–4.40 (4H, multiplet);

4.63 & 4.71 (together 1H, two triplets, J=7.81 & 7.81 Hz);
5.05 & 5.31 (together 1H, two doublets, J=13.18 & 13.18 Hz);
5.22 (1H, doublet, J=2.44 Hz);
5.25 (2H, singlet);
5.35 & 5.43 (together 2H, two doublets, J=12.90 & 12.90 Hz);
7.44 & 7.50 (together 2H, two doublets, J=8.79 & 8.79 Hz);
7.54 (2H, doublet, J=8.06 Hz);
7.57 (2H, doublet, J=8.06 Hz);
8.15–8.28 (6H, multiplet).

PREPARATION 17

4-Nitrobenzyl (1R,5S,6S)-2-{2(S) -[4-(2-4'-nitrobenzyloxycarbonyloxyethyl)-1-piperazinylcarbonyl}-1-(4-nitrobenzyloxycarbonyl) pyrrolidin-4(S)-ylthio}-6-[(R)-1-trimethylsilyloxy)ethyl]-1-methyl-1-carbapen-2-em-3-carboxylate

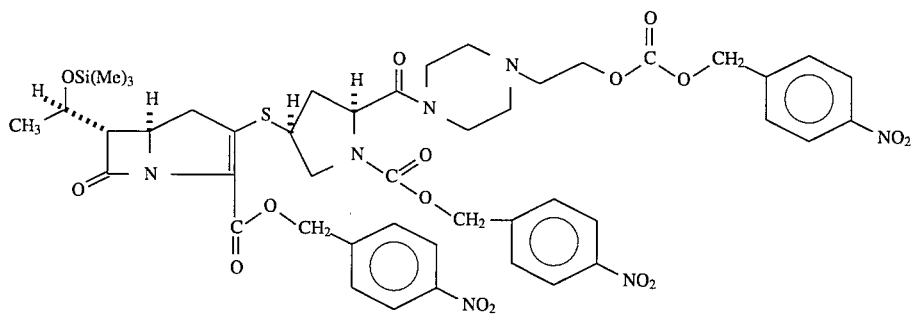

A homogenous mixture of 6.89 g of (3S,4S)-3-[(1R)-1-(trimethylsilyloxy)ethyl]-4-{2(S)-[4-(2-p-nitrobenzyloxycarbonyloxyethyl)piperazin-1-ylcarbonyl]-1-(p-nitrobenzyloxycarbonyl) pyrrolidin-4(S)-yl]-thiocarbonylethyl}-1-(4-nitrobenzyloxyoxalyl)azetidin-2-one (prepared as described in Preparation 16) and 11.2 ml of freshly distilled triethyl phosphite was heated at 60° C. for 4 hours, whilst stirring under an atmosphere of nitrogen. At the end of this time, any excess of triethyl phosphite was removed by distillation at a temperature below 30° C. and under reduced pressure. The residue was washed three times, each time with 50 ml of hexane, and then again three times, each time with 50 ml of diisopropyl ether. The solvent was then finally removed by decantation, and the mixture was dried by evaporation under reduced pressure, to give 6.68 g of an ylide as a brown oil.

5.18 g of this ylide were dissolved in 350 ml of freshly distilled mesitylene, and the solution was heated on an oil bath kept at 170°–175° C. for 7 hours whilst stirring and under an atmosphere of nitrogen. At the end of this time, the reaction mixture was cooled to room temperature and washed with ice-water and with a saturated aqueous solution of sodium chloride, in that order. The resulting mixture was dried over anhydrous magnesium sulfate and treated with active charcoal; the solvent was then removed by distillation under reduced pressure and at a temperature below 45° C. The residue was washed with diisopropyl ether and dried by evaporation under reduced pressure, to give 4.18 g of the title compound as a brown foam.

Infrared Absorption Spectrum (KBr), $v_{max}$ cm$^{-1}$: 1771, 1751, 1712, 1657, 1607, 1522, 1442, 1404 1377, 1347, 1321.

Nuclear Magnetic Resonance Spectrum (CDCl$_3$, 270 MHz), δ ppm:
0.12 (9H, singlet);
1.26 (3H, doublet, J=6.35 Hz);
1.27 (3H, doublet, J=6.35 Hz);
1.81–2.00 (1H, multiplet);
2.32–2.78 (6H, multiplet);
3.20–3.27 (1H, multiplet);
3.27–3.75 (8H, multiplet);
4.00–4.37 (5H, multiplet);
4.63–4.78 (1H, multiplet);
5.07 & 5.30 (together 1H, two doublets, J=13.67 & 13.67 Hz);
5.22 (1H, singlet);
5.26 (2H, singlet);
5.25 & 5.47 (together 2H, two doublets, J=14.15 & 14.15 Hz);
7.44 & 7.51 (together 2H, two doublets, J=8.79 & 8.79 Hz);
7.55 (2H, doublet, J=8.79 Hz);
7.65 (2H, doublet, J=8.79 Hz);
8.18–8.25 (6H, multiplet).

PREPARATION 18

4-Nitrobenzyl (1R,5S,6S)-2-{2(S)-[2-4'-nitrobenzyloxycarbonyloxyethyl) -1-piperazinylcarbonyl]-1-(4-nitrobenzyloxycarbonyl)pyrrolidin-4(S)-ylthio}-6-[(R)-1-hydroxyethyl]-1-methyl-1-carbapen-2-em-3-carboxylate A solution of 0.704 g of potassium fluoride in 11.6 ml of water and then 1.61 ml of acetic acid were added, whilst ice-cooling, to a solution of 4.18 g of 4-nitrobenzyl (1R,5S,6)-2-{2(S)-[4-(2-4'-nitrobenzyloxycarbonyloxyethyl) -1-piperazinylcarbonyl]-1-(4-nitrobenzyloxycarbonyl)pyrrolidin-4(S)-ylthio}-6-[(R)-1-(trimethylsilyloxy) ethyl]-1-methyl-1-carbapen-2-em-3-carboxylate (prepared as described in Preparation 17) in 39 ml of acetone, and the resulting mixture was stirred for 45 minutes. At the end of this time, the reaction mixture was freed from the solvent by distillation under reduced pressure. The resulting residue was mixed with ethyl acetate, and the mixture was washed with water and with a saturated aqueous solution of sodium chloride, in that order. The mixture was dried, and the solvent was removed by distillation under reduced pressure. The residue was washed three times with diethyl ether, to give 2.87 g of the title compound as a powder.

Infrared Absorption Spectrum (KBr), $v_{max}$ cm$^{-1}$: 1769, 1751, 1710, 1653, 1607, 1521, 1443, 1347.

Nuclear Magnetic Resonance Spectrum (CDCl$_3$, 270 MHz), δ ppm:

1.27 & 1.28 (together 3H, two doublets, J=7.33 & 7.33 Hz);
1.37 (3H, doublet, J=6.35 Hz);
1.78–1.98 (1H, multiplet);
2.31–2.80 (7H, multiplet);
3.27 (1H, doublet of doublets, J=6.83 & 2.44 Hz);
3.31–3.76 (8H, multiplet);
4.01–4.33 (5H, multiplet);
4.68 & 4.74 (together 1H, two triplets, J=7.81 & 7.81 Hz);
5.04–5.52 (6H, multiplet);
7.44 & 7.51 (together 2H, two doublets, J=8.79 & 8.79 Hz);
7.55 & 7.65 (together 4H, two doublets, J=8.79 & 8.79 Hz);
8.17–8.25 (6H, multiplet).

The resulting compound can be converted to a known carbapenem derivative having excellent antibacterial activity by deprotecting the hydroxy- and carboxy-protecting groups by conventional means.

PREPARATION 19

Z(O)-1-t-Butyldimethylsilyloxy-1-(2-diethylcarbamoylphenylthio)-1-propene and its E(O)-isomer A solution of 729 mg (2.75 mmole) of S-2-diethylcarbamoylphenyl thiopropionate (prepared as described in Preparation 30), 832 mg (5.52 mmole) of t-butyldimethylsilyl chloride and 621 mg (3.47 mmole) of hexamethylphosphoric triamide in 6 ml of tetrahydrofuran was cooled to −78° C., and 3.0 ml (3.0 mmole) of a 1.0M solution of lithium bis(trimethylsilyl)amide in tetrahydrofuran was added dropwise to the mixture over a period of 7 minutes. The resulting mixture was then stirred at the same temperature for 10 minutes, after which the reaction was terminated by adding 2 ml of a saturated aqueous solution of sodium hydrogencarbonate. The reaction mixture was then mixed with hexane and washed with water to remove tetrahydrofuran and hexamethylphosphoric triamide. The solvent was then removed by distillation under reduced pressure, and the resulting residue was purified by column chromatography through 20 g of alumina, using a 1:1 by volume mixture of methylene chloride and hexane as the eluent, to give 922 mg (yield 88%) of the title compound as a colorless oil. By analysis of the nuclear magnetic resonance spectrum (270 MHz), the product was shown to be a mixture of the Z(O)- and E(O)-isomers in the ratio of 4 to 1.

Nuclear Magnetic Resonance Spectrum (CDCl$_3$, 270 MHz), δ ppm:

0.10 (1.2H, singlet);
0.11 (4.8H, singlet);
0.80 (7.2H, singlet);
0.89 (1.8H, singlet);
1.07 (3H, triplet, J=7 Hz);
1.27 (3H, triplet, J=7 Hz);
1.70 (0.8H, doublet, J=7 Hz);
1.78 (0.2H, doublet, J=7 Hz);
3.16 (1.6H, quartet, J=7 Hz);
3.18 (0.4H, quartet, J=7 Hz);
3.46–3.65 (2H, broad);
5.35 (1H, quartet, J=7 Hz);
7.11–7.20 (2H, multiplet);
7.22–7.32 (1H, multiplet);
7.37–7.45 (1H, multiplet).

PREPARATIONS 20 TO 29

Following a similar procedure to that described in Preparation 19, the following compounds were also prepared.

PREPARATION 20

Z(O)-1-t-Butyldimethylsilyloxy-1-(2-dimethylcarbamoylphenylthio)-1-propene and its E(O)-isomer The yield of the Z(O)-isomer was 85%, and the ratio of the yields of Z(O)-isomer to E(O)-isomer was 4:1.

Nuclear Magnetic Resonance Spectrum (CDCl$_3$, 270 MHz), δ ppm:

0.10 (1.2H, singlet);
0.11 (4.8H, singlet);
0.79 (1.8H, singlet);
0.89 (7.2H, singlet);
1.70 (2.4H, doublet, J=7 Hz);
1.78 (0.6H, doublet, J=7 Hz);
2.88 (3H, singlet);
3.12 (3H, singlet);
5.33 (0.2H, quartet, J=7 Hz);
5.35 (0.8H, quartet, J=7 Hz);
7.15–7.20 (2H, multiplet);
7.24–7.33 (1H, multiplet);
7.40–7.47 (1H, multiplet).

PREPARATION 21

Z(O)-1-t-Butyldimethylsilyloxy-1-(2-dipropylcarbamoylphenylthio)-1-propene and its E(O)-isomer The yield of the Z(O)-isomer was 88%, and the ratio of the yields of Z(O)-isomer to E(O)-isomer was 2:1.

Nuclear Magnetic Resonance Spectrum (CDCl$_3$, 270 MHz), δ ppm:

0.10 (2H, singlet);
0.11 (4H, singlet);
0.73 (3H, triplet, J=7 Hz);
0.81 (3H, singlet);
0.89 (6H, singlet);
1.00 (3H, triplet, J=7 Hz);
1.43–1.60 (2H, multiplet);
1.62–1.80 (2H, multiplet);
1.70 (2H, doublet, J=7 Hz);
1.77 (1H, doublet, J=7 Hz);
3.05 (1.3H, triplet, J=7 Hz);
3.08 (0.7H, triplet, J=7 Hz);
3.46–3.60 (2H, broad singlet);
5.35 (0.67H, quartet, J=7 Hz);
5.37 (0.33H, quartet, J=7 Hz);
7.10–7.19 (2H, multiplet);
7.22–7.31 (1H, multiplet);
7.36–7.31 (1H, multiplet);
7.36–7.44 (1H, multiplet).

PREPARATION 22

Z(O)-1-t-Butyldimethylsilyloxy-1-(2-diisobutylcarbamoylphenylthio)-1-propene and its E(O)-isomer The yield of the Z(O)-isomer was 58%, and the ratio of the yields of Z(O)-isomer to E(O)-isomer was 7:1.

Nuclear Magnetic Resonance Spectrum (CDCl$_3$, 270 MHz), δ ppm:
0.11 (6H, singlet);
0.75 (5.3H, doublet, J=7 Hz);
0.77 (0.7H, doublet, J=7 Hz);
0.82 (1.1H, singlet);
0.90 (7.9H, singlet);
1.03 (6H, doublet, J=7 Hz);
1.71 (2.6H, doublet, J=7 Hz);
1.76 (0.4H, doublet, J=7 Hz);
1.80–1.95 (1H, multiplet);
2.07–2.25 (1H, multiplet);
2.99 (1.75H, doublet, J=8 Hz);
3.02 (0.25H, doublet, J=8 Hz);
3.10–3.70 (2H, broad singlet);
5.36 (0.88H, quartet, J=7 Hz);
5.42 (0.12H, quartet, J=7 Hz);
7.09–7.22 (2H, multiplet);
7.23–7.30 (1H, multiplet);
7.34–7.42 (1H, multiplet).

PREPARATION 23

Z(O)-1-t-Butyldimethylsilyloxy-1-(2-N-methyl-N-phenyl-carbamoylphenylthio)-1-propene and its E(O)-isomer The yield of the Z(O)-isomer was 87%, and the ratio of the yields of Z(O)-isomer to E(O)-isomer was 9:1.

Nuclear Magnetic Resonance Spectrum (CDCl$_3$, 270 MHz), δ ppm:
0.10 (0.6H, singlet);
0.15 (5.4H, singlet);
0.84 (0.9H, singlet);
0.92 (8.1H, singlet);
1.69 (2.7H, doublet, J=7 Hz);
1.79 (0.3H, doublet, J=7 Hz);
3.35–3.55 (3H, broad singlet);
5.34 (0.9H, quartet, J=7 Hz);
5.39 (0.1H, quartet, J=7 Hz);
6.85–7.27 (8H, broad);
7.31–7.38 (1H, broad).

PREPARATION 24

Z(O)-1-t-Butyldimethylsilyloxy-1-[2-(1-piperidyl)-carbonylphenylthio]-1-propene and its E(O)-isomer The yield of the Z(O)-isomer was 94%, and the ratio of the yields of the Z(O)-isomer to E(O)-isomer was 3:1.

Nuclear Magnetic Resonance Spectrum (CDCl$_3$, 270 MHz), δ ppm:
0.10 (1.5H, singlet);
0.11 (4.5H, singlet);
0.80 (2.3H, singlet);
0.89 (6.7H, singlet);
1.40–1.73 (6H, broad);
1.69 (2.25H, doublet, J=7 Hz);
1.77 (0.75H, doublet, J=7 Hz);
3.15–3.28 (2H, broad);
3.55–3.95 (2H, broad);
5.34 (0.25H, quartet, J=7 Hz);
5.35 (0.75H, quartet, J=7 Hz);
7.10–7.19 (2H, multiplet);
7.22–7.32 (1H, multiplet);
7.38–7.46 (1H, multiplet).

PREPARATION 26

Z(O)-1-t-Butyldimethylsilyloxy-1-[2-morpholinocarbonylphenylthio]-1-propene and its E(O)-isomer The yield of the Z(O)-isomer was 99%, and the ratio of the yields of the Z(O)-isomer to E(O)-isomer was 5:1.

Nuclear Magnetic Resonance Spectrum (CDCl$_3$, 270 MHz), δ ppm:
0.10 (1H, singlet);
0.11 (5H, singlet);
0.79 (1.5H, singlet);
0.89 (7.5H, singlet);
1.70 (2.5H, doublet, J=7 Hz);
1.78 (0.5H, doublet, J=7 Hz);
3.18–3.40 (2H, broad);
3.52–3.85 (2H, broad singlet);
3.65–3.90 (4H, broad singlet);
5.34 (0.17H, quartet, J=7 Hz);
5.35 (0.83H, quartet, J=7 Hz);
7.13–7.21 (2H, multiplet);
7.25–7.36 (1H, multiplet);
7.40–7.47 (1H, multiplet).

PREPARATION 27

Z(O)-1-t-Butyldimethylsilyloxy-1-[2-(1-azepinyl)-carbonylphenylthio]-1-propene and its E(O)-isomer The yield of the Z(O)-isomer was 86%, and the ratio of the yields of the Z(O)-isomer to E(O)-isomer was 3:1.

Nuclear Magnetic Resonance Spectrum (CDCl$_3$, 270 MHz), δ ppm:
0.10 (1.5H, singlet);
0.12 (4.5H, singlet);
0.79 (2.3H, singlet);
0.90 (6.7H, singlet);
1.53–1.72 (6H, broad);
1.69 (2.25H, doublet, J=7 Hz);
1.78 (0.75H, doublet, J=7 Hz);
1.75–1.90 (2H, broad);
3.19–3.35 (2H, broad);
3.35–3.80 (2H, broad);
5.33 (0.25H, quartet, J=7 Hz);
5.34 (0.75H, quartet, J=7 Hz);
7.10–7.19 (2H, multiplet);
7.21–7.33 (1H, multiplet);
7.38–7.46 (1H, multiplet).

PREPARATION 28

Z(O)-1-t-Butyldimethylsilyloxy-1-(2-diethylcarbamoyl-6-methylphenylthio)-1-propene and its E(O)-isomer The yield of the Z(O)-isomer was 76%, and the ratio of the yields of the Z(O)-isomer to E(O)-isomer was 11:1.

Nuclear Magnetic Resonance Spectrum (CDCl$_3$, 270 MHz), δ ppm:
0.21 (3H, singlet);
0.23 (3H, singlet);
0.96 (9H, singlet);

1.03 (3H, triplet, J=7 Hz);
1.27 (3H, triplet, J=7 Hz);
1.49 (3H, doublet, J=7 Hz);
2.51 (3H, singlet);
3.08 (1H, doublet of quartets, J=14 & 7 Hz);
3.11 (1H, doublet of quartets, J=14 & 7 Hz);
3.43 (1H, doublet of quartets, J=14 & 7 Hz);
4.12 (1H, quartet, J=7 Hz);
7.08–7.13 (1H, multiplet);
7.25–7.32 (2H, multiplet).

PREPARATION 29

Z(O)-1-t-Butyldimethylsilyloxy-1-[2-diethyl(thiocarbamoyl) -6-methylphenylthio]-1-propene and its E(O)-isomer The yield of the Z(O)-isomer was 100%, and the ratio of the yields of the Z(O)-isomer to E(O)-isomer was 20:1.

Nuclear Magnetic Resonance Spectrum (CDCl$_3$, 270 MHz), δ ppm:
0.12 (3H, singlet);
0.14 (3H, singlet);
0.80 (9/21H, singlet);
0.90 (180/21H, singlet);
1.11 (3H, triplet, J=7 Hz);
1.40 (3H, triplet, J=7 Hz);
1.70 (60/21H, doublet, J=7 Hz);
1.78 (3/21H, doublet, J=7 Hz);
3.29 (1H, doublet of quartets, J=14 & 7 Hz);
3.44 (1H, doublet of quartets, J=14 & 7 Hz);
3.67 (1H, quartet, J=7 & 14 Hz);
4.57 (1H, doublet of quartets, J=7 & 14 Hz);
5.37 (1H, quartet, J=7 Hz);
7.10–7.25 (3H, multiplet);
7.31–7.40 (1H, multiplet).

PREPARATION 30

S-2-Diethylcarbamoylphenyl thiopropionate

Method A

A solution of 34.84 g (0.476 mole) of diethylamine and 70.0 ml (0.502 mole) of triethylamine in 50 ml of methylene chloride was added dropwise, over a period of 1 hour, to an ice-cooled suspension of 71.62 g of (0.209 mole) of 2,2'-dithiobenzoyl chloride in 300 ml of methylene chloride, and the resulting mixture was stirred at the same temperature for a further 30 minutes. At the end of this time, the solvent was removed by distillation under reduced pressure, and the resulting residue was diluted with ethyl acetate. The resulting organic solution was washed with water and with a saturated aqueous solution of sodium chloride, in that order. The solvent was again distilled off to give an amide compound. About 4 g of this amide compound was mixed with 14.36 g (0.220 mole) of zinc powder and 80.0 (0.624 mole) of propionic anhydride, and the mixture was heated at 100° C. for 5 minutes. In the course of this reaction, the zinc in the reaction mixture was activated. The remainder of the amide compound was dissolved in 100 ml of benzene, and the resulting solution was then added dropwise to the reaction mixture at the same temperature over a period of 20 minutes. The resulting mixture was then heated under reflux for 90 minutes, after which it was cooled. The crystals which separated were collected by filtration and washed with ethyl acetate. The filtrate and the washings were combined, and the resulting mixture was washed with water; the solvent was then removed by distillation under reduced pressure. The residue was then subjected to fractional distillation under reduced pressure, to give 106.97 g of the title compound, boiling at 167°–170° C./0.95–1.1 mmHg (12.7–14.7 Pa), representing a total yield of 96% over the two steps.

Infrared Absorption Spectrum (CHCl$_3$), $\nu_{max}$ cm$^{-1}$: 1710, 1635, 1292, 932.

Nuclear Magnetic Resonance Spectrum (CDCl$_3$, 270 MHz), δ ppm:
1.02 (3H, triplet, J=7 Hz);
1.20 (3H, triplet, J=7 Hz);
1.23 (3H, triplet, J=7 Hz);
2.66 (2H, quartet, J=7 Hz);
2.90–3.20 (2H, broad);
3.10–4.00 (2H, broad);
7.29–7.36 (1H, multiplet);
7.40–7.52 (1H, multiplet).

Mass spectrum (m/z): 266 (M$^+$+1), (M$^+$, C$_{14}$H$_{19}$NO$_2$S).

Method B

30B(i) N,N-diethyl-2-benzoylthiobenzamide 2.85 (20.3 mmole) of benzoyl chloride were added dropwise, whilst ice-cooling, to a solution of 3.13 g (20.3 mmole) of thiosalicylic acid and 2.46 g )24.4 mmole) of triethylamine in 60 ml of methylene chloride, and the resulting mixture was stirred at room temperature for 1 hour. At the end of this time, the reaction mixture was washed twice with 0.2N aqueous hydrochloric acid and once with a saturated aqueous solution of sodium chloride, and the solvent was removed by distillation under reduced pressure, to give 5.24 g of benzoylthiobenzoic acid as crude crystals in a quantitative yield. The whole of this product was dissolved in 100 ml of methylene chloride, and 5.45 g (21.3 mmole) of 2-chloro-1-methylpyridinium iodide, 1.78 g (24.4 mmole) of diethylamine and 4.51 g (44.7 mmole) of triethylamine were added, in that order, to the resulting solution, whilst ice-cooling. The resulting mixture was then stirred at room temperature for 20 hours, after which the solvent was removed by distillation under reduced pressure. The residue was partitioned between ethyl acetate and dilute aqueous hydrochloric acid, and the organic layer was washed with water. The solvent was removed by distillation under reduced pressure, and the residue was purified by column chromatography through 120 g of silica gel, using a gradient elution method with mixtures of hexane and acetone ranging from 4:1 to 3:1 by volume as the eluent, to give 4.86 g of the title compound as an oil in a 76% yield.

Nuclear Magnetic Resonance Spectrum (CDCl$_3$, 60 MHz), δ ppm:
0.99 (3H, triplet, J=7 Hz);
1.02 (3H, triplet, J=7 Hz);
3.09 (2H, quartet, J=7 Hz);
3.0–3.9 (2H, broad);
7.2–7.7 (7.5H, multiplet);
7.9–8.2 (1.5H, multiplet).

30B(ii) S-2-Diethylcarbamoylphenyl thiopropionate 0.84 g (15.5 mmole) of sodium methoxide was added, whilst ice-cooling, to a solution of 4.86 g (15.5 mmole) of N,N-diethyl-2-benzoylthiobenzamide [prepared as described in step (i) above] in 60 ml of methanol, and the resulting mixture was stirred for 20 minutes. At the end of this time, the reaction mixture was neutralized by adding about 15 drops of concentrated aqueous hydrochloric acid. Ethanol and was then added, and the solvent was removed by distillation under reduced pressure. In order to eliminate moisture, the residue was mixed with 20 ml of ethanol and 30 ml of benzene and the solvent was removed by distillation under reduced pressure. The resulting residue, containing N,N-diethyl-2-mercaptobenzamide, was suspended in 60 ml of methylene chloride, and 4.30 g (46.5 mmole) of propionyl chloride wand 6.26 g (62.0 mmole) of triethylamine were added, whilst ice-cooling. The reaction mixture was then stirred for 2.5 hours, after which the reaction was terminated by adding water. The reaction mixture was then diluted with methylene chloride and the organic layer was washed first with dilute aqueous hydrochloric acid and then with water. The solvent was removed by distillation under reduced pressure, and the resulting residue was purified by column chromatography through 100 g of silica gel, to give 3.26 g (yield 79%) of the title compound. The product obtained by this method was identical with that prepared in Method A.

PREPARATIONS 31 TO 38

Following the procedure described in Preparation 30 (Method A or B), the following compounds were prepared. In these Preparations, only the infrared carbonyl group absorption is reported.

PREPARATION 31

S-2-Dimethylcarbamoylphenyl thiopropionate

The title compound was obtained in a total yield of 78% for the two steps.

Infrared Absorption Spectrum (liquid), $v_{max}$ cm$^{-1}$: 1709, 1639.

PREPARATION 32

S-2-Dipropylcarbamoylphenyl thiopropionate

The title compound was obtained in a total yield of 93% for the two steps.

Infrared Absorption Spectrum (liquid), $v_{max}$ cm$^{-1}$: 1705, 1632.

PREPARATION 33

S-2-Diisobutylcarbamoylphenyl thiopropionate

The title compound was obtained in a total yield of 99% for the two steps.

Infrared Absorption Spectrum (liquid), $v_{max}$ cm$^{-1}$: 1712, 1635.

PREPARATION 34

S-2-(N-Methyl-N-phenylcarbamoyl)phenyl thiopropionate

The title compound was obtained in a total yield of 96% for the two steps.

Infrared Absorption Spectrum (liquid), $v_{max}$ cm$^{-1}$: 1705, 1645.

PREPARATION 35

S-2-(1-Pyrrolidinylcarbonyl)phenyl thiopropionate

The title compound was obtained in a total yield of 74% for the two steps.

Infrared Absorption Spectrum (liquid), $v_{max}$ cm$^{-1}$: 1702, 1630.

PREPARATION 36

S-2-(1-Piperidylcarbonyl)phenyl thiopropionate

The title compound was obtained in a total yield of 98% for the two steps.

Infrared Absorption Spectrum (liquid), $v_{max}$ cm$^{-1}$: 1702, 1630.

PREPARATION 37

S-2-Morpholinocarbonylphenyl thiopropionate

The title compound was obtained in a total yield of 89% for the two steps.

Infrared Absorption Spectrum (liquid), $v_{max}$ cm$^{-1}$: 1702, 1635.

PREPARATION 38

S-2-(1-Azepinylcarbonyl)phenyl thiopropionate

The title compound was obtained in a total yield of 93% for the two steps.

Infrared Absorption Spectrum (liquid), $v_{max}$ cm$^{-1}$: 1705, 1630.

PREPARATION 39

(3S,4S)-3-[(1R)-1-(t-Butyldimethylsilyloxy)ethyl]-4-{2(S)-[4-(2-p-nitrobenzyloxycarbonyloxyethyl)-piperazin-1-ylcarbonyl]-1-(p-nitrobenzyloxycarbonyl)-pyrrolidin-4(S)-yl]-thiocarbonylethyl}azetidin-2-one A solution of 99 mg (0.20 mmole) of S-2-diethylcarbamoylphenyl 2(R)-{(3S,4S)-3-[1(R)-(t-butyldimethylsilyloxy-)ethyl]-2-oxo-4-azetidinyl}thiopropionate (prepared as described in Example 6), 135 mg (0.22 mmole) of (2S,4S)-2-{4-[2-(4-nitrobenzyloxycarbonyl) oxyethyl]-1-piperazinylcarbonyl}-4-mercapto-1-(4-nitrobenzyloxycarbonyl) pyrrolidine and 30 mg (0.30 mmole) of triethylamine in 2 ml of methylene chloride was stirred at room temperature for 17 hours. At the end of this time, the solvent was removed by distillation under reduced pressure, and the residue was dissolved in ethyl acetate. The resulting solution was washed with a 2N aqueous solution of sodium hydroxide, with water and with a saturated aqueous solution of sodium chloride, in that order. The solvent was then removed by distillation under reduced pressure, and the residue was purified by column chromatography through 25 g of silica gel, using a 3:2 by volume mixture of acetone and hexane as the eluent, to give 182 mg of the title compound as a foam in a quantitative yield.

PREPARATION 40

(3S,4S)-3-[(1R)-1-Hydroxyethyl]-4-{2(S) -[4-(2-p-nitrobenzyloxycarbonyloxyethyl)-piperazin-1-ylcarbonyl]-1-(p-nitrobenzyloxycarbonyl)pyrrolidin-4(S)-yl]-thiocarbonylethyl}azetidin-2-one 24 ml of 3N aqueous hydrochloric acid were added dropwise, whilst ice-cooling and stirring, to a solution of 8.1 g of (3S,4S)-3-[(R)-1-(t-butyldimethylsilyloxy)ethyl ]-4-{1(R)-{2(S)-[4-(2-4'-nitrobenzyloxycarbonyloxyethyl) piperazin-1-ylcarbonyl]-1-(4-nitrobenzyloxycarbonyl) pyrrolidin-4(S)-ylthiocarbonyl}ethyl}-azetidin-2-one (prepared as described in Preparation 39) in 80 ml of methanol, and the mixture was stirred at the same temperature for 30 minutes and then allowed to stand overnight in a refrigerator. At the end of this time, the reaction mixture was ice-cooled and its pH was adjusted to a value of 5 to 6 by the addition of sodium hydrogencarbonate. The mixture was then concentrated by evaporation under reduced pressure, and the resulting residue was mixed with a small amount of water and extracted with ethyl acetate. The aqueous layer was saturated with sodium chloride and extracted with ethyl acetate. The extracts were combined and then freed from the solvent by distillation under reduced pressure. The residue was purified by column chromatography through 150 g of silica gel, using a gradient elution method with mixtures of ethyl acetate and methanol ranging from 20:1 to 10:1 by volume as the eluent, to give 5.9 g of the title compound as a colorless foam.

Infrared Absorption Spectrum (CHCl$_3$), $v_{max}$ cm$^{-1}$: 1752, 1710, 1650, 1607, 1522, 1443, 1404, 1347, 1263.

Nuclear Magnetic Resonance Spectrum (CDCl$_3$, 270 MHz), δ ppm:

1.27 (3H, doublet, J=6.83 Hz);

1.28 (3H, doublet, J=6.35 Hz);

1.82–1.99 (1H, multiplet);

2.10–2.18 (1H, multiplet);

2.40–2.95 (7H, multiplet);

3.03 (1H, doublet of doublets, J=1.95 & 6.35 Hz);

3.37–3.80 (5H, multiplet);

3.78 (1H, doublet of doublets, J=1.95 & 6.84 Hz);

3.95–4.48 (6H, multiplet);

4.68 & 4.73 (together 1H, two triplets, J=8.06 & 7.33 Hz);

5.06 & 6.32 (together 1H, two doublets, J=13.43 & 13.43 Hz);

5.21 (1H, singlet);

5.26 (2H, singlet);

5.99 (1H, broad);

7.45 & 7.50 (together 2H, two doublets, J=8.30 & 8.79 Hz);

7.56 (2H, doublet, J=8.79 Hz);

8.18–8.26 (4H, multiplet).

PREPARATION 41

S-2-diethylaminocarbonyl-6-methylphenyl thiopropionate

Following a procedure similar to that described in Preparation 30 (Method A), the title compound was obtained in a yield of 38%.

Infrared Absorption Spectrum (Kbr), $v_{max}$ cm$^{-1}$: 1703, 1635.

PREPARATION 42

S-2-diethylaminothiocarbonylphenyl thiopropionate 216 mg (0.534 mmole) of Lawesson's reagent were added to a solution of 276 mg (1.04 mmole) of S-2-diethylcarbamoylphenyl thiopropionate (prepared as described in Preparation 30) in 5 ml of toluene, and the resulting mixture was stirred at 100° C. for 20 minutes. It was then cooled, and the resulting mixture was purified by column chromatography through 25 g of silica gel, using a gradient solution method, with mixtures of methylene chloride and hexane ranging from 3:0 to 3:1 by volume as the eluent, to give 386 mg of the title compound, melting at 67.5°–68.5° C.

Infrared Absorption Spectrum (Nujol), $v_{max}$ cm$^{-1}$: 1712, 1505, 1308, 1242, 928.

Nuclear Magnetic Resonance Spectrum (CDCl$_3$, 270 MHz), δ ppm:

1.08 (3H, triplet, J=7 Hz), 1.20 (3H, triplet, J=7 Hz), 1.37 (3H, triplet, J=7 Hz), 2.66 (2H, quartet, J=7 Hz), 3.19 (1H, doublet of quartets, J=14 & 7 Hz), 3.38 (1H, doublet of doublets, J=14 & 7 Hz), 3.70 (1H, doublet of quartets, J=14 & 7 Hz), 4.53 (1H, doublet of doublets, J=14 & 7 Hz), 7.25 (1H, doublet of quartets, J=7 & 3 Hz), 7.31–7.47 (3H, multiplet).

Mass spectrum (m/z): 281 (M$^+$, C$_{14}$H$_{19}$NOS$_2$).

PREPARATION 43

2-Diethylcarbamoylphenyl propionate 2.0 ml (23 mmole) of oxalyl chloride and 0.050 ml of N,N-dimethylformamide were added, whilst ice-cooling, to a solution of 2.40 g (12.4 mmole) of 2-propionyloxybenzoic acid in 24 ml of methylene chloride, and the resulting mixture was stirred for 1 hour. At the end of this time, the solvent and excess oxalyl chloride were removed by distillation under reduced pressure, and 20 ml of methylene chloride were added to the residue, 1.36 g (13.5 mmole) of triethylamine and 986 mg 13.5 mmole) of diethylamine were then added, whilst ice-cooling, to the resulting solution, and the mixture was stirred for 1 hour. The mixture was then diluted with ethyl acetate, and the organic layer was washed with water. The solvent was removed by distillation under reduced pressure, and the residue was purified by column chromatography through 25 g of silica gel, using a gradient elution method, with mixtures of methylene chloride and ethyl acetate ranging from 10:1 to 7:1 by volume as the eluent, to give 3.0 g (yield 97%) of 2-diethylamioncarbonylphenyl propionate as an oil.

Infrared Absorption Spectrum (liquid film), $v_{max}$ cm$^{-1}$: 1765, 1638, 1430, 1293, 1142.

Nuclear Magnetic Resonance Spectrum (CDCl$_3$, 60 MHz), δ ppm:

1.06 (3H, triplet, J=7 Hz), 1.20 (6H, triplet, J=7 Hz), 2.52 (2H, quartet, J=7 Hz), 3.15 (2H, quartet, J=7 Hz), 3.49 (2H, quartet, J=7 Hz), 7.0–7.6 (4, multiplet).

Mass spectrum (m/z): 249 (M$^+$, C$_{14}$H$_{19}$NO$_3$).

EXAMPLE 18

4-Nitrobenzyl (1R,5S,6S)-2-[(3S,5S)-5-dimethylcarbamoyl-1-(4-nitrobenzyloxycarbonyl) -3-pyrrolidinylthio]-1-methyl-6-[1(R)-trimethylsilyloxyethyl]-1-carbapen-2-em-3-carboxylate

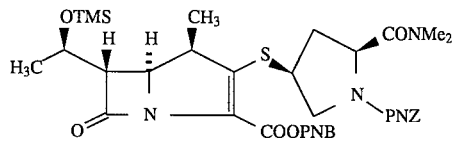

2 ml of a tetrahydrofuran solution containing 68 mg (0.19 mmol) of (2S,4)-2-dimethylcarbamoyl-1-(4-nitrobenzyloxycarbonyl) -4-mercaptopyrrolidine were cooled in tetrahydrofuran solution of bromomagnesium N-isopropyl-N-cyclohexylamide were added dropwise over a period of 2 minutes. The mixture was stirred for a further 10 minutes at this temperature, and then 1 ml of a tetrahydrofuran solution containing 100 mg of 4-nitrobenzyl (1R,5S,6S)-2-(2-diethylcarbamoylphenylsulfinyl)-1-methyl-6-[1(R)-trimethylsilyloxyethyl]-1-carbapen-2-em-3-carboxylate (prepared as described in Example 38) was added. The mixture was stirred for a further 15 minutes at this temperature, after which ice water was added. The reaction mixture was then diluted with ethyl acetate, washed with an aqueous solution of ammonium chloride then with a saturated aqueous solution of sodium chloride. The solvent was then removed by distillation under reduced pressure, and the resulting residue was purified by column chromatography through 10 g of silica gel, eluted with ethyl acetate, to give 94 mg (yield 78%) of the title compound as a foam-like solid.

Infrared Absorption Spectrum (liquid film), $v_{max}$ cm$^{-1}$: 1773, 1711, 1655, 1522, 1345, 1142, 845.

Nuclear Magnetic Resonance Spectrum (CDCl$_3$, 270 MHz) δ ppm:

0.13 (4.5H, singlet);
0.14 (4.5H, singlet);
1.25–1.29 (6H, multiplet);
1.89–2.00 (1H, multiplet);
2.67–2.80 (1H, multiplet);
2.94 (1.5H, singlet);
2.98 (1.5H, singlet);
3.00 (1.5H, singlet);
3.11 (1.5H, singlet);
3.22–3.27 (1H, multiplet);
3.30–3.40 (1H, multiplet);
3.46–3.57 (1H, multiplet);
3.60–3.76 (1H, multiplet);
4.02–4.30 (3, multiplet);
4.72 (0.5H, triplet, J=8 Hz);
4.76 (0.5H, triplet, J=8 Hz);
5.07 (0.5H, doublet, J=14 Hz);
5.22 (1H, singlet);
5.25 (1H, doublet, J=14 Hz);
5.30 (0.5H, doublet, J=14 Hz);
5.46 (1H, doublet, J=14 Hz);
7.44 (1H, doublet, J=9 Hz);
7.52 (1H, doublet, J=9 Hz);
7.65 (2H, doublet, J=9 Hz);
8.20 (1H, doublet, J=9 Hz);
8.21 (3H, doublet, J=9 Hz).

Mass spectrum (m/z): 754 [M$^+$ (C$_{35}$H$_{43}$N$_5$O$_{11}$Ssi)-CH$_3$].

EXAMPLE 19

4-Nitrobenzyl (1R,5S,6S)-2-[(2S,4S)-2-dimethylcarbamoyl-1-(4-nitrobenzyloxycarbonyl) -4-pyrrolidinylthio]-1-methyl-6-[1(R)-butyldimethylsilyloxyethyl]-1-carbapen-2-em-3-carboxylate

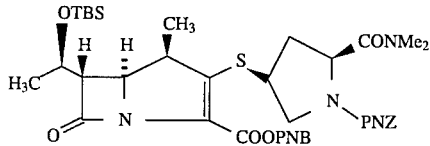

(a) Following a procedure similar to that described in Example 18, but using 4-nitrobenzyl (1R,5S,6S)-2-dimethylcarbamoylphenylsulfinyl) -1-methyl-6-[1(R)-t-butyldimethylsilyloxyethyl]-1-carbapen-2-em-3-carboxylate (prepared as described in Example 39), the title compound was obtained as a foam-like solid in a yield of 86%.

(b) Following a procedure similar to that described in Example 18, but using 4-nitrobenzyl (1R,5S,6S)-2-[2-(2H-1,3,4,5,6,7-hexahydro-1-azepinyl) carbonylphenylsulfinyl]-1-methyl-6-[1(R)-t-butyldimethylsilyloxyethyl] -1-carbapen-2-em-3-carboxylate (prepared as described in Example 41), the title compound was obtained as a foam-like solid in a yield of 83%.

(c) 25 µl (0.144 mmol) of diisopropylethylamine were added to 2 ml of a tetrahydrofuran suspension containing 50 mg (0.071 mmol) of 4-nitrobenzyl (1R,5S,6S)-2-(2-diethylcarbamoylphenylsulfonyl) -1-methyl-6-[1(R)-t-butyldimethyl-silyloxyethyl]-1-carbapen-2-em-3-carboxylate (prepared as described in Example 42), 30 mg (0.086 mmol) of (2S,4S)-dimethylcarbamoyl-1-(4-nitrobenzyloxycarbonyl)-4-mercaptopyrrolidine and 76 mg (0.294 mmol) of a magnesium bromide-diethyl ether complex. The resulting suspension was then stirred for 94 hours. At the end of this time, the reaction solution was diluted with ethyl acetate, washed with water and then with a saturated aqueous solution of sodium chloride. The solvent was then removed by distillation under reduced pressure, and the resulting residue was purified by column chromatography through silica gel, using a 1:1 by volume mixture of methylene chloride and ethyl acetate as the eluent, to obtain 40 mg (yield 69%) of the title compound as a foam-like solid.

(d) Following a procedure similar to that described in Example 18, but using 76 mg of 4-nitrobenzyl (1R,5S, 6S)-2-(2-diethylcarbamoylphenylsulfonyl)-1-methyl -6-[1(R)-t-butyldimethylsilyloxyethyl]-1-carbapen-2-em-3-carboxylate (prepared as described in Example 42) and 46 mg of (2S,4S)-dimethylcarbamoyl-1-(4-nitrobenzyloxycarbonyl)-4-mercaptopyrrolidine, the title compound was obtained in a yield of 78%.

(e) Following a procedure similar to that described in Example 18, but using 101 mg of 4-nitrobenzyl (1R,5S, 6S)-6-[1(R)-t-butyldimethylsilyloxyethyl]-1-methyl-2-[2-(4-nitrobenzyloxycarbonyl)aminoethylsulfinyl]-1-carbapen-2-em-3-carboxylate (prepared as described in Preparation 48) and 61 mg of (2S,4S)-dimethylcarbamoyl-1-(4-nitrobenzyloxycarbonyl)-4-mercaptopyrrolidine, the title compound was obtained in a yield of 83%.

(f) Following a procedure similar to that described in Example 18, 100 mg of 4-nitrobenzyl (1R,5S,6S,)-6-[1(R) -t-butyldimethylsilyloxyethyl]-1-methyl-2-ethylsulfinyl-1-methyl-1-carbapen-2-em-3-carboxylate (prepared as described in Preparation 49) was allowed to react with 79 mg of (2S,4S)-dimethylcarbamoyl-1-(4-nitrobenzyloxycarbonyl)-4-mercaptopyrrolidine, and the product was purified by silica gel column chromatography, using ethyl acetate as the eluent, to give a fraction containing the title compound in a yield of 87%. This fraction, which contained impurities which could not be separated by silica gel column chromatography, showed a purity of 83.5% by as determined the area ratio according to liquid chromatography.

(g) 75 µl of a hexane solution containing 1.6M of butyllithium was added to 1 ml of an ice-cooled toluene solution containing 18 µl (0.13 mmol) of diisopropylamine, and the mixture was stirred for 10 minutes. At the end of this time, 125 µl (0.12 mmol) of a hexane solution containing 0.97M of diethylaluminium chloride was added and the mixture was stirred for a further 20 minutes at this temperature. The diethylaluminium diisopropylamide solution thus obtained was added to 2 ml of an ice-cooled tetrahydrofuran solution containing 43 mg (0.12 mmol) of 2S,4S)-dimethylcarbamoyl-1-(4-nitrobenzyloxycarbonyl)-4-mercaptopyrrolidine, and stirred for 15 minutes at this temperature. At the end of this time, 1 of a tetrahydrofuran solution containing 68 mg (0.10 mmol) of 4-nitrobenzyl (1R,5S,6S)-2-(2-diethylcarbamoylphenylsulfinyl)-1-methyl-6-[1(R)-t-butyldimethylsilyloxyethyl]-1-carbapen-2-em-3-carboxylate (prepared as described in Example 39) was added to the reaction mixture, and the mixture was stirred for 105 minutes. A saturated aqueous solution of ammonium chloride and then ethyl acetate were added, and the precipitate which formed was removed. The organic layer was separated, and washed with water and then with a saturated aqueous solution of sodium chloride. The solvent was then removed by distillation under reduced pressure. The resulting residue was purified by column chromatography through 10 g of silica gel, using a 1:3 by volume mixture of benzene and ethyl acetate as the eluent, to obtain 60 mg of a fraction containing the title compound in a yield of 74%. This fraction showed a plurality of 56% as determined by the area ratio according to liquid chromatography.

The properties of the title compound obtained in (a) to (g) above are shown below.

Infrared Absorption Spectrum (liquid film), $\nu_{max}$ cm$^{-1}$: 1775, 1713, 1657, 1522, 1345, 1142, 837.

Nuclear Magnetic Resonance Spectrum (CDCl$_3$, 270 MHz) δ ppm:

0.07–0.09 (6H, multiplet);
0.85 (4.5H, singlet);
0.87 (4.5H, singlet);
1.23–1.29 (6H, multiplet);
1.88–2.00 (1H, multiplet);
2.67–2.81 (1H, multiplet);
2.94 (1.5H, singlet);
2.98 (1.5H, singlet);
2.99 (1.5H, singlet);
3.11 (1.5H, singlet);
3.23–3.41 (2H, multiplet);
3.46–3.57 (1H, multiplet);
3.61–3.78 (1H, multiplet);
4.03–4.32 (3H, multiplet);
4.73 (0.5H, triplet, J=8 Hz);
4.77 (0.5H, triplet, J=8 Hz);
5.07 (0.5H, doublet, J=13 Hz);
5.22 (1H, singlet);
5.25 (1H, doublet, J=13 Hz);
5.30 (0.5H, doublet, J=13 Hz);
5.45 (1H, doublet, J=13 Hz);
7.45 (1H, doublet, J=9 Hz);
7.52 (1H, doublet, J=9 Hz);
7.65 (2H, doublet, J=9 Hz);
8.20 (1H, doublet, J=9 Hz);
8.21 (3H, doublet, J=9 Hz).
Mass spectrum (m/z): 754 (M$^+$ (C$_{38}$H$_{49}$N$_5$O$_{11}$Ssi)-C$_4$H$_9$)

EXAMPLE 20

4-Nitrobenzyl (1R,5S,6S)-6-[1(R)-t-butyldimethylsilyloxyethyl]-1-methyl -2-{(2S,4S)-2-[4-{2-(4-nitrobenzyloxycarbonyloxy)ethyl}piperazin-1-yl-carbonyl]-1-[(4-nitrobenzyloxycarbonyl)pyrrolidin-4-ylthio]}-1-carbapen-2-em-3-carboxylate

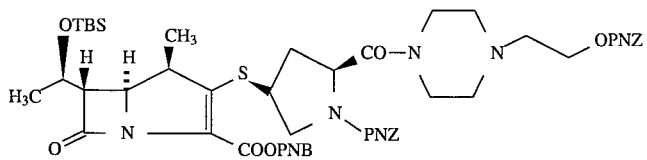

(a) Following a procedure similar to that described in Example 18, but using 4-nitrobenzyl (1R,5S,6S)-2-(2-diethylcarbamoylphenylsulfinyl)-1-methyl-6-[1(R)-t-butyldimethylsilyloxyethyl]-1-carbapen-2-3-carboxylate (prepared as described in Example 39) and (2S,4S)-4-mercapto-2-{4-[2-(4-nitrobenzyloxycarbonyloxy)ethyl]-piperazin-1-ylcarbonyl}-1-(4-nitrobenzyloxycarbonyl)-pyrrolidine as starting materials, in relative proportions similar to those used in that Example, the title compound was obtained in a yield of 86%. Recrystallization of this product from toluene afforded it in the form of crystals, melting at 134°–136° C.

b) Following a procedure similar to that described in of Example 19(c), but using 4-nitrobenzyl (1R,5S,6S)-2-(2-diethylcarbamoylphenylsulfonyl)-1-methyl-6-[1(R)-t-butyldimethylsilyloxyethyl]-1-carbapen-2-3-carboxylate (prepared as described in Example 42) and (2S,4S)-4-mercapto-2-{4-[2-(4-nitrobenzyloxycarbonyloxy)ethyl]-piperazin-1-ylcarbonyl}-1-(4-nitrobenzyloxycarbonyl)-pyrrolidine as starting materials, in relative proportions similar to those used in that Example, the title compound was obtained in a yield of 60%.

Infrared Absorption Spectrum (KBr), $\nu_{max}$ cm$^{-1}$: 1773, 1750, 1709, 1653, 1522, 1345, 1260, 1146, 837.

Nuclear Magnetic Resonance Spectrum (CDCl$_3$, 270 MHz) δ ppm:

0.06–0.09 (6H, multiplet);
0.85 (4.5H, singlet);
0.86 (4.5H, singlet);
1.22–1.29 (6H, multiplet);
1.84–1.99 (1H, multiplet);
2.38–2.81 (7H, multiplet);
3.23–3.77 (8H, multiplet);
4.04–4.32 (5H, multiplet);
4.73 (1H, doublet of triplets, J=14 & 8 Hz);
5.07 (0.5H, doublet, J=14 Hz);
5.22 (1H, singlet);
5.26 (2H, singlet);
5.25 (1H, doublet, J=14 Hz);
5.30 (0.5H, doublet, J=14 Hz);
5.45 (1H, doublet, J=14 Hz);
7.44 (1H, doublet, J=9 Hz);
7.52 (1H, doublet, J=9 Hz);
7.56 (2H, doublet, J=9 Hz);
7.65 (2H, doublet, J=9 Hz);
8.17–8.26 (6H, multiplet).

EXAMPLE 21

4-Nitrobenzyl (1R,5S,6S)-6-[1(R)-t-butyldimethylsilyloxyethyl]-1-methyl -2-{1(S)-[N-(4-nitrobenzyloxycarbonyl)acetimidoyl]pyrrolidin-3-ylthio}-1-carbapen-2-em-3-carboxylate

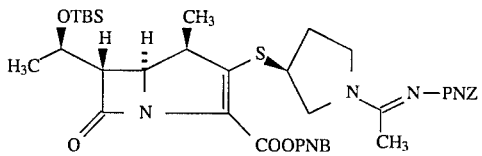

a) Following a procedure similar to that described in Example 18, but using 4-nitrobenzyl (1R,5S,6S)-2-(2-diethylcarbamoylphenylsulfinyl) -1-methyl-6-[1(R)-t-butyldimethylsilyloxyethyl]-1-carbapen-2-em-3-carboxylate (prepared as described in Example 39) and (S)-3-mercapto-1-[N-(4-nitrobenzyloxycarbonyl)acetimidoyl] pyrrolidine as starting materials, in relative proportions similar to those used in that Example, the title compound was obtained in a yield of 79%. Recrystallization from a mixture of diisopropyl ether and ethyl acetate afforded it in the form of crystals, melting at 171°–172.5° C.

(b) 4 ml of a tetrahydrofuran suspension containing 101 mg (1.148 mmol) of 4-nitrobenzyl (1R,5S,6S)-2-(2-diethylcarbamoylphenylsulfinyl) -1-methyl-6-[1(R)-t-butyldimethylsilyloxyethyl]-1-carbapen-2-em-3-carboxylate (prepared as described in Example 39), 106 mg (0.328 mmole) of (S)-3-mercapto-1-[N-(4-nitrobenzyloxycarbonyl) acetimidoyl]pyrrolidine, and 155 mg (0.600 mmol) of a magnesium bromide-diethyl ether complex was stirred for 6 hours. At the end of this time, the reaction mixture was diluted with ethyl acetate, and washed with water and then with a saturated aqueous solution of sodium chloride. The solvent was then removed by distillation under reduced pressure. The resulting residue was purified by column chromatography through 5 g of silica gel. The title compound containing a small amount of impurities was obtained by elution with a 1:1 by volume mixture of hexane and ethyl acetate. This impure compound was purified by additional chromatography through 5 g of silica gel followed by elution with a 1:3 by volume mixture of ethyl acetate and methylene chloride, to afford 74 mg (yield 64%) of the title compound.

(c) Following a procedure similar to that described in Example 19(c), but using 4-nitrobenzyl (1R,5S,6S)-2-(2-diethylcarbamoylphenylsulfonyl) -1-methyl-6-[1(R)-t-butyldimethylsilyloxyethyl]-1-carbapen-2-em-3-carboxylate (prepared as described in Example 42) and (S)-3-mercapto-1-[N-(4-nitrobenzyloxycarbonyl)acetimidoyl]pyrrolidine as starting materials, in relative proportions similar to those used in that Example, the title compound was obtained in a yield of 39%.

Infrared Absorption Spectrum (KBr), $v_{max}$ cm$^{-1}$: 1769, 1694, 1675, 1567, 1520, 1345, 1242, 839.

Nuclear Magnetic Resonance Spectrum (CDCl$_3$, 270 MHz) δ ppm:

0.08 (3H, singlet);
0.09 (3H, singlet);
0.87 (9H, singlet);
1.22–1.31 (6H, multiplet);
1.96–2.16 (1H, multiplet);
2.29 (0.75H, singlet);
2.32 (2.25H, singlet);
2.35–2.51 (1H, multiplet);
3.23–3.35 (2H, multiplet);
3.44–4.05 (5H, multiplet);
4.24–4.32 (2H, multiplet);
5.22 (2H, singlet);
5.24 (1H, doublet, J=14 Hz);
5.45 (1H, doublet, J=14 Hz);
7.56 (2H, doublet, J=9 Hz);
7.65 (2H, doublet, J=9 Hz);
8.19 (2H, doublet, J=9 Hz);
8.21 (2H, doublet, J=9 Hz).

Mass spectrum (m/z): 781 (M$^+$, $C_{37}H_{47}N_5O_{10}SSi$).

EXAMPLE 22

4-Nitrobenzyl (1R,5S,6S)-6-[1(R)-t-butyldimethylsilyloxyethyl]-1-methyl -2-[2-(4-nitrobenzyloxycarbonyl)aminoethylthio]-1-carbapen-2-em-3-carboxylate

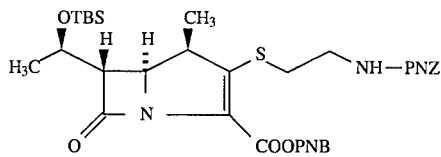

(a) Following a procedure similar to that described in Example 18, but using 4-nitrobenzyl (1R,5S,6S)-2-(2-diethylcarbamoylphenylsulfinyl) -1-methyl-6-[1(R)-t-butyldimethylsilyloxyethyl]-1-carbapen-2-em-3-carboxylate (prepared as described in Example 39) and 2-(4-nitrobenzyloxycarbonyl)aminoethylmercaptan as starting materials, in relative proportions similar to those used in that Example, the title compound was obtained as a foam-like solid in a yield of 92%.

(b) Following a procedure similar to that described in Example 21(b), but using 4-nitrobenzyl (1R,5S,6S)-2-(2-diethylcarbamoylphenylsulfinyl) -1-methyl-6-[1(R)-t-butyldimethylsilyloxyethyl]-1-carbapen-2-em-3-carboxylate (prepared as described in Example 39) and 2-(4-nitrobenzyloxycarbonyl)aminoethylmercaptan as starting materials, in relative proportions similar to those used in that Example, the title compound was obtained in a yield of 83%.

(c) Following a procedure similar to that described in Example 21(b), but using the S-oxide isomer of lower polarity of the 4-nitrobenzyl (1R,5S,6S)-6-[1(R)-t-butyldimethylsilyloxyethyl]-1-methyl-2-phenylsulfinyl-1-carbapen-2-em-3-carboxylate (prepared as described in Preparation 2) and 2-(4-nitrobenzyloxycarbonyl)aminoethylmercaptan as starting materials, in relative proportions similar to those used in that Example, the title compound was obtained in a yield of 81%.

(d) Following the same procedure as that described in (c) above, but using the corresponding S-oxide of higher polarity, the title compound was obtained in a yield of 89%.

(e) Following a procedure similar to that described in Example 19(c), but using 4-nitrobenzyl (1R,5S,6S)-2-(2-diethylcarbamoylphenylsulfonyl)-1-methyl-6-[1(R)-t-butyldimethylsilyloxyethyl]-1-carbapen-2-em-3-carboxylate (prepared as described in Example 42) and 2-(4-nitrobenzyloxycarbonyl)aminoethylmercaptan as starting materials, in relative proportions similar to those used in that Example, the title compound was obtained in a yield of 87%.

(f) Following a procedure similar to that described in Example 19 (c), but using 4-nitrobenzyl (1R,5S,6S)-6-[1(R)-t-butyldimethylsilyloxyethyl]-1-methyl-2-phenylsulfonyl-1-carbapen-2-em-3-carboxylate (prepared as described in Preparation 46) and 2-(4-nitrobenzyloxycarbonyl)aminoethylmercaptan as starting materials, in relative proportions similar to those used in that Example, the title compound was obtained in a yield of 86%.

(g) 0.14 (0.21 mmol) of a cyclohexane solution containing 1.5M of a lithiumdiisopropylamide tetrahydrofuran complex was added to 2 ml of an ice-cooled tetrahydrofuran suspension containing 91 mg (0.352 mmol) of a magnesium bromide-diethyl ether complex, and the resulting mixture was stirred for 10 minutes at this temperature. At the end of this time, 2 ml of a tetrahydrofuran solution containing 55 mg (0.207 mmol) of 2-(4-nitrobenzyloxycarbonyl)aminoethylmercaptan were added to the mixture, which was then stirred for a further 10 minutes in an ice bath. 102 mg (0.174 mmol) of the S-oxide isomer of lower polarity of the 4-nitrobenzyl (1R,5S,6S)-6-[1(R)-t-butyldimethylsilyloxyethyl]-1-methyl-2-phenylsulfinyl-1-carbapen-2-em-3-carboxylate (prepared as described in Preparation 2) and were then added to the mixture, and the mixture was stirred for a further 15 minutes. At the end of this time, a saturated aqueous solution of ammonium chloride was added, and then the mixture was extracted with ethyl acetate. The resulting organic extract was washed first with water and then with a saturated aqueous solution of sodium chloride, after which the solvent was removed by distillation under reduced pressure. The residue was purified by column chromatography through 15 g of silica gel, using a 1:19 by volume mixture of ethyl acetate and hexane as the eluent, to give 104 mg (yield 84%) of the title compound as a foam-like solid.

Infrared Absorption Spectrum (liquid film), $v_{max}$ cm$^{-1}$: 1771, 1723, 1607, 1522, 1347, 1140.

Nuclear Magnetic Resonance Spectrum (CDCl$_3$, 270 MHz) δ ppm:

0.07 (3H, singlet);
0.08 (3H, singlet);
0.86 (9H, singlet);
1.22–1.28 (6H, multiplet);
2.93 (1H, doublet of triplets, J=13 & 7 Hz);
3.11 (1H, doublet of triplets, J=13 & 7 Hz);
3.26 (1H, doublet of doublets, J=3 & 5 Hz);
3.30–3.60 (3H, multiplet);
4.22–4.31 (2H, multiplet);
5.20 (2H, singlet);
5.25 (1H, doublet, J=14 Hz);
5.35 (1H, dull triplet, J=6 Hz);
5.47 (1H, doublet, J=14 Hz);
7.50 (2H, doublet, J=9 Hz);
7.66 (2H, doublet, J=9 Hz);
8.20 (2H, doublet, J=9 Hz);
8.21 (2H, doublet, J=9 Hz).

Mass spectrum (m/z): 714 (M$^+$, C$_{33}$H$_{42}$N$_4$O$_{10}$SSi).

EXAMPLE 23

4-Nitrobenzyl (1R,5S,6S)-6-[1(R)-t-butyldimethylsilyloxyethyl]-1-methyl -2-(4-nitrobenzylthio)-1-carbapen-2-em-3-carboxylate

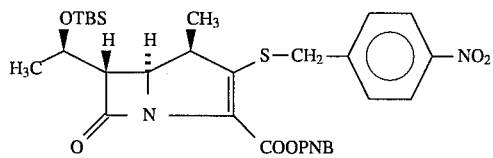

(a) Following a procedure similar to that described in Example 1, but using 4-nitrobenzyl (1R,5S,6S)-2-(2-diethylcarbamoylphenylsulfinyl)-1-methyl -6-[1(R)-t-butyldimethylsilyloxyethyl]-1-carbapen-2-em-3-carboxylate (prepared as described in Example 39) and 4-nitrobenzylmercaptan as starting materials, in relative proportions similar to those used in that Example, the title compound was obtained in a yield of 81%. Recrystallization of this product from a mixture of ethyl acetate and diisopropyl ether the title compound in the form of crystals, melting at 150.5° to 151° C.

(c) Following a procedure similar to that described in Example 21(b), but using 4-nitrobenzyl (1R,5S,6S)-2-(2-diethylcarbamoylphenylsulfinyl) -1-methyl-6-[1(R)-t-butyldimethylsilyloxyethyl]-1-carbapen-2-em-3-carboxylate (prepared as described in Example 39) and 4-nitrobenzylmercaptan as staring materials, in relative proportions similar to those used in that Example, the title compound was obtained in a yield of 88%.

Infrared Absorption Spectrum (KBr), $v_{max}$ cm$^{-1}$: 1773, 1711, 1605, 1522, 1345, 1140.

Nuclear Magnetic Resonance Spectrum (CDCl$_3$, 270 MHz) δ ppm:

0.06 (3H, singlet);
0.08 (3H, singlet);
0.85 (9H, singlet);
1.24 (3H, doublet, J=5 Hz);
1.26 (3H, doublet, J=6 Hz);
3.25 (1H, doublet of doublets, J=2 & 5 Hz);
3.30 (1H, doublet of quartets, J=10 & 6 Hz);
4.11–4.23 (3H, multiplet);
4.25 (1H, quint, J=5 Hz);
5.25 (1H, doublet, J=14 Hz);
5.46 (1H, doublet, J=14 Hz);
7.52 (2H, doublet, J=8 Hz);
7.65 (2H, doublet, J=8 Hz);
8.20 (2H, doublet, J=8 Hz);
8.21 (2H, doublet, J=8 Hz).

Mass spectrum (m/z): 627 (M$^+$, C$_{30}$H$_{37}$N$_3$O$_8$SSi).

EXAMPLE 24

4-Nitrobenzyl (1R,5S,6S)-6-[1(R)-t-butyldimethylsilyloxyethyl]-1-methyl -2-phenylthio-1-carbapen-2-em-3-carboxylate

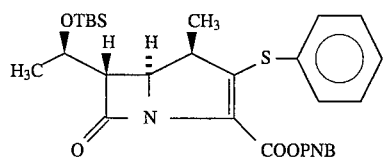

Following a procedure similar to that described in Example 21(b), but using 4-nitrobenzyl (1R,5S,6S)-2-(2-diethylcarbamoylphenylsulfinyl)-1-methyl -6-[1(R)-t-butyldimethylsilyloxyethyl]-1-carbapen-2-em-3-carboxylate (prepared as described in Example 39) and thiophenol as starting materials, in relative proportions similar to those used in that Example, the title compound was obtained as crystals in a yield of 72%. Recrystallization of this product from a mixture of ethyl acetate and hexane afforded crystals of the title compound melting at 149° to 150° C.

Infrared Absorption Spectrum (KBr), $v_{max}$ cm$^{-1}$: 1768, 1694, 1607, 1335, 1136, 839.

Nuclear Magnetic Resonance Spectrum (CDCl$_3$, 270 MHz) δ ppm:
0.06 (6H, singlet);
0.84 (9H, singlet);
0.95 (3H, doublet, J=7 Hz);
1.17 (3H, doublet, J=6 Hz);
3.06 (1H, doublet of quartets, J=10 & 7 Hz);
3.19 (1H, doublet of doublets, J=2 & 5 Hz);
4.19 (1H, doublet of doublets, J=2 & 10 Hz);
4.25 (1H, doublet of quartets, J=5 & 6 Hz);
5.33 (1H, doublet, J=14 Hz);
5.50 (1H, doublet, J=14 Hz);
7.37–7.43 (3H, multiplet);
7.51–7.57 (2H, multiplet);
7.69 (2H, doublet, J=8 Hz);
8.22 (2H, doublet, J=8 Hz).
Mass spectrum (m/z): 568 (M$^+$, C$_{29}$H$_{36}$N$_2$O$_6$SSi).

EXAMPLE 25

4-Nitrobenzyl (1R,5S,6S)-2-[2-(1-perhydroazepinylcarbonyl) phenylthio]-1-methyl-6-[1(R)-t-butyldimethylsilyloxyethyl]-1-carbapen-2-em-3-carboxylate

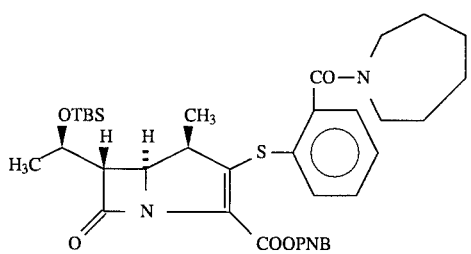

Following a procedure similar to that described in Example 18, but using 4-nitrobenzyl (1R,5S,6S)-2-(2-diethylcarbamoylphenylsulfinyl)-1-methyl -6-[1(R)-t-butyldimethylsilyloxyethyl]-1-carbapen-2-em-3-carboxylate (prepared as described in Example 39) and 2-(1-perhydroazepinylcarbonyl)phenylmercaptan as starting materials, in relative proportions similar to those used in that Example, the title compound was obtained in a yield of 72%. The compound was found to be the same as the compound prepared as described in Example 36 and had the same physicochemical properties.

EXAMPLE 26

4-Nitrobenzyl (1R,5S,6S)-6-[1(R)-t-butyldimethylsilyloxyethyl]-2-ethylthio-1-methyl-1-carbapen-2-em-3-carboxylate

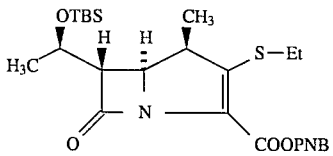

Following a procedure similar to that described in Example 18, but using 4-nitrobenzyl (1R,5S,6S)-2-(2-diethylcarbamoylphenylsulfinyl)-1-methyl -6-[1(R)-t-butyldimethylsilyloxyethyl]-1-carbapen-2-em-3-carboxylate (prepared as described in Example 39) and ethylmercaptan as starting materials, in relative proportions similar to those used in that Example, the title compound was obtained as a crystal in a yield of 83%. Recrystallization of this product from diisopropyl ether afforded the title compound in the form of crystals melting at 121°–121.5° C.

Infrared Absorption Spectrum (KBr), ν$_{max}$ cm$^{-1}$: 1757, 1700, 1522, 1499, 1339, 1215, 1144, 839.

Nuclear Magnetic Resonance Spectrum (CDCl$_3$, 270 MHz) δ ppm:
0.07 (3H, singlet);
0.08 (3H, singlet);
0.86 (9H, singlet);
1.25 (3H, doublet, J=7 Hz);
1.26 (3H, doublet, J=6 Hz);
1.34 (3H, triplet, J=7 Hz);
2.86 (1H, doublet of doublets, J=12 & 7 Hz);
2.90 (1H, doublet of quartets, J=12 & 7 Hz);
3.23 (1H, doublet of doublets, J=3 & 6 Hz);
3.35 (1H, doublet of quartets, J=9 & 7 Hz);
4.20 (1H, doublet of doublets, J=3 & 9 Hz);
4.26 (1H, quartet, J=6 Hz);
5.25 (1H, doublet, J=14 Hz);
5.46 (1H, doublet, J=14 Hz);
7.66 (2H, doublet, J=9 Hz);
8.21 (2H, doublet, J=9 Hz).
Mass spectrum (m/z): 520 (M$^+$, C$_{25}$H$_{36}$N$_2$O$_6$SSi).

EXAMPLE 27

4-Nitrobenzyl (1R,5S,6S)-2-[(3S,5S)-5-dimethylcarbamoyl-1-(4-nitrobenzyloxycarbonyl)-3-pyrrolidinylthio]-1-methyl-5-[1(R)-hydroxyethyl]-1-carbapen-2-em-3-carboxylate

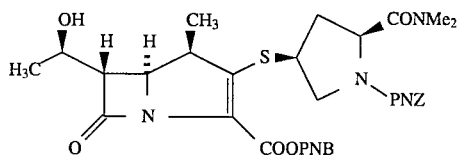

27(a) 4-Nitrobenzyl (1R,5S,6S)-2-(2-diethylcarbamoylphenylsulfinyl)-1-methyl -6-[1(R)-t-hydroxyethyl]-1-carbapen-2-em-3-carboxylate Following a procedure similar to that described in Example 38, but using 467 mg (0.843 mmol) of 4-nitrobenzyl (1R,5S,6S)-2-(2-diethylcarbamoylphenylthio)-1-methyl -6-[1(R)-t-hydroxyethyl]-1-carbapen-2-em-3-carboxylate (prepared as described in Example 37) and 201 mg (0.932 mmol) of m-chloroperbenzoic acid (purity 80%), 464 mg of the title compound were obtained as a crude product. This product was used for the next reaction without further purification.

27(b) 4-Nitrobenzyl (1R,5S,6S)-2-[(3S,5S)-5-diethylcarbamoyl-1-(4-nitrobenzyloxycarbonyl) -3-pyrrolidinylthio]-1-methyl-6-[1(R)-hydroxyethyl]-1-carbapen-2-em-3-carboxylate 3 ml of a tetrahydrofuran solution containing 347 mg (0.982 mmol) of (2S,4S)-dimethylcarbamoyl-1-(4-nitrobenzyloxycarbonyl)-4-mercaptopyrrolidine were cooled in an ice bath, and then 0.97 ml (0.97 mmol) of a tetrahydrofuran solution containing 1M of bromo-magnesium isopropylcyclohexylamide were added dropwise to the cooled solution over a period of 4 minutes, after which the mixture was stirred for 10 minutes. 2 ml of a tetrahydrofuran solution containing 464 mg of the crude 4-nitrobenzyl (1R,5S,6S)-2-(2-diethylcarbamoylphenylsulfinyl)-1-methyl-6-[1(R)-hydroxyethyl]-1-carbapen-2-em-3-carboxylate prepared as described in step (a) above was then added to the solution, and the resulting solution was stirred for a further 30 minutes. At the end of this time, a saturated aqueous solution of ammonium chloride was added, followed by water, and then the reaction mixture was extracted with ethyl acetate 3 times. The organic layers were collected, combined and washed with water and then with a saturated aqueous solution of sodium chloride. The solvent was then removed by distillation under reduced pressure, and the resulting oily residue was subjected to column chromatography through 50 g of silica gel. Elution with a 1:9 by volume mixture of methanol and ethyl acetate afforded 365 mg of the title compound as a foam-like solid (a yield of 62% in terms of the compound of Example 37).

Infrared Absorption Spectrum (KBr), $v_{max}$ cm$^{-1}$: 3500-3300, 1771, 1707, 1649, 1522, 1345, 1140, 855.

Nuclear Magnetic Resonance Spectrum (CDCl$_3$, 270 MHz) δ ppm:

1.25 (1.5H, doublet, J=7 Hz);
1.28 (1.5H, doublet, J=7 Hz);
1.34 (3H, doublet, J=6 Hz);
1.86–1.99 (1H, multiplet);
2.40–3.20 (1H, broad);
2.67–2.81 (1H, multiplet);
2.94 (1.5H, singlet);
2.99 (3H, singlet);
3.11 (1.5H, singlet);
3.23–3.29 (1H, multiplet);
3.34–3.76 (3H, multiplet);
4.04–4.29 (3H, multiplet);
4.73 (0.5H, triplet, J=8 Hz);
4.78 (0.5H, triplet, J=8 Hz);
5.07 (0.5H, doublet, J=14 Hz);
5.21 (1H, singlet);
5.22 (0.5H, doublet, J=14 Hz);
5.23 (1H, doublet, J=14 Hz);
5.48 (1H, doublet, J=14 Hz);
7.43 (1H, doublet, J=8 Hz);
7.51 (1H, doublet, J=8 Hz);
7.64 (2H, doublet, J=8 Hz);
8.20 (1H, doublet, J=9 Hz);
8.17–8.22 (3H, multiplet).

EXAMPLE 28

4-Nitrobenzyl (5S,6S)-6-[1(R)-t-butyldimethylsilyloxyethyl]-2-[(3S,5S)-5-dimethylcarbamoyl-1-(4-nitrobenzyloxycarbonyl) -3-pyrrolidinylthio]-1-carbapen-2-em-3-carboxylate

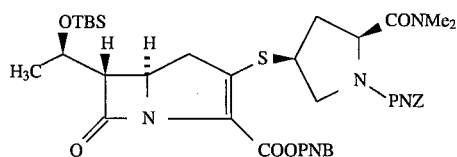

Following a procedure similar to that described in Example 18, but using (2S,4S)-2-dimethylcarbamoyl-1-(4-nitrobenzyloxycarbonyl)-4-mercaptopyrrolidine and the crude 4-nitrobenzyl (5S,6S)-6-[1(R)-t-butyldimethylsilyloxyethyl]-2-phenylsulfinyl-1-carbapen-2-em-3-carboxylate (prepared as described in Preparation 47, but used before purification by column chromatography) as starting materials, in relative proportions similar to those used in that Example, the title compound was obtained as a foam-like solid in a yield of 89%.

Infrared Absorption Spectrum (liquid film), $v_{max}$ cm$^{-1}$: 1179, 1709, 1657, 1522, 1345, 1136, 837.

Nuclear Magnetic Resonance Spectrum (CDCl$_3$, 270 MHz) δ ppm:

0.08–0.09 (6H, multiplet);
0.87 (4.5H, singlet);
0.88 (4.5H, singlet);
1.23–1.27 (3H, multiplet);
1.90–2.03 (1H, multiplet);
2.65–2.79 (1H, multiplet);
2.93 (1.5H, singlet);
2.97 (1.5H, singlet);
2.99 (1.5H, singlet);
3.10 (1.5H, singlet);
3.03–3.30 (3H, multiplet);
3.49–3.71 (2H, multiplet);
4.07–4.30 (3H, multiplet);
4.72 (1H, doublet of triplets, J=14 & 8 Hz);
5.07 (0.5H, doublet, J=14 Hz);
5.23 (1H, singlet);
5.25 (1H, doublet, J=14 Hz);
5.30 (0.5H, doublet, J=14 Hz);
5.44 (1H, doublet, J=14 Hz);
7.44 (1H, doublet, J=9 Hz);
7.52 (1H, doublet, J=9 Hz);
7.64 (2H, doublet, J=9 Hz);
8.19–8.24 (4H, multiplet).

EXAMPLE 29

4-Nitrobenzyl (5R,6S)-6-[1(R)-t-butyldimethylsilyloxyethyl]-2-[(3S,5S)-5-dimethylcarbamoyl-1-(4-nitrobenzyloxycarbonyl) -3-pyrrolidinylthio]-penem-3-carboxylate

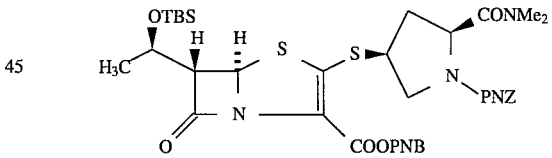

Following a procedure similar to that described in Example 18, but using (2S,4S)-2-dimethylcarbamoyl-1-(4-nitrobenzyloxycarbonyl)-4-mercaptopyrrolidine and 4-nitrobenzyl (5S,6S)-6-[1(R)-t-butyldimethylsilyloxyethyl]-2-ethylsulfinylpenem-3-carboxylate (prepared as described in Preparation 50) as starting materials, in relative proportions similar to those used in that Example, the title compound was obtained as a foam-like solid in a yield of 81%.

Infrared Absorption Spectrum (liquid film), $v_{max}$ cm$^{-1}$: 1788, 1711, 1657, 1522, 1345, 1117, 839.

Nuclear Magnetic Resonance Spectrum (CDCl$_3$, 270 MHz) δ ppm:

0.04 (3H, singlet);
0.07 (3H, singlet);
0.83 (9H, singlet);
1.25 (3H, doublet, J=6 Hz);
1.91–2.05 (1H, multiplet);

2.67–2.85 (1H, multiplet);
2.93 (1.5H, singlet);
2.97 (1.5H, singlet);
2.99 (1.5H, singlet);
3.09 (1.5H, singlet);
3.46–3.60 (1H, multiplet);
3.69–3.80 (2H, multiplet);
4.22–4.40 (2H, multiplet);
4.68–4.79 (1H, multiplet);
5.07 (0.5H, doublet, J=14 Hz);
5.21 (1H, doublet, J=14 Hz);
5.23 (1H, singlet);
5.31 (0.5H, doublet, J=14 Hz);
5.41 (1H, doublet, J=14 Hz);
5.69 (1H, singlet);
7.44 (1H, doublet, J=9 Hz);
7.52 (1H, doublet, J=9 Hz);
7.61 (2H, doublet, J=9 Hz);
8.19–8.24 (4H, multiplet).

EXAMPLE 30

4-Nitrobenzyl (5R,6S)-6-[1(R)-t-butyldimethylsilyloxyethyl]-2-[2-(4-nitrobenzyloxycarbonyl)aminoethylthio]-penem-3-carboxylate

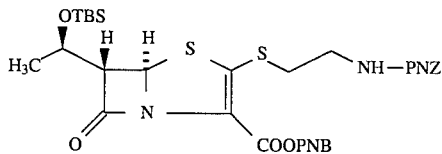

(a) Following a procedure similar to that described in Example 18, but using 4-nitrobenzyl (5R,6S)-6-[1(R)-t-butyldimethylsilyloxyethyl]-2-ethylsulfinylpenem-3-carboxylate (prepared as described in Preparation 50) and 2-(4-nitrobenzyloxycarbonyl)aminoethylmercaptan as starting materials, in relative proportions similar to those used in that Example, the title compound was obtained as a foam-like solid in a yield of 76%.

(b) Following a procedure similar to that described in Example 21(b), but using 4-nitrobenzyl (5R,6S)-6-[1(R)-t-butyldimethylsilyloxyethyl]-2-ethylsulfinyl-penem -3-carboxylate (prepared as described in Preparation 50) and 2-(4-nitrobenzyloxylcarbonyl)aminoethylmercaptan as starting materials, in relative proportions similar to those used in that Example, the title compound was obtained in a yield of 86%.

Infrared Absorption Spectrum (liquid film), $v_{max}$ cm$^{-1}$: 1788, 1725, 1607, 1522, 1347, 1119.

Nuclear Magnetic Resonance Spectrum (CDCl$_3$, 270 MHz), δ ppm:

0.04 (3H, singlet);
0.07 (3H, singlet);
0.83 (9H, singlet);
1.24 (3H, doublet, J=6 Hz);
3.04–3.24 (2H, multiplet);
3.53 (2H, quartet, J=6 Hz);
3.73 (1H, doublet of doublets, J=1 & 4 Hz);
4.36 (1H, doublet of quartets, J=4 & 6 Hz);
5.18–5.27 (1H, multiplet);
5.20 (2H, singlet);
5.21 (1H, doublet, J=14 Hz);
5.42 (1H, doublet, J=14 Hz);
5.67 (1H, doublet, J=1 Hz);
7.50 (2H, doublet, J=9 Hz);
7.62 (2H, doublet, J=9 Hz);
8.20 (2H, doublet, J=9 Hz);
8.22 (2H, doublet, J=9 Hz).

Mass spectrum (m/z): 661 (M$^+$ (C$_{31}$H$_{38}$N$_4$O$_{10}$S$_2$Si)-t-Bu).

EXAMPLE 31

4-Nitrobenzyl (5S,6S)-6-[1(R)-trimethylsiloxyethyl]-2-{(S)-1-[N-(4-nitrobenzyloxycarbonyl)-acetimidoyl]pyrrolidin-3-ylthio}-1-carbapen-2-em-3-carboxylate

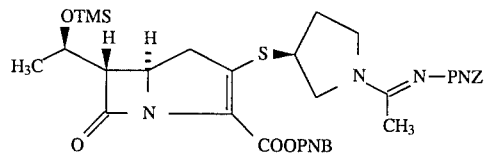

(i) 4-Nitrobenzyl (5S,6S)-6-[1(R)-hydroxyethyl]-2-[2-(4-nitrobenzyloxycarbonyl)aminoethylthio]-1-carbapen-2-em-3-carboxylate was prepared in two steps from thienamycin following the procedure described by S. M. Schmitt et al. [J. Org. Chem. (1980), 45, 1142]. 140 mg (0.239 mmol) of this compound were then dissolved in 2 ml of tetrahydrofuran, and 0.233 ml (1.65 mmol) of triethylamine and 0.147 ml (1.19 mmol) of trimethylsilyl chloride were added to the solution; the resulting mixture was then stirred for 9 hours. Because the starting material did not disappear, a further 0.167 ml (1.20 mmol) of triethylamine and 0.148 ml (1.20 mmol) of trimethylsilyl chloride were added, and the mixture was stirred for a further 1 hour. At the end of this time, the reaction solution was diluted with ethyl acetate, and washed with ice water and then dried with a saturated aqueous solution of sodium chloride. The solvent was then removed by distillation under reduced pressure. The resulting residue was purified by column chromatography through 10 g of silica gel. Elution with a 15:85 by volume mixture of ethyl acetate and methylene chloride yielded 130 mg (83%) of a trimethylsilyl compound in the form of crystals. Recrystallization of these from a mixture of ethyl acetate and hexane afforded crystals of the trimethylsilyl compound melting at 165° to 168° C.

Infrared Absorption Spectrum (KBr), $v_{max}$ cm$^{-1}$: 1773, 1738, 1694, 1607, 1518, 1341, 1140.

Nuclear Magnetic Resonance Spectrum (CDCl$_3$, 270 MHz) δ ppm:

0.14 (9H, singlet);
1.28 (3H, doublet, J=6 Hz);
2.91–3.18 (3H, multiplet);
3.16 (1H, doublet of doublets, J=2 & 6 Hz);
3.27–3.49 (3H, multiplet);
4.11–4.26 (2H, multiplet);
5.20 (2H, singlet);
5.25 (1H, doublet, J=14 Hz);
5.15–5.30 (1H, multiplet);
5.48 (1H, doublet, J=14 Hz);
7.50 (2H, doublet, J=9 Hz);

7.66 (2H, doublet, J=9 Hz);
8.21 (2H, doublet, J=9 Hz);
8.23 (2H, doublet, J=9 Hz).
(ii) Following a procedure similar to that described in Example 38, but using 130 mg of the trimethylsilyl compound obtained as described in step (i) above, 137 mg of a crude S-oxide were obtained.

Infrared Absorption Spectrum (liquid film), $v_{max}$ cm$^{-1}$: 1786, 1721, 1607, 1522, 1349, 1252, 1053.

Nuclear Magnetic Resonance Spectrum (CDCl$_3$, 270 MHz) δ ppm:
0.13 (9H, singlet);
1.25 (1.5H, doublet, J=6 Hz);
1.26 (1.5H, doublet, J=6 Hz);
3.03–3.38 (4.5H, multiplet);
3.52–3.85 (2.5H, multiplet);
4.20–4.45 (2H, multiplet);
3.45–4.07 (5H, multiplet);
4.15–4.27 (2H, multiplet);
5.23 (2H, singlet);
5.24 (1H, doublet, J=14 Hz);
5.48 (1H, doublet, J=14 Hz);
7.56 (2H, doublet, J=9 Hz);
7.65 (2H, doublet, J=9 Hz);
8.20 (2H, doublet, J=9 Hz);
8.22 (2H, doublet, J=9 Hz).

EXAMPLE 32

4-Nitrobenzyl (1R,5S,6S)-6-2-{(3(S)-(4-nitrobenzyloxycarbonyl) aminopyrrolidin-1-ylcarbonyl]-1-methylpyrrolidin-3-ylthio}-6-[1(R)-hydroxyethyl]-1-methyl -1-carbapen-2-em-3-carboxylate

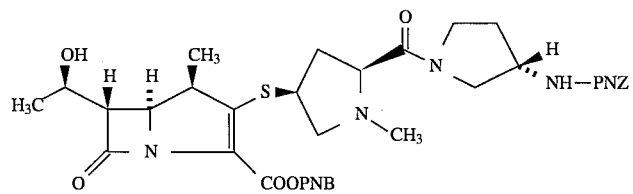

Following a procedure similar to that described in Example 27(b), but using 4-nitrobenzyl (1R,5S,6S)-2-(2-diethylcarbamoylphenylsulfinyl)-1-methyl -6-[1(R)-hydroxyethyl]-1-carbapen-2-em-3-carboxylate [prepared as described in Example 27(a)] and (2S,4S)-4-mercapto-2-[3(S)-4-nitrobenzyloxycarbonyl) aminopyrrolidin-1-ylcarbonyl]-1-methylpyrrolidine as starting materials, in relative proportions similar to those used in that Example, the title compound was obtained as a powder in a yield of 60%.

The physicochemical properties of this compound were in agreement with those of the intermediate 45(a) described in Example 45 of European Patent Publication No. 518 558A.

5.20 (1H, singlet);
5.22 (1H, singlet);
5.26 (0.5H, doublet, J=14 Hz);
5.30 (0.5H, doublet, J=14 Hz);
5.43 (0.5H, doublet, J=14 Hz);
5.47 (0.5H, doublet, J=14 Hz);
5.62–5.70 (1H, multiplet);
7.51 (2H, doublet, J=9 Hz);
7.62 (1H, doublet, J=9 Hz);
7.65 (1H, doublet, J=9 Hz);
8.22 (2H, doublet, J=9 Hz);
8.23 (2H, doublet, J=9 Hz).

(iii) Following a procedure similar to that described in Example 18, but using 137 mg of the crude S-oxide obtained as described in step (ii) above and 84 mg of (S)-3-mercapto-1-[N-(4-nitrobenzyloxycarbonyl)acetimidoyl]pyrrolidine, 126 mg (a yield of 87% calculated in terms of the trimethylsilyl derivative) of the title compound was obtained as crystals. Recrystallization of these from a mixture of ethyl acetate and hexane afforded crystals of the title compound melting at 95° to 96° C. The physicochemical properties of this compound accorded with those of the compound reported by A. Yoshida et al. [Tetrahedron Letters 255, 2793 (1984)].

Infrared Absorption Spectrum (liquid film), $v_{max}$ cm$^{-1}$: 1783, 1700, 1676, 1557, 1520, 1349, 1239, 845.

Nuclear Magnetic Resonance Spectrum (CDCl$_3$), δ ppm:
0.14 (2.25H, singlet);
0.15 (6.75H, singlet);
1.29 (3H, doublet, J=6 Hz);
1.96–2.17 (1H, multiplet);
2.29 (0.75H, singlet);
2.32 (2.25H, singlet);
2.30–2.51 (1H, multiplet);
3.06–3.31 (3H, multiplet);

EXAMPLE 33

4-Nitrobenzyl (1R,5S,6S)-2-[(RS)-5-oxo-3-pyrrolidinylthio]-6-[1(R)-hydroxyethyl]-1-methyl-1-carbapen-2-em-3-carboxylate

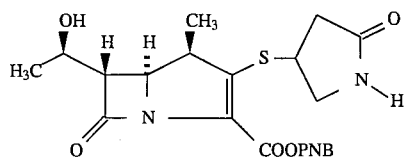

Following a procedure similar to that described in Example 27(b), but using 4-nitrobenzyl (1R,5S,6S)-2-(2-diethylcarbamoylphenylsulfinyl)-1-methyl -6-[1(R)-hydroxyethyl]-1-carbapen-2-em-3-carboxylate [prepared as described in Example 27(a)] and 4-mercapto-2-oxo-pyrrolidine as starting materials, in relative proportions similar to those used in that Example, the title compound was obtained as a powder in a yield of 59%.

The physicochemical properties of this compound were in agreement with those of the intermediate described in Example 11 of Japanese Patent Publication No. Hei 2-49783.

EXAMPLE 34

4-Nitrobenzyl (1R,5S,6S)-2-(2-diethylcarbamoylphenylthio) -1-methyl-6-[1(R)-trimethylsilyloxyethyl]-1-carbapen-2-em-3-carboxylate

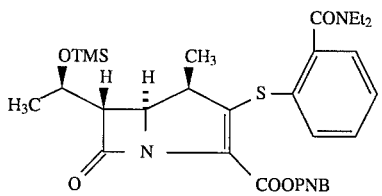

8 ml of methylene chloride solution containing 492 mg (1.09 mmol) of S-2-diethylcarbamoylphenyl 2(R)-[(2S,3S)-3-[1(R)-(trimethylsilyloxy)ethyl]-4-oxo-2-azetidinyl]thiopropionate (prepared as described in Preparation 1) and 0.46 ml (3.30 mmol) of triethylamine were cooled in a salt-ice bath, and then 797 mg (3.27 mmol) of p-nitrobenzyloxyoxalyl chloride were added to the solution. The resulting mixture was then allowed to react for 15 minutes at this temperature. At the end of this time, 0.25 ml (3.27 mmol) of isopropanol was added, and the reaction mixture was stirred for 10 minutes at this temperature to decompose any excess of the acid chloride. The reaction solution was then diluted with ethyl acetate, and washed twice with water and then twice with a saturated aqueous solution of sodium chloride. The solvent was then removed by distillation under reduced pressure. The resulting residue was suspended in toluene, and insoluble matter was filtered off. Toluene was then removed by distillation under reduced pressure, 784 mg (4.40 mmol) of dipropyl ethylphosphonite were added to the residue, and the mixture was stirred for 140 minutes at room temperature. At the end of this time, excess reagent was removed by distillation under reduced pressure, and the residue was dissolved in 65 ml of xylene and heated under reflux for 3 hours. The solvent was then removed by distillation under reduced pressure, and the resulting residue was purified by column chromatography through 50 g of silica gel. The title compound containing a small amount of impurities was obtained by elution with a 1:2 by volume mixture of ethyl acetate and hexane. Further purification by column chromatography under the same conditions yielded 535 mg (78%) of the title compound. Recrystallization of this product from diisopropyl ether afforded the title compound in the form of colorless crystals melting at 202°–203° C.

Infrared Absorption Spectrum (liquid film), $v_{max}$ cm$^{-1}$: 1761, 1695, 1630, 1342, 1207.

Nuclear Magnetic Resonance Spectrum (CDCl$_3$, 270 MHz) δ ppm:

0.10 (9H, singlet);

1.01 (3H, triplet, J=7 Hz)

0.29–1.20 (6H, multiplet);

1.20 (3H, doublet, J=6 Hz);

3.06 (2H, quartet, J=7 Hz);

3.05–3.28 (3H, multiplet);

3.45–3.80 (1H, broad singlet);

4.18–4.25 (2H, multiplet);

5.27 (1H, doublet, J=14 Hz);

5.47 (1H, doublet, J=14 Hz);

7.32–7.65 (4H, multiplet);

7.68 (2H, doublet, J=9 Hz);

8.21 (2H, doublet, J=9 Hz).

Mass spectrum (m/z): 625 (M$^+$, C$_{31}$H$_{39}$N$_3$O$_7$SSi).

EXAMPLE 35

4-Nitrobenzyl (1R,5S,6S)-2-(2-diethylcarbamoylphenylthio) -1-methyl-6-[1(R)-t-butyldimethylsilyloxyethyl] -1-carbapen-2-em-3-carboxylate

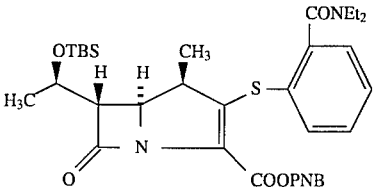

Following a procedure similar to that described in Example 34, but using S-2-diethylcarbamoylphenyl 2(R)-[(2S,3S)-3-[1(R)-t-butyldimethylsilyloxyethyl]-4-oxo-2-azetidinyl]thiopropionate (prepared as described in Preparation 52 of this specification and also in Example 1 of Japanese Patent Application No. Hei 4-174099) as a starting material, in a relative amount similar to that used in that Example, the title compound was obtained in a yield of 80%. Recrystallization of this product from diisopropyl ether afforded the title compound in the form of crystals melting at 166°–166.5° C.

Infrared Absorption Spectrum (Nujol-trade mark), $v_{max}$ cm$^{-1}$: 1762, 1693, 1633, 1340, 1210.

Nuclear Magnetic Resonance Spectrum (CDCl$_3$, 270 MHz) δ ppm:

0.06 (6H, singlet);

0.84 (9H, singlet);

1.01 (3H, triplet, J=7 Hz);

0.93–1.20 (6H, multiplet);

1.16 (3H, doublet, J=6 Hz);

3.00–3.30 (3H, multiplet);

3.07 (2H, quartet, J=7 Hz);

3.40–3.90 (1H, multiplet);

4.21–4.33 (2H, multiplet);

5.28 (1H, doublet, J=14 Hz);

5.44 (1H, doublet, J=14 Hz);

7.27–7.65 (4, multiplet);

7.67 (2H, doublet, J=9 Hz);

8.21 (2H, doublet, J=9 Hz).

Mass spectrum (m/z): 667 (M$^+$, C$_{34}$H$_{45}$N$_3$O$_7$SSi).

EXAMPLE 36

4-Nitrobenzyl (1R,5S,6S)-2-[2-(1-perhydroazepinylcarbonyl) phenylthio]-1-methyl-6-[1(R)-t-butyldimethylsilyloxyethyl]-1-carbapen-2-em-3-carboxylate

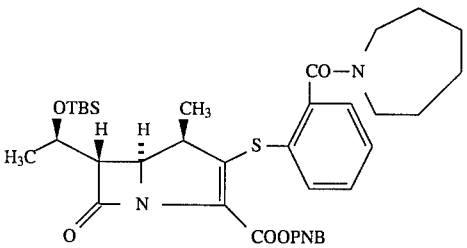

Following a procedure similar to that described in Example 34, but using S-2-(1-perhydroazepinylcarbonylphenyl 2(R)-{(2S,3S)-3-[1(R)-t-butyldimethylsilyloxyethyl]-4-oxo-2-azetidinyl}thiopropionate (prepared as described in Example 9 of Japanese Patent Application No. Hei 5-174099) as a starting material, in a relative amount similar to that used in that Example, the title compound was obtained in a yield of 70%. Recrystallization of this product from diisopropyl ether gave the title compound in the form of crystals melting at 210°–211° C.

Infrared Absorption Spectrum (KBr), $v_{max}$ cm$^{-1}$: 1757, 1700, 1632, 1341, 1212, 1138.

Nuclear Magnetic Resonance Spectrum (CDCl$_3$, 270 MHz) δ ppm:

0.06 (6H, singlet);
0.85 (9H, singlet);
0.95–1.08 (3, multiplet);
1.16 (3H, doublet, J=6 Hz);
1.40–1.85 (8H, multiplet);
3.04–3.34 (5H, multiplet);
3.45–3.65 (1H, broad singlet);
4.20–4.36 (2H, multiplet);
5.29 (1H, doublet, J=14 Hz);
5.46 (1H, doublet, J=14 Hz);
7.30–7.65 (4H, multiplet);
7.68 (2H, doublet, J=9 Hz);
8.22 (2H, doublet, J=9 Hz).
Mass spectrum (m/z): 693 (M$^+$, C$_{36}$H$_{47}$N$_3$O$_7$SSi).

EXAMPLE 37

4-Nitrobenzyl (1R,5S,6S)-2-(2-diethylcarbamoylphenylthio) -1-methyl-6-[1(R)-hydroxyethyl]-1-carbapen-2-em-3-carboxylate

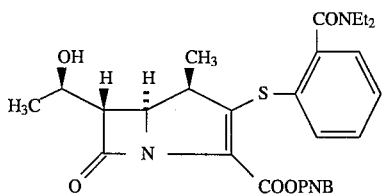

41 mg (0.195 mmol) of citric acid hydrate were added to 30 ml of a solution of 1.072 g (1.71 mmol) of 4-nitrobenzyl (1R,5S,6S)-2-(2-diethylcarbamoylphenylthio) -1-methyl-6-[1(R)-trimethylsilyloxyethyl]-1-carbapen-2-em-3-carboxylate (prepared as described in Example 34) in a 2:1 by volume mixture of methanol and methylene chloride, and the mixture was stirred for 20 minutes at room temperature. At the end of this time, the reaction solution was condensed by distillation under reduced pressure. The resulting residue was purified by column chromatography through 25 g of silica gel. Elution with ethyl acetate afforded 970 mg (quantitative yield) of the title compound as a colorless foam-like solid.

Infrared Absorption Spectrum (neat), $v_{max}$ cm$^{-1}$: 3600-3200 (broad), 1771, 1707, 1612, 1345, 1207.

Nuclear Magnetic Resonance Spectrum (CDCl$_3$, 270 MHz) δ ppm:

1.00 (3H, triplet, J=7 Hz);
0.94–1.15 (6H, multiplet);
1.30 (3H, doublet, J=6 Hz);
3.05 (2H, quartet, J=7 Hz);
3.10–3.28 (3H, multiplet);
3.45–3.80 (1H, broad singlet);
4.20 (1H, quintet, J=7 Hz);
4.25 (1H, doublet of doublets, J=2 & 9 Hz);
5.27 (1H, doublet, J=14 Hz);
5.48 (1H, doublet, J=14 Hz);
7.31–7.65 (4H, multiplet);
7.67 (2H, doublet, J=9 Hz);
8.22 (2H, doublet, J=9 Hz).
Mass spectrum (m/z): 553 (M$^+$, C$_{28}$H$_{31}$N$_3$O$_7$S).

EXAMPLE 38

4-Nitrobenzyl (1R,5S,6S)-2-(2-diethylcarbamoylphenylsulfinyl) -1-methyl-6-[1(R)-trimethylsilyloxyethyl]-1-carbapen-2-em-3-carboxylate

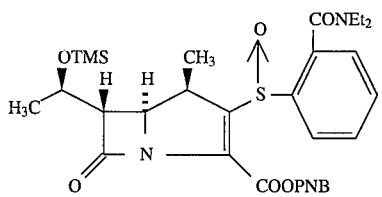

122 mg (1.45 mmol) of sodium hydrogencarbonate were added to 6 ml of a methylene chloride solution containing 304 mg (0.486 mmol) of 4-nitrobenzyl (1R,5S,6S)-2-(2-diethylcarbamoylphenylthio) -1-methyl-6-[1(R)-trimethylsilyloxyethyl]-1-carbapen-2-em-3-carboxylate (prepared as described in Example 34). The mixture was then placed in an ice bath while 105 mg (0.487 mmol) of m-chloroperbenzoic acid (80% purity) were added, with stirring. The reaction mixture was stirred for 1 hour at the same temperature, after which it was diluted with methylene chloride and washed with an ice-cooled dilute aqueous solution of sodium hydrogencarbonate. The solvent was then removed by distillation under reduced pressure. The resulting residue was purified by column chromatography through 25 g of silica gel. Elution with a 2:1 by volume mixture of ethyl acetate and hexane afforded 260 mg (yield 83%) of the title compound as a foam-like solid.

Infrared Absorption Spectrum (liquid film), $v_{max}$ cm$^{-1}$: 1788, 1734, 1630, 1522, 1061.

Nuclear Magnetic Resonance Spectrum (CDCl$_3$, 270 MHz) δ ppm:

0.08 (5.4H, singlet);
0.10 (3.6H, singlet);
1.04–1.27 (12H, multiplet);
2.98–3.53 (5.6H, multiplet);
3.67 (0.4H, doublet of quartets, J=11 & 7 Hz);
4.16–4.23 (1H, multiplet);
4.26 (0.6H, doublet of doublets, J=10 & 3 Hz);
4.34 (0.4H, doublet of doublets, J=10 & 3 Hz);
5.35 (0.4H, doublet, J=14 Hz);
5.38 (0.6H, doublet, J=14 Hz);
5.46 (0.4H, doublet, J=14 Hz);
5.50 (0.6H, doublet, J=14 Hz);
7.27–7.36 (1H, multiplet);
7.50–7.73 (4H, multiplet);
7.84–7.90 (0.4H, multiplet);
8.15–8.26 (2.6H, multiplet).
Mass spectrum (m/z): 641 (M$^+$, C$_{31}$H$_{39}$N$_3$O$_8$SSi).

EXAMPLE 39

4-Nitrobenzyl (1R,5S,6S)-2-(2-diethylcarbamoylphenylsulfinyl) -1-methyl-6-[1(R)-t-butyldimethylsilyloxyethyl] -1-carbapen-2-em-3-carboxylate

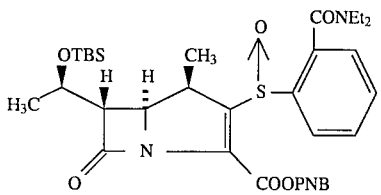

Following a procedure similar to that described in Example 38, but using 4-nitrobenzyl (1R,5S,6S)-2-(2-diethylcarbamoylphenylthio) -1-methyl-6-[1(R)-t-butyldimethylsilyloxyethyl]-1-carbapen-2-em-3-carboxylate (prepared as described in Example 35) as a starting material, in a relative amount similar to that used in that Example, the title compound was obtained as a foam-like solid in a yield of 87%.

Infrared Absorption Spectrum (Nujol), $v_{max}$ cm$^{-1}$: 1788, 1735, 1630, 1523, 1058.

Nuclear Magnetic Resonance Spectrum (CDCl$_3$, 270 MHz) δ ppm:

0.03–0.06 (6H, multiplet);
0.83 (4.5H, singlet);
0.84 (4.5H, singlet);
1.05–1.27 (12H, multiplet);
2.98–3.56 (5.5H, multiplet);
3.59 (0.5H, doublet of quartets, J=10 & 7 Hz);
4.20–4.38 (1H, multiplet);
4.30 (0.5H, doublet of doublets, J=11 & 3 Hz);
4.39 (0.5H, doublet of doublets, J=11 & 3 Hz);
5.34 (0.5H, doublet, J=14 Hz);
5.38 (0.5H, doublet, J=14 Hz);
5.45 (0.5H, doublet, J=14 Hz);
5.49 (0.5H, doublet, J=14 Hz);
7.29–7.36 (1H, multiplet);
7.50–7.71 (4H, multiplet);
7.85–7.89 (0.5H, multiplet);
8.15–8.25 (2.5H, multiplet).

Mass spectrum (m/z): 683 (M$^+$, C$_{34}$H$_{45}$N$_3$O$_8$SSi).

EXAMPLE 40

4-Nitrobenzyl (1R,5S,6S)-2-(2-diethylcarbamoylphenylsulfinyl) -1-methyl-6-[1(R)-hydroxyethyl]-1-carbapen-2-em-3-carboxylate

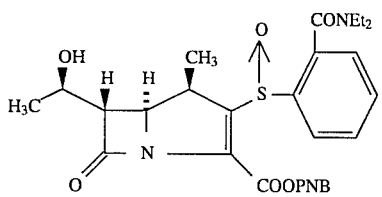

10 ml of a methylene chloride solution containing 554 mg (1.00 mmol) of 4-nitrobenzyl (1R,5S,6S)-2-(2-diethylcarbamoylphenylthio) -1-methyl-6-[1(R)-hydroxyethyl]-1-carbapen-2-em-3-carboxylate (prepared as described in Example 37) were cooled in an ice bath, and then 1.5 ml (1.5 mmol) of a 1m aqueous solution of sodium hydrogencarbonate and then 215 mg (1.00 mmol) of m-chloroperbenzoic acid (80% purity) were added, and the reaction solution was stirred for 90 minutes at the same temperature. At the end of this time, an aqueous solution of sodium sulfite was added to the reaction solution, and the mixture was stirred for 10 minutes to complete the reaction. The reaction solution was then diluted with methylene chloride, ice-cooled, washed with an aqueous solution of sodium hydrogencarbonate and condensed by evaporation under reduced pressure. The resulting residue was purified by column chromatography through 50 g of silica gel. Elution with ethyl acetate afforded 145 mg (yield 25%) of an isomer of the title compound of lower polarity (the isomer is a result of the configuration of the S-oxide), followed by 96 mg (yield 17%) of a higher polarity isomer of the title compound, both as foam-like solids.

Lower Polarity S-Oxide

Infrared Absorption Spectrum (liquid film), $v_{max}$ cm$^-$: 3500–3300, 1786, 1732, 1624, 1522, 1200, 1061.

Nuclear Magnetic Resonance Spectrum (CDCl$_3$, 270 MHz) δ ppm:

1.02–1.11 (6H, multiplet);
1.24 (6H, triplet, J=7 Hz);
3.01 (1H, doublet of quartets, J=10 & 7 Hz);
3.12 (2H, quartet, J=7 Hz);
3.18–3.30 (1H, multiplet);
3.32 (1H, doublet of doublets, J=3 & 6 Hz);
3.39–3.52 (1H, multiplet);
4.19 (1H, quintet, 6 Hz);
4.28 (1H, doublet of doublets, J=3 & 10 Hz);
5.38 (1H, doublet, J=14 Hz);
5.52 (1H, doublet, J=14 Hz);
7.33 (1H, doublet of doublets, J=1 & 8 Hz);
7.58 (1H, doublet of triplets, J=1 & 8 Hz);
7.66 (1H, doublet of triplets, J=1 & 8 Hz);
7.70 (2H, doublet, J=9 Hz);
8.16 (1H, doublet of doublets, J=1 & 8 Hz);
8.24 (2H, doublet, J=9 Hz).

Higher Polarity S-Oxide

Infrared Absorption Spectrum (liquid film), $v_{max}$ cm$^-$: 3500–3300, 1786, 1734, 1624, 1522, 1198, 1061.

Nuclear Magnetic Resonance Spectrum (CDCl$_3$, 270 MHz) δ ppm:

0.83 (3H, doublet, J=7 Hz);
1.09 (3H, triplet, J=7 Hz);
1.18 (3H, triplet, J=7 Hz);
1.28 (3H, doublet, J=6 Hz);
3.18 (2H, quartet, J=7 Hz);
3.20–3.35 (1H, multiplet);
3.40–3.53 (1H, multiplet);
3.47 (1H, doublet of doublets, J=3 & 6 Hz);
3.70 (1H, doublet of quartets, J=10 & 7 Hz);
4.25 (1H, quintet, 6 Hz);
4.38 (1H, doublet of doublets, J=3 & 10 Hz);
5.34 (1H, doublet, J=13 Hz);
5.48 (1H, doublet, J=13 Hz);
7.28–7.32 (1H, multiplet);

7.48–7.56 (2H, multiplet);
7.65 (2H, doublet, J=9 Hz);
7.85–7.91 (1H, multiplet);
8.22 (2H, doublet, J=9 Hz).
Mass spectrum (m/z): 551 [M⁺ (C₂₈H₃₁N₅O₈S).H₂O].

EXAMPLE 41

4-Nitrobenzyl (1R,6S,6S)-2-[2-(1-perhydroazepinylcarbonyl) phenylsulfinyl]-1-methyl-6-[1(R)-t-butyldimethylsilyloxyethyl]-1-carbapen-2-em-3-carboxylate

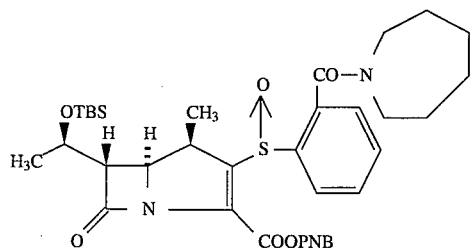

Following a procedure similar to that described in Example 38, but using 4-nitrobenzyl (1R,5S,6S)-2-[2-(1-perhydroazepinylcarbonyl) phenylthio]-1-methyl-6-[1(R)-t-butyldimethylsilyloxyethyl]-1-carbapen-2-em-3-carboxylate (prepared as described in Example 36) as a starting material, in a relative amount similar to that used in that Example, the title compound was obtained as a foam-like solid in a yield of 89%.

Infrared Absorption Spectrum (liquid film), $v_{max}$ cm⁻: 1790, 1734, 1628, 1524, 1347, 1061.

Nuclear Magnetic Resonance Spectrum (CDCl₃, 270 MHz) δ ppm:

0.03, 0.04, 0.05, 0.06 (total 6H, each singlet);
0.75 (1.5H, doublet, J=7 Hz);
0.83 (4.5H, singlet);
0.84 (4.5H, singlet);
1.13 (1.5H, doublet, J=6 Hz);
1.16 (1.5H, doublet, J=6 Hz);
1.28 (1.5H, doublet, J=7 Hz);
1.44–1.80 (8H, multiplet);
3.00 (0.5H, doublet of quartets, J=10 & 7 Hz);
3.11–3.37 (3.5H, multiplet);
3.41–3.50 (1H, multiplet);
3.60–3.77 (1H, multiplet);
4.19–4.31 (1.5H, multiplet);
4.38 (0.5H, doublet of doublets, J=10 & 3 Hz);
5.33 (0.5H, doublet, J=14 Hz);
5.40 (0.5H, doublet, J=14 Hz);
5.46 (0.5H, doublet, J=14 Hz);
5.49 (0.5H, doublet, J=14 Hz);
7.27–7.32 (0.5H, multiplet);
7.36 (0.5H, doublet of doublets, J=7 & 1 Hz);
7.48–7.60 (1.5H, multiplet);
7.63–7.73 (2.5H, multiplet);
7.93–7.96 (0.5H, multiplet);
8.15 (0.5H, doublet of doublets, J=8 & 1 Hz);
8.22 (1H, doublet, J=9 Hz);
8.23 (1H, doublet, J=9 Hz).
Mass spectrum (m/z): 709 (M⁺, C₃₆H₄₇N₃O₈SSi).

EXAMPLE 42

4-Nitrobenzyl (1R,5S,6S)-2-(2-diethylcarbamoylphenylsulfonyl) -1-methyl-6-[1(R)-t-butyldimethylsilyloxyethyl]-1-carbapen-2-em-3-carboxylate

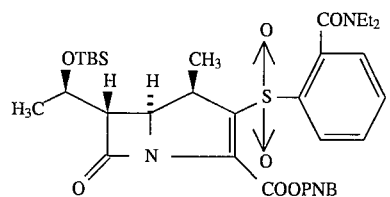

3 ml of a methylene chloride solution containing 157 mg (0.235 mmol) of 4-nitrobenzyl (1R,5S,6S)-2-(2-diethylcarbamoylphenylthio) -1-methyl-6-[1(R)-t-butyldimethylsilyloxyethyl]-1-carbapen-2-em-3-carboxylate (prepared as described in Example 35) was cooled in an ice bath, and 78 mg (0.93 mmol) of sodium hydrogencarbonate and then 78 mg (0.52 mmol) of m-chloroperbenzoic acid (80% purity) were added to the cooled solution. The reaction mixture was then stirred for 20 minutes at the same temperature and for 3.5 hours at room temperature. At then end of this time, an aqueous solution of sodium sulfite was added to the reaction mixture, and the mixture was stirred for 10 minutes to complete the reaction. The reaction solution was then diluted with methylene chloride, washed with an aqueous solution of sodium hydrogencarbonate and condensed with evaporation under reduced pressure. The resulting residue was purified by column chromatography through 15 g of silica gel. Elution with a 4:6 by volume mixture of ethyl acetate and hexane afforded 148 mg (yield 90%) of the title compound as a foam-like solid.

Infrared Absorption Spectrum (liquid film), $v_{max}$ cm⁻: 1794, 1748, 1636, 1524, 1320, 1266, 1161.

Nuclear Magnetic Resonance Spectrum (CDCl₃, 270 MHz) δ ppm:

0.03 (3H, singlet);
0.05 (3H, singlet);
0.83 (9H, singlet);
1.06 (3H, triplet, J=7 Hz);
1.16 (3H, doublet, J=6 Hz);
1.20–1.43 (6H, multiplet);
3.01–3.19 (2H, multiplet);
3.24–3.84 (4H, multiplet);
4.19–4.28 (1H, multiplet);
4.42–4.52 (1H, multiplet);
5.39 (2H, singlet);
7.25–7.34 (1H, singlet);
7.48–7.65 (2H, multiplet);
7.62 (2H, doublet, J=9 Hz);
8.11 (1H, doublet, J=8 Hz);
8.21 (2H, doublet, J=9 Hz).
Mass spectrum (m/z): 700 [M⁺ (C₃₄H₄₅N₃O₉Ssi)+1].

PREPARATION 44

S-2-Diethylcarbamoylphenyl 2(R)-[(2S,3S)-3-(1 R)-(trimethylsilyloxy) ethyl]-4-oxo-3-azetidinyl)-thiopropionate

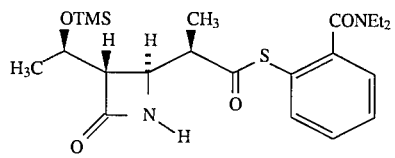

5 ml of 2N aqueous hydrochloric acid were added to 20 ml of a tetrahydrofuran solution containing 1.002 g (2.03) of S-2-diethylcarbamoylphenyl 2(R)-[(2S,3S)-3-(1 R)-t-tyldimethylsilyloxyethyl]-4-oxo-2-azetidinyl]-thiopropionate (prepared as described in Preparation 52 of this specification and also in Example 1 of Japanese Patent Application No. Hei 4-174099), and the mixture was heated for 3 hours at 50° C. At the end of this time, the reaction solution was cooled and extracted with ethyl acetate. The organic extract was washed with a saturated aqueous solution of sodium hydrogencarbonate, with water and then with a saturated aqueous solution of sodium chloride, in that order, after which the solvent was removed by distillation under reduced pressure. The resulting desilylated compound was dissolved in 10 ml of tetrahydrofuran, and 0.60 ml (4.30 mmol) of triethylamine and 0.53 ml of trimethylsilyl chloride were added to the resulting solution. The reaction mixture was then stirred for 80 minutes at room temperature and then for 100 minutes at 40° C. At the end of this time, the reaction mixture was cooled, diluted with ethyl acetate and washed with twice ice water and then once with a saturated aqueous solution of sodium chloride. The solvent was then removed by distillation under reduced pressure. The resulting residue was purified by column chromatography through 50 g of silica gel, using a gradient elution method, with mixtures of ethyl acetate and hexane in ratios ranging from 3:2 to 4:1 by volume as the eluent, to give 742 mg (yield 81%) of the title compound as a foam-like solid.

Infrared Absorption Spectrum (liquid film), $v_{max}$ cm⁻: 3250, 1760, 1700, 1625.

Nuclear Magnetic Resonance Spectrum (CDCl$_3$, 270 MHz) δ ppm:

0.12 (9H, singlet);
1.03 (3H, triplet, J=7 Hz);
1.23 (3H, doublet, J=6 Hz);
1.25 (3H, triplet, J=7 Hz);
1.22–1.31 (3H, multiplet);
2.95–3.12 (4H, multiplet);
3.25–3.85 (2H, multiplet);
3.90 (1H, doublet of doublets, J=2 & 4 Hz);
4.14 (1H, quintet, J=6 Hz);
6.07–6.18 (1H, broad singlet);
7.32–7.35 (1H, multiplet);
7.41–7.51 (3H, multiplet).
Mass spectrum (m/z): 450 (M⁺, C$_{22}$H$_{34}$N$_2$O$_4$Ssi).

EXAMPLE 45

4-Nitrobenzyl (1R,5S,6S)-6-[1(R)-t-butyldimethylsilyloxyethyl]-1-methyl-2-phenylsulfinyl-1-carbapen-2-em-3-carboxylate

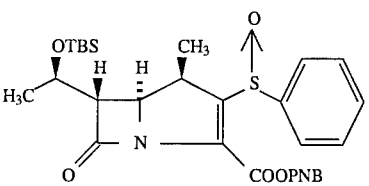

Following a procedure similar to that described in Example 38, but using 4-nitrobenzyl (1R,5S,6S)-6-[1(R)-t-butyldimethylsilyloxyethyl]-1-methyl-2-phenylthio-1-carbapen-2-em-3-carboxylate (prepared as described in Example 24) as a starting material, in a relative amount similar to that used in that Preparation, and then purifying the product by silica gel column chromatography, using a gradient elution method, with mixtures of diethyl ether and methylene chloride in ratios ranging from 5:95 to 20:80 by volume as the eluent, the lower polarity S-oxide was obtained as crystals in a yield of 62%, and the higher polarity S-oxide was obtained as a foam-like solid in a yield of 30%.

Recrystallization of the lower polarity S-oxide from a mixture of ethyl acetate and hexane afforded crystals of that isomer melting at 150°–151° C.

Isomer of Lower Polarity

Infrared Absorption Spectrum (Kbr), $v_{max}$ cm⁻: 1796, 1715, 1528, 1335, 1044, 839.

Nuclear Magnetic Resonance Spectrum (CDCl$_3$, 270 MHz) δ ppm:

0.06 (3H, singlet);
0.77 (3H, singlet);
0.73 (3H, doublet, J=7 Hz);
0.85 (9H, singlet);
1.18 (3, doublet, J=6 Hz);
3.27 (1H, doublet of doublets, J=3 & 5 Hz);
3.90 (1H, doublet of quartets, J=11 & 7 Hz);
4.23 (1H, doublet of quartets, J=5 & 6 Hz);
4.41 (1H, doublet of doublets, J=3 & 11 Hz);
5.36 (1H, doublet, J=14 Hz);
5.56 (1H, doublet, J=14 Hz);
7.46–7.53 (3H, multiplet);
7.66 (2H, doublet, J=9 Hz);
7.72–7.78 (2H, multiplet);
8.24 (2H, doublet, J=9 Hz).

Isomer of Higher Polarity

Infrared Absorption Spectrum (liquid film), $v_{max}$ cm⁻: 1788, 1730, 1524, 1319, 1273, 1047, 837.

Nuclear Magnetic Resonance Spectrum (CDCl$_3$, 270 MHz) δ ppm:

0.04 (3H, singlet);
0.05 (3H, singlet);
0.83 (9H, singlet);
1.15 (3H, doublet, J=6 Hz);
1.39 (3H, triplet, J=7 Hz);
3.16 (1H, doublet of quartets, J=10 & 7 Hz);

3.39 (1H, doublet of doublets, J=3 & 4 Hz);

4.16 (1H, doublet of doublets, J=3 & 10 Hz);

4.26 (1H, doublet of quartets, J=4 & 6 Hz);

5.40 (1H, doublet, J=14 Hz);

5.49 (1H, doublet, J=14 Hz);

7.51–7.58 (3H, multiplet);

7.68 (2H, doublet, J=9 Hz);

7.68–7.73 (2, multiplet);

8.23 (2H, doublet, J=9 Hz).

Mass spectrum (m/z): both isomers: 584 ($M^+$, $C_{29}H_{36}N_2O_7SSi$).

PREPARATION 46

4-Nitrobenzyl (1R,5S,6S)-6-[1(R)-t-butyldimethylsilyloxyethyl]-1-methyl-2-phenylsulfonyl-1-carbapen-2-em-3-carboxylate

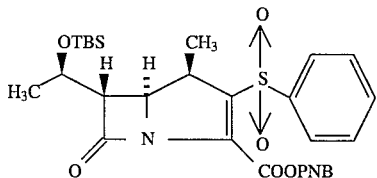

Following a procedure similar to that described in Example 28, but using the isomer of higher polarity of 4-nitrobenzyl (1R,5S,6S)-6-[1(R)-t-butyldimethylsilyloxyethyl]-1-methyl-2-phenylsulfinyl-1-carbapen-2-em-3-carboxylate (prepared as described in Preparation 45) as a starting material, in a relative amount similar to that used in that Preparation, the title compound was obtained as a foam-like solid in a yield of 87%.

Infrared Absorption Spectrum (liquid film), $v_{max}$ cm$^-$: 1796, 1750, 1524, 1316, 1264, 1161, 1079, 837.

Nuclear Magnetic Resonance Spectrum (CDCl$_3$, 270 MHz) δ ppm:

0.03 (3H, singlet);

0.05 (3H, singlet);

0.84 (9H, singlet);

1.16 (3H, doublet, J=6 Hz);

1.19 (3H, doublet, J=7 Hz);

3.40 (1H, doublet, J=11 & 7 Hz);

3.46–3.52 (1H, multiplet);

4.23 (1H, doublet of quartets, J=4 & 6 Hz);

4.44 (1H, doublet of doublets, J=4 & 11 Hz);

5.45 (2H, singlet);

7.51–7.58 (2H, multiplet);

7.60–7.68 (3H, multiplet);

8.00 (2H, doublet, J=9 Hz);

8.23 (2H, doublet, J=9 Hz).

Mass spectrum (m/z): 543 [$M^+$ ($C_{29}H_{36}N_2O_8SSi$)-t-Bu].

PREPARATION 47

4-Nitrobenzyl (5S,6S)-6-[1(R)-t-butyldimethylsilyloxyethyl]-2-phenylsulfinyl-1-carbapen-2-em-3-carboxylate

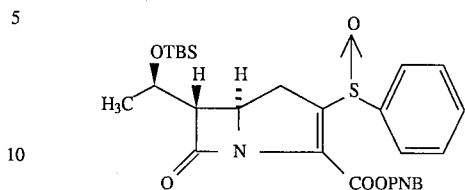

Following a procedure similar to that described in Example 38 but using 4-nitrobenzyl (5S,6S)-6-[1(R)-t-butyldimethylsilyloxyethyl]-2-phenylthio-1-carbapen-2-em-3-carboxylate [Tetrahedron Letters 25, 2793 (1984)] as a starting material, in a relative amount similar to that used in that Example. The product was separated and purified by silica gel column chromatography eluted with a 4:6 by volume mixture of ethyl acetate and hexane, to give the lower polarity S-oxide as crystals in a yield of 43%, and the higher polarity S-oxide as a foam-like solid in a yield of 48%. Recrystallization of the lower polarity S-oxide from diisopropyl ether afforded it in the form of crystals melting at 111.5°–114° C.

Isomer of Lower Polarity

Infrared Absorption Spectrum (KBr), $v_{max}$ cm$^-$: 1786, 1723, 1607, 1526, 1323, 1206, 1044, 837.

Nuclear Magnetic Resonance Spectrum (CDCl$_3$, 270 MHz) δ ppm:

0.05 (3H, singlet);

0.06 (3H, singlet);

0.85 (9H, singlet);

1.17 (3H, doublet, J=6 Hz);

2.55 (3H, doublet of doublets, J=9 & 18 Hz);

3.08 (1H, doublet of doublets, J=3 & 5 Hz);

3.51 (1H, doublet of doublets, J=11 & 18 Hz);

4.18 (1H, doublet of quartets, J=5 & 6 Hz);

4.37 (1H, doubled doublet of doublets, J=3, 9 & 11 Hz);

5.37 (1H, doublet, J=14 Hz);

5.54 (1H, doublet, J=14 Hz);

7.48–7.54 (3H, multiplet);

7.65 (2H, doublet, J=9 Hz);

7.70–7.77 (2H, multiplet);

8.24 (2H, doublet, J=9 Hz).

Mass spectrum (m/z): 570 ($M^+$, $C_{28}H_{34}N_2O_7SSi$).

Isomer of Higher Polarity

Infrared Absorption Spectrum (liquid film), $v_{max}$ cm$^-$: 1790, 1723, 1607, 1524, 1322, 1269, 1044, 837.

Nuclear Magnetic Resonance Spectrum (CDCl$_3$, 270 MHz) δ ppm:

0.05 (3H, singlet);

0.06 (3H, singlet);

0.84 (9H, singlet);

1.18 (3H, doublet, J=6 Hz);

2.80 (3H, doublet of doublets, J=11 & 19 Hz);

3.29 (1H, doublet of doublets, J=8 & 19 Hz);

3.34 (1H, triplet, J=3 Hz);

4.17–4.30 (2H, multiplet);

5.40 (1H, doublet, J=14 Hz);

5.49 (1H, doublet, J=14 Hz);

7.49–7.55 (3H, multiplet);

7.68 (2H, doublet, J=9 Hz);

7.70–7.76 (2H, multiplet);

8.23 (2H, doublet, J=9 Hz).

PREPARATION 48

4-Nitrobenzyl (1R,5S,6S)-6-[1(R)-t-butyldimethylsilyloxy-ethyl]-1-methyl-2-[2-(4-nitrobenzyloxycarbonyl)-aminoethylsulfinyl]-1-carbapen-2-em-3-carboxylate

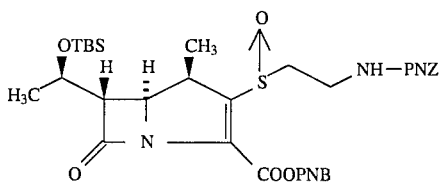

Following a procedure similar to that described in Example 38, but using 4-nitrobenzyl (1R,5S,6S)-6-[1(R)-t-butyldimethylsilyloxyethyl]-1-methyl-2-[2-(4-nitrobenzyloxycarbonyl)-aminoethylthio]-1-carbapen-2-em-3-carboxylate (prepared as described in Example 22) as a starting material, in a relative amount similar to that used in that Example, the title compound was obtained as a foam-like solid in a yield of 92%.

Infrared Absorption Spectrum (liquid film), $v_{max}$ cm⁻: 1786, 1721, 1607, 1522, 1347, 1254, 1048.

Nuclear Magnetic Resonance Spectrum (CDCl₃, 270 MHz) δ ppm:

0.07 (3H, singlet);

0.09 (3H, singlet);

0.86 (9H, singlet);

1.23 (1.5H, doublet, J=6 Hz);

1.24 (1.5H, doublet, J=6 Hz);

1.39 (1.5H, doublet, J=7 Hz);

1.40 (1.5H, doublet, J=7 Hz);

3.12–3.45 (3H, multiplet);

3.60–3.92 (3H, multiplet);

4.29 (1H, quartet, J=6 Hz);

4.34 (0.5H, doublet of doublets, J=3 & 10 Hz);

4.46 (0.5H, doublet of doublets, J=3 & 10 Hz);

5.14–5.46 (2H, multiplet);

5.23 (2H, singlet);

5.68–5.77 (1H, multiplet);

7.51 (1H, doublet, J=9 Hz);

7.52 (1H, doublet, J=9 Hz);

7.61 (1H, doublet, J=9 Hz);

7.66 (1H, doublet, J=9 Hz);

8.20–8.24 (4H, multiplet).

Mass spectrum (m/z): 705 [M⁺ (C₃₃H₄₂N₄O₁₁SSi)-CH₃].

PREPARATION 49

4-Nitrobenzyl (1R,5S,6S)-6-[1(R)-t-butyldimethylsilyloxy-ethyl]-1-methyl-2-ethylsulfinyl-1-methyl-1-carbapen-2-em-3-carboxylate

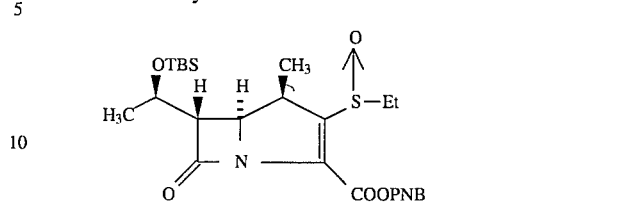

Following a procedure similar to that described in Example 38, but using 4-nitrobenzyl (1R,5S,6S)-6-[1(R)-t-butyldimethylsilyloxyethyl]-2-ethylthio-1-methyl-1-carbapen-2-em-3-carboxylate (prepared as described in Example 26) as a starting material, in a relative amount similar to that used in that Example, the title compound was obtained as a foam-like solid in a yield of 92%.

Infrared Absorption Spectrum (liquid film), $v_{max}$ cm⁻: 1784, 1715, 1524, 1333, 1055, 837.

Nuclear Magnetic Resonance Spectrum (CDCl₃, 270 MHz) δ ppm:

0.08 (3.6H, singlet);

0.09 (2.4H, singlet);

0.86 (9H, singlet);

1.24 (3H, doublet, J=6 Hz);

1.39 (3H, doublet, J=7 Hz);

1.41 (1.8H, triplet, J=7 Hz);

1.44 (1.2H, doublet, J=7 Hz);

2.93–3.10 (2H, multiplet);

3.38 (0.6H, doublet of doublets, J=3 & 5 Hz);

3.41 (0.4H, doublet of doublets, J=3 & 5 Hz);

3.61 (0.6H, doublet of doublets, J=10 & 7 Hz);

3.85 (0.4H, doublet of quartets, J=10 & 7 Hz);

4.23–4.34 (1.6H, multiplet);

4.42 (0.4H, doublet of doublets, J=3 & 10 Hz);

5.27 (0.4H, doublet, J=14 Hz);

5.32 (0.6H, doublet, J=14 Hz);

5.41 (0.6H, doublet, J=14 Hz);

5.44 (0.4H, doublet, J=14 Hz);

7.63 (1.2H, doublet, J=9 Hz);

7.66 (0.8H, doublet, J=9 Hz);

8.23 (2H, doublet, J=9 Hz).

Mass spectrum (m/z): 479 (M⁺ (C₂₅H₃₆N₂O₇SSi)-t-Bu).

PREPARATION 50

4-Nitrobenzyl (5R,6S)-6-[1(R)-t-butyldimethylsilyloxy-ethyl]-2-ethylsulfinylpenem-3-carboxylate

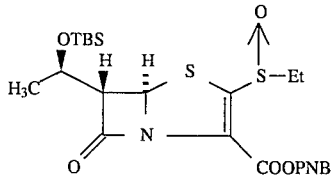

20 ml of a methylene chloride solution containing 1.039 g (1.98 mmol) of 4-nitrobenzyl (5R,6S)-6-[1(R)-t-butyldimethylsilyloxyethyl]-2-ethylthiopenem-3-carboxylate was cooled in an ice bath and 469 mg of m-chloroperbenzoic acid (purity 80%) was added carefully over a period of 5 minutes to the cooled solution. The reaction mixture was stirred for 30 minutes at the same temperature and then a further 88 mg of m-chloroperbenzoic acid (purity 80%) (making a total of 557 mg, 2.58 mmol) were added, and the mixture was stirred for a further 15 minutes. At the end of this time, the reaction mixture was diluted with methylene chloride and washed with a dilute aqueous solution of sodium hydrogencarbonate. The organic layer was condensed by evaporation under reduced pressure, and the resulting residue was purified by column chromatography through 50 g of silica gel. Elution with a 4:6 by volume mixture of ethyl acetate and hexane afforded, in order, the following:

202 mg (yield 19%) of an S-oxide lower polarity as a foam-like solid;

336 mg (31% yield) of a mixture of the S-oxides of lower and higher polarity in a ratio of 1:3, and 72 mg (7% yield) of an S-oxide of higher polarity as a foam-like solid.

In Examples 29 and 30, all three of the fractions separated by column chromatography were recombined for use as the starting materials.

Isomer of Lower Polarity

Infrared Absorption Spectrum (liquid film), $v_{max}$ cm⁻: 1796, 1701, 1524, 1323, 1063.

Nuclear Magnetic Resonance Spectrum (CDCl$_3$, 270 MHz) δ ppm:

0.05 (3H, singlet);
0.08 (3H, singlet);
0.84 (9H, singlet);
1.26 (3H, doublet, J=6 Hz);
1.44 (3H, triplet, J=7 Hz);
3.10 (2H, quartet, J=7 Hz);
3.92 (1H, doublet of doublets, J=1 & 3 Hz);
4.28 (1H, doublet of quartets, J=3 & 6 Hz);
5.26 (1H, doublet, J=14 Hz);
5.38 (1H, doublet, J=14 Hz);
5.73 (1H, doublet, J=1 Hz);
7.62 (2H, doublet, J=9 Hz);
8.23 (2H, doublet, J=9 Hz).

Isomer of Higher Polarity

Infrared Absorption Spectrum (liquid film), $v_{max}$ cm⁻: 1794, 1702, 1524, 1321, 1063.

Nuclear Magnetic Resonance Spectrum (CDCl$_3$, 270 MHz) δ ppm:

0.04 (3H, singlet);
0.07 (3H, singlet);
0.82 (9H, singlet);
1.26 (3H, doublet, J=6 Hz);
1.44 (3H, triplet, J=7 Hz);
3.13 (2H, doublet of quartets, J=4 & 8 Hz);
3.90 (1H, doublet of doublets, J=2 & 4 Hz);
4.27 (1H, doublet of quartets, J=4 & 6 Hz);
5.22 (1H, doublet, J=14 Hz);
5.41 (1H, doublet, J=14 Hz);
5.85 (1H, doublet, J=2 Hz);
7.59 (2H, doublet, J=9 Hz);
8.23 (2H, doublet, J=9 Hz).

PREPARATION 51

4-Nitrobenzyl (1R,5S,6S)-2-[(3S,6-S)-5-dimethylcarbamoyl-1-(4-nitrobenzyloxycarbonyl)-3-pyrrolidinylthio]-1-methyl-6-[1(R)-hydroxyethyl]-1-carbapen-2-em-3-carboxylate

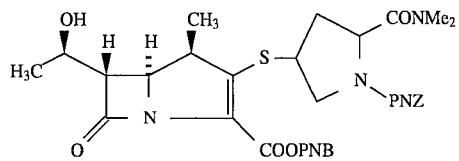

8 mg (0.039 mmol) of citric acid hydrate were added to 2 ml of a solution containing 55 mg of 4-nitrobenzyl (1R,5S,6S)-2-[(3S,5-S)-5-dimethylcarbamoyl-1-(4-nitrobenzyloxycarbonyl)-3-pyrrolidinylthio]-1-methyl-6-[1(R)-trimethylsilyloxyethyl]-1-carbapen-2-em-3-carboxylate (prepared as described in Example 18) in methanol, and the resulting mixture was stirred at room temperature for 35 minutes. At the end of this time, the solvent was removed by distillation under reduced pressure, and the residue was purified by column chromatography through 5 g of silica gel, using a 1:9 by volume mixture of methanol and ethyl acetate as the eluent, to give 42 mg (yield 84%) of the title compound as a vitreous solid.

The physicochemical properties of this compound were in agreement with those of the compound prepared as described in Example 27.

PREPARATION 52

S-2-Diethylcarbamoylphenyl 2(R)-{2S,3S) -3-[1(R)-(t-butyldimethylsilyloxy)ethyl]-4-oxo-2-azetidinyl}thiopropionate

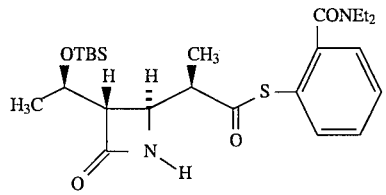

52(a) 1-t-Butyldimethylsilyloxy-1-(2-diethylcarbamoyl)-phenylthio-1-propene 1.7 ml (12.2 mmol) of triethylamine were added to a solution of 3.20 g (12.1 mmol) of S-(2-diethylcarbamoyl)phenyl thiopropionate, which is described in Referential Example 12 of Japanese Patent Kokai Application No. Hei 4-174099, and 3.64 g (24.1 mmol) of t-butyldimethylsilyl chloride in a mixture of 12 ml of dimethylformamide and 12 ml of tetrahydrofuran, and the resulting mixture was stirred at room temperature for 3 minutes. At the end of this time, the solution was cooled to −78° C., and 12.1 ml of a 1.0M tetrahydrofuran solution of lithium bis(trimethylsilyl)amide were added dropwise over a period of 20 minutes. The mixture was then stirred at the same temperature for 30 minutes, after which 10 ml of a saturated aqueous solution of sodium hydrogencarbonate were added. The reaction mixture was then extracted with hexane, and the extract was washed twice with water, once with a 2N aqueous solution of sodium hydroxide, three times with water and once with a saturated aqueous solution of sodium chloride, in that order. The extract was then dried over anhydrous magnesium sulfate, and the solvent was removed by distillation under reduced pressure. The resulting residue was again dissolved in hexane, and the solution was mixed with 9.0 g of aluminum oxide for chromatography and then stirred for 15 minutes. The aluminum oxide was removed from the mixture by filtration, and the aluminum oxide was washed with hexane. The filtrate and the washings were combined and the solvent was removed by distillation under reduced pressure, to give 4.24 g of Z(O)-1-t-butyldimethylsilyloxy-1-(2-diethylcarbamoyl) phenylthio-1-propene. Analysis by nuclear magnetic resonance spectroscopy (270 MHz) showed that the ratio of the Z(O)-isomer to the E(O)-isomer in the product was more than 20.

52(b) S-2-Diethylcarbamoylphenyl 2(R)-{(2S,3)-3-[1(R)-(t-butyldimethylsilyloxy)ethyl]-4-oxo-2-azetidinyl}thiopropionate 1.49 g (10.9 mmol) of anhydrous zinc chloride were added to a solution of 4.24 g of Z(O)-1-t-butyldimethylsilyloxy-1-(2-diethylcarbamoyl) phentylthio-1-propene [prepared as described in step (a) above] and 1.57 g (5.47 mmol) of (3R,4S)-3-[1(R)-t-butyldimethylsilyloxyethyl]-4-acetoxy-2-azetidinone in 55 ml of methylene chloride, and the resulting mixture was heated under reflux for 40 minutes. At the end of this time, the reaction mixture was cooled to room temperature, and the solvent was removed by distillation under reduced pressure. The residue was dissolved in ethyl acetate, and the solution was washed three times with water and once with a saturated aqueous solution of sodium chloride. The mixture was then dried over anhydrous magnesium sulfate, after which the solvent was removed by distillation under reduced pressure, and the residue was recystallized from about 10 ml of diisopropyl ether, to give 2.08 g (yield 77%) of the title compound as crystals, melting at 130.5°–132° C.

Nuclear Magnetic Resonance Spectrum (CDCl$_3$, 270 MHz), δ ppm:

0.08 (6H, singlet);
0.87 (9H, singlet);
1.03 (4H, triplet, J=7 Hz);
1.21 (3H, doublet, J=6 Hz);
1.25 (3H, triplet, J=7 Hz);
1.29 (3H, doublet, J=7 Hz);
2.96–3.15 (4H, multiplet);
3.20–3.85 (2H, broad);
3.96 (1H, dd, J=2, 4 Hz);
4.19 (1H, quintet, J=6 Hz);
5.90–6.10 (1H, broad singlet);
7.30–7.35 (1H, multiplet);
7.41–7.51 (3H, multiplet).

Mass spectrum (m/z): 492 (M$^+$, C$_{25}$H$_{40}$N$_2$O$_4$SSi).

We claim:

1. A compound selected from the group consisting of 4-nitrobenzyl-2-(2-diethylcarbamoylphenylthio)-1-methyl-6-(1-trimethylsilyloxyethyl)-1-carbapen -2-em-3-carboxylate, 4-nitrobenzyl-2-(2-diethylcarbamoylphenylsulfinyl)-1-methyl-6-(1-trimethylsilyloxyethyl)-1-carbapen -2-em-3-carboxylate, 4-nitrobenzyl-2-(2-diethylcarbamoylphenylsulfonyl)-1-methyl-6-(1-trimethylsilyloxyethyl)-1-carbapen -2-em-3-carboxylate, 4-nitrobenzyl-2-(2-diethylcarbamoylphenylthio)-1-methyl-6-(1-hydroxyethyl)-1-carbapen -2-em-3-carboxylate, 4-nitrobenzyl-2-(2-diethylcarbamoylphenylsulfinyl)-1-methyl-6-(1-hydroxyethyl)-1-carbapen -2-em-3-carboxylate, 4-nitrobenzyl-2-(2-diethylcarbamoylphenylsulfonyl)-1-methyl-6-(1-hydroxyethyl)-1-carbapen -2-em-3-carboxylate, 4-nitrobenzyl-2-[2-(1-perhydroazepinylcarbonyl)phenylthio ]-1-methyl-6-(1-trimethylsilyloxyethyl)-1-carbapen-2-em-3-carboxylate, 4-nitrobenzyl-2-[2-(1-perhydroazepinylcarbonyl)phenylsulfinyl ]-1-methyl-6-(1-trimethylsilyloxyethyl)-1-carbapen-2-em-3-carboxylate, 4-nitrobenzyl-2-[2-(1-perhydroazepinylcarbonyl)phenylsulfonyl ]-1-methyl-6-(1-trimethylsilyloxyethyl)-1-carbapen-2-em-3-carboxylate, 4-nitrobenzyl-2-[2-(1-perhydroazepinylcarbonyl)phenylthio ]-1-methyl-6-(1-hydroxyethyl)-1-carbapen-2-em-3-carboxylate, 4-nitrobenzyl-2-[2-(1-perhydroazepinylcarbonyl)phenylsulfinyl ]-1-methyl-6-(1-hydroxyethyl)-1-carbapen-2-em-3-carboxylate and 4-nitrobenzyl-2-[2-(1-perhydroazepinylcarbonyl)phenylsulfonyl ]-1-methyl-6-(1-hydroxyethyl)-1-carbapen-2-em-3-carboxylate;

or a pharmaceutically acceptable salt thereof or a pharmaceutically acceptable ester thereof.

2. The compound of claim 1, which is 4-nitrobenzyl-2-(2-diethylcarbamoylphenylthio)-1-methyl-6-(1-trimethylsilyloxyethyl)-1-carbapen -2-em-3-carboxylate.

3. The compound of claim 1, which is 4-nitrobenzyl-2-(2-diethylcarbamoylphenylsulfinyl)-1-methyl-6-(1-trimethylsilyloxyethyl)-1-carbapen -2-em-3-carboxylate.

4. The compound of claim 1, which is 4-nitrobenzyl-2-(2-diethylcarbamoylphenylsulfonyl)-1-methyl-6-(1-trimethylsilyloxyethyl)-1-carbapen -2-em-3-carboxylate.

5. The compound of claim 1, which is 4-nitrobenzyl-2-(2-diethylcarbamoylphenylthio)-1-methyl-6-(1-hydroxyethyl)-1-carbapen -2-em-3-carboxylate.

6. The compound of claim 1, which is 4-nitrobenzyl-2-(2-diethylcarbamoylphenylsulfinyl)-1-methyl-6-(1-hydroxyethyl)-1-carbapen -2-em-3-carboxylate.

7. The compound of claim 1, which is 4-nitrobenzyl-2-(2-diethylcarbamoylphenylsulfonyl)-1-methyl-6-(1-hydroxyethyl)-1-carbapen -2-em-3-carboxylate.

8. The compound of claim 1, which is 4-nitrobenzyl-2-[2-(1-perhydroazepinylcarbonyl)phenylthio ]-1-methyl-6-(1-trimethylsilyloxyethyl)-1-carbapen-2-em-3-carboxylate.

9. The compound of claim 1, which is 4-nitrobenzyl-2-[2-(1-perhydroazepinylcarbonyl)phenylsulfinyl ]-1-methyl-6-(1-trimethylsilyloxyethyl)-1-carbapen-2-em-3-carboxylate.

10. The compound of claim 1, which is 4-nitrobenzyl-2-[2-(1-perhydroazepinylcarbonyl)phenylsulfonyl ]-1-methyl-6-(1-trimethylsilyloxyethyl)-1-carbapen-2-em-3-carboxylate.

11. The compound of claim 1, which is 4-nitrobenzyl-2-[2-(1-perhydroazepinylcarbonyl)phenylthio ]-1-methyl-6-(1-hydroxyethyl)-1-carbapen-2-em-3-carboxylate.

12. The compound of claim 1, which is 4-nitrobenzyl-2-[2-(1-perhydroazepinylcarbonyl)phenylsulfinyl ]-1-methyl-6-(1-hydroxyethyl)-1-carbapen-2-em-3-carboxylate.

13. The compound of claim 1, which is 4-nitrobenzyl-2-[2-(1-perhydroazepinylcarbonyl)phenylsulfonyl ]-1-methyl-6-(1-hydroxyethyl)-1-carbapen-2-em-3-carboxylate.

* * * * *